US010562935B2

(12) United States Patent
Luyt et al.

(10) Patent No.: US 10,562,935 B2
(45) Date of Patent: Feb. 18, 2020

(54) STAPLED PEPTIDES AND USES THEREOF

(71) Applicant: London Health Sciences Centre Research Inc., London (CA)

(72) Inventors: Leonard Luyt, London (CA); Eva Turley, London (CA); Alexandra Hauser-Kawaguchi, Toronto (CA); Emily Rodrigues, Hamilton (CA)

(73) Assignee: London Health Sciences Centre Research Inc., London (CA)

( * ) Notice: Subject to any disclaimer, the term of this patent is extended or adjusted under 35 U.S.C. 154(b) by 93 days.

(21) Appl. No.: 15/559,953

(22) PCT Filed: Mar. 21, 2016

(86) PCT No.: PCT/IB2016/051587
§ 371 (c)(1),
(2) Date: Sep. 20, 2017

(87) PCT Pub. No.: WO2016/151478
PCT Pub. Date: Sep. 29, 2016

(65) Prior Publication Data
US 2018/0170967 A1    Jun. 21, 2018
US 2019/0092816 A9    Mar. 28, 2019

Related U.S. Application Data

(60) Provisional application No. 62/135,951, filed on Mar. 20, 2015.

(51) Int. Cl.
*A61K 38/08*    (2019.01)
*A61K 38/10*    (2006.01)
(Continued)

(52) U.S. Cl.
CPC ............... *C07K 7/64* (2013.01); *A61K 38/08* (2013.01); *A61K 38/10* (2013.01); *A61K 38/177* (2013.01);
(Continued)

(58) Field of Classification Search
CPC .... A61K 38/08; A61K 38/10; A61K 38/1709; A61K 38/177; C07K 7/06; C07K 7/08; C07K 14/47; C07K 14/705
See application file for complete search history.

(56) References Cited

U.S. PATENT DOCUMENTS 6,271,344 B1    8/2001  Turley
6,429,291 B1    8/2002  Turley et al.
(Continued)

FOREIGN PATENT DOCUMENTS

CA    2160603 C    4/1996
CA    2237051 A    6/1999
(Continued)

OTHER PUBLICATIONS

Sequence Listing for WO 2011/150495 published on Dec. 8, 2011, 16 pages.
(Continued)

*Primary Examiner* — Jeffrey E. Russel
(74) *Attorney, Agent, or Firm* — Stinson LLP

(57) ABSTRACT

Cyclized peptides derived from the hyaluronan binding region of RHAMM are provided. Pharmaceutical compositions and methods for using the peptides and pharmaceutical compositions are also provided. The peptides and pharmaceutical compositions can be used for the treatment of cancer, inflammatory disorders, autoimmune disorders, and fibrotic disorders.

24 Claims, 36 Drawing Sheets

Specification includes a Sequence Listing.

(51) Int. Cl.
| | |
|---|---|
| A61K 38/17 | (2006.01) |
| C07K 7/06 | (2006.01) |
| C07K 7/08 | (2006.01) |
| C07K 14/705 | (2006.01) |
| C07K 7/64 | (2006.01) |

(52) U.S. Cl.
CPC ............... *C07K 7/06* (2013.01); *C07K 7/08* (2013.01); *C07K 14/705* (2013.01)

(56) References Cited

U.S. PATENT DOCUMENTS

| | | | |
|---|---|---|---|
| 6,864,235 | B1 | 3/2005 | Turley et al. |
| 6,911,429 | B2 | 6/2005 | Cruz et al. |
| 8,044,022 | B2 | 10/2011 | Kolodka et al. |
| 8,093,217 | B2 | 1/2012 | Toole et al. |
| 8,715,653 | B2 | 5/2014 | Turley et al. |
| 9,090,659 | B2 | 7/2015 | Luyt et al. |
| 2002/0127227 | A1 | 9/2002 | Holmes et al. |
| 2003/0100490 | A1 | 5/2003 | Cruz et al. |
| 2003/0170755 | A1 | 9/2003 | Schmitt et al. |
| 2004/0010812 | A1 | 1/2004 | Turley et al. |
| 2004/0037834 | A1 | 2/2004 | Woloski et al. |
| 2005/0058646 | A1 | 3/2005 | Turley et al. |
| 2007/0179085 | A1 | 8/2007 | Savani |
| 2009/0030180 | A1 | 1/2009 | Kolodka et al. |
| 2010/0062000 | A1 | 3/2010 | Turley et al. |
| 2010/0143382 | A1 | 6/2010 | Turley et al. |
| 2010/0290989 | A1 | 11/2010 | Tolg et al. |
| 2013/0259807 | A1 | 10/2013 | Bissell et al. |
| 2014/0179616 | A1 | 6/2014 | Turley et al. |
| 2015/0284433 | A1 | 10/2015 | Turley et al. |

FOREIGN PATENT DOCUMENTS

| | | |
|---|---|---|
| EP | 0 950 708 A2 | 10/1999 |
| WO | 93/21312 A1 | 10/1993 |
| WO | 97/24111 A2 | 7/1997 |
| WO | 97/38098 A1 | 10/1997 |
| WO | 02/100428 A1 | 12/2002 |
| WO | 03/033535 A2 | 4/2003 |
| WO | 2006/130974 A1 | 12/2006 |
| WO | 2008/140586 A2 | 11/2008 |
| WO | 2011/150495 A1 | 12/2011 |
| WO | 2012/031015 A1 | 3/2012 |
| WO | 2014/082042 A2 | 5/2014 |
| WO | 2015/184125 A1 | 12/2015 |

OTHER PUBLICATIONS

Shepherd, N. E., et al., "Single Turn Peptide Alpha Helices with Exceptional Stability in Water," Journal of the American Chemical Society, 2005, pp. 2974-2983, vol. 127, No. 9.
Sokolowska, M., et al., "Low Molecular Weight Hyaluronan Activates Cytosolic Phospholipase A(sub2)alpha and Eicosanoid Production in Monocytes and Macrophages," The Journal of Biological Chemistry, 2014, pp. 4470-4488, vol. 289, No. 7.
Takeda, M., et al., "Ligand-Induced Structural Changes of the CD44 Hyaluronan-Binding Domain Revealed by NMR," The Journal of Biological Chemistry, 2006, pp. 40089-40095, vol. 281, No. 52.
Tammi, M. I., et al., "Hyaluronan and Homeostasis: A Balancing Act," The Journal of Biological Chemistry, 2002, pp. 4581-4584, vol. 277, No. 7.
Teriete, P., et al., "Structure of the Regulatory Hyaluronan Binding Domain in the Inflammatory Leukocyte Homing Receptor CD44," Molecular Cell, 2004, pp. 483-496, vol. 13, No. 4.
Tolg, C., et al., "Genetic Deletion of Receptor for Hyaluronan-Mediated Motility (Rhamm) Attenuates the Formation of Aggressive Fibromatosis (Desmoid Tumor)," Oncogene, Oct. 2003, pp. 6873-6882, vol. 22, No. 44.

Tolg, C., et al., "Rhamm −/− Fibroblasts are Defective in CD44-Mediated ERK1,2 Motogenic Signaling, Leading to Defective Skin Wound Repair," The Journal of Cell Biology, 2006, pp. 1017-1028, vol. 175, No. 6.
Tolg, C., et al., "A RHAMM Mimetic Peptide Blocks Hyaluronan Signaling and Reduces Inflammation and Fibrogenesis in Excisional Skin Wounds," The American Journal of Pathology, 2012, pp. 1250-1270, vol. 181, No. 4.
Tolg, C., et al., "Hyaluronan and RHAMM in Wound Repair and the "Cancerization" of Stromal Tissues," BioMed Research International, 2014, 18 pages, Article ID 103923, vol. 2014.
Toole, B. P., "Hyaluronan: From Extracellular Glue to Pericellular Cue," Nature Reviews Cancer, Jul. 2004, pp. 528-539, vol. 4, No. 7.
Turley, E. A., "Purification of a Hyaluronate-Binding Protein Fraction that Modifies Cell Social Behavior," Biochemical and Biophysical Research Communications, Oct. 1982, pp. 1016-1024, vol. 108, No. 3.
Turley, E. A., et al., "Expression and Function of a Receptor for Hyaluronan-Mediated Motility on Normal and Malignant B Lymphocytes," Blood, Jan. 1993, pp. 446-453, vol. 81, No. 2.
Turley, E. A., et al., "Signaling Properties of Hyaluronan Receptors," The Journal of Biological Chemistry, 2002, pp. 4589-4592, vol. 277, No. 7.
Yang, B., et al, "Identification of Two Hyaluronan-Binding Domains in the Hyaluronan Receptor RHAMM," The Journa of Biological Chemistry, 1993, pp. 8617-8623, vol. 268, No. 12.
Yang, B., et al., "Identification of a Common Hyaluronan Binding Motif in the Hyaluronan Binding Proteins RHAMM, CD44 and Link Protein," The EMBO Journal, 1994, pp. 286-296, vol. 13, No. 2.
Zaleski, K. J., et al., "Hyaluronic Acid Binding Peptides Prevent Experimental Staphylococcal Wound Infection," Antimicrobial Agents and Chemotherapy, Nov. 2006, pp. 3856-3860, vol. 50, No. 11.
Zhang, S. et al., "The Hyaluronan Receptor RHAMM Regulates Extracellular-Regulated Kinase," The Journal of Biological Chemistry, May 1998, pp. 11342-11348, vol. 273, No. 18.
Ziebell, M. R., et al., "Interactions of Peptide Mimics of Hyaluronic Acid with the Receptor for Hyaluronan Mediated Motility (RHAMM)," Journal of Computer-Aided Molecular Designs, 2004, pp. 597-614, vol. 18, No. 10.
Adamia, S., et al., "Hyaluronan and Hyaluronan Synthases: Potential Therapeutic Targets in Cancer," Current Drug Targets. Cardiovascular & Haematological Disorders, 2005, pp. 3-14, vol. 5, No. 1.
Aitken, K., et al., "Stretch-Induced Bladder Smooth Muscle Cell (SMC) Proliferation is Mediated by RHAMM-Dependent Extracellular-Regulated Kinase (erk) Signaling," Urology, Jun. 2001, p. 109, vol. 57, Issue 6, Supplement 1.
Arispe, N., et al., "Efficiency of Histidine-Associating Compounds for Blocking the Alzheimer's Abeta Channel Activity and Cytotoxicity," Biophysical Journal, 2008, pp. 4879-4889, vol. 95, No. 10.
Assmann, V., et al., "The Human Hyaluronan Receptor RHAMM is Expressed as an Intracellular Protein in Breast Cancer Cells," Journal of Cell Science, 1998, pp. 1685-1694, vol. 111, Part 12.
Assmann, V., et al., "The Intracellular Hyaluronan Receptor RHAMM/ IHABP Interacts with Microtubules and Actin Filaments," Journal of Cell Science, 1999, pp. 3943-3954, vol. 112, Part 22.
Bissell, D. M., "Chronic Liver Injury, TGF-beta, and Cancer," Experimental & Molecular Medicine, 2001, pp. 179-190, vol. 33, No. 4.
Bollyky, P. L., et al., "The Role of Hyaluronan and the Extracellular Matrix in Islet Inflammation and Immune Regulation," Current Diabetes Reports, Oct. 2012, pp. 471-480, vol. 12, No. 5.
Casalegno-Garduno, R., et al., "Clinical Peptide Vaccination Trials for Leukemia Patients," Expert Review of Vaccines, Jun. 2011, pp. 785-799, vol. 10, No. 6.
Cheon, S. S., et al., "beta-Catenin Stabilization Dysregulates Mesenchymal Cell Proliferation, Motility, and Invasiveness and Causes Aggressive Fibromatosis and Hyperplastic Cutaneous Wounds," Proceedings of the National Academy of Sciences of the United States of America, 2002, pp. 6973-6978, vol. 99, No. 10.

(56) References Cited

OTHER PUBLICATIONS

Cheung, W. F., et al., "Receptor for Hyaluronan-Mediated Motility (RHAMM), A Hyaladherin that Regulates Cell Responses to Growth Factors," Biochemical Society Transactions, 1999, pp. 135-142, vol. 27, No. 2.

Correa, D. H. A., et al., "The Use of Circular Dichroism Spectroscopy to Study Protein Folding, Form and Function," African Journal of Biochemistry Research, May 2009, pp. 164-173, vol. 3, No. 5.

Ebid, R., et al., "Hyaluronan Is Not a Ligand but a Regulator of Toll-Like Receptor Signaling in Mesangial Cells: Role of Extracellular Matrix in Innate Immunity," ISRN Nephrology, 2014, 11 pages, Article ID 714081, vol. 2014.

Esguerra, K. V., et al., "Tubulin Derived Peptides as Optical Imaging Probes Targeting RHAMM," The Journal of Nuclear Medicine, May 2010, 2 pages, vol. 51, Supplement 2, Abstract No. 394.

Evanko, S. P., et al., "Hyaluronan-Dependent Pericellular Matrix," Advanced Drug Delivery Reviews, 2007, pp. 1351-1365, vol. 59, No. 13.

Foley, J. P., et al., "Toll-Like Receptor 2 (TLR2), Transforming Growth Factor-beta, Hyaluronan (HA), and Receptor for HA-Mediated Motility (RHAMM) Are Required for Surfactant Protein A—Stimulated Macrophage Chemotaxis," The Journal of Biological Chemistry, 2012, pp. 37406-37419, vol. 287, No. 44.

Geneseq, "RHAMM/Erk I Competitive Binding Peptide D5," XP-002718746, retrieved from EBI accession No. GSP: ADC02454, Database accession No. ADC02454, Dec. 18, 2003, 1 page.

Geneseq, "Heparin Binding Protein Associated Amino Acid Sequence, SEQ ID No. 65," XP-002718747, retrieved from EBI Accession No. GSP:ADY52132, Database Accession No. ADY52132, Mar. 3, 2005, 1 page.

Geneseq, "Structural Peptide Seq ID No. 23563," XP-002718745, retrieved from EBI Accession No. GSP:AJG37689, Database Accession No. AJG37689, Aug. 30, 2007, 1 page.

GenScript, "Peptide Modifications," Oct. 2007, 2 pages.

Greiner, J., et al., "RHAMM/CD168-R3 Peptide Vaccination of HLA-A2+ Patients with Acute Myeloid Leukemia (AML), Myelodysplastic Syndrome (MDS) and Multiple Myeloma (MM)," Blood, 2005, p. 2781, vol. 106, No. 11, Abstract only.

Greiner, J., et al., "Identification and Characterization of Epitopes of the Receptor for Hyaluronic Acid-Mediated Motility (RHAMM/CD168) Recognized by CD8+ T Cells of HLA-A2-Positive Patients with Acute Myeloid Leukemia," Blood, 2005, pp. 938-945, vol. 106, No. 3.

Hall, C. L., et al., "Overexpression of the Hyaluronan Receptor RHAMM is Transforming and is Also Required for H-ras Transformation," Cell, Jul. 1995, pp. 19-26, vol. 82, No. 1.

Hall, C. L., et al., "pp60(c-src) is Required for Cell Locomotion Regulated by the Hyaluronanreceptor RHAMM," Oncogene, 1996, pp. 2213-2224, vol. 13, No. 10.

Hall, C. L., et al., "Fibroblasts Require Protein Kinase C Activation to Respond to Hyaluronan with Increased Locomotion," Matrix Biology, Jun. 2001, pp. 183-192, vol. 20, No. 3.

Hardwick, C., et al., "Molecular Cloning of a Novel Hyaluronan Receptor that Mediates Tumor Cell Motility," The Journal of Cell Biology, 1992, pp. 1343-1350, vol. 117, No. 6.

Hill, D. R., et al., "Human Milk Hyaluronan Enhances Innate Defense of the Intestinal Epithelium," The Journal of Thological Chemistry, 2013, pp. 29090-29104, vol. 288, No. 40.

Houston, M. E., et al., "Lactam Bridge Stabilization of alpha-Helical Peptides: Ring Size, Orientation and Positional Effects," Journal of Peptide Science, 1995, pp. 274-282, vol. 1, No. 4.

Huang, C., et al., "MAP Kinases and Cell Migration," Journal of Cell Science, Sep. 2004, pp. 4619-4628, vol. 117, Part 20.

International Search Report and Written Opinion issued for PCT/IB2016/051587 dated Jun. 22, 2016, 18 pages.

Isidro-Llobet, A., et al., "Amino Acid-Protecting Groups," Chemical Reviews, 2009, pp. 2455-2504, vol. 109.

Kaya, G., et al., "Selective Suppression of CD44 in Keratinocytes of Mice Bearing an Antisense CD44 Transgene Driven by a Tissue-Specific Promoter Disrupts Hyaluronate Metabolism in the Skin and Impairs Keratinocyte Proliferation," Genes & Development, Apr. 1997, pp. 996-1007, vol. 11, No. 8.

Lee, J. C., et al., "Modulation of the Local Neutrophil Response by a Novel Hyaluronic Acid-Binding Peptide Reduces Bacterial Burden During Staphylococcal Wound Infection," Infection and Immunity, Oct. 2010, pp. 4176-4186, vol. 78, No. 10.

Li, H., et al., "Adult Bone-Marrow-Derived Mesenchymal Stem Cells Contribute to Wound Healing of Skin Appendages," Cell and Tissue Research, 2006, pp. 725-736, vol. 326, No. 3.

Lovvorn, H. N., et al., "Hyaluronan Receptor Expression Increases in Fetal Excisional Skin Wounds and Correlates with Fibroplasia," Journal of Pediatric Surgery, 1998, pp. 1062-1069, vol. 33, No. 7.

Luo, P., et al., "Mechanism of Helix Induction by Trifluoroethanol: A Framework for Extrapolating the Helix-Forming Properties of Peptides from Trifluoroethanol/Water Mixtures Back to Water," Biochemistry, 1997, pp. 8413-8421, vol. 36, No. 27.

Maxwell, C. A., et al., "RHAMM is a Centrosomal Protein that Interacts with Dynein and Maintains Spindle Pole Stability," Molecular Biology of the Cell, 2003, pp. 2262-2276, vol. 14, No. 6.

Mummert, M. E., et al., "Development of a Peptide Inhibitor of Hyaluronan-Mediated Leukocyte Trafficking," The Journal of Experimental Medicine, Sep. 2000, pp. 769-779, vol. 192, No. 6.

Nedvetzki, S., et al., "RHAMM, A Receptor for Hyaluronan-Mediated Motility, Compensates for CD44 in Inflamed CD44-Knockout Mice: A Different Interpretation of Redundancy," Proceedings of the National Academy of Sciences of the United States of America, 2004, pp. 18081-18086, vol. 101, No. 52.

Jiang, D., et al., "Hyaluronan as an Immune Regulator in Human Diseases," Physiological Reviews, 2011, pp. 221-264, vol. 91, No. 1.

Orian-Rousseau, V., "CD44, A Therapeutic Target for Metastasising Tumours," European Journal of Cancer, 2010, pp. 1271-1277, vol. 46, No. 7.

Peer, D., et al., "Tumor-Targeted Hyaluronan Nanoliposomes Increase the Antitumor Activity of Liposomal Doxorubicin in Syngeneic and Human Xenograft Mouse Tumor Models," Neoplasia, Jul.-Aug. 2004, pp. 343-353, vol. 6, No. 4.

Pelton, J. T., et al., "Spectroscopic Methods for Analysis of Protein Secondary Structure," Analytical Biochemistry, 2000, pp. 167-176, vol. 277.

Petrey, A. C., et al., "Hyaluronan, A Crucial Regulator of Inflammation," Frontiers in Immunology, Mar. 2014, pp. 1-13, Article 101, vol. 5.

Rezvani, K., et al., "Vaccination Strategies in Lymphomas and Leukaemias," Drugs, 2011, pp. 1659-1674, vol. 71, No. 13.

Rodrigues, E., "Stapled Peptides for the Stabilization of the Receptor for Hyaluronan Mediated Motility," Thesis submitted to the Department of Chemistry of the University of Western Ontario, Mar. 2015, 41 pages.

Rodrigues, E., et al., "Stapled Peptides for the Stabilization of the Receptor for Hyaluronan Mediated Motility," 43rd Southern Ontario Undergraduate Student Chemistry Conference, Abstract No. 48/S02/IB235, Mar. 21, 2015, p. 22.

Samuel, S. K., et al., "TGF-beta 1 Stimulation of Cell Locomotion Utilizes the Hyaluronan Receptor RHAMM and Hyaluronan," The Journal of Cell Biology, Nov. 1993, pp. 749-758, vol. 123, No. 3.

Savani, R. C., et al., "Migration of Bovine Aortic Smooth Muscle Cells After Wounding Injury. The Role of Hyaluronan and RHAMM," The Journal of Clinical Investigation, Mar. 1995, pp. 1158-1168, vol. 95, No. 3.

Savani, R. C., et al., "A Role for Hyaluronan in Macrophage Accumulation and Collagen Deposition After Bleomycin-Induced Lung Injury," American Journal of Respiratory Cell and Molecular Biology, Oct. 2000, pp. 475-484, vol. 23, No. 4.

Schmits, R., et al., "CD44 Regulates Hematopoietic Progenitor Distribution, Granuloma Formation, and Tumorigenicity," Blood, Sep. 1997, pp. 2217-2233, vol. 90, No. 6.

Ac-VSKLRSQLVKRKQN-NH$_2$ (132; SEQ ID NO: 2)

Ac-(cyclo-4,8)-VSK[ERSQK]VKRKQN-NH$_2$ (150; SEQ ID NO: 7, wherein X$_1$ is E and X$_2$ is K)

Ac-(cyclo-5,9)-VSKL[ESQLK]KRKQN-NH₂ (151; SEQ ID NO: 8, wherein X₁ is E and X₂ is K)

Ac-(cyclo-6,10)-VSKLR[EQLVK]RKQN-NH₂ (152; SEQ ID NO: 9, wherein X₁ is E and X₂ is K)

H-(cyclo-6,10)-VSKLR[EQLVK]RKQN-NH$_2$ (153; SEQ ID NO: 10, wherein X$_1$ is E and X$_2$ is K)

Ac-(cyclo-5,9)-VSKL[KSQLE]KRKQN-NH$_2$ (154; SEQ ID NO: 8, wherein X$_1$ is K and X$_2$ is E)

Ac-(cyclo-6,10)-VSKLR[KQLVE]RKQN-NH$_2$ (155; SEQ ID NO: 9, wherein X$_1$ is K and X$_2$ is E)

Ac-(cyclo-5,9)-VSKL[ESQLK]KRKQN-NH$_2$ (151; SEQ ID NO: 8, wherein X$_1$ is E and X$_2$ is K)

Ac-(cyclo-5,9)-VSKL[KSQLE]KRKQN-NH$_2$ (154; SEQ ID NO: 8, wherein X$_1$ is K and X$_2$ is E)

Ac-(cyclo-6,10)-VSKLR[EQLVK]RKQN-NH$_2$ (152; SEQ ID NO: 9, wherein X$_1$ is E and X$_2$ is K)

Ac-(cyclo-6,10)-VSKLR[KQLVE]RKQN-NH$_2$ (155; SEQ ID NO: 9, wherein X$_1$ is E and X$_2$ is K)

Ac-NLKQKIKHVVKLKDE-NH$_2$ (156; SEQ ID NO: 4)

Ac-(cyclo-4,8)-NLK[EKIKK]VVKLKDE-NH$_2$ (157; SEQ ID NO: 15, wherein X$_1$ is E and X$_2$ is K)

Ac-(cyclo-5,9)-NLKQ[EIKHK]VKLKDE-NH$_2$ (158; SEQ ID NO: 16, wherein X$_1$ is E and X$_2$ is K)

Ac-(cyclo-6,10)-NLKQK[EKHVK]KLKDE-NH$_2$ (159; SEQ ID NO: 17, wherein X$_1$ is E and X$_2$ is K)

Ac-(cyclo-7,11)-NLKQKI[EHVVK]LKDE-NH$_2$ (160; SEQ ID NO: 18, wherein X$_1$ is E and X$_2$ is K)

Ac-(cyclo-8,12)-NLKQKIK[EVVKK]KDE-NH$_2$ (161; SEQ ID NO: 16, wherein X$_1$ is E and X$_2$ is K)

Ac-KIKHVVKLKDENSQLKSEVSKLRSQLVKRK-NH$_2$ (265; SEQ ID NO: 5)

Ac-(cyclo-10-14, cyclo-15-19)-KIKHVVKLK[EENSK][EKSEK]SKLRSQLVKRK-NH$_2$
(266; SEQ ID NO: 26, wherein X$_1$ is E, X$_2$ is K, X$_3$ is E, and X$_4$ is K)

Ac-(cyclo-11-15, cyclo-16-20)-KIKHVVKLKD[ENSQK][ESEVK]KLRSQLVKRK-NH$_2$
(267; SEQ ID NO 27, wherein X$_1$ is E, X$_2$ is K, X$_3$ is E, and X$_4$ is K)

Ac-(cyclo-10-14, cyclo-15-19)-KIKHVVKLK[EENSK][KKSEE]SKLRSQLVKRK-NH$_2$
(268; SEQ ID NO: 26, wherein X$_1$ is E, X$_2$ is K, X$_3$ is K, and X$_4$ is E)

Ac-(cyclo-10-14, cyclo-15-19)-KIKHVVKLK[KENSE][EKSEK]SKLRSQLVKRK-NH$_2$
(269; SEQ ID NO: 27, wherein X$_1$ is K, X$_2$ is E, X$_3$ is E, and X$_4$ is K)

Ac-NLKQKIKHVVKLKDENSQLKSEVSKLRSQLVKRKQN-NH$_2$ (275; SEQ ID NO: 6)

Ac-(cyclo-28-32)-NLKQKIKHVVKLKDENSQLKSEVSKLR[EQLVK]RKQN-NH$_2$
(277; SEQ ID NO: 28, wherein X$_1$ is E and X$_2$ is K)

Ac-(cyclo-7-11, cyclo-28-32)- NLKQKI[EHVVK]LKDENSQLKSEVSKLR[EQLVK]RKQN-NH$_2$
(278; SEQ ID NO: 29, wherein X$_1$ is E, X$_2$ is K, X$_3$ is E, and X$_4$ is K)

SEQUENCE LISTING

```
<160> NUMBER OF SEQ ID NOS: 33

<210> SEQ ID NO 1
<211> LENGTH: 62
<212> TYPE: PRT
<213> ORGANISM: Mus musculus

<400> SEQUENCE: 1

Arg Asp Ser Tyr Ala Gln Leu Leu Gly His Gln Asn Leu Lys Gln Lys
1               5                   10                  15

Ile Lys His Val Val Lys Leu Lys Asp Glu Asn Ser Gln Leu Lys Ser
            20                  25                  30

Glu Val Ser Lys Leu Arg Ser Gln Leu Val Lys Arg Lys Gln Asn Glu
```

```
                35                  40                  45
Leu Arg Leu Gln Gly Glu Leu Asp Lys Ala Leu Gly Ile Arg
    50                  55                  60

<210> SEQ ID NO 2
<211> LENGTH: 14
<212> TYPE: PRT
<213> ORGANISM: Mus musculus

<400> SEQUENCE: 2

Val Ser Lys Leu Arg Ser Gln Leu Val Lys Arg Lys Gln Asn
1               5                   10

<210> SEQ ID NO 3
<211> LENGTH: 20
<212> TYPE: PRT
<213> ORGANISM: Mus musculus

<400> SEQUENCE: 3

Lys Ser Glu Val Ser Lys Leu Arg Ser Gln Leu Val Lys Arg Lys Gln
1               5                   10                  15

Asn Glu Leu Arg
            20

<210> SEQ ID NO 4
<211> LENGTH: 15
<212> TYPE: PRT
<213> ORGANISM: Mus musculus

<400> SEQUENCE: 4

Asn Leu Lys Gln Lys Ile Lys His Val Val Lys Leu Lys Asp Glu
1               5                   10                  15

<210> SEQ ID NO 5
<211> LENGTH: 30
<212> TYPE: PRT
<213> ORGANISM: Mus musculus

<400> SEQUENCE: 5

Lys Ile Lys His Val Val Lys Leu Lys Asp Glu Asn Ser Gln Leu Lys
1               5                   10                  15

Ser Glu Val Ser Lys Leu Arg Ser Gln Leu Val Lys Arg Lys
            20                  25                  30

<210> SEQ ID NO 6
<211> LENGTH: 36
<212> TYPE: PRT
<213> ORGANISM: Mus musculus

<400> SEQUENCE: 6

Asn Leu Lys Gln Lys Ile Lys His Val Val Lys Leu Lys Asp Glu Asn
1               5                   10                  15

Ser Gln Leu Lys Ser Glu Val Ser Lys Leu Arg Ser Gln Leu Val Lys
            20                  25                  30

Arg Lys Gln Asn
        35

<210> SEQ ID NO 7
<211> LENGTH: 14
<212> TYPE: PRT
<213> ORGANISM: Artificial Sequence
<220> FEATURE:
<223> OTHER INFORMATION: Synthetic construct
```

```
<220> FEATURE:
<221> NAME/KEY: misc_feature
<222> LOCATION: (4)..(4)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: misc_feature
<222> LOCATION: (8)..(8)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 7

Val Ser Lys Xaa Arg Ser Gln Xaa Val Lys Arg Lys Gln Asn
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (9)..(9)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 8

Val Ser Lys Leu Xaa Ser Gln Leu Xaa Lys Arg Lys Gln Asn
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (10)..(10)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 9

Val Ser Lys Leu Arg Xaa Gln Leu Val Xaa Arg Lys Gln Asn
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa can be glutamic acid, lysine, ornithine,
```

L-2-aminoadipic acid, allylglycine, alanine derivative S5, alanine
        derivative R8, or alanine derivative R5
<220> FEATURE:
<221> NAME/KEY: MISC_FEATURE
<222> LOCATION: (11)..(11)
<223> OTHER INFORMATION: Xaa can be glutamic acid, lysine, ornithine,
        L-2-aminoadipic acid, allylglycine, alanine derivative S5, alanine
        derivative R8, or alanine derivative R5

<400> SEQUENCE: 10

Val Ser Lys Leu Arg Ser Xaa Leu Val Lys Xaa Lys Gln Asn
1               5                   10

<210> SEQ ID NO 11
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Xaa can be glutamic acid, lysine, ornithine,
        L-2-aminoadipic acid, allylglycine, alanine derivative S5, alanine
        derivative R8, or alanine derivative R5
<220> FEATURE:
<221> NAME/KEY: MISC_FEATURE
<222> LOCATION: (16)..(16)
<223> OTHER INFORMATION: Xaa can be glutamic acid, lysine, ornithine,
        L-2-aminoadipic acid, allylglycine, alanine derivative S5, alanine
        derivative R8, or alanine derivative R5

<400> SEQUENCE: 11

Lys Ser Glu Val Ser Lys Leu Arg Xaa Gln Leu Val Lys Arg Lys Xaa
1               5                   10                  15

Asn Glu Leu Arg
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa can be glutamic acid, lysine, ornithine,
        L-2-aminoadipic acid, allylglycine, alanine derivative S5, alanine
        derivative R8, or alanine derivative R5
<220> FEATURE:
<221> NAME/KEY: MISC_FEATURE
<222> LOCATION: (17)..(17)
<223> OTHER INFORMATION: Xaa can be glutamic acid, lysine, ornithine,
        L-2-aminoadipic acid, allylglycine, alanine derivative S5, alanine
        derivative R8, or alanine derivative R5

<400> SEQUENCE: 12

Lys Ser Glu Val Ser Lys Leu Arg Ser Xaa Leu Val Lys Arg Lys Gln
1               5                   10                  15

Xaa Glu Leu Arg
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (11)..(11)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (18)..(18)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 13

Lys Ser Glu Val Ser Lys Leu Arg Ser Gln Xaa Val Lys Arg Lys Gln
1               5                   10                  15

Asn Xaa Leu Arg
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (7)..(7)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 14

Asn Leu Xaa Gln Lys Ile Xaa His Val Val Lys Leu Lys Asp Glu
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthtic construct
<220> FEATURE:
<221> NAME/KEY: MISC_FEATURE
<222> LOCATION: (4)..(4)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (8)..(8)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 15

Asn Leu Lys Xaa Lys Ile Lys Xaa Val Val Lys Leu Lys Asp Glu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)

```
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (9)..(9)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 16

Asn Leu Lys Gln Xaa Ile Lys His Xaa Val Lys Leu Lys Asp Glu
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (10)..(10)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 17

Asn Leu Lys Gln Lys Xaa Lys His Val Xaa Lys Leu Lys Asp Glu
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (11)..(11)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 18

Asn Leu Lys Gln Lys Ile Xaa His Val Val Xaa Leu Lys Asp Glu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (8)..(8)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
```

<221> NAME/KEY: MISC_FEATURE
<222> LOCATION: (12)..(12)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 19

Asn Leu Lys Gln Lys Ile Lys Xaa Val Val Lys Xaa Lys Asp Glu
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (11)..(11)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 20

Asn Leu Lys Xaa Lys Ile Lys His Val Val Xaa Leu Lys Asp Glu
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (12)..(12)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 21

Asn Leu Lys Gln Xaa Ile Lys His Val Val Lys Xaa Lys Asp Glu
1               5                   10                  15

<210> SEQ ID NO 22
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (10)..(10)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (17)..(17)
<223> OTHER INFORMATION: Xaa can be glutamic acid, lysine, ornithine,
      L-2-aminoadipic acid, allylglycine, alanine derivative S5, alanine derivative R8, or alanine derivative R5

<400> SEQUENCE: 22

Lys Ile Lys His Val Val Lys Leu Lys Xaa Glu Asn Ser Gln Leu Lys
1               5                   10                  15

Xaa Glu Val Ser Lys Leu Arg Ser Gln Leu Val Lys Arg Lys
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (11)..(11)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (18)..(18)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 23

Lys Ile Lys His Val Val Lys Leu Lys Asp Xaa Asn Ser Gln Leu Lys
1               5                   10                  15

Ser Xaa Val Ser Lys Leu Arg Ser Gln Leu Val Lys Arg Lys
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (12)..(12)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (19)..(19)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 24

Lys Ile Lys His Val Val Lys Leu Lys Asp Glu Xaa Ser Gln Leu Lys
1               5                   10                  15

Ser Glu Xaa Ser Lys Leu Arg Ser Gln Leu Val Lys Arg Lys
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (13)..(13)
<223> OTHER INFORMATION: Xaa can be glutamic acid, lysine, ornithine,
      L-2-aminoadipic acid, allylglycine, alanine derivative S5, alanine
      derivative R8, or alanine derivative R5

```
<220> FEATURE:
<221> NAME/KEY: MISC_FEATURE
<222> LOCATION: (20)..(20)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 25

Lys Ile Lys His Val Val Lys Leu Lys Asp Glu Asn Xaa Gln Leu Lys
1               5                   10                  15

Ser Glu Val Xaa Lys Leu Arg Ser Gln Leu Val Lys Arg Lys
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Synthtic construct
<220> FEATURE:
<221> NAME/KEY: MISC_FEATURE
<222> LOCATION: (10)..(10)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (14)..(15)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (19)..(19)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 26

Lys Ile Lys His Val Val Lys Leu Lys Xaa Glu Asn Ser Xaa Xaa Lys
1               5                   10                  15

Ser Glu Xaa Ser Lys Leu Arg Ser Gln Leu Val Lys Arg Lys
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (11)..(11)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (15)..(16)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (20)..(20)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 27

Lys Ile Lys His Val Val Lys Leu Lys Asp Xaa Asn Ser Gln Xaa Xaa
1               5                   10                  15
```

```
Ser Glu Val Xaa Lys Leu Arg Ser Gln Leu Val Lys Arg Lys
            20                  25                  30

<210> SEQ ID NO 28
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (28)..(28)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (32)..(32)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 28

Asn Leu Lys Gln Lys Ile Lys His Val Val Lys Leu Lys Asp Glu Asn
1               5                   10                  15

Ser Gln Leu Lys Ser Glu Val Ser Lys Leu Arg Xaa Gln Leu Val Xaa
            20                  25                  30

Arg Lys Gln Asn
        35

<210> SEQ ID NO 29
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (11)..(11)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (28)..(28)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (32)..(32)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 29

Asn Leu Lys Gln Lys Ile Xaa His Val Val Xaa Leu Lys Asp Glu Asn
1               5                   10                  15

Ser Gln Leu Lys Ser Glu Val Ser Lys Leu Arg Xaa Gln Leu Val Xaa
            20                  25                  30

Arg Lys Gln Asn
        35
```

```
<210> SEQ ID NO 30
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(27)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (31)..(31)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 30

Asn Leu Lys Gln Lys Ile Lys His Val Val Lys Leu Lys Asp Glu Asn
1               5                   10                  15

Ser Gln Leu Lys Ser Glu Val Ser Lys Leu Xaa Ser Gln Leu Xaa Lys
            20                  25                  30

Arg Lys Gln Asn
        35

<210> SEQ ID NO 31
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (11)..(11)
<223> OTHER INFORMATION: Xaa can be glutamic acid, lysine, ornithine,
      L-2-aminoadipic acid, allylglycine, alanine derivative S5, alanine
      derivative R8, or alanine derivative R5

<400> SEQUENCE: 31

Asn Leu Lys Gln Lys Ile Xaa His Val Val Xaa Leu Lys Asp Glu Asn
1               5                   10                  15

Ser Gln Leu Lys Ser Glu Val Ser Lys Leu Arg Ser Gln Leu Val Lys
            20                  25                  30

Arg Lys Gln Asn
        35

<210> SEQ ID NO 32
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (7)..(7)
<223> OTHER INFORMATION: Xaa can be glutamic acid, lysine, ornithine,
      L-2-aminoadipic acid, allylglycine, alanine derivative S5, alanine
      derivative R8, or alanine derivative R5
<220> FEATURE:
<221> NAME/KEY: MISC_FEATURE
<222> LOCATION: (11)..(11)
<223> OTHER INFORMATION: Xaa can be glutamic acid, lysine, ornithine,
      L-2-aminoadipic acid, allylglycine, alanine derivative S5, alanine
```

```
        derivative R8, or alanine derivative R5
<220> FEATURE:
<221> NAME/KEY: MISC_FEATURE
<222> LOCATION: (27)..(27)
<223> OTHER INFORMATION: Xaa can be glutamic acid, lysine, ornithine,
        L-2-aminoadipic acid, allylglycine, alanine derivative S5, alanine
        derivative R8, or alanine derivative R5
<220> FEATURE:
<221> NAME/KEY: MISC_FEATURE
<222> LOCATION: (31)..(31)
<223> OTHER INFORMATION: Xaa can be glutamic acid, lysine, ornithine,
        L-2-aminoadipic acid, allylglycine, alanine derivative S5, alanine
        derivative R8, or alanine derivative R5

<400> SEQUENCE: 32

Asn Leu Lys Gln Lys Ile Xaa His Val Val Xaa Leu Lys Asp Glu Asn
1               5                   10                  15

Ser Gln Leu Lys Ser Glu Val Ser Lys Leu Xaa Ser Gln Leu Xaa Lys
            20                  25                  30

Arg Lys Gln Asn
        35

<210> SEQ ID NO 33
<211> LENGTH: 38
<212> TYPE: PRT
<213> ORGANISM: Mus musculus

<400> SEQUENCE: 33

His Gln Asn Leu Lys Gln Lys Ile Lys His Val Val Lys Leu Lys Asp
1               5                   10                  15

Glu Asn Ser Gln Leu Lys Ser Glu Val Ser Lys Leu Arg Ser Gln Leu
            20                  25                  30

Val Lys Arg Lys Gln Asn
        35
```

STAPLED PEPTIDES AND USES THEREOF

CROSS-REFERENCE TO RELATED APPLICATIONS

This application is a U.S. National of PCT Application No. PCT/IB2016/051587, filed on Mar. 21, 2016, which claims priority to U.S. Provisional Application No. 62/135,951, filed Mar. 20, 2015. Each of the above-cited applications is incorporated herein by reference in its entirety.

FIELD OF THE INVENTION

The present invention generally relates to cyclized peptides derived from the hyaluronan (HA)- and protein-binding region of RHAMM. The invention further relates to pharmaceutical compositions containing the peptides, and methods of using the peptides to detect the presence of HA in cells, for diagnosis of disorders or conditions associated with elevated levels of HA, for treatment of disorders or conditions associated with elevated levels of HA, for inhibiting proliferation or motility of cells, for inhibiting migration of cells, for preventing metastasis, for inhibiting inflammation, for inhibiting cellular invasion and for inhibiting fibrosis.

BACKGROUND OF THE INVENTION

Native hyaluronan (HA) is ubiquitous in its tissue distribution and in its high molecular form has anti-inflammatory properties [1-3]. HA fragments, which are produced as a result of tissue stress and oxygen/nitrogen free radical formation, function as pro-inflammatory Danger Associated Molecular Pattern molecules (DAMP) that interact with HA receptors and Toll-like receptors to promote monocyte maturation into macrophages, macrophage chemotaxis, and production of pro-inflammatory chemokines and iNOS [1, 2, 4]. Both CD44 and RHAMM (Receptor for Hyaluronan-Mediated Motility) have been functionally linked to Toll Like receptors 2 or 4 in the regulation of these macrophage functions [5-8]. Although CD44 clearly plays a key role in pro-inflammatory responses, CD44 is ubiquitous in its expression increasing the possibility of off target adverse effects [9] and its complex mechanisms for binding to HA present challenges [10, 11] to the design of antagonists. Collectively, these have limited the use of CD44 as a clinical target. In contrast to CD44, RHAMM is not constitutively expressed in most homeostatic tissues. Instead, RHAMM expression and in particular its cell surface display occurs transiently following tissue injury but is chronic in diseases involving sustained inflammation [3]. Not unexpectedly, the safety profile for RHAMM peptides is therefore good [12, 13]. Furthermore, HA binding to RHAMM, which occurs over a short sequence and depends on ionic interactions [14], is readily competed with peptide mimics.

Shorter versions of RHAMM have been proposed as pharmaceutically relevant peptides. However, it is well known that short linear peptides containing only natural L amino acids have very limited stability against protease hydrolysis in vivo.

SUMMARY OF THE INVENTION

A peptide is provided. The peptide comprises at least a portion of a RHAMM HA binding domain (HABD). The peptide has a length of at least 7 amino acids. The peptide includes one or more amino acid substitutions relative to the sequence of a HABD of a naturally occurring RHAMM protein. The one or more substitutions occur at position i, i+4, and/or i+7. The substitution allows for the formation of a covalent bond between the amino acid at position i and the amino acid at position i+4 or i+7.

Another peptide is provided. The peptide has a length of 20 amino acids or fewer. The peptide comprises an amino acid sequence having at least 75% identity to the amino acid sequence NLKQKIKHVVKLKDE (SEQ ID NO: 4).

Yet another peptide is provided. The peptide has a length of 20 amino acids or fewer. The peptide comprises an amino acid sequence having at least 70% sequence identity to the amino acid sequence VSKLRSQLVKRKQN (SEQ ID NO: 2). The peptide is acetylated at its amino-terminus.

Any of the peptides can further comprise a detectable label.

A pharmaceutical composition is provided. The pharmaceutical composition comprises one or more of any of the peptides and a pharmaceutically acceptable carrier.

A method for detecting the presence of hyaluronic acid in cells, tissues, or organs is provided. The method comprises contacting any of the peptides comprising a detectable label with the cell, tissue, or organ. An imaging technique is applied for detecting the detectable label.

A method for diagnosing a subject of a disorder or condition associated with elevated levels of hyaluronic acid (HA) or RHAMM is provided. The method comprises obtaining a cell or tissue sample from the subject. The sample is contacted with any of the peptides that comprises a detectable label. An imaging technique is applied for detecting the label in the sample. Detection of elevated HA levels in the sample indicates a positive diagnosis of the disorder or condition.

A method for treating a subject suffering from a disorder or condition associated with elevated levels of hyaluronic acid (HA) or RHAMM is provided. The method comprises administering to the subject an effective amount of one or more peptides of any of the peptides or any of the pharmaceutical compositions.

A method of inhibiting proliferation or motility of cells that express elevated levels of RHAMM or that have elevated levels of HA is provided. The method comprises contacting the cells with an effective amount of one or more of any of the peptides or any of the pharmaceutical compositions.

A method of preventing metastasis in a subject having cancer is provided. The method comprises administering to the subject an effective amount of one or more of any of the peptides or any of the pharmaceutical compositions.

A method for inhibiting migration of cells is provided. The method comprises contacting the cells with an effective amount of one or more of any of the peptides or any of the pharmaceutical compositions.

A method for inhibiting inflammation is provided. The method comprises contacting cells with an effective amount of one or more of any of the peptides or any of the pharmaceutical compositions.

A method for inhibiting cellular invasion is provided. The method comprises contacting cells with an effective amount of one or more of any of the peptides or any of the pharmaceutical compositions.

A method for inhibiting fibrosis is provided. The method comprises contacting cells with an effective amount of one or more of any of the peptides or any of the pharmaceutical compositions.

Other objects and features will be in part apparent and in part pointed out hereinafter.

BRIEF DESCRIPTION OF THE DRAWINGS

Corresponding reference characters indicate corresponding parts throughout the drawings.

Definitions

When the articles "a," "an," "one," "the," and "said" are used herein, they mean "at least one" or "one or more" unless otherwise indicated.

The term "amino acid" as used herein is meant to include both naturally occurring and synthetic (non-naturally occurring) amino acids.

The term "standard amino acid" as used herein refers to any of the twenty standard L-amino acids that are commonly found in naturally occurring peptides in humans and animals, namely the L-isomers of alanine (Ala or A), Arginine (Arg or R), asparagine (Asn or N), aspartic acid (Asp or D), cysteine (Cys or C), glutamic acid (Glu or E), glutamine (Glu or Q), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

The term "non-standard amino acid" as used herein refers to any amino acid other than the standard amino acids, regardless of whether it is prepared synthetically or isolated or otherwise derived from a natural source. Thus, the term "non-standard amino acid" encompasses both naturally occurring amino acids that are not standard amino acids, as well as non-naturally occurring amino acids.

The term "naturally occurring amino acid" as used herein includes all twenty of the standard L-amino acids that are commonly found in naturally occurring peptides, as well as any other amino acid found in nature. Examples of non-standard naturally occurring amino acids include, but are not limited to ornithine and L-2-aminoadipic acid. Naturally occurring non-standard amino acids typically do not participate in protein translation at the ribosome of a cell in nature. However, they occur in nature and may participate in other physiological processes.

The term "non-naturally occurring amino acid" as used herein refers to any amino acid that does not occur in nature but instead is generated through chemical synthesis or through chemical modification of a naturally occurring amino acid.

The terms "comprising," "including," and "having" are intended to be inclusive and mean that there may be additional elements other than the listed elements.

The term "effective amount" as used herein refers to an amount sufficient to induce a detectable therapeutic response in a subject.

Figures 1, 2:
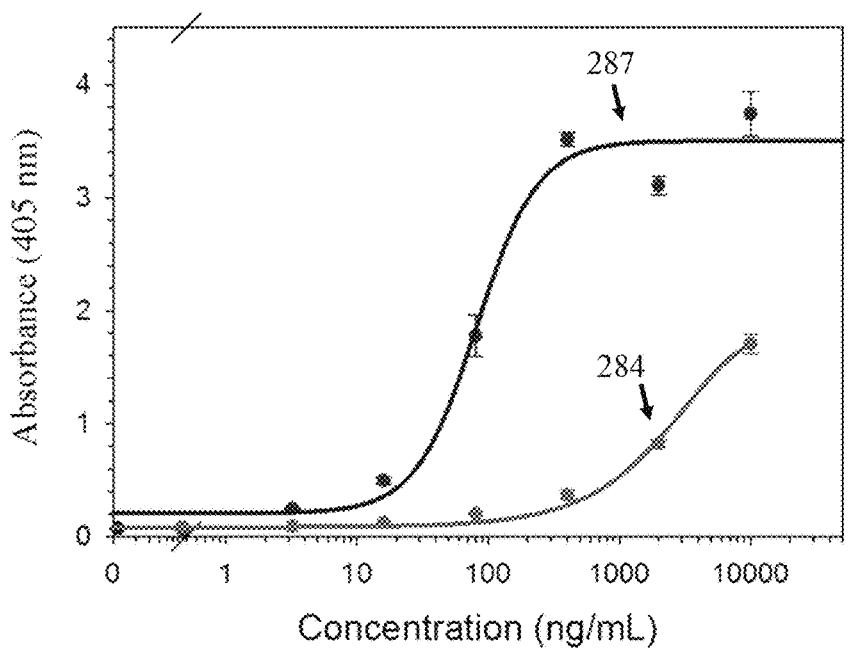
FIG. 1 shows the sequence for amino acids 706-767 of RHAMM. This sequence is also referred to herein as "7 kDa RHAMM." Two minimal HA binding domains are shown the boxes labeled "BD1" and "BD2." The lowercase letters under the sequence indicate helical regions ("h"), coiled regions ("c"), and extended strands ("e").
FIG. 2 provides illustrative ELISA results.
Figure 11:
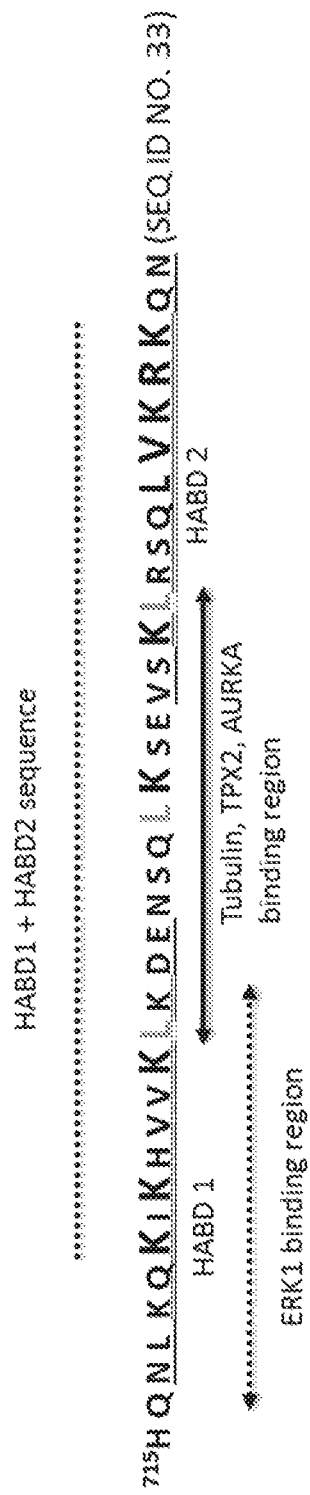
FIG. 11 illustrates the RHAMM HA binding region.

Unless otherwise specified, the terms "HABD1" and "HABD2" as used herein refer to the minimal hyaluronan-binding domains of RHAMM as depicted in FIGS. 1 and 11.

The term "peptide" as used herein refers a short chain of amino acids linked to one another via peptide bonds. Peptides generally have a length of fewer than about 50 amino acids.

The term "isolated peptide" as used herein refers to a peptide which is substantially separated from other cellular components.

The terms "stapled peptide" and "cyclized peptide" are used interchangeably herein to refer to a peptide that includes a covalent bond between the side chains of two amino acids in the peptide, or between the amino-terminal nitrogen of a peptide and an amino acid side chain of another amino acid within the peptide. The term "peptide staple" refers to the covalent bond between the two amino acid side chains.

The terms "i," "i+4," and "i+7" as used herein refer to the positions of the amino acids within the peptide that become covalently bonded to one another upon formation of the staple. The "i" position refers to the position of the amino acid that is nearest to the amino terminus of the peptide. The "i+4" position is 4 amino acids downstream (4 amino acids further towards the carboxy-terminus) of the "i" position, and the "i+7" position is 7 amino acids downstream of the "i" position. Upon formation of the staple, a covalent bond is formed between the amino acid at position i and the amino acid at position i+4 or i+7.

The term "RHAMM" as used herein refers to a Receptor for Hyaluronic Acid Mediated Motility, also known as CD 168. RHAMM is a non-integral cell surface (CD 168) and intracellular hyaluronan binding protein that promotes cell motility in vitro and whose expression is strongly upregulated in aggressive tumors [WO 2008/140587].

The term "subject" as used herein refers to any mammal, including both humans and non-human mammals.

DESCRIPTION OF THE PREFERRED EMBODIMENTS

The present invention relates to peptides derived from the hyaluronan (HA)- and protein-binding region of RHAMM and cyclized derivatives of such peptides. FIGS. 1 and 11 depict the HA-binding region of RHAMM. FIG. 1 shows amino acids 706-767 of the mouse RHAMM sequence. In FIG. 1, the minimal HA binding domains are indicated shown the boxes labeled "BD1" and "BD2." The lowercase letters under the sequence indicate helical regions ("h"), coiled regions ("c"), and extended strands ("e").

FIG. 11 provides a more detailed depiction of the HA- and protein-binding region of RHAMM. RHAMM regulates cell motility and stem cell differentiation. These functions have been linked to the HA binding capability of RHAMM and also its intracellular association with proteins such as ERK, TPX2, AURKA and tubulin. As shown in FIG. 11, The HA binding sequence of RHAMM contains two domains (underlined sequences, HA-binding domain 1 (HABD1) and HA-binding domain 2 (HABD2) that contribute to binding to HA. These are separated by a leucine zipper (leucines that form zipper are in grey and whole region is denoted by a solid double arrow) that is required for binding of RHAMM to tubulin, TPX2 and AURKA. The second HA domain (HABD2) contains the most sequences that are thought to be required for HA binding and is more important for binding to HA than HABD1. The amino acids that have been shown to be involved in HA binding (either by site directed mutagenesis or computer modelling) are enlarged. HABD1 also contains sequence that is involved in docking of the MAP kinase ERK1 to RHAMM, as shown by site directed mutagenesis. This region is identified by a dotted double arrow. Minimal HA binding sequences are marked by double underlines.

Stapled Peptides

Stapled peptides include a covalent bond between the side chains of two amino acids in the peptide. Peptide stapling can be used to physically constrain a peptide into a specific conformation (e.g., to physically constrain a peptide into its native alpha-helical state). This can in turn enhance the pharmacological properties of a peptide by helping to retain the native structure needed to interact with a target molecule, increasing cell penetration, and/or protecting the peptide from proteolytic degradation.

Peptide stapling was used to constrain alpha-helical structures in peptides derived from the HA-binding region of RHAMM. These peptides contained HABD1 ("HABD1" peptides), HABD2 ("HABD2" peptides), or most or all of HABD1 and all of HABD2 ("HABD1+HABD2" peptides). Since the alpha helical structures of the HABD1 and HABD2 of RHAMM are predicted to be required for HA binding and since the HA binding properties of RHAMM are known to be key to its biological activity, a variety of stapled peptides were developed that can be grouped into HABD1, HABD2, and sequences containing both HABD1 and HABD2 (HABD1+HABD2). The leucine zipper and HABD1 are also regions of protein:protein interactions that require alpha helicity. Therefore, stapling these peptides could also increase the ability of the peptides to affect these interactions. The peptides thus have potentially multiple protein partners with which they may compete. It was unknown prior to the present invention whether short alpha-helical segments of RHAMM would allow for retention of HA binding and/or biological activity.

When peptide staples are used to physically constrain a peptide into its native alpha-helical state, it is desirable to form the staple between the i and i+4 positions of a peptide or between the i and i+7 positions of a peptide. This because upon formation of the alpha helix, the amino acid side chains of the amino acids at the i, i+4, and i+7 positions will be located on the same face of the helix.

Figure 3:
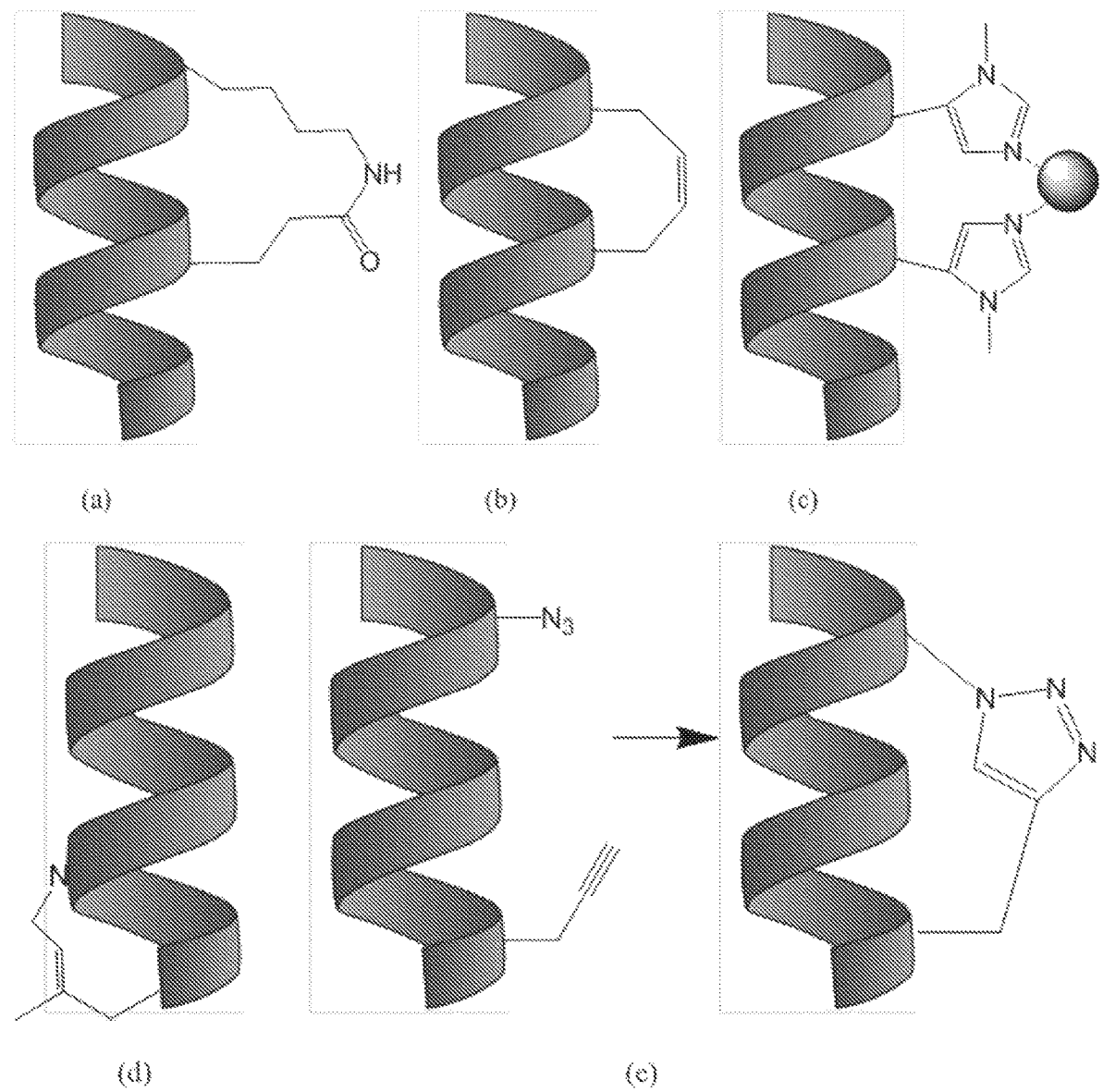
FIG. 3 depicts: (a) a lactam bridge; (b) a hydrocarbon bridge; (c) a metal-ion clip; (d) a hydrogen bond surrogate; and (e) formation of a heterocycle bridge by azide-alkyne cycloaddition.

A number of different types of peptide staples can be used. FIG. 3 illustrates several types of peptide staples: (a) a lactam bridge; (b) a hydrocarbon bridge; (c) a metal-ion clip; (d) a hydrogen bond surrogate; and (e) a heterocycle bridge. Any of these types of staples, or other peptide staples known in the art, can be used in connection with any of the peptides described herein.

Figure 7:
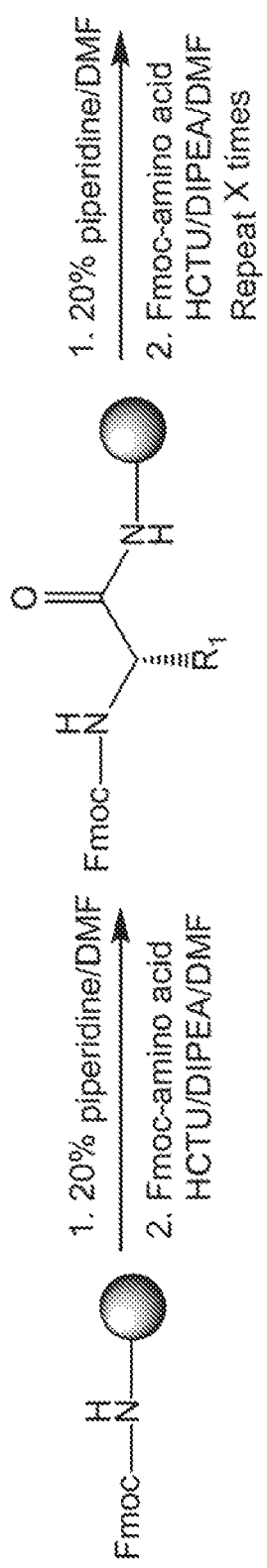
FIG. 7 provides an illustrative reaction scheme for synthesis of a peptide containing glutamic acid residues protected with allylester (Glu(OAll)) and lysine residues protected with alloxycarbonyl (Lys(Alloc)) protecting groups.
Figure 8:
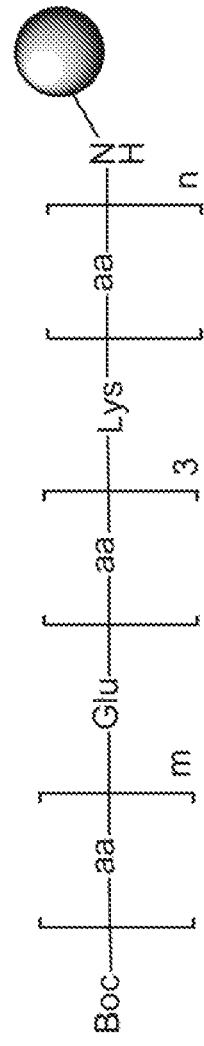
FIG. 8 provides an illustrative reaction scheme for deprotection of Glu(OAll) and Lys(Alloc) residues in a peptide and formation of a lactam bridge.
Figure 8:
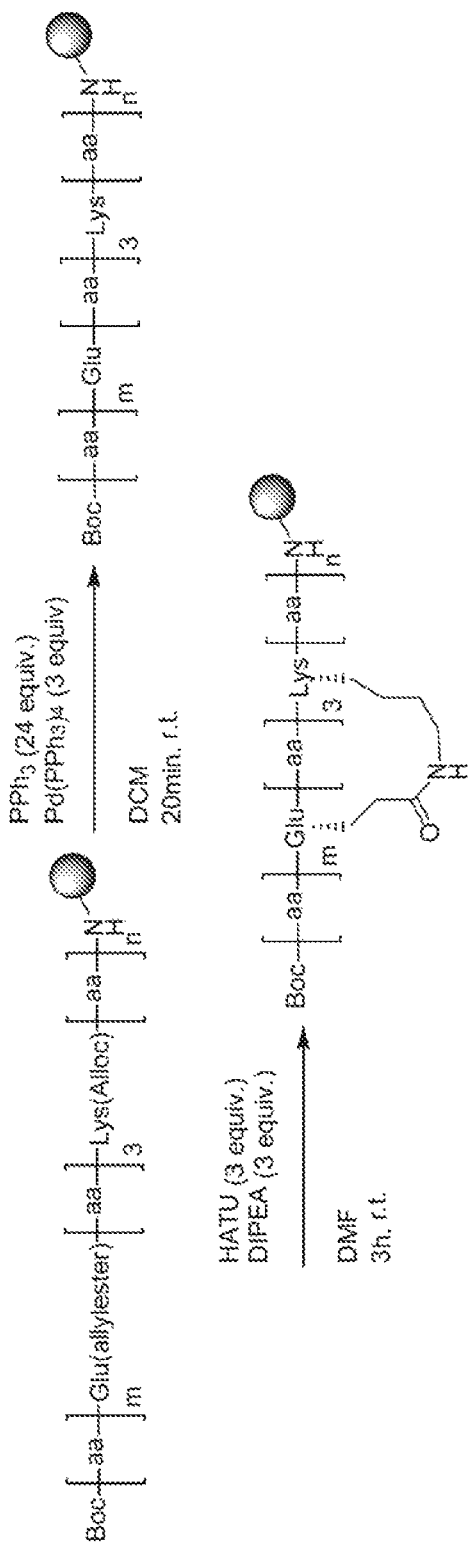
Figure 9:
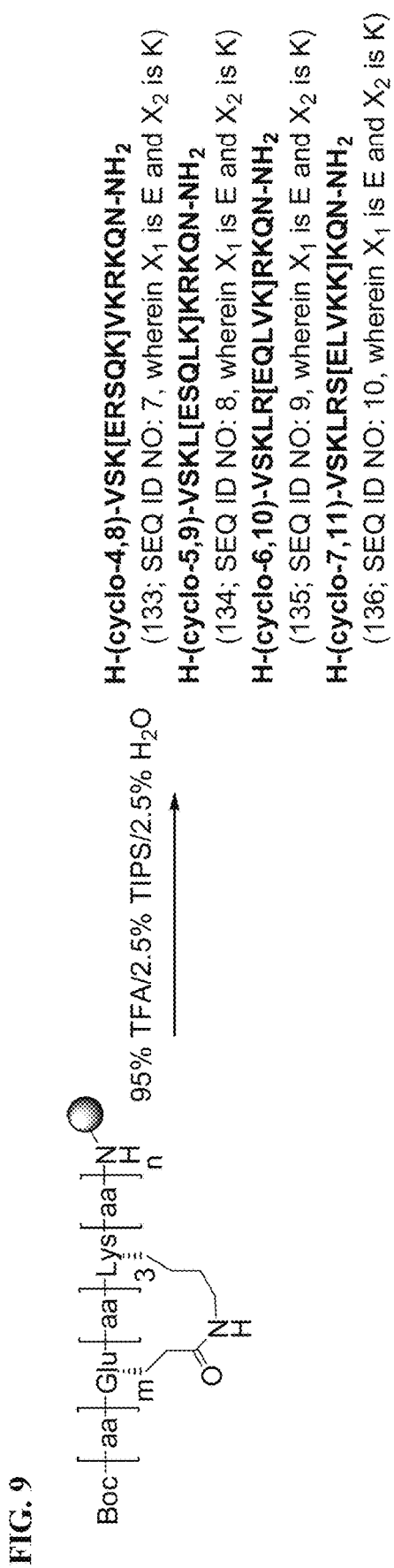
FIG. 9 provides an illustrative reaction scheme for deprotection of remaining protecting groups in a synthesized peptide and cleavage of peptides off of resin to obtain lactam bridged cyclic peptides.

Lactam bridges can be formed glutamic acid and lysine residues of a peptides. The glutamic acid and lysine residues may be present in the native sequence of the peptide. Alternatively, amino acid substitutions for glutamic acid and/or lysine at the desired positions of the peptide or may be introduced at the desired positions during peptide synthesis. When glutamic acid and lysine are used to form lactam bridges, protected versions of these amino acids are introduced into the peptide during synthesis. In particular, ester-protected glutamic acid (Glu(OAll)) residues and allyloxycarbonyl-protected lysine residues can be used. Following peptide synthesis, the protecting groups are removed and the lactam bridge is formed between the glutamic acid and lysine residues. This process is illustrated in FIGS. 7-9.

Thus, for example, a glutamic acid can be introduced at position i, and a lysine introduced at position i+4, allow for formation of a lactam bridge between the i and i+4 residues. Alternatively, a glutamic acid can be introduced at position i, and a lysine introduced at position i+7, such that a lactam bridge can be formed between the i and i+7 residues.

Using a glutamic acid residue at the i position and a lysine residue at the i+4 or i+7 position is the typical way to form this type of lactam bridge. However, the order of the lysine and glutamic acid residues can also be reversed. For example, a lysine residue can be introduced at position i of a peptide and a glutamic acid residue can be introduced at the i+4 or i+7 position of the peptide. This type of staple is referred to herein as a "reverse" lactam bridge, since the typical order of the glutamic acid and lysine residues is reversed.

Lactam bridges can also be formed between ornithine (Orn) and L-2-aminoadipic acid (Aad) residues. The ornithine and L-2-aminoadipic acid residues can be introduced at the desired positions during peptide synthesis, and then the lactam bridge can be formed using standard methods known in the art.

Hydrocarbon bridges (e.g., olefin bridges) can be formed between two allylglycine residues in a peptide. Allylglycine (AllylGly) has the following structure:

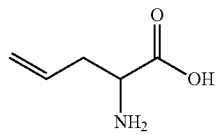

Two allylglycine residues can be introduced into a peptide at the desired positions, and then the hydrocarbon bridge can be formed using standard methods known in the art. When allylglycine residues are used for formation of hydrocarbon bridges, the substitutions are preferably made at the i and i+4 positions of the peptide.

Hydrocarbon bridges can also be formed using the alanine derivatives S5, R8, and/or R5. The alanine derivatives R5 and R8 both have the following structure:

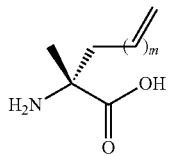

In R8 m is 5. In R5, m is 2. The alanine derivatives S5 has the structure shown below, wherein n is 2:

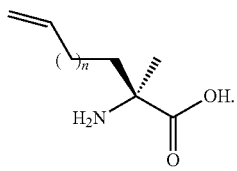

The following preferred configurations can be used to create hydrocarbon bridges in peptides using the alanine derivatives S5, R8, and/or R5: (1) substitution at position i of a peptide with an S5 residue and substitution at position i+4 with another S5 residue; (2) substitution at position i of a peptide with an R5 residue and substitution at position i+4 with another R5 residue; or (3) substitution at position i of a peptide with an R8 residue and substitution at position i+7 with an S5 residue. It has also been reported that substitution at the i position with an R5 residue and substitution at the i+3 position with an S5 residue can also be used for helix stabilization.

Figure 4:
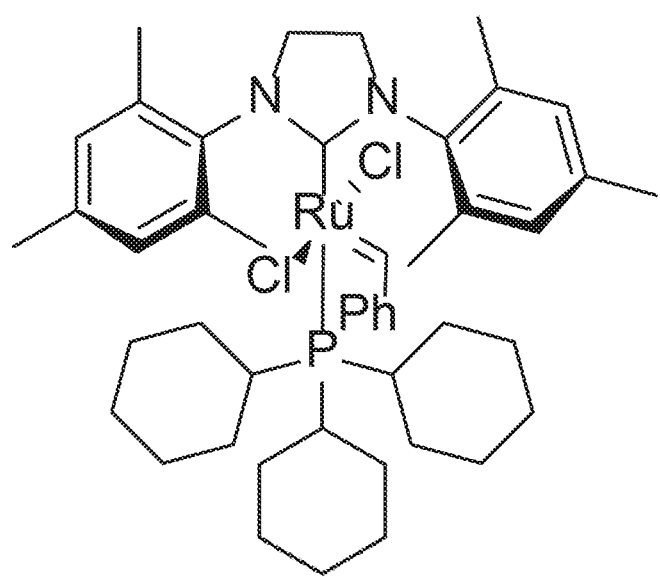
FIG. 4 provides the structure for the Grubbs ruthenium catalyst.

Following introduction of the alanine derivatives or allylglycine residues at the desired positions of the peptide, a hydrocarbon bridge can be formed between the olefin tether side chains of these amino acids. The olefin tethers can react with a Grubbs ruthenium catalyst (see FIG. 4) to complete the ring closing reaction.

In a metal-ion clip, a bridge is formed through coordinate bonds to a metal-ion (e.g., a rhenium, ruthenium, or palladium ion).

In a hydrogen bond surrogate, a hydrocarbon bridge is formed between the amino-terminal nitrogen atom of a peptide to an amino acid side chain.

Another type of peptide staple is a heterocycle bridge. Heterocycle bridges are formed through a cycloaddition reaction between two amino acids, for example azide-alkyne cycloaddition as shown in panel (e) of FIG. 3.

Peptides can be synthesized that contain two or more of any of the peptide staples discussed above. For example, to prepare a peptide having multiple lactam bridge staples, the peptide is synthesized until the amino acid residue at the end of the first staple. With the N-terminal Fmoc protecting group still present, the Alloc and Allyl protecting groups are deprotected and cyclized to form the first staple. Peptide synthesis is then continued and deprotection and cyclization are repeated to form the second staple.

The present invention is directed to a peptide comprising at least a portion of a RHAMM HA binding domain (HABD). The peptide has a length of at least 7 amino acids. The peptide includes one or more amino acid substitutions relative to the sequence of a HABD of a naturally occurring RHAMM protein. The one or more substitutions occur at position i, i+4, and/or i+7. The substitution allows for the formation of a covalent bond between the amino acid at position i and the amino acid at position i+4 or i+7.

The substitution at position i, i+4, and/or i+7 can comprise a substitution with a standard amino acid.

The substitution at position i, i+4, and/or i+7 can comprise a substitution with a non-standard amino acid.

The non-standard amino acid can comprise a naturally occurring amino acid.

The non-standard amino acid can comprise a non-naturally occurring amino acid.

The amino acid at position i is preferably covalently bonded to the amino acid at position i+4 or i+7.

For example, the amino acid at position i can be covalently bonded to the amino acid at position i+4.

Alternatively, the amino acid at position i can be covalently bonded to the amino acid at position i+7.

The covalent bond can comprise a lactam bridge, a hydrocarbon bridge, a metal-ion clip, a hydrogen bond surrogate, or a heterocycle bridge.

The covalent bond suitably comprises a lactam bridge or a hydrocarbon bridge.

For example, the covalent bond can comprise a lactam bridge.

Where the covalent bond comprises a lactam bridge, the one or more amino acid substitutions can comprise a substitution with a glutamic acid residue, a lysine residue, or a combination thereof.

For example, where the covalent bond comprises a lactam bridge, the one or more amino acid substitutions can comprise a substitution with a glutamic acid residue at position i.

Where the covalent bond comprises a lactam bridge, the one or more amino acid substitutions can comprise a substitution with a glutamic acid residue at position i+4.

Where the covalent bond comprises a lactam bridge, the one or more amino acid substitutions can comprise a substitution with a glutamic acid residue at position i+7.

Where the covalent bond comprises a lactam bridge, the one or more amino acid substitutions can comprise a substitution with a lysine residue at position i.

Where the covalent bond comprises a lactam bridge, the one or more amino acid substitutions can comprise a substitution with a lysine residue at position i+4.

Where the covalent bond comprises a lactam bridge, the one or more amino acid substitutions can comprise a substitution with a lysine residue at position i+7.

Where the covalent bond comprises a lactam bridge and the one or more amino acid substitutions comprises the substitution with the glutamic acid residue at position i, the sequence of the HABD of the naturally occurring RHAMM protein can comprise a lysine residue at position i+4 or position i+7. For example, the sequence of the HABD of the naturally occurring RHAMM protein can comprises the lysine residue at position i+4.

Where the covalent bond comprises a lactam bridge and the one or more amino acid substitutions comprises the substitution with the lysine residue at position i+4 or i+7, the sequence of the HABD of the naturally occurring RHAMM protein can comprise a glutamic acid residue at position i.

Where the covalent bond comprises a lactam bridge and the one or more amino acid substitutions comprises the substitution with the lysine residue at position i, the sequence of the HABD of the naturally occurring RHAMM protein can comprise a glutamic acid residue at position i+4 or i+7.

Where the covalent bond comprises a lactam bridge and the one or more amino acid substitutions comprises the substitution with the glutamic acid residue at position i+4 or i+7, the sequence of the HABD of the naturally occurring RHAMM protein can comprise a lysine residue at position i.

Where the covalent bond comprises a lactam bridge and the one or more amino acid substitutions comprises the substitution with a glutamic acid residue at position i, the one or more amino acid substitutions can further comprise the substitution with the lysine residue at position i+4 or the substitution with the lysine residue at position i+7. For example, the substitution with the lysine residue can be at position i+4.

Where the covalent bond comprises a lactam bridge and the one or more amino acid substitutions comprises the substitution with a lysine residue at position i, the one or more substitutions can further comprise the substitution with the glutamic acid residue at position i+4 or the substitution with the glutamic acid residue at position i+7.

Where the covalent bond comprises a lactam bridge, the one or more amino acid substitutions can comprise a substitution with an ornithine residue at position i and a substitution with an L-2-aminoadipic acid residue at position i+4 or i+7.

Alternatively, where the covalent bond comprises a lactam bridge, the one or more amino acid substitutions can comprise a substitution with an L-2-aminoadipic acid residue at position i and a substitution with an ornithine residue at position i+4 or i+7.

The covalent bond can comprise a hydrocarbon bridge. Where the covalent bond comprises the hydrocarbon bridge, the one or more amino acid substitutions can comprise substitutions with allylglycine residues at positions i and i+4.

Where the covalent bond comprises the hydrocarbon bridge, the one or more substitutions can comprise substitutions with alanine derivative S5 residues at positions i and i+4.

Where the covalent bond comprises the hydrocarbon bridge, the one or more substitutions can comprise a substitution with alanine derivative R8 at position i and a substitution with alanine derivative S5 at one of positions i+4 and i+7.

Where the covalent bond comprises the hydrocarbon bridge, the one or more substitutions can comprise substitutions with alanine derivative R5 residues at positions i and i+4.

Any of the peptides can comprise two or more staples. For example, the peptide can comprise one or more first substitutions at a first position i, a first position i+4, and/or a first position i+7, wherein the one or more first substitutions allows for the formation of a covalent bond between the amino acid at first position i and the amino acid at first position i+4 or first position i+7; and one or more second substitutions at a second position i, a second position i+4, and/or a second position i+7, wherein the one or more second substitutions allows for the formation of a covalent bond between the amino acid at second position i and the amino acid at second position i+4 or second position i+7.

Any of the peptides can have a length of at least 8 amino acids.

Any of the peptides can have a length of at least 9 amino acids.

Any of the peptides can have a length of at least 10 amino acids.

Any of the peptides can have a length of at least 11 amino acids.

Any of the peptides can have a length of at least 12 amino acids.

Any of the peptides can have a length of at least 13 amino acids.

Any of the peptides can have a length of at least 14 amino acids.

Any of the peptides preferably has a length of 50 amino acids or fewer.

For example, any of the peptides can have a length of 45 amino acids or fewer.

Any of the peptides can have a length of 40 amino acids or fewer.

Any of the peptides can have a length of 36 amino acids or fewer.

Any of the peptides can have a length of 30 amino acids or fewer.

Any of the peptides can have a length of 20 amino acids or fewer.

Any of the peptides can have a length of 19 amino acids or fewer.

Any of the peptides can have a length of 18 amino acids or fewer.

Any of the peptides can have a length of 17 amino acids or fewer.

Any of the peptides can have a length of 16 amino acids or fewer.

Any of the peptides can have a length of 15 amino acids or fewer.

Any of the peptides can have a length of 14 amino acids or fewer.

For example, any of the peptides can have a length of 8-16 amino acids.

In any of the peptides, the RHAMM HABD can comprises amino acids 14 to 24 of SEQ ID NO: 1.

In any of the peptides, the RHAMM HABD can comprise amino acids 36 to 45 of SEQ ID NO: 1.

In any of the peptides, the RHAMM HABD can comprise amino acids 14 to 24 and amino acids 36 to 45 of SEQ ID NO: 1.

In any of the peptides, the amino acid sequence of the peptide can comprise a sequence selected from SEQ ID NOs. 2-6, wherein the sequence includes the one or more amino acid substitutions.

In any of the peptides, the amino acid sequence of the peptide can consist of a sequence selected from SEQ ID NOs. 2-6, wherein the sequence includes the one or more amino acid substitutions.

Any of the peptides can comprise an amino acid sequence selected from SEQ ID NOs. 7-32.

Any of the peptides can consist of an amino acid sequence selected from SEQ ID NOs. 7-32.

The amino acid sequence of the peptide can comprise VSKX$_1$RSQX$_2$VKRKQN (SEQ ID NO: 7), wherein X$_1$ is glutamic acid and X$_2$ is lysine, and wherein X$_1$ is covalently bonded to X$_2$.

The amino acid sequence of the peptide can consist of VSKX$_1$RSQX$_2$VKRKQN (SEQ ID NO: 7), wherein X$_1$ is glutamic acid and X$_2$ is lysine, and wherein X$_1$ is covalently bonded to X$_2$.

The amino acid sequence of the peptide can comprise VSKLX$_1$SQLX$_2$KRKQN (SEQ ID NO: 8), wherein X$_1$ is glutamic acid and X$_2$ is lysine, and wherein X$_1$ is covalently bonded to X$_2$.

The amino acid sequence of the peptide can consist of VSKLX$_1$SQLX$_2$KRKQN (SEQ ID NO: 8), wherein X$_1$ is glutamic acid and X$_2$ is lysine, and wherein X$_1$ is covalently bonded to X$_2$.

The amino acid sequence of the peptide can comprise VSKLRX$_1$QLVX$_2$RKQN (SEQ ID NO: 9), wherein X$_1$ is glutamic acid and X$_2$ is lysine, and wherein X$_1$ is covalently bonded to X$_2$.

The amino acid sequence of the peptide can consist of VSKLRX$_1$QLVX$_2$RKQN (SEQ ID NO: 9), wherein X$_1$ is glutamic acid and X$_2$ is lysine, and wherein X$_1$ is covalently bonded to X$_2$.

The amino acid sequence of the peptide can comprise VSKLRSX$_1$LVKX$_2$KQN (SEQ ID NO: 10), wherein X$_1$ is glutamic acid and X$_2$ is lysine, and wherein X$_1$ is covalently bonded to X$_2$.

The amino acid sequence of the peptide can consist of VSKLRSX$_1$LVKX$_2$KQN (SEQ ID NO: 10), wherein X$_1$ is glutamic acid and X$_2$ is lysine, and wherein X$_1$ is covalently bonded to X$_2$.

The amino acid sequence of the peptide can comprise VSKX$_1$RSQX$_2$VKRKQN (SEQ ID NO: 7), wherein X$_1$ is lysine and X$_2$ is glutamic acid, and wherein X$_1$ is covalently bonded to X$_2$.

The amino acid sequence of the peptide can consist of VSKX$_1$RSQX$_2$VKRKQN (SEQ ID NO: 7), wherein X$_1$ is lysine and X$_2$ is glutamic acid, and wherein X$_1$ is covalently bonded to X$_2$.

The amino acid sequence of the peptide can comprise VSKLX$_1$SQLX$_2$KRKQN (SEQ ID NO: 8), wherein X$_1$ is lysine and X$_2$ is glutamic acid, and wherein X$_1$ is covalently bonded to X$_2$.

The amino acid sequence of the peptide can consist of VSKLX$_1$SQLX$_2$KRKQN (SEQ ID NO: 8), wherein X$_1$ is lysine and X$_2$ is glutamic acid, and wherein X$_1$ is covalently bonded to X$_2$.

The amino acid sequence of the peptide can comprise VSKLRX$_1$QLVX$_2$RKQN (SEQ ID NO: 9), wherein X$_1$ is lysine and X$_2$ is glutamic acid, and wherein X$_1$ is covalently bonded to X$_2$.

The amino acid sequence of the peptide can consist of VSKLRX$_1$QLVX$_2$RKQN (SEQ ID NO: 9), wherein X$_1$ is lysine and X$_2$ is glutamic acid, and wherein X$_1$ is covalently bonded to X$_2$.

The amino acid sequence of the peptide can comprise VSKLRSX$_1$LVKX$_2$KQN (SEQ ID NO: 10), wherein X$_1$ is lysine and X$_2$ is glutamic acid, and wherein X$_1$ is covalently bonded to X$_2$.

The amino acid sequence of the peptide can consist of VSKLRSX$_1$LVKX$_2$KQN (SEQ ID NO: 10), wherein X$_1$ is lysine and X$_2$ is glutamic acid, and wherein X$_1$ is covalently bonded to X$_2$.

The amino acid sequence of the peptide can comprise VSKX$_1$RSQX$_2$VKRKQN (SEQ ID NO: 7), wherein X$_1$ is ornithine and X$_2$ is L-2-aminoadipic acid, and wherein X$_1$ is covalently bonded to X$_2$.

The amino acid sequence of the peptide can consist of VSKX$_1$RSQX$_2$VKRKQN (SEQ ID NO: 7), wherein X$_1$ is ornithine and X$_2$ is L-2-aminoadipic acid, and wherein X$_1$ is covalently bonded to X$_2$.

The amino acid sequence of the peptide can comprise VSKLX$_1$SQLX$_2$KRKQN (SEQ ID NO: 8), wherein X$_1$ is ornithine and X$_2$ is L-2-aminoadipic acid, and wherein X$_1$ is covalently bonded to X$_2$.

The amino acid sequence of the peptide can consist of VSKLX$_1$SQLX$_2$KRKQN (SEQ ID NO: 8), wherein X$_1$ is ornithine and X$_2$ is L-2-aminoadipic acid, and wherein X$_1$ is covalently bonded to X$_2$.

The amino acid sequence of the peptide can comprise VSKLRX$_1$QLVX$_2$RKQN (SEQ ID NO: 9), wherein X$_1$ is ornithine and X$_2$ is L-2-aminoadipic acid, and wherein X$_1$ is covalently bonded to X$_2$.

The amino acid sequence of the peptide can consist of VSKLRX$_1$QLVX$_2$RKQN (SEQ ID NO: 9), wherein X$_1$ is ornithine and X$_2$ is L-2-aminoadipic acid, and wherein X$_1$ is covalently bonded to X$_2$.

The amino acid sequence of the peptide can comprise VSKLRSX$_1$LVKX$_2$KQN (SEQ ID NO: 10), wherein X$_1$ is ornithine and X$_2$ is L-2-aminoadipic acid, and wherein X$_1$ is covalently bonded to X$_2$.

The amino acid sequence of the peptide can consist of VSKLRSX$_1$LVKX$_2$KQN (SEQ ID NO: 10), wherein X$_1$ is ornithine and X$_2$ is L-2-aminoadipic acid, and wherein X$_1$ is covalently bonded to X$_2$.

The amino acid sequence of the peptide can comprise VSKX$_1$RSQX$_2$VKRKQN (SEQ ID NO: 7), wherein X$_1$ is L-2-aminoadipic acid and X$_2$ is ornithine, and wherein X$_1$ is covalently bonded to X$_2$.

The amino acid sequence of the peptide can consist of VSKX$_1$RSQX$_2$VKRKQN (SEQ ID NO: 7), wherein X$_1$ is L-2-aminoadipic acid and X$_2$ is ornithine, and wherein X$_1$ is covalently bonded to X$_2$.

The amino acid sequence of the peptide can comprise VSKLX$_1$SQLX$_2$KRKQN (SEQ ID NO: 8), wherein X$_1$ is L-2-aminoadipic acid and X$_2$ is ornithine, and wherein X$_1$ is covalently bonded to X$_2$.

The amino acid sequence of the peptide can consist of VSKLX$_1$SQLX$_2$KRKQN (SEQ ID NO: 8), wherein X$_1$ is L-2-aminoadipic acid and X$_2$ is ornithine, and wherein X$_1$ is covalently bonded to X$_2$.

The amino acid sequence of the peptide can comprise VSKLRX$_1$QLVX$_2$RKQN (SEQ ID NO: 9), wherein X$_1$ is L-2-aminoadipic acid and X$_2$ is ornithine, and wherein X$_1$ is covalently bonded to X$_2$.

The amino acid sequence of the peptide can consist of VSKLRX$_1$QLVX$_2$RKQN (SEQ ID NO: 9), wherein X$_1$ is L-2-aminoadipic acid and X$_2$ is ornithine, and wherein X$_1$ is covalently bonded to X$_2$.

The amino acid sequence of the peptide can comprise VSKLRSX$_1$LVKX$_2$KQN (SEQ ID NO: 10), wherein X$_1$ is L-2-aminoadipic acid and X$_2$ is ornithine, and wherein X$_1$ is covalently bonded to X$_2$.

The amino acid sequence of the peptide can consist of VSKLRSX$_1$LVKX$_2$KQN (SEQ ID NO: 10), wherein X$_1$ is L-2-aminoadipic acid and X$_2$ is ornithine, and wherein X$_1$ is covalently bonded to X$_2$.

The amino acid sequence of the peptide can comprise VSKX$_1$RSQX$_2$VKRKQN (SEQ ID NO: 7), wherein X$_1$ and X$_2$ are both alanine derivative S5, and wherein X$_1$ is covalently bonded to X$_2$.

The amino acid sequence of the peptide can consist of VSKX$_1$RSQX$_2$VKRKQN (SEQ ID NO: 7), wherein X$_1$ and X$_2$ are both alanine derivative S5, and wherein X$_1$ is covalently bonded to X$_2$.

The amino acid sequence of the peptide can comprise VSKLX$_1$SQLX$_2$KRKQN (SEQ ID NO: 8), wherein X$_1$ and X$_2$ are both alanine derivative S5, and wherein X$_1$ is covalently bonded to X$_2$.

The amino acid sequence of the peptide can consist of VSKLX₁SQLX₂KRKQN (SEQ ID NO: 8), wherein X₁ and X₂ are both alanine derivative S5, and wherein X₁ is covalently bonded to X₂.

The amino acid sequence of the peptide can comprise VSKLRX₁QLVX₂RKQN (SEQ ID NO: 9), wherein X₁ and X₂ are both alanine derivative S5, and wherein X₁ is covalently bonded to X₂.

The amino acid sequence of the peptide can consist of VSKLRX₁QLVX₂RKQN (SEQ ID NO: 9), wherein X₁ and X₂ are both alanine derivative S5, and wherein X₁ is covalently bonded to X₂.

The amino acid sequence of the peptide can comprise VSKLRSX₁LVKX₂KQN (SEQ ID NO: 10), wherein X₁ and X₂ are both alanine derivative S5, and wherein X₁ is covalently bonded to X₂.

The amino acid sequence of the peptide can consist of VSKLRSX₁LVKX₂KQN (SEQ ID NO: 10), wherein X₁ and X₂ are both alanine derivative S5, and wherein X₁ is covalently bonded to X₂.

The amino acid sequence of the peptide can comprise VSKX₁RSQX₂VKRKQN (SEQ ID NO: 7), wherein X₁ and X₂ are both allylglycine, and wherein X₁ is covalently bonded to X₂.

The amino acid sequence of the peptide can consist of VSKX₁RSQX₂VKRKQN (SEQ ID NO: 7), wherein X₁ and X₂ are both allylglycine, and wherein X₁ is covalently bonded to X₂.

The amino acid sequence of the peptide can comprise VSKLX₁SQLX₂KRKQN (SEQ ID NO: 8), wherein X₁ and X₂ are both allylglycine, and wherein X₁ is covalently bonded to X₂.

The amino acid sequence of the peptide can consist of VSKLX₁SQLX₂KRKQN (SEQ ID NO: 8), wherein X₁ and X₂ are both allylglycine, and wherein X₁ is covalently bonded to X₂.

The amino acid sequence of the peptide can comprise VSKLRX₁QLVX₂RKQN (SEQ ID NO: 9), wherein X₁ and X₂ are both allylglycine, and wherein X₁ is covalently bonded to X₂.

The amino acid sequence of the peptide can consist of VSKLRX₁QLVX₂RKQN (SEQ ID NO: 9), wherein X₁ and X₂ are both allylglycine, and wherein X₁ is covalently bonded to X₂.

The amino acid sequence of the peptide can comprise VSKLRSX₁LVKX₂KQN (SEQ ID NO: 10), wherein X₁ and X₂ are both allylglycine, and wherein X₁ is covalently bonded to X₂.

The amino acid sequence of the peptide can consist of VSKLRSX₁LVKX₂KQN (SEQ ID NO: 10), wherein X₁ and X₂ are both allylglycine, and wherein X₁ is covalently bonded to X₂.

The amino acid sequence of the peptide can comprise NLKX₁KIKX₂VVKLKDE (SEQ ID NO: 15), wherein X₁ is glutamic acid and X₂ is lysine, and wherein X₁ is covalently bonded to X₂.

The amino acid sequence of the peptide can consist of NLKX₁KIKX₂VVKLKDE (SEQ ID NO: 15), wherein X₁ is glutamic acid and X₂ is lysine, and wherein X₁ is covalently bonded to X₂.

The amino acid sequence of the peptide can comprise NLKQX₁KHX₂VKLKDE (SEQ ID NO: 16), wherein X₁ is glutamic acid and X₂ is lysine, and wherein X₁ is covalently bonded to X₂.

The amino acid sequence of the peptide can consist of NLKQX₁KHX₂VKLKDE (SEQ ID NO: 16), wherein X₁ is glutamic acid and X₂ is lysine, and wherein X₁ is covalently bonded to X₂.

The amino acid sequence of the peptide can comprise NLKQKX₁KHVX₂KLKDE (SEQ ID NO: 17), wherein X₁ is glutamic acid and X₂ is lysine, and wherein X₁ is covalently bonded to X₂.

The amino acid sequence of the peptide can consist of NLKQKX₁KHVX₂KLKDE (SEQ ID NO: 17), wherein X₁ is glutamic acid and X₂ is lysine, and wherein X₁ is covalently bonded to X₂.

The amino acid sequence of the peptide can comprise NLKQKIX₁HVVX₂LKDE (SEQ ID NO: 18), wherein X₁ is glutamic acid and X₂ is lysine, and wherein X₁ is covalently bonded to X₂.

The amino acid sequence of the peptide can consist of NLKQKIX₁HVVX₂LKDE (SEQ ID NO: 18), wherein X₁ is glutamic acid and X₂ is lysine, and wherein X₁ is covalently bonded to X₂.

The amino acid sequence of the peptide can comprise NLKQKIKX₁VVKX₂KDE (SEQ ID NO: 19), wherein X₁ is glutamic acid and X₂ is lysine, and wherein X₁ is covalently bonded to X₂.

The amino acid sequence of the peptide can consist of NLKQKIKX₁VVKX₂KDE (SEQ ID NO: 19), wherein X₁ is glutamic acid and X₂ is lysine, and wherein X₁ is covalently bonded to X₂.

The amino acid sequence of the peptide can comprise NLKX₁KIKX₂VVKLKDE (SEQ ID NO: 15), wherein X₁ is lysine and X₂ is glutamic acid, and wherein X₁ is covalently bonded to X₂.

The amino acid sequence of the peptide can consist of NLKX₁KIKX₂VVKLKDE (SEQ ID NO: 15), wherein X₁ is lysine and X₂ is glutamic acid, and wherein X₁ is covalently bonded to X₂.

The amino acid sequence of the peptide can comprise NLKQX₁IKHX₂VKLKDE (SEQ ID NO: 16), wherein X₁ is lysine and X₂ is glutamic acid, and wherein X₁ is covalently bonded to X₂.

The amino acid sequence of the peptide can consist of NLKQX₁IKHX₂VKLKDE (SEQ ID NO: 16), wherein X₁ is lysine and X₂ is glutamic acid, and wherein X₁ is covalently bonded to X₂.

The amino acid sequence of the peptide can comprise NLKQKX₁KHVX₂KLKDE (SEQ ID NO: 17), wherein X₁ is lysine and X₂ is glutamic acid, and wherein X₁ is covalently bonded to X₂.

The amino acid sequence of the peptide can consist of NLKQKX₁KHVX₂KLKDE (SEQ ID NO: 17), wherein X₁ is lysine and X₂ is glutamic acid, and wherein X₁ is covalently bonded to X₂.

The amino acid sequence of the peptide can comprise NLKQKIX₁HVVX₂LKDE (SEQ ID NO: 18), wherein X₁ is lysine and X₂ is glutamic acid, and wherein X₁ is covalently bonded to X₂.

The amino acid sequence of the peptide can consist of NLKQKIX₁HVVX₂LKDE (SEQ ID NO: 18), wherein X₁ is lysine and X₂ is glutamic acid, and wherein X₁ is covalently bonded to X₂.

The amino acid sequence of the peptide can comprise NLKQKIKX₁VVKX₂KDE (SEQ ID NO: 19), wherein X₁ is lysine and X₂ is glutamic acid, and wherein X₁ is covalently bonded to X₂.

The amino acid sequence of the peptide can consist of NLKQKIKX$_1$VVKX$_2$KDE (SEQ ID NO: 19), wherein X$_1$ is lysine and X$_2$ is glutamic acid, and wherein X$_1$ is covalently bonded to X$_2$.

The amino acid sequence of the peptide can comprise NLKX$_1$KIKX$_2$VVKLKDE (SEQ ID NO: 15), wherein X$_1$ is ornithine and X$_2$ is L-2-aminoadipic acid, and wherein X$_1$ is covalently bonded to X$_2$.

The amino acid sequence of the peptide can consist of NLKX$_1$KIKX$_2$VVKLKDE (SEQ ID NO: 15), wherein X$_1$ is ornithine and X$_2$ is L-2-aminoadipic acid, and wherein X$_1$ is covalently bonded to X$_2$.

The amino acid sequence of the peptide can comprise NLKQX$_1$IKHX$_2$VKLKDE (SEQ ID NO: 16), wherein X$_1$ is ornithine and X$_2$ is L-2-aminoadipic acid, and wherein X$_1$ is covalently bonded to X$_2$.

The amino acid sequence of the peptide can consist of NLKQX$_1$IKHX$_2$VKLKDE (SEQ ID NO: 16), wherein X$_1$ is ornithine and X$_2$ is L-2-aminoadipic acid, and wherein X$_1$ is covalently bonded to X$_2$.

The amino acid sequence of the peptide can comprise NLKQKX$_1$KHVX$_2$KLKDE (SEQ ID NO: 17), wherein X$_1$ is ornithine and X$_2$ is L-2-aminoadipic acid, and wherein X$_1$ is covalently bonded to X$_2$.

The amino acid sequence of the peptide can consist of NLKQKX$_1$KHVX$_2$KLKDE (SEQ ID NO: 17), wherein X$_1$ is ornithine and X$_2$ is L-2-aminoadipic acid, and wherein X$_1$ is covalently bonded to X$_2$.

The amino acid sequence of the peptide can comprise NLKQKIX$_1$HVVX$_2$LKDE (SEQ ID NO: 18), wherein X$_1$ is ornithine and X$_2$ is L-2-aminoadipic acid, and wherein X$_1$ is covalently bonded to X$_2$.

The amino acid sequence of the peptide can consist of NLKQKIX$_1$HVVX$_2$LKDE (SEQ ID NO: 18), wherein X$_1$ is ornithine and X$_2$ is L-2-aminoadipic acid, and wherein X$_1$ is covalently bonded to X$_2$.

The amino acid sequence of the peptide can comprise NLKQKIKX$_1$VVKX$_2$KDE (SEQ ID NO: 19), wherein X$_1$ is ornithine and X$_2$ is L-2-aminoadipic acid, and wherein X$_1$ is covalently bonded to X$_2$.

The amino acid sequence of the peptide can consist of NLKQKIKX$_1$VVKX$_2$KDE (SEQ ID NO: 19), wherein X$_1$ is ornithine and X$_2$ is L-2-aminoadipic acid, and wherein X$_1$ is covalently bonded to X$_2$.

The amino acid sequence of the peptide can comprise NLKX$_1$KIKX$_2$VVKLKDE (SEQ ID NO: 15), wherein X$_1$ is L-2-aminoadipic acid and X$_2$ is ornithine, and wherein X$_1$ is covalently bonded to X$_2$.

The amino acid sequence of the peptide can consist of NLKX$_1$KIKX$_2$VVKLKDE (SEQ ID NO: 15), wherein X$_1$ is L-2-aminoadipic acid and X$_2$ is ornithine, and wherein X$_1$ is covalently bonded to X$_2$.

The amino acid sequence of the peptide can comprise NLKQX$_1$IKHX$_2$VKLKDE (SEQ ID NO: 16), wherein X$_1$ is L-2-aminoadipic acid and X$_2$ is ornithine, and wherein X$_1$ is covalently bonded to X$_2$.

The amino acid sequence of the peptide can consist of NLKQX$_1$IKHX$_2$VKLKDE (SEQ ID NO: 16), wherein X$_1$ is L-2-aminoadipic acid and X$_2$ is ornithine, and wherein X$_1$ is covalently bonded to X$_2$.

The amino acid sequence of the peptide can comprise NLKQKX$_1$KHVX$_2$KLKDE (SEQ ID NO: 17), wherein X$_1$ is L-2-aminoadipic acid and X$_2$ is ornithine, and wherein X$_1$ is covalently bonded to X$_2$.

The amino acid sequence of the peptide can consist of NLKQKX$_1$KHVX$_2$KLKDE (SEQ ID NO: 17), wherein X$_1$ is L-2-aminoadipic acid and X$_2$ is ornithine, and wherein X$_1$ is covalently bonded to X$_2$.

The amino acid sequence of the peptide can comprise NLKQKIX$_1$HVVX$_2$LKDE (SEQ ID NO: 18), wherein X$_1$ is L-2-aminoadipic acid and X$_2$ is ornithine, and wherein X$_1$ is covalently bonded to X$_2$.

The amino acid sequence of the peptide can consist of NLKQKIX$_1$HVVX$_2$LKDE (SEQ ID NO: 18), wherein X$_1$ is L-2-aminoadipic acid and X$_2$ is ornithine, and wherein X$_1$ is covalently bonded to X$_2$.

The amino acid sequence of the peptide can comprise NLKQKIKX$_1$VVKX$_2$KDE (SEQ ID NO: 19), wherein X$_1$ is L-2-aminoadipic acid and X$_2$ is ornithine, and wherein X$_1$ is covalently bonded to X$_2$.

The amino acid sequence of the peptide can consist of NLKQKIKX$_1$VVKX$_2$KDE (SEQ ID NO: 19), wherein X$_1$ is L-2-aminoadipic acid and X$_2$ is ornithine, and wherein X$_1$ is covalently bonded to X$_2$.

The amino acid sequence of the peptide can comprise NLKX$_1$KIKX$_2$VVKLKDE (SEQ ID NO: 15), wherein X$_1$ and X$_2$ are both alanine derivative S5, and wherein X$_1$ is covalently bonded to X$_2$.

The amino acid sequence of the peptide can consist of NLKX$_1$KIKX$_2$VVKLKDE (SEQ ID NO: 15), wherein X$_1$ and X$_2$ are both alanine derivative S5, and wherein X$_1$ is covalently bonded to X$_2$.

The amino acid sequence of the peptide can comprise NLKQX$_1$IKHX$_2$VKLKDE (SEQ ID NO: 16), wherein X$_1$ and X$_2$ are both alanine derivative S5, and wherein X$_1$ is covalently bonded to X$_2$.

The amino acid sequence of the peptide can consist of NLKQX$_1$IKHX$_2$VKLKDE (SEQ ID NO: 16), wherein X$_1$ and X$_2$ are both alanine derivative S5, and wherein X$_1$ is covalently bonded to X$_2$.

The amino acid sequence of the peptide can comprise NLKQKX$_1$KHVX$_2$KLKDE (SEQ ID NO: 17), wherein X$_1$ and X$_2$ are both alanine derivative S5, and wherein X$_1$ is covalently bonded to X$_2$.

The amino acid sequence of the peptide can consist of NLKQKX$_1$KHVX$_2$KLKDE (SEQ ID NO: 17), wherein X$_1$ and X$_2$ are both alanine derivative S5, and wherein X$_1$ is covalently bonded to X$_2$.

The amino acid sequence of the peptide can comprise NLKQKIX$_1$HVVX$_2$LKDE (SEQ ID NO: 18), wherein X$_1$ and X$_2$ are both alanine derivative S5, and wherein X$_1$ is covalently bonded to X$_2$.

The amino acid sequence of the peptide can consist of NLKQKIX$_1$HVVX$_2$LKDE (SEQ ID NO: 18), wherein X$_1$ and X$_2$ are both alanine derivative S5, and wherein X$_1$ is covalently bonded to X$_2$.

The amino acid sequence of the peptide can comprise NLKQKIKX$_1$VVKX$_2$KDE (SEQ ID NO: 19), wherein X$_1$ and X$_2$ are both alanine derivative S5, and wherein X$_1$ is covalently bonded to X$_2$.

The amino acid sequence of the peptide can consist of NLKQKIKX$_1$VVKX$_2$KDE (SEQ ID NO: 19), wherein X$_1$ and X$_2$ are both alanine derivative S5, and wherein X$_1$ is covalently bonded to X$_2$.

The amino acid sequence of the peptide can comprise NLKX$_1$KIKX$_2$VVKLKDE (SEQ ID NO: 15), wherein X$_1$ and X$_2$ are both allylglycine, and wherein X$_1$ is covalently bonded to X$_2$.

The amino acid sequence of the peptide can consist of NLKX$_1$KIKX$_2$VVKLKDE (SEQ ID NO: 15), wherein X$_1$ and X$_2$ are both allylglycine, and wherein X$_1$ is covalently bonded to X$_2$.

The amino acid sequence of the peptide can comprise NLKQX$_1$IKHX$_2$VKLKDE (SEQ ID NO: 16), wherein X$_1$ and X$_2$ are both allylglycine, and wherein X$_1$ is covalently bonded to X$_2$.

The amino acid sequence of the peptide can consist of NLKQX$_1$IKHX$_2$VKLKDE (SEQ ID NO: 16), wherein X$_1$ and X$_2$ are both allylglycine, and wherein X$_1$ is covalently bonded to X$_2$.

The amino acid sequence of the peptide can comprise NLKQKX$_1$KHVX$_2$KLKDE (SEQ ID NO: 17), wherein X$_1$ and X$_2$ are both allylglycine, and wherein X$_1$ is covalently bonded to X$_2$.

The amino acid sequence of the peptide can consist of NLKQKX$_1$KHVX$_2$KLKDE (SEQ ID NO: 17), wherein X$_1$ and X$_2$ are both allylglycine, and wherein X$_1$ is covalently bonded to X$_2$.

The amino acid sequence of the peptide can comprise NLKQKIX$_1$HVVX$_2$LKDE (SEQ ID NO: 18), wherein X$_1$ and X$_2$ are both allylglycine, and wherein X$_1$ is covalently bonded to X$_2$.

The amino acid sequence of the peptide can consist of NLKQKIX$_1$HVVX$_2$LKDE (SEQ ID NO: 18), wherein X$_1$ and X$_2$ are both allylglycine, and wherein X$_1$ is covalently bonded to X$_2$.

The amino acid sequence of the peptide can comprise NLKQKIKX$_1$VVKX$_2$KDE (SEQ ID NO: 19), wherein X$_1$ and X$_2$ are both allylglycine, and wherein X$_1$ is covalently bonded to X$_2$.

The amino acid sequence of the peptide can consist of NLKQKIKX$_1$VVKX$_2$KDE (SEQ ID NO: 19), wherein X$_1$ and X$_2$ are both allylglycine, and wherein X$_1$ is covalently bonded to X$_2$.

The amino acid sequence of the peptide can comprise NLKX$_1$KIKHVVX$_2$LKDE (SEQ ID NO: 20), wherein X$_1$ is glutamic acid and X$_2$ is lysine, and wherein X$_1$ is covalently bonded to X$_2$.

The amino acid sequence of the peptide can consist of NLKX$_1$KIKHVVX$_2$LKDE (SEQ ID NO: 20), wherein X$_1$ is glutamic acid and X$_2$ is lysine, and wherein X$_1$ is covalently bonded to X$_2$.

The amino acid sequence of the peptide can comprise NLKQX$_1$IKHVVKX$_2$KDE (SEQ ID NO: 21), wherein X$_1$ is glutamic acid and X$_2$ is lysine, and wherein X$_1$ is covalently bonded to X$_2$.

The amino acid sequence of the peptide can consist of NLKQX$_1$IKHVVKX$_2$KDE (SEQ ID NO: 21), wherein X$_1$ is glutamic acid and X$_2$ is lysine, and wherein X$_1$ is covalently bonded to X$_2$.

The amino acid sequence of the peptide can comprise NLKX$_1$KIKHVVX$_2$LKDE (SEQ ID NO: 20), wherein X$_1$ is lysine and X$_2$ is glutamic acid, and wherein X$_1$ is covalently bonded to X$_2$.

The amino acid sequence of the peptide can consist of NLKX$_1$KIKHVVX$_2$LKDE (SEQ ID NO: 20), wherein X$_1$ is lysine and X$_2$ is glutamic acid, and wherein X$_1$ is covalently bonded to X$_2$.

The amino acid sequence of the peptide can comprise NLKQX$_1$IKHVVKX$_2$KDE (SEQ ID NO: 21), wherein X$_1$ is lysine and X$_2$ is glutamic acid, and wherein X$_1$ is covalently bonded to X$_2$.

The amino acid sequence of the peptide can consist of NLKQX$_1$IKHVVKX$_2$KDE (SEQ ID NO: 21), wherein X$_1$ is lysine and X$_2$ is glutamic acid, and wherein X$_1$ is covalently bonded to X$_2$.

The amino acid sequence of the peptide can comprise NLKX$_1$KIKHVVX$_2$LKDE (SEQ ID NO: 20), wherein X$_1$ is ornithine and X$_2$ is L-2-aminoadipic acid, and wherein X$_1$ is covalently bonded to X$_2$.

The amino acid sequence of the peptide can consist of NLKX$_1$KIKHVVX$_2$LKDE (SEQ ID NO: 20), wherein X$_1$ is ornithine and X$_2$ is L-2-aminoadipic acid, and wherein X$_1$ is covalently bonded to X$_2$.

The amino acid sequence of the peptide can comprise NLKQX$_1$IKHVVKX$_2$KDE (SEQ ID NO: 21), wherein X$_1$ is ornithine and X$_2$ is L-2-aminoadipic acid, and wherein X$_1$ is covalently bonded to X$_2$.

The amino acid sequence of the peptide can consist of NLKQX$_1$IKHVVKX$_2$KDE (SEQ ID NO: 21), wherein X$_1$ is ornithine and X$_2$ is L-2-aminoadipic acid, and wherein X$_1$ is covalently bonded to X$_2$.

The amino acid sequence of the peptide can comprise NLKX$_1$KIKHVVX$_2$LKDE (SEQ ID NO: 20), wherein X$_1$ is L-2-aminoadipic acid and X$_2$ is ornithine, and wherein X$_1$ is covalently bonded to X$_2$.

The amino acid sequence of the peptide can consist of NLKX$_1$KIKHVVX$_2$LKDE (SEQ ID NO: 20), wherein X$_1$ is L-2-aminoadipic acid and X$_2$ is ornithine, and wherein X$_1$ is covalently bonded to X$_2$.

The amino acid sequence of the peptide can comprise NLKQX$_1$IKHVVKX$_2$KDE (SEQ ID NO: 21), wherein X$_1$ is L-2-aminoadipic acid and X$_2$ is ornithine, and wherein X$_1$ is covalently bonded to X$_2$.

The amino acid sequence of the peptide can consist of NLKQX$_1$IKHVVKX$_2$KDE (SEQ ID NO: 21), wherein X$_1$ is L-2-aminoadipic acid and X$_2$ is ornithine, and wherein X$_1$ is covalently bonded to X$_2$.

The amino acid sequence of the peptide can comprise NLKX$_1$KIKHVVX$_2$LKDE (SEQ ID NO: 20), wherein X$_1$ is alanine derivative R8 and X$_2$ is alanine derivative S5, and wherein X$_1$ is covalently bonded to X$_2$.

The amino acid sequence of the peptide can consist of NLKX$_1$KIKHVVX$_2$LKDE (SEQ ID NO: 20), wherein X$_1$ is alanine derivative R8 and X$_2$ is alanine derivative S5, and wherein X$_1$ is covalently bonded to X$_2$.

The amino acid sequence of the peptide can comprise NLKQX$_1$IKHVVKX$_2$KDE (SEQ ID NO: 21), wherein X$_1$ is alanine derivative R8 and X$_2$ is alanine derivative S5, and wherein X$_1$ is covalently bonded to X$_2$.

The amino acid sequence of the peptide can consist of NLKQX$_1$IKHVVKX$_2$KDE (SEQ ID NO: 21), wherein X$_1$ is alanine derivative R8 and X$_2$ is alanine derivative S5, and wherein X$_1$ is covalently bonded to X$_2$.

The amino acid sequence of the peptide can comprise KSEVSKLRX$_1$QLVKRKX$_2$NELR (SEQ ID NO: 11), wherein X$_1$ is glutamic acid and X$_2$ is lysine, and wherein X$_1$ is covalently bonded to X$_2$.

The amino acid sequence of the peptide can consist of KSEVSKLRX$_1$QLVKRKX$_2$NELR (SEQ ID NO: 11), wherein X$_1$ is glutamic acid and X$_2$ is lysine, and wherein X$_1$ is covalently bonded to X$_2$.

The amino acid sequence of the peptide can comprise KSEVSKLRSX$_1$LVKRKQX$_2$ELR (SEQ ID NO: 12), wherein X$_1$ is glutamic acid and X$_2$ is lysine, and wherein X$_1$ is covalently bonded to X$_2$.

The amino acid sequence of the peptide can consist of KSEVSKLRSX$_1$LVKRKQX$_2$ELR (SEQ ID NO: 12), wherein X$_1$ is glutamic acid and X$_2$ is lysine, and wherein X$_1$ is covalently bonded to X$_2$.

The amino acid sequence of the peptide can comprise KSEVSKLRSQX$_1$VKRKQNX$_2$LR (SEQ ID NO: 13), wherein X$_1$ is glutamic acid and X$_2$ is lysine, and wherein X$_1$ is covalently bonded to X$_2$.

The amino acid sequence of the peptide can consist of KSEVSKLRSQX$_1$VKRKQNX$_2$LR (SEQ ID NO: 13), wherein X$_1$ is glutamic acid and X$_2$ is lysine, and wherein X$_1$ is covalently bonded to X$_2$.

The amino acid sequence of the peptide can comprise KSEVSKLRX$_1$QLVKRKX$_2$NELR (SEQ ID NO: 11), wherein X$_1$ is lysine and X$_2$ is glutamic acid, and wherein X$_1$ is covalently bonded to X$_2$.

The amino acid sequence of the peptide can consist of KSEVSKLRX$_1$QLVKRKX$_2$NELR (SEQ ID NO: 11), wherein X$_1$ is lysine and X$_2$ is glutamic acid, and wherein X$_1$ is covalently bonded to X$_2$.

The amino acid sequence of the peptide can comprise KSEVSKLRSX$_1$LVKRKQX$_2$ELR (SEQ ID NO: 12), wherein X$_1$ is lysine and X$_2$ is glutamic acid, and wherein X$_1$ is covalently bonded to X$_2$.

The amino acid sequence of the peptide can consist of KSEVSKLRSX$_1$LVKRKQX$_2$ELR (SEQ ID NO: 12), wherein X$_1$ is lysine and X$_2$ is glutamic acid, and wherein X$_1$ is covalently bonded to X$_2$.

The amino acid sequence of the peptide can comprise KSEVSKLRSQX$_1$VKRKQNX$_2$LR (SEQ ID NO: 13), wherein X$_1$ is lysine and X$_2$ is glutamic acid, and wherein X$_1$ is covalently bonded to X$_2$.

The amino acid sequence of the peptide can consist of KSEVSKLRSQX$_1$VKRKQNX$_2$LR (SEQ ID NO: 13), wherein X$_1$ is lysine and X$_2$ is glutamic acid, and wherein X$_1$ is covalently bonded to X$_2$.

The amino acid sequence of the peptide can comprise KSEVSKLRX$_1$QLVKRKX$_2$NELR (SEQ ID NO: 11), wherein X$_1$ is ornithine and X$_2$ is L-2-aminoadipic acid, and wherein X$_1$ is covalently bonded to X$_2$.

The amino acid sequence of the peptide can consist of KSEVSKLRX$_1$QLVKRKX$_2$NELR (SEQ ID NO: 11), wherein X$_1$ is ornithine and X$_2$ is L-2-aminoadipic acid, and wherein X$_1$ is covalently bonded to X$_2$.

The amino acid sequence of the peptide can comprise KSEVSKLRSX$_1$LVKRKQX$_2$ELR (SEQ ID NO: 12), wherein X$_1$ is ornithine and X$_2$ is L-2-aminoadipic acid, and wherein X$_1$ is covalently bonded to X$_2$.

The amino acid sequence of the peptide can consist of KSEVSKLRSX$_1$LVKRKQX$_2$ELR (SEQ ID NO: 12), wherein X$_1$ is ornithine and X$_2$ is L-2-aminoadipic acid, and wherein X$_1$ is covalently bonded to X$_2$.

The amino acid sequence of the peptide can comprise KSEVSKLRSQX$_1$VKRKQNX$_2$LR (SEQ ID NO: 13), wherein X$_1$ is ornithine and X$_2$ is L-2-aminoadipic acid, and wherein X$_1$ is covalently bonded to X$_2$.

The amino acid sequence of the peptide can consist of KSEVSKLRSQX$_1$VKRKQNX$_2$LR (SEQ ID NO: 13), wherein X$_1$ is ornithine and X$_2$ is L-2-aminoadipic acid, and wherein X$_1$ is covalently bonded to X$_2$.

The amino acid sequence of the peptide can comprise KSEVSKLRX$_1$QLVKRKX$_2$NELR (SEQ ID NO: 11), wherein X$_1$ is L-2-aminoadipic acid and X$_2$ is ornithine, and wherein X$_1$ is covalently bonded to X$_2$.

The amino acid sequence of the peptide can consist of KSEVSKLRX$_1$QLVKRKX$_2$NELR (SEQ ID NO: 11), wherein X$_1$ is L-2-aminoadipic acid and X$_2$ is ornithine, and wherein X$_1$ is covalently bonded to X$_2$.

The amino acid sequence of the peptide can comprise KSEVSKLRSX$_1$LVKRKQX$_2$ELR (SEQ ID NO: 12), wherein X$_1$ is L-2-aminoadipic acid and X$_2$ is ornithine, and wherein X$_1$ is covalently bonded to X$_2$.

The amino acid sequence of the peptide can consist of KSEVSKLRSX$_1$LVKRKQX$_2$ELR (SEQ ID NO: 12), wherein X$_1$ is L-2-aminoadipic acid and X$_2$ is ornithine, and wherein X$_1$ is covalently bonded to X$_2$.

The amino acid sequence of the peptide can comprise KSEVSKLRSQX$_1$VKRKQNX$_2$LR (SEQ ID NO: 13), wherein X$_1$ is L-2-aminoadipic acid and X$_2$ is ornithine, and wherein X$_1$ is covalently bonded to X$_2$.

The amino acid sequence of the peptide can consist of KSEVSKLRSQX$_1$VKRKQNX$_2$LR (SEQ ID NO: 13), wherein X$_1$ is L-2-aminoadipic acid and X$_2$ is ornithine, and wherein X$_1$ is covalently bonded to X$_2$.

The amino acid sequence of the peptide can comprise KSEVSKLRX$_1$QLVKRKX$_2$NELR (SEQ ID NO: 11), wherein X$_1$ is alanine derivative R8 and X$_2$ is alanine derivative S5, and wherein X$_1$ is covalently bonded to X$_2$.

The amino acid sequence of the peptide can consist of KSEVSKLRX$_1$QLVKRKX$_2$NELR (SEQ ID NO: 11), wherein X$_1$ is alanine derivative R8 and X$_2$ is alanine derivative S5, and wherein X$_1$ is covalently bonded to X$_2$.

The amino acid sequence of the peptide can comprise KSEVSKLRSX$_1$LVKRKQX$_2$ELR (SEQ ID NO: 12), wherein X$_1$ is alanine derivative R8 and X$_2$ is alanine derivative S5, and wherein X$_1$ is covalently bonded to X$_2$.

The amino acid sequence of the peptide can consist of KSEVSKLRSX$_1$LVKRKQX$_2$ELR (SEQ ID NO: 12), wherein X$_1$ is alanine derivative R8 and X$_2$ is alanine derivative S5, and wherein X$_1$ is covalently bonded to X$_2$.

The amino acid sequence of the peptide can comprise KSEVSKLRSQX$_1$VKRKQNX$_2$LR (SEQ ID NO: 13), wherein X$_1$ is alanine derivative R8 and X$_2$ is alanine derivative S5, and wherein X$_1$ is covalently bonded to X$_2$.

The amino acid sequence of the peptide can consist of KSEVSKLRSQX$_1$VKRKQNX$_2$LR (SEQ ID NO: 13), wherein X$_1$ is alanine derivative R8 and X$_2$ is alanine derivative S5, and wherein X$_1$ is covalently bonded to X$_2$.

The amino acid sequence of the peptide can comprise KIKHVVKLKX$_1$ENSQLKX$_2$EVSKLRSQLVKRK (SEQ ID NO: 22), wherein X$_1$ is glutamic acid and X$_2$ is lysine, and wherein X$_1$ is covalently bonded to X$_2$.

The amino acid sequence of the peptide can consist of KIKHVVKLKX$_1$ENSQLKX$_2$EVSKLRSQLVKRK (SEQ ID NO: 22), wherein X$_1$ is glutamic acid and X$_2$ is lysine, and wherein X$_1$ is covalently bonded to X$_2$.

The amino acid sequence of the peptide can comprise KIKHVVKLKDX$_1$NSQLKSX$_2$VSKLRSQLVKRK (SEQ ID NO: 23), wherein X$_1$ is glutamic acid and X$_2$ is lysine, and wherein X$_1$ is covalently bonded to X$_2$.

The amino acid sequence of the peptide can consist of KIKHVVKLKDX$_1$NSQLKSX$_2$VSKLRSQLVKRK (SEQ ID NO: 23), wherein X$_1$ is glutamic acid and X$_2$ is lysine, and wherein X$_1$ is covalently bonded to X$_2$.

The amino acid sequence of the peptide can comprise KIKHVVKLKDEX$_1$SQLKSEX$_2$SKLRSQLVKRK (SEQ ID NO: 24), wherein X$_1$ is glutamic acid and X$_2$ is lysine, and wherein X$_1$ is covalently bonded to X$_2$.

The amino acid sequence of the peptide can consist of KIKHVVKLKDEX$_1$SQLKSEX$_2$SKLRSQLVKRK (SEQ ID NO: 24), wherein X$_1$ is glutamic acid and X$_2$ is lysine, and wherein X$_1$ is covalently bonded to X$_2$.

The amino acid sequence of the peptide can comprise KIKHVVKLKDENX$_1$QLKSEVX$_2$KLRSQLVKRK (SEQ ID NO: 25), wherein X$_1$ is glutamic acid and X$_2$ is lysine, and wherein X$_1$ is covalently bonded to X$_2$.

The amino acid sequence of the peptide can consist of KIKHVVKLKDENX$_1$QLKSEVX$_2$KLRSQLVKRK (SEQ ID NO: 25), wherein X$_1$ is glutamic acid and X$_2$ is lysine, and wherein X$_1$ is covalently bonded to X$_2$.

The amino acid sequence of the peptide can comprise KIKHVVKLKX$_1$ENSQLKX$_2$EVSKLRSQLVKRK (SEQ ID NO: 22), wherein X$_1$ is lysine and X$_2$ is glutamic acid, and wherein X$_1$ is covalently bonded to X$_2$.

The amino acid sequence of the peptide can consist of KIKHVVKLKX$_1$ENSQLKX$_2$EVSKLRSQLVKRK (SEQ ID NO: 22), wherein X$_1$ is lysine and X$_2$ is glutamic acid, and wherein X$_1$ is covalently bonded to X$_2$.

The amino acid sequence of the peptide can comprise KIKHVVKLKDX$_1$NSQLKSX$_2$VSKLRSQLVKRK (SEQ ID NO: 23), wherein X$_1$ is lysine and X$_2$ is glutamic acid, and wherein X$_1$ is covalently bonded to X$_2$.

The amino acid sequence of the peptide can consist of KIKHVVKLKDX$_1$NSQLKSX$_2$VSKLRSQLVKRK (SEQ ID NO: 23), wherein X$_1$ is lysine and X$_2$ is glutamic acid, and wherein X$_1$ is covalently bonded to X$_2$.

The amino acid sequence of the peptide can comprise KIKHVVKLKDEX$_1$SQLKSEX$_2$SKLRSQLVKRK (SEQ ID NO: 24), wherein X$_1$ is lysine and X$_2$ is glutamic acid, and wherein X$_1$ is covalently bonded to X$_2$.

The amino acid sequence of the peptide can consist of KIKHVVKLKDEX$_1$SQLKSEX$_2$SKLRSQLVKRK (SEQ ID NO: 24), wherein X$_1$ is lysine and X$_2$ is glutamic acid, and wherein X$_1$ is covalently bonded to X$_2$.

The amino acid sequence of the peptide can comprise KIKHVVKLKDENX$_1$QLKSEVX$_2$KLRSQLVKRK (SEQ ID NO: 25), wherein X$_1$ is lysine and X$_2$ is glutamic acid, and wherein X$_1$ is covalently bonded to X$_2$.

The amino acid sequence of the peptide can consist of KIKHVVKLKDENX$_1$QLKSEVX$_2$KLRSQLVKRK (SEQ ID NO: 25), wherein X$_1$ is lysine and X$_2$ is glutamic acid, and wherein X$_1$ is covalently bonded to X$_2$.

The amino acid sequence of the peptide can comprise KIKHVVKLKX$_1$ENSQLKX$_2$EVSKLRSQLVKRK (SEQ ID NO: 22), wherein X$_1$ is ornithine and X$_2$ is L-2-aminoadipic acid, and wherein X$_1$ is covalently bonded to X$_2$.

The amino acid sequence of the peptide can consist of KIKHVVKLKX$_1$ENSQLKX$_2$EVSKLRSQLVKRK (SEQ ID NO: 22), wherein X$_1$ is ornithine and X$_2$ is L-2-aminoadipic acid, and wherein X$_1$ is covalently bonded to X$_2$.

The amino acid sequence of the peptide can comprise KIKHVVKLKDX$_1$NSQLKSX$_2$VSKLRSQLVKRK (SEQ ID NO: 23), wherein X$_1$ is ornithine and X$_2$ is L-2-aminoadipic acid, and wherein X$_1$ is covalently bonded to X$_2$.

The amino acid sequence of the peptide can consist of KIKHVVKLKDX$_1$NSQLKSX$_2$VSKLRSQLVKRK (SEQ ID NO: 23), wherein X$_1$ is ornithine and X$_2$ is L-2-aminoadipic acid, and wherein X$_1$ is covalently bonded to X$_2$.

The amino acid sequence of the peptide can comprise KIKHVVKLKDEX$_1$SQLKSEX$_2$SKLRSQLVKRK (SEQ ID NO: 24), wherein X$_1$ is ornithine and X$_2$ is L-2-aminoadipic acid, and wherein X$_1$ is covalently bonded to X$_2$.

The amino acid sequence of the peptide can consist of KIKHVVKLKDEX$_1$SQLKSEX$_2$SKLRSQLVKRK (SEQ ID NO: 24), wherein X$_1$ is ornithine and X$_2$ is L-2-aminoadipic acid, and wherein X$_1$ is covalently bonded to X$_2$.

The amino acid sequence of the peptide can comprise KIKHVVKLKDENX$_1$QLKSEVX$_2$KLRSQLVKRK (SEQ ID NO: 25), wherein X$_1$ is ornithine and X$_2$ is L-2-aminoadipic acid, and wherein X$_1$ is covalently bonded to X$_2$.

The amino acid sequence of the peptide can consist of KIKHVVKLKDENX$_1$QLKSEVX$_2$KLRSQLVKRK (SEQ ID NO: 25), wherein X$_1$ is ornithine and X$_2$ is L-2-aminoadipic acid, and wherein X$_1$ is covalently bonded to X$_2$.

The amino acid sequence of the peptide can comprise KIKHVVKLKX$_1$ENSQLKX$_2$EVSKLRSQLVKRK (SEQ ID NO: 22), wherein X$_1$ is L-2-aminoadipic acid and X$_2$ is ornithine, and wherein X$_1$ is covalently bonded to X$_2$.

The amino acid sequence of the peptide can consist of KIKHVVKLKX$_1$ENSQLKX$_2$EVSKLRSQLVKRK (SEQ ID NO: 22), wherein X$_1$ is L-2-aminoadipic acid and X$_2$ is ornithine, and wherein X$_1$ is covalently bonded to X$_2$.

The amino acid sequence of the peptide can comprise KIKHVVKLKDX$_1$NSQLKSX$_2$VSKLRSQLVKRK (SEQ ID NO: 23), wherein X$_1$ is L-2-aminoadipic acid and X$_2$ is ornithine, and wherein X$_1$ is covalently bonded to X$_2$.

The amino acid sequence of the peptide can consist of KIKHVVKLKDX$_1$NSQLKSX$_2$VSKLRSQLVKRK (SEQ ID NO: 23), wherein X$_1$ is L-2-aminoadipic acid and X$_2$ is ornithine, and wherein X$_1$ is covalently bonded to X$_2$.

The amino acid sequence of the peptide can comprise KIKHVVKLKDEX$_1$SQLKSEX$_2$SKLRSQLVKRK (SEQ ID NO: 24), wherein X$_1$ is L-2-aminoadipic acid and X$_2$ is ornithine, and wherein X$_1$ is covalently bonded to X$_2$.

The amino acid sequence of the peptide can consist of KIKHVVKLKDEX$_1$SQLKSEX$_2$SKLRSQLVKRK (SEQ ID NO: 24), wherein X$_1$ is L-2-aminoadipic acid and X$_2$ is ornithine, and wherein X$_1$ is covalently bonded to X$_2$.

The amino acid sequence of the peptide can comprise KIKHVVKLKDENX$_1$QLKSEVX$_2$KLRSQLVKRK (SEQ ID NO: 25), wherein X$_1$ is L-2-aminoadipic acid and X$_2$ is ornithine, and wherein X$_1$ is covalently bonded to X$_2$.

The amino acid sequence of the peptide can consist of KIKHVVKLKDENX$_1$QLKSEVX$_2$KLRSQLVKRK (SEQ ID NO: 25), wherein X$_1$ is L-2-aminoadipic acid and X$_2$ is ornithine, and wherein X$_1$ is covalently bonded to X$_2$.

The amino acid sequence of the peptide can comprise KIKHVVKLKX$_1$ENSQLKX$_2$EVSKLRSQLVKRK (SEQ ID NO: 22), wherein X$_1$ is alanine derivative R8 and X$_2$ is alanine derivative S5, and wherein X$_1$ is covalently bonded to X$_2$.

The amino acid sequence of the peptide can consist of KIKHVVKLKX$_1$ENSQLKX$_2$EVSKLRSQLVKRK (SEQ ID NO: 22), wherein X$_1$ is alanine derivative R8 and X$_2$ is alanine derivative S5, and wherein X$_1$ is covalently bonded to X$_2$.

The amino acid sequence of the peptide can comprise KIKHVVKLKDX$_1$NSQLKSX$_2$VSKLRSQLVKRK (SEQ ID NO: 23), wherein X$_1$ is alanine derivative R8 and X$_2$ is alanine derivative S5, and wherein X$_1$ is covalently bonded to X$_2$.

The amino acid sequence of the peptide can consist of KIKHVVKLKDX$_1$NSQLKSX$_2$VSKLRSQLVKRK (SEQ ID NO: 23), wherein X$_1$ is alanine derivative R8 and X$_2$ is alanine derivative S5, and wherein X$_1$ is covalently bonded to X$_2$.

The amino acid sequence of the peptide can comprise KIKHVVKLKDEX$_1$SQLKSEX$_2$SKLRSQLVKRK (SEQ ID NO: 24), wherein X$_1$ is alanine derivative R8 and X$_2$ is alanine derivative S5, and wherein X$_1$ is covalently bonded to X$_2$.

The amino acid sequence of the peptide can consist of KIKHVVKLKDEX$_1$SQLKSEX$_2$SKLRSQLVKRK (SEQ ID NO: 24), wherein $X_1$ is alanine derivative R8 and $X_2$ is alanine derivative S5, and wherein $X_1$ is covalently bonded to $X_2$.

The amino acid sequence of the peptide can comprise KIKHVVKLKDENX$_1$QLKSEVX$_2$KLRSQLVKRK (SEQ ID NO: 25), wherein $X_1$ is alanine derivative R8 and $X_2$ is alanine derivative S5, and wherein $X_1$ is covalently bonded to $X_2$.

The amino acid sequence of the peptide can consist of KIKHVVKLKDENX$_1$QLKSEVX$_2$KLRSQLVKRK (SEQ ID NO: 25), wherein $X_1$ is alanine derivative R8 and $X_2$ is alanine derivative S5, and wherein $X_1$ is covalently bonded to $X_2$.

The amino acid sequence of the peptide can comprise KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can consist of KIKHVVKLKDX$_1$NSQX$_2$X$_3$SEVX$_4$KLRSQLVKRK (SEQ ID NO: 27), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can comprise KIKHVVKLKX$_1$ENSX$_2$X$_3$KSEX$_4$SKLRSQLVKRK (SEQ ID NO: 26), wherein $X_1$ is lysine, $X_2$ is glutamic acid, $X_3$ is lysine, $X_4$ is glutamic acid, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$ is lysine, $X_2$ is glutamic acid, $X_3$ is lysine, $X_4$ is glutamic acid, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$ is lysine, $X_2$ is glutamic acid, $X_3$ is lysine, $X_4$ is glutamic acid, and wherein $X_1$ is covalently bonded to $X_2$ and $X_3$ is covalently bonded to $X_4$.

The amino acid sequence of the peptide can consist of IKHVVKLKDX$_1$NSQX$_2$X$_3$SEVX$_4$KLRSQLVKRK (SEQ ID NO: 27), wherein $X_1$ is lysine, $X_2$ is glutamic acid, $X_3$ is lysine, $X_4$ is glutamic acid, and wherein $X_1$ is covalently bonded to $X_2$ and $X_3$ is covalently bonded to $X_4$.

The amino acid sequence of the peptide can comprise KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is lysine, $X_4$ is glutamic acid, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is lysine, $X_4$ is glutamic acid, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$ is glutamic acid, $X_2$ is lysine, $X_3$ is lysine, $X_4$ is glutamic acid, and wherein $X_1$ is covalently bonded to $X_2$ and $X_3$ is covalently bonded to $X_4$.

The amino acid sequence of the peptide can consist of KIKHVVKLKDX$_1$NSQX$_2$X$_3$SEVX$_4$KLRSQLVKRK (SEQ ID NO: 27), wherein $X_1$ is glutamic acid, $X_2$ is lysine, $X_3$ is lysine, $X_4$ is glutamic acid, and wherein $X_1$ is covalently bonded to $X_2$ and $X_3$ is covalently bonded to $X_4$.

The amino acid sequence of the peptide can comprise KIKHVVKLKX$_1$ENSX$_2$X$_3$KSEX$_4$SKLRSQLVKRK (SEQ ID NO: 26), wherein $X_1$ is lysine, $X_2$ is glutamic acid, $X_3$ is glutamic acid, $X_4$ is lysine, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$ is lysine, $X_2$ is glutamic acid, $X_3$ is glutamic acid, $X_4$ is lysine, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$ is lysine, $X_2$ is glutamic acid, $X_3$ is glutamic acid, $X_4$ is lysine, and wherein $X_1$ is covalently bonded to $X_2$ and $X_3$ is covalently bonded to $X_4$.

The amino acid sequence of the peptide can consist of KIKHVVKLKDX$_1$NSQX$_2$X$_3$SEVX$_4$KLRSQLVKRK (SEQ ID NO: 27), wherein $X_1$ is lysine, $X_2$ is glutamic acid, $X_3$ is glutamic acid, $X_4$ is lysine, and wherein $X_1$ is covalently bonded to $X_2$ and $X_3$ is covalently bonded to $X_4$.

The amino acid sequence of the peptide can comprise KIKHVVKLKX$_1$ENSX$_2$X$_3$KSEX$_4$SKLRSQLVKRK (SEQ ID NO: 26), wherein $X_1$ is ornithine, $X_2$ is L-2-aminoadipic acid, $X_3$ is ornithine, $X_4$ is L-2-aminoadipic acid, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$ is ornithine, $X_2$ is L-2-aminoadipic acid, $X_3$ is ornithine, $X_4$ is L-2-aminoadipic acid, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$ is ornithine, $X_2$ is L-2-aminoadipic acid, $X_3$ is ornithine, $X_4$ is L-2-aminoadipic acid, and wherein $X_1$ is covalently bonded to $X_2$ and $X_3$ is covalently bonded to $X_4$.

The amino acid sequence of the peptide can consist of KIKHVVKLKDX$_1$NSQX$_2$X$_3$SEVX$_4$KLRSQLVKRK (SEQ ID NO: 27), wherein $X_1$ is ornithine, $X_2$ is L-2-aminoadipic acid, $X_3$ is ornithine, $X_4$ is L-2-aminoadipic acid, and wherein $X_1$ is covalently bonded to $X_2$ and $X_3$ is covalently bonded to $X_4$.

The amino acid sequence of the peptide can comprise KIKHVVKLKX$_1$ENSX$_2$X$_3$KSEX$_4$SKLRSQLVKRK (SEQ ID NO: 26), wherein $X_1$ is L-2-aminoadipic acid, $X_2$ is ornithine, $X_3$ is L-2-aminoadipic acid, $X_4$ is ornithine, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$ is L-2-aminoadipic acid, $X_2$ is ornithine, $X_3$ is L-2-aminoadipic acid, $X_4$ is ornithine, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$ is L-2-aminoadipic acid, $X_2$ is ornithine, $X_3$ is L-2-aminoadipic acid, $X_4$ is ornithine, and wherein $X_1$ is covalently bonded to $X_2$ and $X_3$ is covalently bonded to $X_4$.

The amino acid sequence of the peptide can consist of KIKHVVKLKDX$_1$NSQX$_2$X$_3$SEVX$_4$KLRSQLVKRK (SEQ ID NO: 27), wherein $X_1$ is L-2-aminoadipic acid, $X_2$ is ornithine, $X_3$ is L-2-aminoadipic acid, $X_4$ is ornithine, and wherein $X_1$ is covalently bonded to $X_2$ and $X_3$ is covalently bonded to $X_4$.

The amino acid sequence of the peptide can comprise KIKHVVKLKX$_1$ENSX$_2$X$_3$KSEX$_4$SKLRSQLVKRK (SEQ ID NO: 26), wherein $X_1$ is ornithine, $X_2$ is L-2-aminoadipic acid, $X_3$ is L-2-aminoadipic acid, $X_4$ is ornithine, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$ is ornithine, $X_2$ is L-2-aminoadipic acid, $X_3$ is L-2-aminoadipic acid, $X_4$ is ornithine, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$ is ornithine, $X_2$ is L-2-aminoadipic acid, $X_3$ is L-2-aminoadipic acid, $X_4$ is ornithine, and wherein $X_1$ is covalently bonded to $X_2$ and $X_3$ is covalently bonded to $X_4$.

The amino acid sequence of the peptide can consist of KIKHVVKLKDX$_1$NSQX$_2$X$_3$SEVX$_4$KLRSQLVKRK (SEQ ID NO: 27), wherein $X_1$ is ornithine, $X_2$ is L-2-aminoadipic acid, $X_3$ is L-2-aminoadipic acid, $X_4$ is ornithine, and wherein $X_1$ is covalently bonded to $X_2$ and $X_3$ is covalently bonded to $X_4$.

The amino acid sequence of the peptide can comprise KIKHVVKLKX$_1$ENSX$_2$X$_3$KSEX$_4$SKLRSQLVKRK (SEQ ID NO: 26), wherein $X_1$ is L-2-aminoadipic acid, $X_2$ is ornithine, $X_3$ is ornithine, $X_4$ is L-2-aminoadipic acid, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$ is L-2-aminoadipic acid, $X_2$ is ornithine, $X_3$ is ornithine, $X_4$ is L-2-aminoadipic acid, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$ is L-2-aminoadipic acid, $X_2$ is ornithine, $X_3$ is ornithine, $X_4$ is L-2-aminoadipic acid, and wherein $X_1$ is covalently bonded to $X_2$ and $X_3$ is covalently bonded to $X_4$.

The amino acid sequence of the peptide can consist of KIKHVVKLKDX$_1$NSQX$_2$X$_3$SEVX$_4$KLRSQLVKRK (SEQ ID NO: 27), wherein $X_1$ is L-2-aminoadipic acid, $X_2$ is ornithine, $X_3$ is ornithine, $X_4$ is L-2-aminoadipic acid, and wherein $X_1$ is covalently bonded to $X_2$ and $X_3$ is covalently bonded to $X_4$.

The amino acid sequence of the peptide can comprise KIKHVVKLKX$_1$ENSX$_2$X$_3$KSEX$_4$SKLRSQLVKRK (SEQ ID NO: 26), wherein $X_1$, $X_2$, $X_3$, and $X_4$ are each allylglycine, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$, $X_2$, $X_3$, and $X_4$ are each allylglycine, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$, $X_2$, $X_3$, and $X_4$ are each allylglycine, and wherein $X_1$ is covalently bonded to $X_2$ and $X_3$ is covalently bonded to $X_4$.

The amino acid sequence of the peptide can consist of KIKHVVKLKDX$_1$NSQX$_2$X$_3$SEVX$_4$KLRSQLVKRK (SEQ ID NO: 27), wherein $X_1$, $X_2$, $X_3$, and $X_4$ are each allylglycine, and wherein $X_1$ is covalently bonded to $X_2$ and $X_3$ is covalently bonded to $X_4$.

The amino acid sequence of the peptide can comprise KIKHVVKLKX$_1$ENSX$_2$X$_3$KSEX$_4$SKLRSQLVKRK (SEQ ID NO: 26), wherein $X_1$, $X_2$, $X_3$, and $X_4$ are each alanine derivative S5, and wherein $X_1$ is covalently bonded to $X_2$ and $X_3$ is covalently bonded to $X_4$.

The amino acid sequence of the peptide can consist of KIKHVVKLKX$_1$ENSX$_2$X$_3$KSEX$_4$SKLRSQLVKRK (SEQ ID NO: 26), wherein $X_1$, $X_2$, $X_3$, and $X_4$ are each alanine derivative S5, and wherein $X_1$ is covalently bonded to $X_2$ and $X_3$ is covalently bonded to $X_4$.

The amino acid sequence of the peptide can comprise KIKHVVKLKDX$_1$NSQX$_2$X$_3$SEVX$_4$KLRSQLVKRK (SEQ ID NO: 27), wherein $X_1$, $X_2$, $X_3$, and $X_4$ are each alanine derivative S5, and wherein $X_1$ is covalently bonded to $X_2$ and $X_3$ is covalently bonded to $X_4$.

The amino acid sequence of the peptide can consist of KIKHVVKLKDX$_1$NSQX$_2$X$_3$SEVX$_4$KLRSQLVKRK (SEQ ID NO: 27), wherein $X_1$, $X_2$, $X_3$, and $X_4$ are each alanine derivative S5, and wherein $X_1$ is covalently bonded to $X_2$ and $X_3$ is covalently bonded to $X_4$.

The amino acid sequence of the peptide can comprise NLKQKIKHVVKLKDENSQLKSEVSKLRX$_1$QLVX$_2$RKQN (SEQ ID NO: 28), wherein $X_1$ is glutamic acid and $X_2$ is lysine, and wherein $X_1$ is covalently bonded to $X_2$.

The amino acid sequence of the peptide can consist of NLKQKIKHVVKLKDENSQLKSEVSKLRX$_1$QLVX$_2$RKQN (SEQ ID NO: 28), wherein $X_1$ is glutamic acid and $X_2$ is lysine, and wherein $X_1$ is covalently bonded to $X_2$.

The amino acid sequence of the peptide can comprise NLKQKIX$_1$HVVX$_2$LKDENSQLKSEVSKLRX$_3$QLVX$_4$RKQN (SEQ ID NO: 29), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can consist of NLKQKIX$_1$HVVX$_2$LKDENSQLKSEVSKLRX$_3$QLVX$_4$RKQN (SEQ ID NO: 29), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can comprise NLKQKIKHVVKLKDENSQLKSEVSKLX$_1$SQLX$_2$KRKQN (SEQ ID NO: 30), wherein $X_1$ is glutamic acid and $X_2$ is lysine, and wherein $X_1$ is covalently bonded to $X_2$.

The amino acid sequence of the peptide can consist of NLKQKIKHVVKLKDENSQLKSEVSKLX$_1$SQLX$_2$KRKQN (SEQ ID NO: 30), wherein $X_1$ is glutamic acid and $X_2$ is lysine, and wherein $X_1$ is covalently bonded to $X_2$.

The amino acid sequence of the peptide can comprise NLKQKIX$_1$HVVX$_2$LKDENSQLKSEVSKLRSQLVKRKQN (SEQ ID NO: 31), wherein $X_1$ is glutamic acid and $X_2$ is lysine, and wherein $X_1$ is covalently bonded to $X_2$.

The amino acid sequence of the peptide can consist of NLKQKIX$_1$HVVX$_2$LKDENSQLKSEVSKLRSQLVKRKQN (SEQ ID NO: 31), wherein $X_1$ is glutamic acid and $X_2$ is lysine, and wherein $X_1$ is covalently bonded to $X_2$.

The amino acid sequence of the peptide can comprise LKQKIX$_1$HVVX$_2$LKDENSQLKSEVSKLX$_3$SQLX$_4$KRKQN (SEQ ID NO: 32), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can consist of LKQKIX$_1$HVVX$_2$LKDENSQLKSEVSKLX$_3$SQLX$_4$KRKQN (SEQ ID NO: 32), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

For example, the amino acid sequence of the peptide can comprise or consist of:

VSKX$_1$RSQX$_2$VKRKQN (SEQ ID NO: 7), wherein $X_1$ is glutamic acid and $X_2$ is lysine, and wherein $X_1$ is covalently bonded to $X_2$;

VSKLX$_1$SQLX$_2$KRKQN (SEQ ID NO: 8), wherein $X_1$ is glutamic acid and $X_2$ is lysine, and wherein $X_1$ is covalently bonded to $X_2$;

VSKLRX$_1$QLVX$_2$RKQN (SEQ ID NO: 9), wherein $X_1$ is glutamic acid and $X_2$ is lysine, and wherein $X_1$ is covalently bonded to $X_2$;

VSKLRSX$_1$LVKX$_2$KQN (SEQ ID NO: 10), wherein $X_1$ is glutamic acid and $X_2$ is lysine, and wherein $X_1$ is covalently bonded to $X_2$;

VSKLX$_1$SQLX$_2$KRKQN (SEQ ID NO: 8), wherein $X_1$ is lysine and $X_2$ is glutamic acid, and wherein $X_1$ is covalently bonded to $X_2$;

VSKLRX$_1$QLVX$_2$RKQN (SEQ ID NO: 9), wherein $X_1$ is lysine and $X_2$ is glutamic acid, and wherein $X_1$ is covalently bonded to $X_2$;

NLKX$_1$KIKX$_2$VVKLKDE (SEQ ID NO: 15), wherein $X_1$ is glutamic acid and $X_2$ is lysine, and wherein $X_1$ is covalently bonded to $X_2$;

NLKQX$_1$IKHX$_2$VKLKDE (SEQ ID NO: 16), wherein $X_1$ is glutamic acid and $X_2$ is lysine, and wherein $X_1$ is covalently bonded to $X_2$;

NLKQKX$_1$KHVX$_2$KLKDE (SEQ ID NO: 17), wherein $X_1$ is glutamic acid and $X_2$ is lysine, and wherein $X_1$ is covalently bonded to $X_2$;

NLKQKIX$_1$HVVX$_2$LKDE (SEQ ID NO: 18), wherein $X_1$ is glutamic acid and $X_2$ is lysine, and wherein $X_1$ is covalently bonded to $X_2$;

NLKQKIKX$_1$VVKX$_2$KDE (SEQ ID NO: 19), wherein $X_1$ is glutamic acid and $X_2$ is lysine, and wherein $X_1$ is covalently bonded to $X_2$;

KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$;

KIKHVVKLKDX$_1$NSQX$_2$X$_3$SEVX$_4$KLRSQLVKRK (SEQ ID NO: 27), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$;

KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is lysine, $X_4$ is glutamic acid, and wherein $X_1$ is covalently bonded to $X_2$ and $X_3$ is covalently bonded to $X_4$;

KIKHVVKLKX$_1$ENSX$_2$X$_3$KSEX$_4$SKLRSQLVKRK (SEQ ID NO: 26), wherein $X_1$ is lysine, $X_2$ is glutamic acid, $X_3$ is glutamic acid, $X_4$ is lysine, and wherein $X_1$ is covalently bonded to $X_2$ and $X_3$ is covalently bonded to $X_4$;

NLKQKIKHVVKLKDENSQLKSEVSKLRX$_1$QLVX$_2$RKQN (SEQ ID NO: 28), wherein $X_1$ is glutamic acid and $X_2$ is lysine, and wherein $X_1$ is covalently bonded to $X_2$; or NLKQKIX$_1$HVVX$_2$LKDENSQLKSEVSKLRX$_3$QLVX$_4$RKQN (SEQ ID NO: 29), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can comprise or consist of:

VSKX$_1$RSQX$_2$VKRKQN (SEQ ID NO: 7), wherein $X_1$ is glutamic acid and $X_2$ is lysine, and wherein $X_1$ is covalently bonded to $X_2$;

VSKLX$_1$SQLX$_2$KRKQN (SEQ ID NO: 8), wherein $X_1$ is glutamic acid and $X_2$ is lysine, and wherein $X_1$ is covalently bonded to $X_2$;

VSKLRX$_1$QLVX$_2$RKQN (SEQ ID NO: 9), wherein $X_1$ is glutamic acid and $X_2$ is lysine, and wherein $X_1$ is covalently bonded to $X_2$;

VSKLRSX$_1$LVKX$_2$KQN (SEQ ID NO: 10), wherein $X_1$ is glutamic acid and $X_2$ is lysine, and wherein $X_1$ is covalently bonded to $X_2$;

NLKQX$_1$IKHX$_2$VKLKDE (SEQ ID NO: 16), wherein $X_1$ is glutamic acid and $X_2$ is lysine, and wherein $X_1$ is covalently bonded to $X_2$;

NLKQKX$_1$KHVX$_2$KLKDE (SEQ ID NO: 17), wherein $X_1$ is glutamic acid and $X_2$ is lysine, and wherein $X_1$ is covalently bonded to $X_2$;

NLKQKIX$_1$HVVX$_2$LKDE (SEQ ID NO: 18), wherein $X_1$ is glutamic acid and $X_2$ is lysine, and wherein $X_1$ is covalently bonded to $X_2$;

KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$;

NLKQKIKHVVKLKDENSQLKSEVSKLRX$_1$QLVX$_2$RKQN (SEQ ID NO: 28), wherein $X_1$ is glutamic acid and $X_2$ is lysine, and wherein $X_1$ is covalently bonded to $X_2$; or NLKQKIX$_1$HVVX$_2$LKDENSQLKSEVSKLRX$_3$QLVX$_4$RKQN (SEQ ID NO: 29), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can comprise or consist of:

VSKLRSX$_1$LVKX$_2$KQN (SEQ ID NO: 10), wherein $X_1$ is glutamic acid and $X_2$ is lysine, and wherein $X_1$ is covalently bonded to $X_2$;

VSKLX$_1$SQLX$_2$KRKQN (SEQ ID NO: 8), wherein $X_1$ is lysine and $X_2$ is glutamic acid, and wherein $X_1$ is covalently bonded to $X_2$;

NLKX$_1$KIKX$_2$VVKLKDE (SEQ ID NO: 15), wherein $X_1$ is glutamic acid and $X_2$ is lysine, and wherein $X_1$ is covalently bonded to $X_2$;

KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$;

KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is lysine, $X_4$ is glutamic acid, and wherein $X_1$ is covalently bonded to $X_2$ and $X_3$ is covalently bonded to $X_4$;

KIKHVVKLKX$_1$ENSX$_2$X$_3$KSEX$_4$SKLRSQLVKRK (SEQ ID NO: 26), wherein $X_1$ is lysine, $X_2$ is glutamic acid, $X_3$ is glutamic acid, $X_4$ is lysine, and wherein $X_1$ is covalently bonded to $X_2$ and $X_3$ is covalently bonded to $X_4$;

NLKQKIKHVVKLKDENSQLKSEVSKLRX$_1$QLVX$_2$RKQN (SEQ ID NO: 28), wherein $X_1$ is glutamic acid and $X_2$ is lysine, and wherein $X_1$ is covalently bonded to $X_2$; or NLKQKIX$_1$HVVX$_2$LKDENSQLKSEVSKLRX$_3$QLVX$_4$RKQN (SEQ ID NO: 29), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can comprise or consist of:

VSKX$_1$RSQX$_2$VKRKQN (SEQ ID NO: 7), wherein $X_1$ is glutamic acid and $X_2$ is lysine, and wherein $X_1$ is covalently bonded to $X_2$;

VSKLRX$_1$QLVX$_2$RKQN (SEQ ID NO: 9), wherein $X_1$ is glutamic acid and $X_2$ is lysine, and wherein $X_1$ is covalently bonded to $X_2$; or NLKQKIKX$_1$VVKX$_2$KDE (SEQ ID NO: 19), wherein $X_1$ is glutamic acid and $X_2$ is lysine, and wherein $X_1$ is covalently bonded to $X_2$.

The amino acid sequence of the peptide can comprise or consist of:

VSKX$_1$RSQX$_2$VKRKQN (SEQ ID NO: 7), wherein $X_1$ is glutamic acid and $X_2$ is lysine, and wherein $X_1$ is covalently bonded to $X_2$;

VSKLX$_1$SQLX$_2$KRKQN (SEQ ID NO: 8), wherein $X_1$ is glutamic acid and $X_2$ is lysine, and wherein $X_1$ is covalently bonded to $X_2$;

VSKLRX$_1$QLVX$_2$RKQN (SEQ ID NO: 9), wherein $X_1$ is glutamic acid and $X_2$ is lysine, and wherein $X_1$ is covalently bonded to $X_2$;

VSKLRSX$_1$LVKX$_2$KQN (SEQ ID NO: 10), wherein $X_1$ is glutamic acid and $X_2$ is lysine, and wherein $X_1$ is covalently bonded to $X_2$;

NLKX$_1$KIKX$_2$VVKLKDE (SEQ ID NO: 15), wherein $X_1$ is glutamic acid and $X_2$ is lysine, and wherein $X_1$ is covalently bonded to $X_2$;

NLKQX$_1$IKHX$_2$VKLKDE (SEQ ID NO: 16), wherein $X_1$ is glutamic acid and $X_2$ is lysine, and wherein $X_1$ is covalently bonded to $X_2$;

NLKQKX$_1$KHVX$_2$KLKDE (SEQ ID NO: 17), wherein $X_1$ is glutamic acid and $X_2$ is lysine, and wherein $X_1$ is covalently bonded to $X_2$;

NLKQKIKX$_1$VVKX$_2$KDE (SEQ ID NO: 19), wherein $X_1$ is glutamic acid and $X_2$ is lysine, and wherein $X_1$ is covalently bonded to $X_2$;

KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$;

KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is lysine, $X_4$ is glutamic acid, and wherein $X_1$ is covalently bonded to $X_2$ and $X_3$ is covalently bonded to $X_4$;

KIKHVVKLKX$_1$ENSX$_2$X$_3$KSEX$_4$SKLRSQLVKRK (SEQ ID NO: 26), wherein $X_1$ is lysine, $X_2$ is glutamic acid, $X_3$ is glutamic acid, $X_4$ is lysine, and wherein $X_1$ is covalently bonded to $X_2$ and $X_3$ is covalently bonded to $X_4$;

NLKQKIKHVVKLKDENSQLKSEVSKLRX$_1$QLVX$_2$RKQN (SEQ ID NO: 28), wherein $X_1$ is glutamic acid and $X_2$ is lysine, and wherein $X_1$ is covalently bonded to $X_2$; or NLKQKIX$_1$HVVX$_2$LKDENSQLKSEVSKLRX$_3$QLVX$_4$RKQN (SEQ ID NO: 29), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can comprise or consist of:

VSKLX$_1$SQLX$_2$KRKQN (SEQ ID NO: 8), wherein $X_1$ is glutamic acid and $X_2$ is lysine, and wherein $X_1$ is covalently bonded to $X_2$;

VSKLRX$_1$QLVX$_2$RKQN (SEQ ID NO: 9), wherein $X_1$ is glutamic acid and $X_2$ is lysine, and wherein $X_1$ is covalently bonded to $X_2$;

NLKQX$_1$IKHX$_2$VKLKDE (SEQ ID NO: 16), wherein $X_1$ is glutamic acid and $X_2$ is lysine, and wherein $X_1$ is covalently bonded to $X_2$;

NLKQKIKX$_1$VVKX$_2$KDE (SEQ ID NO: 19), wherein $X_1$ is glutamic acid and $X_2$ is lysine, and wherein $X_1$ is covalently bonded to $X_2$;

KIKHVVKLKX$_1$ENSX$_2$X$_3$KSEX$_4$SKLRSQLVKRK (SEQ ID NO: 26), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$;

KIKHVVKLKX$_1$ENSX$_2$X$_3$KSEX$_4$SKLRSQLVKRK (SEQ ID NO: 26), wherein $X_1$ is lysine, $X_2$ is glutamic acid, $X_3$ is glutamic acid, $X_4$ is lysine, and wherein $X_1$ is covalently bonded to $X_2$ and $X_3$ is covalently bonded to $X_4$;

NLKQKIKHVVKLKDENSQLKSEVSKLRX$_1$QLVX$_2$RKQN (SEQ ID NO: 28), wherein $X_1$ is glutamic acid and $X_2$ is lysine, and wherein $X_1$ is covalently bonded to $X_2$; or NLKQKIX$_1$HVVX$_2$LKDENSQLKSEVSKLRX$_3$QLVX$_4$RKQN (SEQ ID NO: 29), wherein $X_1$ is glutamic acid, $X_2$ is lysine, $X_3$ is glutamic acid, $X_4$ is lysine, and wherein $X_1$ is covalently bonded to $X_2$ and $X_3$ is covalently bonded to $X_4$.

The amino acid sequence of the peptide can comprise or consist of:

VSKLRX$_1$QLVX$_2$RKQN (SEQ ID NO: 9), wherein $X_1$ is glutamic acid and $X_2$ is lysine, and wherein $X_1$ is covalently bonded to $X_2$;

NLKQKIKX$_1$VVKX$_2$KDE (SEQ ID NO: 19), wherein $X_1$ is glutamic acid and $X_2$ is lysine, and wherein $X_1$ is covalently bonded to $X_2$; or NLKQKIKHVVKLKDENSQLKSEVSKLRX$_1$QLVX$_2$RKQN (SEQ ID NO: 28), wherein X$_1$ is glutamic acid and X$_2$ is lysine, and wherein X$_1$ is covalently bonded to X$_2$.

The amino acid sequence of the peptide can comprise or consist of:

VSKX$_1$RSQX$_2$VKRKQN (SEQ ID NO: 7), wherein X$_1$ is glutamic acid and X$_2$ is lysine, and wherein X$_1$ is covalently bonded to X$_2$;

VSKLRX$_1$QLVX$_2$RKQN (SEQ ID NO: 9), wherein X$_1$ is glutamic acid and X$_2$ is lysine, and wherein X$_1$ is covalently bonded to X$_2$;

NLKX$_1$KIKX$_2$VVKLKDE (SEQ ID NO: 15), wherein X$_1$ is glutamic acid and X$_2$ is lysine, and wherein X$_1$ is covalently bonded to X$_2$;

NLKQX$_1$IKHX$_2$VKLKDE (SEQ ID NO: 16), wherein X$_1$ is glutamic acid and X$_2$ is lysine, and wherein X$_1$ is covalently bonded to X$_2$;

NLKQKX$_1$KHVX$_2$KLKDE (SEQ ID NO: 17), wherein X$_1$ is glutamic acid and X$_2$ is lysine, and wherein X$_1$ is covalently bonded to X$_2$;

NLKQKIKX$_1$VVKX$_2$KDE (SEQ ID NO: 19), wherein X$_1$ is glutamic acid and X$_2$ is lysine, and wherein X$_1$ is covalently bonded to X$_2$;

KIKHVVKLKX$_1$ENSX$_2$X$_3$KSEX$_4$SKLRSQLVKRK (SEQ ID NO: 26), wherein X$_1$ is glutamic acid, X$_2$ is lysine, X$_3$ is glutamic acid, X$_4$ is lysine, and wherein X$_1$ is covalently bonded to X$_2$ and X$_3$ is covalently bonded to X$_4$; or NLKQKIKHVVKLKDENSQLKSEVSKLRX$_1$QLVX$_2$RKQN (SEQ ID NO: 28), wherein X$_1$ is glutamic acid and X$_2$ is lysine, and wherein X$_1$ is covalently bonded to X$_2$.

The amino acid sequence of the peptide can comprise or consist of:

VSKX$_1$RSQX$_2$VKRKQN (SEQ ID NO: 7), wherein X$_1$ is glutamic acid and X$_2$ is lysine, and wherein X$_1$ is covalently bonded to X$_2$;

VSKLRX$_1$QLVX$_2$RKQN (SEQ ID NO: 9), wherein X$_1$ is glutamic acid and X$_2$ is lysine, and wherein X$_1$ is covalently bonded to X$_2$;

VSKLRSX$_1$LVKX$_2$KQN (SEQ ID NO: 10), wherein X$_1$ is glutamic acid and X$_2$ is lysine, and wherein X$_1$ is covalently bonded to X$_2$;

KIKHVVKLKX$_1$ENSX$_2$X$_3$KSEX$_4$SKLRSQLVKRK (SEQ ID NO: 26), wherein X$_1$ is glutamic acid, X$_2$ is lysine, X$_3$ is glutamic acid, X$_4$ is lysine, and wherein X$_1$ is covalently bonded to X$_2$ and X$_3$ is covalently bonded to X$_4$; or KIKHVVKLKX$_1$ENSX$_2$X$_3$KSEX$_4$SKLRSQLVKRK (SEQ ID NO: 26), wherein X$_1$ is glutamic acid, X$_2$ is lysine, X$_3$ is lysine, X$_4$ is glutamic acid, and wherein X$_1$ is covalently bonded to X$_2$ and X$_3$ is covalently bonded to X$_4$.

The amino acid sequence of the peptide can comprise or consist of:

VSKX$_1$RSQX$_2$VKRKQN (SEQ ID NO: 7), wherein X$_1$ is glutamic acid and X$_2$ is lysine, and wherein X$_1$ is covalently bonded to X$_2$;

VSKLRX$_1$QLVX$_2$RKQN (SEQ ID NO: 9), wherein X$_1$ is glutamic acid and X$_2$ is lysine, and wherein X$_1$ is covalently bonded to X$_2$;

NLKX$_1$KIKX$_2$VVKLKDE (SEQ ID NO: 15), wherein X$_1$ is glutamic acid and X$_2$ is lysine, and wherein X$_1$ is covalently bonded to X$_2$;

NLKQX$_1$IKHX$_2$VKLKDE (SEQ ID NO: 16), wherein X$_1$ is glutamic acid and X$_2$ is lysine, and wherein X$_1$ is covalently bonded to X$_2$;

KIKHVVKLKX$_1$ENSX$_2$X$_3$KSEX$_4$SKLRSQLVKRK (SEQ ID NO: 26), wherein X$_1$ is glutamic acid, X$_2$ is lysine, X$_3$ is glutamic acid, X$_4$ is lysine, and wherein X$_1$ is covalently bonded to X$_2$ and X$_3$ is covalently bonded to X$_4$.

For example, the amino acid sequence of the peptide can comprise VSKLRX$_1$QLVX$_2$RKQN (SEQ ID NO: 9), wherein X$_1$ is glutamic acid and X$_2$ is lysine, and wherein X$_1$ is covalently bonded to X$_2$.

The amino acid sequence of the peptide can consist of VSKLRX$_1$QLVX$_2$RKQN (SEQ ID NO: 9), wherein X$_1$ is glutamic acid and X$_2$ is lysine, and wherein X$_1$ is covalently bonded to X$_2$.

The peptides of the invention can include dimers and trimers of the peptides. A multimer according to the invention can either be a homomer, consisting of a multitude of the same peptide, or a heteromer consisting of different peptides.

Alternatively or in addition, the peptides can contain additional stabilizing flanking sequences. Stabilizing flanking sequences can increase the biological availability of the peptides.

Furthermore, the peptides can also encompass functionally equivalent variants or analogues of the peptides of the present invention. This includes peptides having peptides having one or more conservative or non-conservative amino acid substitutions as compared to the sequences of the peptides described herein. The substitution is preferably a conservative substitution, and does not negatively impact the biological or structural properties of the peptide (e.g., ability to bind to HA).

Functional analogues may be generated by conservative or non-conservative amino acid substitutions. Amino acid substitutions may be generally based on the relative similarity of the amino acid side-chain substituents, for example, their hydrophobicity, hydrophilicity, charge, size and the like. Thus, within the scope of the invention, conservative amino acid changes means an amino acid change at a particular position which may be of the same type as originally present; i.e. a hydrophobic amino acid exchanged for a hydrophobic amino acid, a basic amino acid for a basic amino acid, etc. Examples of conservative substitutions may include, without limitation, the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes may result in functional analogues in that they may not significantly alter the overall charge and/or configuration of the peptide. Examples of such conservative changes are well-known to the skilled artisan and are within the scope of the present invention. Conservative substitution may also include the use of a chemically derivatized residue in place of a non-derivatized residue provided that the resulting peptide is a biologically functional equivalent to the peptides of the invention.

Linear Peptides

The invention also relates to linear (non-cyclized) peptides.

A peptide is provided. The peptide has a length of 20 amino acids or fewer. The peptide comprises an amino acid sequence having at least 75% identity to the amino acid sequence NLKQKIKHVVKLKDE (SEQ ID NO: 4).

The amino acid sequence of the peptide can comprise one or more conservative amino acid substitutions relative to SEQ ID NO: 4.

For example, the amino acid sequence of the peptide can comprises a single conservative amino acid substitution relative to SEQ ID NO: 4.

The peptide can comprise an amino acid sequence having at least 80% identity to SEQ ID NO: 4.

The peptide can comprise an amino acid sequence having at least 85% identity to SEQ ID NO: 4.

The peptide can comprise an amino acid sequence having at least 90% identity to SEQ ID NO: 4.

The peptide can comprise an amino acid sequence having 100% identity to SEQ ID NO: 4.

The peptide can have a length of 19 amino acids or fewer.
The peptide can have a length of 18 amino acids or fewer.
The peptide can have a length of 17 amino acids or fewer.
The peptide can have a length of 16 amino acids or fewer.
The amino acid sequence of the peptide can consist of SEQ ID NO: 4.

Another peptide is provided. The peptide has a length of 20 amino acids or fewer. The peptide comprises an amino acid sequence having at least 70% sequence identity to the amino acid sequence VSKLRSQLVKRKQN (SEQ ID NO: 2). The peptide is acetylated at its amino-terminus.

The peptide can comprise one or more conservative amino acid substitutions relative to SEQ ID NO: 2.

For example, the amino acid sequence of the peptide can comprise a single conservative amino acid substitution relative to SEQ ID NO: 2.

The peptide can comprise an amino acid sequence having at least 75% identity to SEQ ID NO: 2.

The peptide can comprise an amino acid sequence having at least 85% identity to SEQ ID NO: 2.

The peptide can comprise an amino acid sequence having at least 90% identity to SEQ ID NO: 2.

The peptide can comprise an amino acid sequence having 100% identity to SEQ ID NO: 2.

The peptide can have a length of 19 amino acids or fewer.
The peptide can have a length of 18 amino acids or fewer.
The peptide can have a length of 17 amino acids or fewer.
The peptide can have a length of 16 amino acids or fewer.
The peptide can have a length of 15 amino acids or fewer.
The amino acid sequence of the peptide can consist of SEQ ID NO: 2.

Additional Peptide Modifications

Any of the linear or stapled peptides described herein can also include various chemical modifications.

For example, any of the peptides can be amidated at its carboxy-terminus.

Alternatively or in addition, any of the peptides can be acetylated at its amino-terminus.

Amino-terminal acetylation and carboxy-terminal amidation reduce the overall charge of a peptide, which can increase stability because the terminal acetylation/amidation generates a closer mimic of the native protein. Therefore, these modifications can increase the biological activity of a peptide.

Other modifications can also be made to any of the peptides described herein. For example, the peptide can be phosphorylated, glycosylated, PEGylated, lipidated, functionalized with a cellulose or a modified cellulose, or a combination thereof.

The peptide can comprise one or more D amino acids.

Labeled Peptides

Any of the peptides described herein can further comprise a detectable label.

Use of a detectable label allows the peptides to be used for detecting HA in a sample (e.g., in a cell, tissue, or organ).

For example, the peptide can be conjugated to the detectable label.

The detectable label can biotin, a magnetic label, a paramagnetic label, a radioactive label, a fluorescent label, a radiodense label, an enzyme, a hapten, and a combination thereof.

The hapten can comprise digoxigenin.

The paramagnetic label can comprise a gadolinium label.

The label can comprise biotin. For example, the peptide can be labeled with biotin at its amino terminus.

Where the peptide is labeled with biotin, the peptide preferably further comprises a 2-[2-(2-aminoethoxy)ethoxy] acetic acid (AEEA) linker between the peptide and the biotin. The AEEA linker separates the peptide from the biotin, thereby allowing the peptide to interact with a target (e.g., HA) without steric hindrance from the much larger biotin molecule.

Where the label comprises a radioactive label, the radioactive label can comprise a tritium label, a carbon-11 label, a fluorine-18 label, a phosphorus-32 label, a scandium-44 label, a copper-64 label, a gallium-68 label, a yttrium-86 label, a zirconium-89 label, a technetium-99m label, an indium-111 label, an iodine-123 label, an iodine-124 label, an iodine-125 label, or an iodine-131 label.

Suitable magnetic labels include DYNANBEADS.

Suitable fluorescent labels include fluorescein, rhodamine, and Texas-red.

Suitable enzyme labels include alkaline phosphatase, horseradish peroxidase, and other enzymes commonly used in enzyme-linked immunosorbent (ELISA) assays.

The peptide can be conjugated to a cytotoxic molecule or radioactive molecule.

The peptides of the present invention may be covalently or non-covalently coupled to a solid carrier such as a microsphere of gold or polystyrene, a slide, chip or to a wall of a microtiter plate. The peptides may be labelled directly or indirectly with a label selected from but not limited to biotin, fluorescein and an enzyme such as horseradish peroxidase.

Illustrative Linear and Stapled Peptides

Table 1 below provides sequences and structures for a number of linear and stapled peptides containing HABD1, HABD2, or most or all of HABD1 and all of HABD2. Brackets denote the positions of the residues that form the staple. For example, in the peptide H-(cyclo-4,8)-VSK[ERSQK]VKRKQN-NH$_2$ (SEQ ID NO: 7, wherein X$_1$ is glutamic acid and X$_2$ is lysine), there is a lactam bridge staple between the glutamic acid residue at amino acid 4 of the peptide and the lysine residue at amino acid 8 of the peptide.

Those skilled in the art will recognize that the list provided in Table 1 below is not exhaustive and that other stapled peptides are also within the scope of the present invention.

TABLE 1

Illustrative linear and stapled peptides

| Region | Type of Staple | Sequence | SEQ ID NO. | X₁ | X₂ | X₃ | X₄ |
|---|---|---|---|---|---|---|---|
| HABD2 (i, 1 + 4) | | VS-KLRSQLVKRK-QN | 2 | — | — | — | — |
| | Lactm (Glu-Lys) | H-(cyclo-4,8)-VSK[ERSQK]-VKRKQN-NH₂ | 7 | Glu | Lys | — | — |
| | | H-(cyclo-5,9)-VSKL[ERSQLK]KRKQN-NH₂ | 8 | Glu | Lys | — | — |
| | | H-(cyclo-6,10)-VSKLR[EQLVK]RKQN-NH₂ | 9 | Glu | Lys | — | — |
| | | H-(cyclo-7,11)-VSKLRS[ELVKK]KQN-NH₂ | 10 | Glu | Lys | — | — |
| | | H-(cyclo-4,8)-VSK[KRSQE]VKRKQN-NH₂ | 7 | Lys | Glu | — | — |
| | | H-(cyclo-5,9)-VSKL[KSQLE]EKRQN-NH₂ | 8 | Lys | Glu | — | — |
| | | H-(cyclo-6,10)-VSKLR[KQLVE]RKQN-NH₂ | 9 | Lys | Glu | — | — |
| | | H-(cyclo-7,11)-VSKLRS[KLVKE]KQN-NH₂ | 10 | Lys | Alu | — | — |
| | Lactm (Orn-Aad) | H-(cyclo-4,8)-VSK[(Orn)RSQ(Aad)]VKRKQN-NH₂ | 7 | Orn | Aad | — | — |
| | | H-(cyclo-5,9)-VSKL[(Orn)SQL(Aad)]KRKQN-NH₂ | 8 | Orn | Aad | — | — |
| | | H-(cyclo-6,10)-VSKLR[(Orn)QLV(Aad)]RKQN-NH₂ | 9 | Orn | Aad | — | — |
| | | H-(cyclo-7,11)-VSKLRS[(Orn)LVK(Aad)]KQN-NH₂ | 10 | Orn | Aad | — | — |
| | | H-(cyclo-4,8)-VSK[(Aad)RSQ(Orn)]VKRKQN-NH₂ | 7 | Aad | Orn | — | — |
| | | H-(cyclo-5,9)-VSKL[(Aad)SQL(Orn)]KRKQN-NH₂ | 8 | Aad | Orn | — | — |
| | | H-(cyclo-6,10)-VSKLR[(Aad)QLV(Orn)]RKQN-NH₂ | 9 | Aad | Orn | — | — |
| | | H-(cyclo-7,11)-VSKLRS[(Aad)LVK(Orn)]KQN-NH₂ | 10 | Aad | Orn | — | — |
| | Hydocarbon | | | | | | |
| (i, 1 + 4) | Alanine derivatives | H-(cyclo-4,8)-VSK[S5RSQS5]VKRKQN-NH₂ | 7 | S5 | S5 | — | — |
| | | H-(cyclo-5,9)-VSKL[S5SQLS5]KRKQN-NH₂ | 8 | S5 | S5 | — | — |
| | | H-(cyclo-6,10)-VSKLR[S5QLVS5]RKQN-NH₂ | 9 | S5 | S5 | — | — |
| | | H-(cyclo-7,10)-VSKLRS[S5LVKS5]KQN-NH₂ | 10 | S5 | S5 | — | — |
| | Ally|glycine | H-(cyclo-4,8)-VSK[(Ally|Gly)RSQ(Ally|Gly)]VKRKQN-NH₂ | 7 | Ally|Gly | Ally|Gly | — | — |
| | | H-(cyclo-5,9)-VSKL[(Ally|Gly)SQL(Ally|Gly)]KRKQN-NH₂ | 8 | Ally|Gly | Ally|Gly | — | — |
| | | H-(cyclo-6,10)-VSKLR[(Ally|Gly)QLV(Ally|Gly)]RKQN-NH₂ | 9 | Ally|Gly | Ally|Gly | — | — |
| | | H-(cyclo-7,11)-VSKLRS[(Ally|Gly)LVK(Ally|Gly)]KQN-NH₂ | 10 | Ally|Gly | Ally|Gly | — | — |
| HABD1 (i, 1 + 4) | | NL-KQKIHVVKLK-DE | 4 | — | — | — | — |
| | Lactm (Glu-Lys) | H-(cyclo-4,8)-NKL[EKIKK]VVKLDE-NH₂ | 15 | Glu | Lys | — | — |
| | | H-(cyclo-5,9)-NKLQ[EIKHK]VKLKDE-NH₂ | 16 | Glu | Lys | — | — |
| | | H-(cyclo-6,10)-NLKQK[EHVK]KLKDE-NH₂ | 17 | Glu | Lys | — | — |
| | | H-(cyclo-7,11)-NLKQKI[EHVVK]LKDE-NH₂ | 18 | Glu | Lys | — | — |
| | | H-(cyclo-8,12)-NLKQKIK[EVVKK]KDE-NH₂ | 19 | Glu | Lys | — | — |
| | | H-(cyclo-4,8)-NLK[KKIKE]VVKLDE-NH₂ | 15 | Lys | Glu | — | — |
| | | H-(cyclo-5,9)-NLKQ[KIKHE]VKLKDE-NH₂ | 16 | Lys | Glu | — | — |
| | | H-(cyclo-6,10)-NLKQK[KHVE]KLKDE-NH₂ | 17 | Lys | Glu | — | — |
| | | H-(cyclo-7,11)-NLKQKI[KHVVE]LKDE-NH₂ | 18 | Lys | Glu | — | — |
| | | H-(cyclo-8,12)-NLKQKIK[KVVKE]KDE-NH₂ | 19 | Lys | Glu | — | — |
| | Lactm (Orn-Aad) | H-(cyclo-4,8)-NLK[(Orn)KIK(Aad)]VVKLDE-NH₂ | 15 | Orn | Aad | — | — |
| | | H-(cyclo-5,9)-NLKQ[(Orn)IKH(Aad)]VKLKDE-NH₂ | 16 | Orn | Aad | — | — |
| | | H-(cyclo-6,10)-NLKQK[(Orn)KHV(Aad)]KLKDE-NH₂ | 17 | Orn | Aad | — | — |
| | | H-(cyclo-7,11)-NLKQKI[(Orn)HVV(Aad)]LKDE-NH₂ | 18 | Orn | Aad | — | — |
| | | H-(cyclo-8,12)-NLKQKIK[(Orn)VVK(Aad)]KDE-NH₂ | 19 | Orn | Aad | — | — |
| | | H-(cyclo-4,8)-NLK[(Aad)KIK(Orn)]VVKLDE-NH₂ | 15 | Aad | Orn | — | — |

TABLE 1-continued

Illustrative linear and stapled peptides

| Region | Type of Staple | Sequence | SEQ ID NO. | $X_1$ | $X_2$ | $X_3$ | $X_4$ |
|---|---|---|---|---|---|---|---|
| | | H-(cyclo-5,9)-NLKQ[(Aad)IKH(Orn)]VKLKDE-NH$_2$ | 16 | Aad | Orn | — | — |
| | | H-(cyclo-6,10)-NLKQK[(Aad)KHV(Orn)]KLKDE-NH$_2$ | 17 | Aad | Orn | — | — |
| | | H-(cyclo-7,11)-NLKQKI[(Aad)HVV(Orn)]LKDE-NH$_2$ | 18 | Aad | Orn | — | — |
| | | H-(cyclo-8,12)-NLKQKIK[(Aad)VVK(Orn)]KDE-NH$_2$ | 19 | Aad | Orn | — | — |
| | Hydocarbon | | | | | | |
| (i, 1 + 4) | Alanine derivatives | H-(cyclo-4,8)-NLK[S5KIKS5]VVKLKDE-NH$_2$ | 15 | S5 | S5 | — | — |
| | | H-(cyclo-5,9)-NLKQ[S5IKHS5]VKLKDE-NH$_2$ | 16 | S5 | S5 | — | — |
| | | H-(cyclo-6,10)-NLKQK[S5KHVS5]KLKDE-NH$_2$ | 17 | S5 | S5 | — | — |
| | | H-(cyclo-7,11)-NLKQKI[S5HVVS5]LKDE-NH$_2$ | 18 | S5 | S5 | — | — |
| | | H-(cyclo-8,12)-NLKQKIK[S5VVKS5]KDE-NH$_2$ | 19 | S5 | S5 | — | — |
| | Ally\|Glyine | H-(cyclo-4,8)-NLK[(Ally\|Gly)KIK(Ally\|Gly)]VVKLKDE-NH$_2$ | 15 | Ally\|Gly | Ally\|Gly | — | — |
| | | H-(cyclo-5,9)-NLKQ[(Ally\|Gly)IKH(Ally\|Gly)]VKLKDE-NH$_2$ | 16 | Ally\|Gly | Ally\|Gly | — | — |
| | | H-(cyclo-6,10)-NLKQK[(Ally\|Gly)KHV(Ally\|Gly)]KLKDE-NH$_2$ | 17 | Ally\|Gly | Ally\|Gly | — | — |
| | | H-(cyclo-7,11)-NLKQKI[(Ally\|Gly)HVV(Ally\|Gly)]LKDE-NH$_2$ | 18 | Ally\|Gly | Ally\|Gly | — | — |
| | | H-(cyclo-8,12)-NLKQKIK[(Ally\|Gly)VVK(Ally\|Gly)]KDE-NH$_2$ | 19 | Ally\|Gly | Ally\|Gly | — | — |
| (i, 1 + 7) | Lactum (Glu-Lys) | H-(cyclo-4,11)-NLK[EKIKHVVK]LKDE-NH$_2$ | 20 | Glu | Lys | — | — |
| | | H-(cyclo-5,12)-NLKQ[EIKHVVKK]KDE-NH$_2$ | 21 | Glu | Lys | — | — |
| | | H-(cyclo-4,11)-NLK[KKIKHVVE]LKDE-NH$_2$ | 20 | Lys | Glu | — | — |
| | | H-(cyclo-5,12)-NLKQ[KIKHVVE]KDE-NH$_2$ | 21 | Lys | Glu | — | — |
| | Lactam (Orn-Aad) | H-(cyclo-4,11)-NLK[(Orn)KIKHVV(Aad)]LKDE-NH$_2$ | 20 | Orn | Aad | — | — |
| | | H-(cyclo-5,12)-NLKQ[(Orn)IKHVV(Aad)]KDE-NH$_2$ | 21 | Orn | Aad | — | — |
| | | H-(cyclo-4,11)-NLK[(Aad)KIKHVV(Orn)]LKDE-NH$_2$ | 20 | Aad | Orn | — | — |
| | | H-(cyclo-5,12)-NLKQ[(Aad)IKHVV(Orn)]KDE-NH$_2$ | 21 | Aad | Orn | — | — |
| | Hydocarbon | | | | | | |
| | Alanine derivatives | H-(cyclo-4,11)-NLK[R8KIKHVVS5]LKDE-NH$_2$ | 20 | R8 | S5 | — | — |
| | | H-(cyclo-5,12)-NLKQ[R8IKHVKS5]KDE-NH$_2$ | 21 | R8 | S5 | — | — |
| HABD2 | | KSEVS-KLRSQLVKRK-QNELR | 3 | — | — | — | — |
| (i, 1 + 7) | Lactam (Glu-Lys) | H-(cyclo-9,16)-KSEVSKLR[EQLVKRKK]NELR-NH$_2$ | 11 | Glu | Lys | — | — |
| | | H-(cyclo-10,17)-KSEVSKLRS[ELVKRKQK]ELR-NH$_2$ | 12 | Glu | Lys | — | — |
| | | H-(cyclo-11,18)-KSEVSKLRSQ[EVKRKQNK]LR-NH$_2$ | 13 | Glu | Lys | — | — |
| | | H-(cyclo-9,16)-KSEVSKLR[KQLVKRKE]NELR-NH$_2$ | 11 | Lys | Glu | — | — |
| | | H-(cyclo-10,17)-KSEVSKLRS[KLVKRKQE]ELR-NH$_2$ | 12 | Lys | Glu | — | — |
| | | H-(cyclo-11,18)-KSEVSKLRSQ[KVKRKQNE]LR-NH$_2$ | 13 | Lys | Glu | — | — |
| | Lactam (Orn-Aad) | H-(cyclo-9,16)-KSEVSKLR[(Orn)QLVKRK(Aad)]NELR-NH$_2$ | 11 | Orn | Aad | — | — |
| | | H-(cyclo-10,17)-KSEVSKLRS[(Orn)LVKRKQ(Aad)]ELR-NH$_2$ | 12 | Orn | Aad | — | — |
| | | H-(cyclo-11,18)-KSEVSKLRSQ[(Orn)VKRKQN(Aad)]LR-NH$_2$ | 13 | Orn | Aad | — | — |
| | | H-(cyclo-9,16)-KSEVSKLR[(Aad)QLVKRK(Orn)]NELR-NH$_2$ | 11 | Aad | Orn | — | — |
| | | H-(cyclo-10,17)-KSEVSKLRS[(Aad)LVKRKQ(Orn)]ELR-NH$_2$ | 12 | Aad | Orn | — | — |
| | | H-(cyclo-11,18)-KSEVSKLRSQ[(Aad)VKRKQN(Orn)]LR-NH$_2$ | 13 | Aad | Orn | — | — |

TABLE 1-continued

Illustrative linear and stapled peptides

| Region | Type of Staple | Sequence | SEQ ID NO. | X₁ | X₂ | X₃ | X₄ |
|---|---|---|---|---|---|---|---|
| | Hydrocarbon | | | | | | |
| | Alanine derivatives | H-(cyclo-9-16)-KSEVSKLR[R8QLVKRKS5]NELR-NH₂ | 11 | R8 | S5 | — | — |
| | | H-(cyclo-10-17)-KSEVSKLRS[R8LVKRKQS5]ELR-NH₂ | 12 | R8 | S5 | — | — |
| | | H-(cyclo-11-18)-KSEVSKLRSQ[R8VKRKQNS5]LR-NH₂ | 13 | R8 | S5 | — | — |
| HABD1 + HABD2 | | KIKHVVKLK-DENSQLKSEVS-KLRSQLVKRK | 5 | — | — | — | — |
| | Lactam (Glu-Lys) | H-(cyclo-10-17)-KIKHVVKLK[ENSQLKE]EVSKLRSQLVKRK-NH₂ | 22 | Glu | Lys | — | — |
| | | H-(cyclo-11-18)-KIKHVVKLKD[ENSQLKK]VSKLRSQLVKRK-NH₂ | 23 | Glu | Lys | — | — |
| | | H-(cyclo-12-19)-KIKHVVKLKDE[ESQLKSEK]SKLRSQLVKRK-NH₂ | 24 | Glu | Lys | — | — |
| | | H-(cyclo-13-20)-KIKHVVKLKDEN[EQLKSEVK]KLRSQLVKRK-NH₂ | 25 | Glu | Lys | — | — |
| | | H-(cyclo-10-17)-KIKHVVKLK[KNSQLKE]EVSKLRSQLVKRK-NH₂ | 22 | Lys | Glu | — | — |
| | | H-(cyclo-11-18)-KIKHVVKLKD[KNSQLKSE]VSKLRSQLVKRK-NH₂ | 23 | Lys | Glu | — | — |
| | | H-(cyclo-12-19)-KIKHVVKLKDE[KSQLKSEE]SKLRSQLVKRK-NH₂ | 24 | Lys | Glu | — | — |
| | | H-(cyclo-13-20)-KIKHVVKLKDEN[KQLKSEVE]KLRSQLVKRK-NH₂ | 25 | Lys | Glu | — | — |
| | Lactam (Orn-Aad) | H-(cyclo-10-17)-KIKHVVKLK[(Orn)ENSQLK(Aad)]EVSKLRSQLVKRK-NH₂ | 22 | Orn | Aad | — | — |
| | | H-(cyclo-11-18)-KIKHVVKLKD[(Orn)NSQLKS(Aad)]VSKLRSQLVKRK-NH₂ | 23 | Orn | Aad | — | — |
| | | H-(cyclo-12-19)-KIKHVVKLKDE[(Orn)SQLKSE(Aad)]SKLRSQLVKRK-NH₂ | 24 | Orn | Aad | — | — |
| | | H-(cyclo-13-20)-KIKHVVKLKDEN[(Orn)QLKSEV(Aad)]KLRSQLVKRK-NH₂ | 25 | Orn | Aad | — | — |
| | | H-(cyclo-10-17)-KIKHVVKLK[(Aad)ENSQLK(Orn)]EVSKLRSQLVKRK-NH₂ | 22 | Aad | Orn | — | — |
| | | H-(cyclo-11-18)-KIKHVVKLKD[(Aad)NSQLKS(Orn)]VSKLRSQLVKRK-NH₂ | 23 | Aad | Orn | — | — |
| | | H-(cyclo-12-19)-KIKHVVKLKDE[(Aad)SQLKSE(Orn)]SKLRSQLVKRK-NH₂ | 24 | Aad | Orn | — | — |
| | | H-(cyclo-13-20)-KIKHVVKLKDEN[(Aad)QLKSEV(Orn)]KLRSQLVKRK-NH₂ | 25 | Aad | Orn | — | — |
| | Hydrocarbon | | | | | | |
| | Alanine derivatives | H-(cyclo-10-17)-KIKHVVKLK[R8ENSQLKS5]EVSKLRSQLVKRK-NH₂ | 22 | R8 | S5 | — | — |
| | | H-(cyclo-11-18)-KIKHVVKLKD[R8NSQLKSS5]VSKLRSQLVKRK-NH₂ | 23 | R8 | S5 | — | — |
| | | H-(cyclo-12-19)-KIKHVVKLKDE[R8SQLKSES5]SKLRSQLVKRK-NH₂ | 24 | R8 | S5 | — | — |
| | | H-(cyclo-13-20)-KIKHVVKLKDEN[R8QLKSEVS5]KLRSQLVKRK-NH₂ | 25 | R8 | S5 | — | — |
| (i, 1 + 4) (i, 1 + 4) | Lactam (Glu-Lys) | H-(cyclo-10-14, cyclo-15-19)-KIKHVVKLK[EKSEK]|EKSEK]SKLRSQLVKRK-NH₂ | 26 | Glu | Lys | Glu | Lys |
| | | H-(cylco-11-15, cyclo-16-20)-KIKHVVKLKD[EENSK]|EKSEK]SKLRSQLVKRK-NH₂ | 27 | Glu | Lys | Glu | Lys |
| | | KIKHVVKLKD[ENSQK]|ESEVK]KLRSQLVKRK-NH₂ | 26 | Lys | Glu | Lys | Glu |
| | | H-(cyclo-10-14, cyclo-15-19)-KIKHVVKLK[KENSE]|KKSEE]SKLRSQLVKRK-NH₂ | 27 | Lys | Glu | Lys | Glu |
| | | H-(cyclo-11-15, cyclo-16-20)-KIKHVVKLK[KENSE]|KSEVE]KLRSQLVKRK-NH₂ | 26 | Glu | Glu | Lys | Lys |
| | | H-(cyclo-10-14, cyclo-15-19)-KIKHVVKLK[EENSK]|KSEVE]KLRSQLVKRK-NH₂ | 27 | Glu | Glu | Lys | Lys |
| | | H-(cyclo-11-15, cyclo-16-20)-KIKHVVKLK[KENSQ]|KSEVK]KLRSQLVKRK-NH₂ | 26 | Lys | Glu | Glu | Lys |
| | | H-(cyclo-10-14, cyclo-15-19)-KIKHVVKLK[EKSEK]|KLRSQLVKRK-NH₂ | | | | | |
| | | H-(cyclo-11-15, cyclo-16-20)-KIKHVVKLK[KNSQE]|ESEVK]KLRSQLVKRK-NH₂ | 27 | Lys | Glu | Glu | Lys |

TABLE 1-continued

Illustrative linear and stapled peptides

| Region | Type of Staple | Sequence | SEQ ID NO. | X₁ | X₂ | X₃ | X₄ |
|---|---|---|---|---|---|---|---|
| | Lactam (Orn-Aad) | H-(cylco-10-14, cyclo-15-19)-KIKHVVKLK[(Orn)ENS(Aad)][(Orn)KSE(Aad)SKLRSQLVKRK-NH₂ | 26 | Orn | Aad | Orn | Aad |
| | | H-(cyclo-11-15, cyclo-16-20)-KIKHVVKLKD[(Orn)NSQ(Aad)][(Orn)SEV(Aad)KLRSQLVKRK-NH₂ | 27 | Orn | Aad | Orn | Aad |
| | | H-(cylco-10-14, cyclo-15-19)-KIKHVVKLK[(Aad)ENS(Orn)][(Aad)KSE(Orn)SKLRSQLVKRK-NH₂ | 26 | Aad | Orn | Aad | Orn |
| | | H-(cyclo-11-15, cyclo-16-20)-KIKHVVKLKD[(Aad)NSQ(Orn)][(Aad)SEV(Orn)KLRSQLVKRK-NH₂ | 27 | Aad | Orn | Aad | Orn |
| | | H-(cylco-10-14, cyclo-15-19)-KIKHVVKLK[(Orn)ENS(Aad)][(Aad)KSE(Orn)SKLRSQLVKRK-NH₂ | 26 | Orn | Aad | Aad | Orn |
| | | H-(cyclo-11-15, cyclo-16-20)-KIKHVVKLKD[(Orn)NSQ(Aad)][(Aad)SEV(Orn)KLRSQLVKRK-NH₂ | 27 | Orn | Aad | Aad | Orn |
| | | H-(cylco-10-14, cyclo-15-19)-KIKHVVKLK[(Aad)ENS(Orn)][(Orn)KSE(Aad)SKLRSQLVKRK-NH₂ | 26 | Aad | Orn | Orn | Aad |
| | | H-(cyclo-11-15, cyclo-16-20)-KIKHVVKLKD[(Aad)NSQ(Orn)][(Orn)SEV(Aad)KLRSQLVKRK-NH₂ | 27 | Aad | Orn | Orn | Aad |
| | Hydrocarbon Ally\|glycine | H-(cylco-10-14, cyclo-15-19)-KIKHVVKLK[(Ally\|gly)ENS(Ally\|gly)][(Ally\|gly)KSE(Ally\|gly)]SKLRSQLVKRK-NH₂ | 26 | Ally\|gly | Ally\|gly | Ally\|gly | Ally\|gly |
| | | H-(cyclo-11-15, cyclo-16-20)-KIKHVVKLKD[(Ally\|gly)NSQ(Ally\|gly)][(Ally\|gly)SEV(Ally\|gly)]KLRSQLVKRK-NH₂ | 27 | Ally\|gly | Ally\|gly | Ally\|gly | Ally\|gly |
| | Alanine derivatives | H-(cylco-10-14, cyclo-15-19)-KIKHVVKLK[s5ENSs5][s5KSEs5]SKLRSQLVKRK-NH₂ | 26 | S5 | S5 | S5 | S5 |
| | | H-(cyclo-11-15, cyclo-16-20)-KIKHVVKLKD[s5NSQs5][s5SEVs5]KLRSQLVKRK-NH₂ | 27 | S5 | S5 | S5 | S5 |
| HABD1 + HABD2 (i, 1 + 4) | | NL-KQKIHVVKLK-DENSQLKSEVS-KLRSQLVKRK-QN | 6 | — | — | — | — |
| | Lactam (Glu-Lys) | H-(cyclo-28-32)-NLKQKIHVKHVVKLKDENSQLKSEVSKLR[EQLVK]RKQN-NH₂ | 28 | Glu | Lys | — | — |
| | | H-(cyclo-27-31)-NLKQKIHVKHVVKLKDENSQLKSEVSKL[ESQLK]KRKQN-NH₂ | 30 | Glu | Lys | — | — |
| | | H-(cyclo-7-11)-NLKQKI[EHVVK]LKDENSQLKSEVSKLRSQLVKRK-NH₂ | 31 | Glu | Lys | — | — |
| | | H-(cyclo-28-32)-NLKQKIHVKHVVKLKDENSQLKSEVSKLR[KQLVE]RKQN-NH₂ | 28 | Lys | Glu | — | — |
| | | H-(cyclo-27-31)-NLKQKIHVKHVVKLKDENSQLKSEVSKL[KSQLE]KRKQN-NH₂ | 30 | Lys | Glu | — | — |
| | | H-(cyclo-7-11)-NLKQKI[KHVVE]LKDENSQLKSEVSKLRSQLVKRK-NH₂ | 31 | Lys | Glu | — | — |

TABLE 1-continued

Illustrative linear and stapled peptides

| Region | Type of Staple | Sequence | SEQ ID NO. | $X_1$ | $X_2$ | $X_3$ | $X_4$ |
|---|---|---|---|---|---|---|---|
| | Lactam (Orn-Aad) | H-(cyclo-28-32)-NLKQKIKHVVKLKDENSQLKSEVSKLR(Orn)QLV(Aad)]RKQN-NH$_2$ | 28 | Orn | Aad | — | — |
| | | H-(cyclo-27-31)-NLKQKIKHVVKLKDENSQLKSEVSKL[(Orn)SQL(Aad)]KRKQN-NH$_2$ | 30 | Orn | Aad | — | — |
| | | H-(cyclo-7-11)-NLKQKI[(Orn)HVV(Aad)]LKDENSQLKSEVSKLRSQLVKRKQN-NH$_2$ | 31 | Orn | Aad | — | — |
| | | H-(cyclo-28-32)-NLKQKIKHVVKLKDENSQLKSEVSKLR[(Aad)QLV(Orn)]RKQN-NH$_2$ | 28 | Aad | Orn | — | — |
| | | H-(cyclo-27-31)-NLKQKIKHVVKLKDENSQLKSEVSKL[(Aad)SQL(Orn)]KRKQN-NH$_2$ | 30 | Aad | Orn | — | — |
| | | H-(cyclo-7-11)-NLKQKI[(Aad)HVV(Orn)]LKDENSQLKSEVSKLRSQLVKRKQN-NH$_2$ | 31 | Aad | Orn | — | — |
| | Hydrocarbon Ally/glycine | H-(cyclo-28-32)-NLKQKIKHVVKLKDENSQLKSEVSKLR[(Ally\|Gly)QLV(Ally\|Gly)]RKQN-NH$_2$ | 28 | Ally\|Gly | Ally\|Gly | — | — |
| | | H-(cyclo-27-31)-NLKQKIKHVVKLKDENSQLKSEVSKL[(Ally\|Gly)SQL(Ally\|Gly)]KRKQN-NH$_2$ | 30 | Ally\|Gly | Ally\|Gly | — | — |
| | | H-(cyclo-7-11)-NLKQKI[(Ally\|Gly)HVV(Ally\|Gly)]LKDENSQLKSEVSKLRSQLVKRKQN-NH$_2$ | 31 | Ally\|Gly | Ally\|Gly | — | — |
| | Alanine derivatives | H-(cyclo-28-32)-NLKQKIKHVVKLKDENSQLKSEVSKLR[S5QLVS5]RKQN-NH$_2$ | 28 | S5 | S5 | — | — |
| | | H-(cyclo-27-31)-NLKQKIKHVVKLKDENSQLKSEVSKL[S5SQLS5]KRKQN-NH$_2$ | 30 | S5 | S5 | — | — |
| | | H-(cyclo-7-11)-NLKQKI[S5HVVS5]LKDENSQLKSEVSKLRSQLVKRKQN-NH$_2$ | 31 | S5 | S5 | — | — |
| (i, i + 4) (i, i + 4) | Lactam (Glu-Lys) | H-(cyclo-7-11, cyclo-28-32)-NLKQKI[EHVVK]LKDENSQLKSEVSKLR[EQLVK]RKQN-NH$_2$ | 29 | Glu | Lys | Glu | Lys |
| | | H-(cyclo-7-11, cyclo-27-31)-NLKQKI[EHVVK]LKDENSQLKSEVSKL[ESQLK]KRKQN-NH$_2$ | 32 | Glu | Lys | Glu | Lys |
| | | H-(cyclo-7-11, cyclo-28-32)-NLKQKI[EHVVE]LKDENSQLKSEVSKLR[KQLVE]RKQN-NH$_2$ | 29 | Lys | Glu | Lys | Glu |
| | | H-(cyclo-7-11, cyclo-27-31)-NLKQKI[EHVVE]LKDENSQLKSEVSKL[KSQLE]KRKQN-NH$_2$ | 32 | Lys | Glu | Lys | Glu |
| | | H-(cyclo-7-11, cyclo-28-32)-NLKQKI[EHVVE]LKDENSQLKSEVSKLR[KQLVE]RKQN-NH$_2$ | 29 | Glu | Lys | Lys | Glu |
| | | H-(cyclo-7-11, cyclo-27-31)-NLKQKI[EHVVE]LKDENSQLKSEVSKL[KSQLE]KRKQN-NH$_2$ | 32 | Glu | Lys | Lys | Glu |
| | | H-(cyclo-7-11, cyclo-28-32)-NLKQKI[KHVVE]LKDENSQLKSEVSKLR[EQLVE]RKQN-NH$_2$ | 29 | Lys | Glu | Glu | Lys |
| | | H-(cyclo-7-11, cyclo-27-31)-NLKQKI[KHVVE]LKDENSQLKSEVSKL[ESQLE]KRKQN-NH$_2$ | 32 | Lys | Glu | Glu | Lys |

TABLE 1-continued

Illustrative linear and stapled peptides

| Region | Type of Staple | Sequence | SEQ ID NO. | X₁ | X₂ | X₃ | X₄ |
|---|---|---|---|---|---|---|---|
| | Lactam (Orn-Aad) | H-(cyclo-7-11, cyclo-28-32)-NLKQKI[(Orn)HVV(Aad)]LKDENSQLKSEVSKLR[(Orn)QLV(Aad)]RKQN-NH₂ | 29 | Orn | Aad | Orn | Aad |
| | | H-(cyclo-7-11, cyclo-27-31)-NLKQKI[(Orn)HVV(Aad)]LKDENSQLKSEVSKL[(Orn)SQL(Aad)]KRKQN-NH₂ | 32 | Orn | Aad | Orn | Aad |
| | | H-(cyclo-7-11, cyclo-28-32)-NLKQKI[(Aad)HVV(Orn)]LKDENSQLKSEVSKLR[(Aad)SQL(Orn)]RKQN-NH₂ | 29 | Aad | Orn | Aad | Orn |
| | | H-(cyclo-7-11, cyclo-27-31)-NLKQKI[(Aad)HVV(Orn)]LKDENSQLKSEVSKL[(Aad)SQL(Orn)]KRKQN-NH₂ | 32 | Aad | Orn | Aad | Orn |
| | | H-(cyclo-7-11, cyclo-28-32)-NLKQKI[(Orn)HVV(Aad)]LKDENSQLKSEVSKLR[(Aad)QLV(Orn)]RKQN-NH₂ | 29 | Orn | Aad | Aad | Orn |
| | | H-(cyclo-7-11, cyclo-27-31)-NLKQKI[(Orn)HVV(Aad)]LKDENSQLKSEVSKL[(Aad)SQL(Orn)]KRKQN-NH₂ | 32 | Orn | Aad | Aad | Orn |
| | | H-(cyclo-7-11, cyclo-28-32)-NLKQKI[(Aad)HVV(Orn)]LKDENSQLKSEVSKLR[(Orn)QLV(Aad)]RKQN-NH₂ | 29 | Aad | Orn | Orn | Aad |
| | | H-(cyclo-7-11, cyclo-27-31)-NLKQKI[(Aad)HVV(Orn)]LKDENSQLKSEVSKL[(Orn)SQL(Aad)]KRKQN-NH₂ | 32 | Aad | Orn | Orn | Aad |
| | Hydrocarbon Ally\|glycine | H-(cyclo-7-11, cyclo-28-32)-NLKQKI[(Ally\|Gly)HVV(Ally\|Gly)]LKDENSQLKSEVSKLR[(Ally\|Gly)QLV(Ally\|Gly)]RKQN-NH₂ | 29 | Ally\|Gly | Ally\|Gly | Ally\|Gly | Ally\|Gly |
| | | H-(cyclo-7-11, cyclo-27-31)-NLKQKI[(Ally\|Gly)HVV(Ally\|Gly)]LKDENSQLKSEVSKL[(Ally\|Gly)SQL(Ally\|Gly)]KRKQN-NH₂ | 32 | Ally\|Gly | Ally\|Gly | Ally\|Gly | Ally\|Gly |
| | Alanine derivatives | H-(cyclo-7-11, cyclo-28-32)-NLKQKI[(S5HVVS5)]LKDENSQLKSEVSKLR[S5QLVS5]RKQN-NH₂ | 29 | S5 | S5 | S5 | S5 |
| | | H-(cyclo-7-11, cyclo-27-31)-NLKQKI[(S5HVVS5)]LKDENSQLKSEVSKL[S5SQLS5]KRKQN-NH₂ | 32 | S5 | S5 | S5 | S5 |

Pharmaceutical Compositions

The invention is further directed to pharmaceutical compositions comprising one or more of the peptides and a pharmaceutically acceptable carrier.

The compositions can be used for administration of the peptides to a subject.

The pharmaceutical composition can further comprise an adjuvant. The adjuvant can enhance the biological activity of the one or more peptides.

The pharmaceutical composition can further comprise hyaluronic acid (HA). For example, pharmaceutical composition can comprise high molecular weight HA (e.g., an HA having an average molecular weight of at least 500 kDa).

The one or more peptides can be provided in a liposome (e.g., an immunoliposome) or lipid formulation.

The pharmaceutical composition can be formulated for injection (e.g., intramuscular, subcutaneous, intravenous, or intraperitoneal injection), oral administration, topical administration, transdermal administration, intranasal administration, or inhalation.

Pharmaceutically acceptable carriers are well known to those skilled in the art and include, for example, sterile saline, lactose, sucrose, calcium phosphate, gelatin, dextrin, agar, pectin, peanut oil, olive oil, sesame oil, and deionised water.

The pharmaceutical composition can comprise one or more stabilizers. For example, the stabilizer can comprise a carbohydrate (e.g., sorbitol, mannitol, starch, sucrose, dextrin, glucose, or a combination thereof), a protein such as albumin or casein, and/or a buffer (e.g., an alkaline phosphate).

Compositions for injection may include one or more pharmaceutically acceptable vehicles or diluents. Compositions for injection can comprise buffered solutions that have a suitable pH and are iso-osmotic with physiological fluids. Any pharmaceutically suitable diluent may be used in the composition for injections (e.g., distilled water, a salt solution, and/or a buffer solution). Compositions for injection may be prepared by conventional volume-weight procedures. A certain amount of the peptide may be diluted to the necessary volume with a diluent or solvent. The solution may then filtered through sterilized filters and then bottled or ampouled. The resultant solution is suitably a stable transparent liquid, and preferably does not contain any chemical or other impurities.

Therapeutic and Diagnostic Uses

The peptides and pharmaceutical compositions can be used in a number of therapeutic or diagnostic methods.

A method for detecting the presence of hyaluronic acid (HA) in cells, tissues, or organs is provided. The method comprises contacting any of the peptides with the cell, tissue, or organ and applying an imaging technique for detecting the detectable label.

The method for detecting the presence of HA in cells can further comprise administering the peptide to a subject.

Where the peptide is administered to a subject, the detectable label suitably comprises a radionuclide and the imaging technique comprises SPECT, CT and PET.

The method can comprise administering the peptide to the subject by intravenous injection, intramuscular injection, subcutaneous injection, intraperitoneal injection, orally, intranasally, or by implantation of the probe into the tissue or organ of interest.

Alternatively, the method for detecting the presence of HA in cells, tissues, or organs can comprise obtaining a cell or tissue sample from a subject and applying the imaging technique ex vivo.

In any of the methods for detecting the presence of HA in cells, the cells suitably comprise macrophages or tumor cells.

The peptides can also be used for diagnosing a subject of a disorder or condition associated with elevated levels of HA. Alternatively, the peptides can be used in methods for diagnosing a subject of a disorder or condition associated with elevated levels of factors that increase RHAMM expression (e.g., growth factors).

A method for diagnosing a subject of a disorder or condition associated with elevated levels of hyaluronic acid (HA) or RHAMM is provided. The method comprises obtaining a cell or tissue sample from the subject, contacting the sample with any of the peptides, and applying an imaging technique for detecting the label in the sample. Detection of elevated HA levels in the sample indicates a positive diagnosis of the disorder or condition.

The disorder or condition can comprise a fibrotic disorder, cancer, an inflammatory disorder, or a combination thereof.

A method for treating a subject suffering from a disorder or condition associated with elevated levels of hyaluronic acid (HA) or RHAMM is provided. The method comprises administering to the subject an effective amount of one or more of any of the peptides or any of the pharmaceutical compositions.

The peptide can be conjugated to a cytotoxic molecule.

The disorder or condition can comprise cancer, an inflammatory disorder, an autoimmune disorder, or a fibrotic disorder (e.g., a fibrotic disorder associated with tissue trauma such as tissue scarring).

Where the disorder or condition comprises cancer, the method can further comprise administering a conventional cancer therapy to the subject. For example, the conventional cancer therapy can be selected from a cancer vaccine, chemotherapy, immunotherapy, radiation therapy or combinations thereof.

RHAMM is present on circulating tumor cells and HA plays a role in metastasis. Thus, the peptides can be used to prevent metastasis.

A method of preventing metastasis in a subject having cancer is provided. The method comprises administering to the subject an effective amount of one or more of any of the peptides or any of the pharmaceutical compositions.

A method for inhibiting proliferation or motility of cells that express elevated levels of RHAMM or that have elevated levels of HA is provided. The method comprises contacting the cells with an effective amount of one or more of any of the peptides or any of the pharmaceutical compositions.

In the method for inhibiting proliferation or motility of cells that express elevated levels of RHAMM or that have elevated levels of HA, the cells are suitably cancer cells.

A method for inhibiting migration of cells is provided. The method comprises comprising contacting the cells with an effective amount of one or more of any of the peptides or any of the pharmaceutical compositions.

A method for inhibiting inflammation is provided. The method comprises contacting cells with an effective amount of one or more of any of the peptides or any of the pharmaceutical compositions.

A method for inhibiting cellular invasion is provided. The method comprises contacting cells with an effective amount of one or more of any of the peptides or any of the pharmaceutical compositions.

A method for inhibiting fibrosis is provided. The method comprises comprising contacting cells with an effective amount of one or more of any of the peptides or any of the pharmaceutical compositions.

In any of the methods for inhibiting migration of cells, inhibiting inflammation, inhibiting cellular invasion, or inhibiting fibrosis, the cells suitably display RHAMM or another HA-binding protein.

The methods for inhibiting migration of cells, inhibiting inflammation, inhibiting cellular invasion, or inhibiting fibrosis can be carried out in vitro or in vivo.

Having described the invention in detail, it will be apparent that modifications and variations are possible without departing from the scope of the invention defined in the appended claims.

EXAMPLES

The following non-limiting examples are provided to further illustrate the present invention.

Example 1

The second HABD (residues 553-562) has been identified as having greater affinity for HA than the first HABD (residues 531-541) (FIG. 1). For this reason, a peptide having the sequence VSKLRSQLVKRKQN (SEQ ID NO: 2), which contains the second HABD, was synthesized first. The peptide was synthesized with and without substitutions at positions i and/or i+4 with glutamic acid and lysine residues to allow for formation of the staple or with allyl-glycine residues to allow for formation of a hydrocarbon staple. For peptides with the substitution(s), ring closing metathesis was carried out to promote adoption of an α-helical conformation. The peptides were then analyzed by circular dichroism (CD) spectroscopy in order to quantify the amount of α-helicity, and determine the efficiency of hydrocarbon and lactam staples in facilitating secondary structure formation and improving stability. The cyclized peptides that show the best α-helical structure as determined by CD spectroscopy were then be analyzed by enzyme-linked immunosorbant assay (ELISA) to determine the extent of binding affinity to HA.

Results

Synthesis of RHAMMHA-Binding Domain

Figure 5:
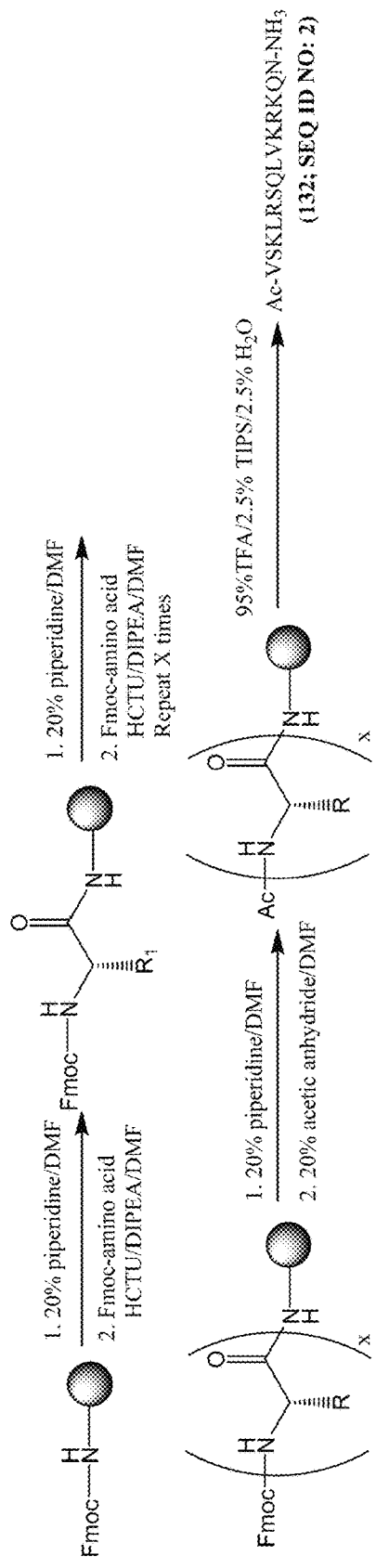
FIG. 5 provides an illustrative reaction scheme for standard Fmoc solid-phase peptide synthesis (SPPS).

The natural amino acid sequence of the peptide that was taken from the second HABD of native RHAMM was synthesized by standard Fmoc solid-phase peptide synthesis (SPPS) (FIG. 5).

The N-terminus Fmoc-group was removed with 20% piperidine in DMF, while all amino acids with reactive side chains were protected with acid labile orthogonal groups (such as tert-butyl (tBu) and 2,2,4,6,7-pentamethyldihydrobenzofurane (Pbf)). The N-terminus of the compound was acetylated in order to prevent the molecule from having a charged terminus, allowing it to better mimic the native protein, as well as to improve its stability in vivo by protecting it from exopeptidase degradation [19]. The final peptide was purified and characterized by liquid-chromatography-mass spectrometry (LC-MS) (Table 2).

TABLE 2

Characterization of synthesized natural second HA binding domain of RHAMM

| Compound No. (SEQ ID NO.) | Sequence | [M + 2H]$^{2+}$ Expected | [M + 2H]$^{2+}$ Observed | Purity* | Yield |
|---|---|---|---|---|---|
| 132 (SEQ ID NO: 2) | Ac-VSKLRSQLVKRKQN-NH2 | 863.0384 | 863.0952 | >95% | 21% |

*Purity is determined by integrating the area under the purified LC curve

Synthesis of Hydrocarbon Bridges

Figure 6:
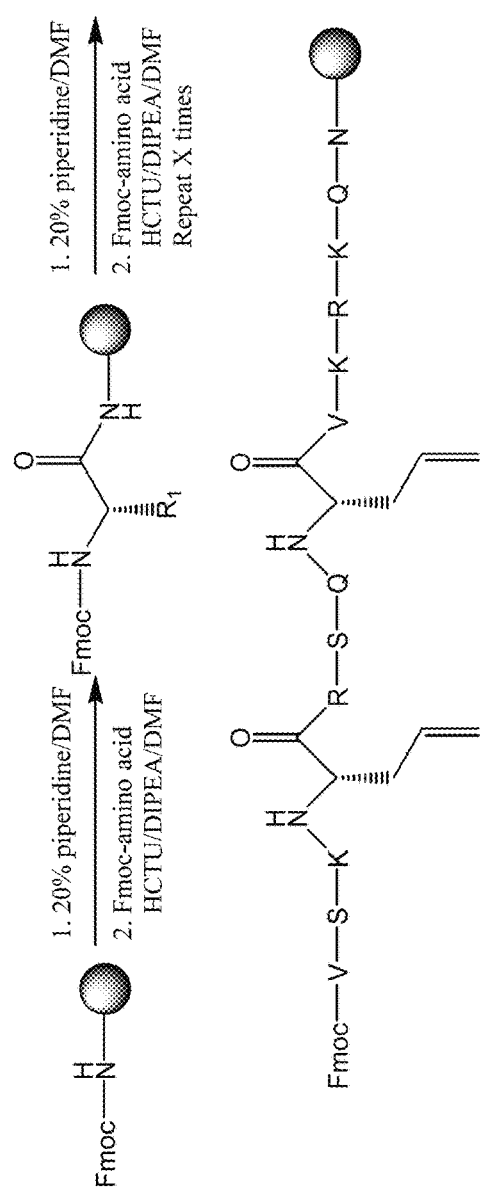
FIG. 6 provides an illustrative reaction scheme for synthesis of a peptide having allyl glycine substitutions that allow for cyclization of the peptide.

Amino acids at positions i and i+4 in the RHAMM HABD2 were substituted with allyl glycine to create the peptides having hydrocarbon bridges illustrated below in Table 3. Synthesis of the peptide is possible by manual or automated SPPS according to the scheme shown in FIG. 6.

TABLE 3

| Structure | [M + 2H]$^{2+}$ Expected | [M + 2H]$^{2+}$ Observed | SEQ ID NO: |
|---|---|---|---|
| Ac—V—S—K—N(H)—C(=O)—R—S—Q—N(H)—C(=O)—V—K—R—K—Q—N—NH₂ (with hydrocarbon staple between the two α-carbons) | 812.49 | 812.37 | 7, where X₁ and X₂ are both allylglycine |

TABLE 3-continued

| Structure | [M + 2H]$^{2+}$ Expected | [M + 2H]$^{2+}$ Observed | SEQ ID NO: |
|---|---|---|---|
| Ac—V—S—K—L—[cyclic structure]—S—Q—L—[cyclic]—K—R—K—Q—N—NH$_2$ | N/A | N/A | 8, where X$_1$ and X$_2$ are both allylglycine |
| Ac—V—S—K—L—R—[cyclic]—Q—L—V—[cyclic]—R—K—Q—N—NH$_2$ | N/A | N/A | 9, where X$_1$ and X$_2$ are both allylglycine |
| Ac—V—S—K—L—R—S—[cyclic]—L—V—K—[cyclic]—K—Q—N—NH$_2$ | N/A | N/A | 10, where X$_1$ and X$_2$ are both allylglycine |

Synthesis of Lactam Bridge

Peptides having lactam bridges within RHAMM HABD2 were synthesized by substituting an amino acid residue at position i and i+4 with glutamic acid and lysine (or in the case of compound 152, only making a substitution with a glutamic acid residue at the i position, since a lysine occurs at the i+4 position in the native sequence). Glutamic acid residues protected with allylester (Glu(OAll)) and lysine residues protected with alloxycarbonyl (Lys(Alloc)) protecting groups were used. Peptides were synthesized by solid-phase peptide synthesis according to the scheme shown in FIG. 7. These Glu(OAll) and Lys(Alloc) protecting groups allow for the selective deprotection of the glutamic acid and lysine residues so that they can be subsequently coupled together in order to create the lactam bridge. Deprotection was carried out using a palladium (0) catalyst under basic conditions (FIG. 8).

The remaining protecting groups were removed and the peptide was cleaved off of the solid support after the lactam bridge staple was in place, in order to obtain the free cyclized peptide of the second HABD of RHAMM (FIG. 9).

These peptides were successfully purified and characterized (Table 4). The yields for the cyclized peptides were sacrificed in order to ensure high purity of the final compounds.

TABLE 4

Characterization of synthesized lactam bridge second HA binding domain of RHAMM

| Compound Number (SEQ ID NO.) | Sequence | [M + 2H]$^{2+}$ Expected | [M + 2H]$^{2+}$ Observed |
|---|---|---|---|
| 133 (SEQ ID NO: 7, where X$_1$ is glutamic acid and X$_2$ is lysine) | H-(cyclo-4,8)-VSK[ERSQK]VKRKQN-NH$_2$ | 848.5087 | 848.6129 |
| 134 (SEQ ID NO: 8, where X$_1$ is glutamic acid and X$_2$ is lysine) | H-(cyclo-5,9)-VSKL[ESQLK]KRKQN-NH$_2$ | 834.0030 | 834.0885 |
| 135 (SEQ ID NO: 9, where X$_1$ is glutamic acid and. X$_2$ is lysine) | H-(cyclo-6,10)-VSKLR[EQLVK]RKQN-NH$_2$ | 854.0293 | 854.6246 |
| 136 (SEQ ID NO: 10, where X$_1$ is glutamic acid and X$_2$ is lysine) | H-(cyclo-7,11)-VSKLRS[ELVKK]QN-NH$_2$ | 819.5129 | 819.5986 |

The N-terminus of the lactam-bridged peptides was not acetylated because a Boc-protecting group was placed at the N-terminus in order to minimize the number of by-products that formed during the lactam bridging reaction. In normal peptide synthesis, an Fmoc group protects the N-terminus of the peptide chain; however, Fmoc-deprotection requires only mild basic conditions [16]. Removal of the Boc protecting group, on the other hand, requires harsh acidic conditions (20-50% TFA) [22]. Therefore, the Boc-protected N-terminus of the peptide is protected until all modifications are completed and the peptide is removed from its solid support in the final global deprotection step.

Circular Dichroism (CD)

Figure 10:
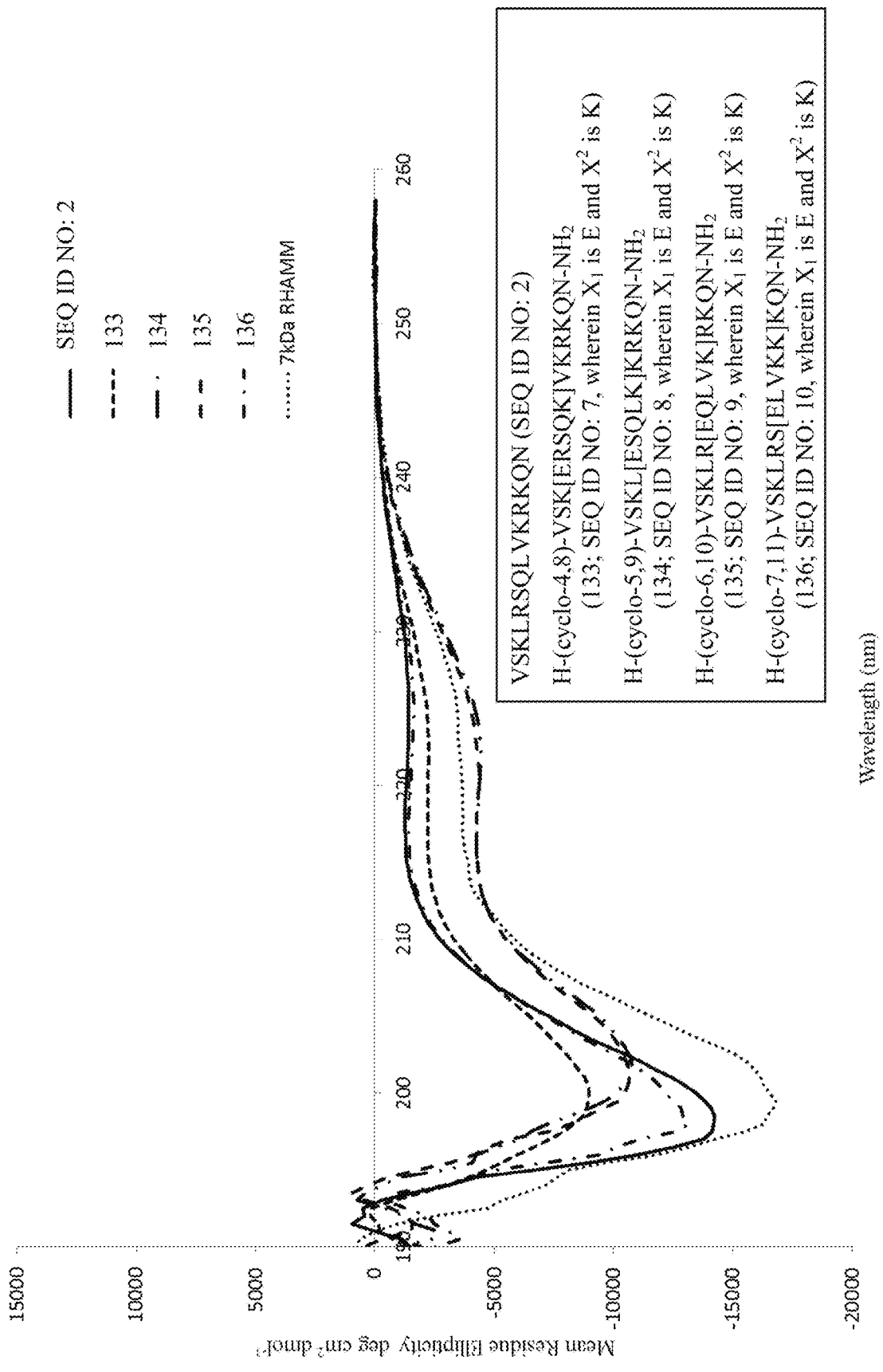
FIG. 10 provides illustrative circular dichroism (CD) spectra for 7 kDa RHAMM (SEQ ID NO: 1) and the linear peptide VSKLRSQLVKRKQN (SEQ ID NO: 2) and cyclized variants thereof.

The compounds synthesized in this example (Compounds 132-136) were analyzed by CD spectroscopy in order to analyze the amount of α-helicity that each peptide possessed (FIG. 10). A typical CD spectrum for an α-helix shows two minima at around 222 and 208 nm, as well as a maximum at approximately 192 nm. In addition, a large mean residue ellipticity indicates greater α-helical character [17]. Compound 132 shows minimal α-helical character (FIG. 10). This was predicted to be the case, as there is a lack of contributing residues that might form a hydrophobic core, thereby helping to stabilize the secondary structure of the linear peptide [14]. For this reason, bridges were introduced into the peptides. An increase in α-helix structure was observed in those peptides where the bridges were introduced towards the center of the peptide (134 and 135), as there is a greater minimum at both 222 nm and 208 nm and a more distinct maximum at 192 nm. Bridges placed towards the end of the peptides (133 and 136) did not seem to stabilize the respective peptides, and facilitate the formation of an α-helix shape, as their spectra are comparable to that of the uncycled peptide. The differences in α-helicity induced by the bridges placed at different points within each peptide may be due to the differences in their primary sequences. Specifically, two amino acids (at the i and i+4 position) have to be replaced in order to form the lactam bridge. In compound 133, leucine was replaced at both the i and i+4 position; while in compound 136, glutamine was replaced at the i position and aspartic acid was replaced at i+4. Leucine and glutamine are proposed to be helix-stabilizing residues [17]. Without these residues in the sequence, the α-helical structure may become less stable, and therefore result in a weaker α-helical signal. Effectiveness of stapling for α-helix formation is case dependent, and there is currently little agreement in literature about the most effective ring sizes or composition [17].

A larger portion of the RHAMM protein was used as the reference for α-helical character of the truncated peptides. 7 kDa RHAMM (SEQ ID NO: 1) is a mini protein that is composed of 62 amino acids, which was derived from the C-terminus of the full-length RHAMM sequence. It contains both HABDs, and is predicted to have almost complete α-helix shape, similar to that of native full-length RHAMM.

A peptide's α-helicity can be quantified using equations 1-3:

$$f_H = [([\theta]_{obs222} - [\theta]_c)/([\theta]_{max222} - [\theta]_c)] \quad \text{(Equation 1)}$$

$$[\theta]_c = 2220 + 53T \quad \text{(Equation 2)}$$

$$[\theta]_{max222} = (-44000 + 250T)(1 - k/N) \quad \text{(Equation 3)}$$

where $f_H$ is the ratio of the average number of helical hydrogen bonds divided by the total number of hydrogen bonds that can be found in a peptide, T is the temperature in degrees Celsius, N is the number of residues in the peptide and k is a constant of ellipticity when 100% of the structure is α-helical (3 for carboxyamidated peptides) [17-19]. Table 5 summarizes the quantification of helicity of each of the peptides analyzed (FIG. 10).

TABLE 5

Molar Ellipticities ([θ] deg cm² dmol⁻¹ residue⁻¹) at λ = 222, 208, and 192 nm ratios of ellipticities at 222/208 nm, and fraction helicity for compound 1-2d and 7 kDa RHAMM at a concentration of 0.5 mM in Milli-Q water

| Compound | $[\theta]_{222}$ | $[\theta]_{208}$ | $[\theta]_{192}$ | $[\theta]_{222}/[\theta]_{208}$ | $f_H$ |
|---|---|---|---|---|---|
| 132 | −1339.76 | −4944.38 | −433.48 | 0.27 | 0.13 |
| 133 | −2260.92 | −5010.81 | 1733.35 | 0.45 | 0.17 |
| 134 | −4403.89 | −7685.97 | 1002.14 | 0.57 | 0.22 |
| 135 | −4400.73 | −7906.16 | 1245.85 | 0.55 | 0.22 |
| 136 | −1568.07 | −5084.93 | 1437.80 | 0.30 | 0.14 |
| 7 kDa RHAMM | −4046.60 | −7553.76 | 1839.66 | 0.46 | 0.18 |

Milli-Q water was chosen as the solvent in which all peptides would be dissolved for CD spectroscopy, as it is a UV invisible solvent, which is a requirement of the analytical technique [20], and it represents RHAMM's natural environment in the body. Luo and Baldwin [18] stated that when peptides are taken out of their native protein sequence, they usually show little to no helical formation in water alone. For this reason, TFE/H₂O solutions are commonly used in studies to observe the α-helix characteristics, and may improve the helical nature of the peptides observed here. However, a helix-stabilizing solvent, such as TFE, would not be as contextually relevant, as there are no solvent stabilizing effects in the body. Thus use of TFE would tend to produce skewed results and not be representative of the peptide's natural behavior.

Example 2

HA binding ELISA

Experimental

Biotinylated peptides included a 2-[2-(2-aminoethoxy)ethoxy]acetic acid (AEEA) spacer to separate the peptide sequence from the biotin molecule. Five milligrams of biotin-labeled peptide was dissolved in 1 mL phosphate-buffered saline (PBS). This stock solution was further dissolved in 1× Tris-buffered saline (TBS) to generate peptide solutions of 50 µg/mL, 10 µg/mL, 2 µg/mL, 0.4 µg/mL, 0.08 µg/mL, and 0.016 µg/mL. Diluted peptides were added to HA coated ELISA plates (200 µl/well, triplicates, ECHELON kit K-1200). The ELISA plate was incubated over night at 40° C. 200 µL of 1× TBS was used as a negative control. Wells were washed 3 times with 200 µL 1× TBS and then 100 µL pre-diluted streptavidin-HRP (LSAB2 Streptavidin-HRP, DAKO K1016) was added to each well and the ELISA plate was incubated for 1 hour at room temperature. Wells were washed 3 times with 200 µL 1× TBS and 100 µL, 3,3',5,5'-tetramethylbenzidine (TMB) solution (ECHELON kit K-4800) was added. After a 20 minute incubation at room temperature, 50 µL 1N H₂SO₄ stop solution was added. Absorbance was measured at 450 nm using a SYNERGY H4 (BioTek) plate reader. Average and standard deviation was calculated and results were graphed using EXCEL software.

Results

The peptides shown below in Table 6 were evaluated for their affinity to hyaluronan (HA) using ELISA (enzyme-linked immunosorbent assay) analysis.

TABLE 6

| Peptide structure | Compound number (SEQ ID NO.) |
|---|---|
| Biotin-AEEA-VSKERSQLVKRKQN-NH$_2$ | 284 (SEQ ID NO: 2) |
| Biotin-AEEA-(cyclo-6-10)-VSKLR[EQLVK]RKQN-NH$_2$ | 287 (SEQ ID NO: 9, wherein X$_1$ is glutamic acid and X$_2$ is lysine) |

HA coated ELISA plates were used, with incubation of varying concentrations of the test peptides and the analysis was carried out in triplicate for each concentration. It was discovered that the linear peptide sequence (284) that includes the HA binding domain 2, did interact with HA; however, high peptide concentration was required. The peptide analogue (287), having a lactam bridge, was found to have a more significant interaction, with a concentration of only 80 ng/mL concentration required in order to have equivalent interaction to that of the linear peptide, which required a concentration of 10 μg/mL. The cyclic constraint was able to provide a preferential conformation resulting in improved HA affinity. The ELISA results are shown in FIG. 2.

Example 3

Summary

Peptides containing one or both of the RHAMM hyaluronan binding domains (HABD) were designed with macrocyclic constraints in an effort to develop short alpha-helical peptides with retained hyaluronan (HA) interaction. Stapled peptides were synthesized and alpha-helicity was determined by CD spectroscopy. For both HABD1 and HABD2 regions, 14-mer and 15-mer macrocyclic peptides were discovered with alpha-helical character in water, significantly improved as compared to the linear sequence. In particular for HABD2, compound 151 in water had alpha-helical character equal to that of the linear peptide when in the helix stabilizing solvent trifluoroethanol (TFE). Longer RHAMM derived peptides were also prepared as macrocyclic structures, with compound 266, containing two stapled constraints, showing the best improvement in helicity.

Methods

Peptide Synthesis

Fmoc-based solid-phase synthesis was carried out manually and automatically through the use of a BIOTAGE SYRO WAVE automated peptide synthesizer. Synthesis was done on a 0.1 mmol scale with 0.52 mmol/g Fmoc-Rink amide MBHA resin and a 3-fold excess of the protected amino acids. The resin was allowed to swell in dichloromethane (DCM) (2.0 mL, 15 min) and then solvent was removed. The resin was then rinsed with dimethylformamide (DMF) (1.0 mL, 1 min), and after removal of the solvent, deprotection of the Fmoc group was performed by adding a solution of 20% piperidine/DMF (1.5 mL) to the resin and vortexing for 5 minutes. The resin was then washed with three times with DMF (2.0 mL, vortex 30 sec) and then the resin was vortexed for 15 min with 20% piperidine/DMF (1.5 mL). The resin was then washed with DMF six times to remove any unreacted products (2.0 mL, vortex 30 sec). A Kaiser test was performed after the Fmoc removal to verify the presence of a free primary amino group. The desired Fmoc-protected amino acid (0.3 mmol) and the coupling reagent HCTU (0.3 mmol) was dissolved in DMF (1.5 mL) and added to the resin. The mixture was allowed to vortex for 30 seconds and then N,N-diisopropylethylamine (DIPEA) (0.6 mmol) was added to the mixture and the mixture was allowed to vortex for 1 hour. This deprotection/amino acid coupling cycle was repeated until the desired amino acid sequence was obtained. After the final amino acid was coupled, the resin was washed three times with DMF (2.0 mL, vortex 30 sec) and then 3 times with DCM (2.0 mL, vortex 30 sec) and then dried under vacuum and stored in the freezer. The removal of the final Fmoc protecting group on the N-terminus is achieved using the same procedure for the other deprotections as previously described. To determine if the correct peptide has been synthesized, a microcleave was performed before full cleavage off the resin. A small amount of resin (<5 mg) was added to a small peptide vessel and 95% trifluoroacetic acid/2.5% triisopropylsilane/2.5% water (500 μL) was added. The mixture was allowed to vortex for 3-4 hours, and the resulting liquid was precipitated with cold tert-butyl methyl ether (TBME) (2 mL). The precipitate was centrifuged and the mother liquor was decanted off and the pellet was dissolved in water (2 mL) and frozen and the lyophilized. If the correct peptide was synthesized as determined by analytical HPLC/MS, then a full cleavage of all of the resin was performed. The procedure for full cleaves was the same as a microcleave. A solution of 95% trifluoroacetic acid/2.5% triisopropylsilane/2.5% water (3 mL) was added to the resin and vortexed for 4-6 hours. The solution was drained, precipitated in TBME (20 mL) and centrifuged. The mother liquor was decanted and the pellet is dissolved in water (20 mL) and lyophilized to obtain the crude fully deprotected peptide.

Kiaser Test

To qualitatively test whether a free amine was present (after a Fmoc-deprotection, amino acid coupling, or alloc/allylester deprotection), a Kaiser test was performed. A small amount of resin (<5 mg) was taken and placed in a small test tube. To the test tube, solutions of: Phenol:EtOH (8:2 v/v), 0.001M KCN:pyridine (2:98 v/v) and ninhydrin in EtOH (5% w/v) were added. The test tube was heated to 70° C. and the presence of a free amine was indicated by the resin beads turning blue. The indication of no free amine was determined by the presence of clear/yellow resin beads.

Deprotection of Allyloxycarbonyl (Alloc) and Allylester (OAll) Protecting Groups Selective deprotection of the allyloxycarbonyl and the allylester protecting groups was accomplished by adding DCM (4.5 mL) to the resin-bound peptide and shaking gently for 10 minutes. After addition of phenylsilane (24 equiv.), the peptide vessel was flushed with nitrogen and allowed to react for 5 minutes. Then, tetrakis(triphenylphosphine) palladium (0) (0.1 equiv.) was added to the mixture and the peptide vessel was again flushed with nitrogen, and the reaction was allowed to proceed for 10 minutes. Next, the peptide-resin was washed with DCM (4×30 s), followed by a series of washings with DCM, DMF, MeOH, DMF, DCM (30 s each).

Lactam Bridge Formation

After the resin-bound peptide was selectively alloc and allylester deprotected, HATU (3 equiv.) was dissolved in DMF (1.5 mL) and allowed to vortex for 30 seconds. DIPEA (6 equiv.) was then added to the peptide vessel in order for the lactam bridge to be made and the reaction was vortexed for 2 hours. Final washings with DMF and DCM (2.0 ml, 3×30 s each) were performed to remove any residual reactants.

Purification of Peptides by RP-HPLC/ESI-MS Peptides were analyzed using a reverse-phase analytical HPLC column (Agilent Zorbax SB-C8 column 4.6×150 mm, 3.5 μm). This system was equipped with a Waters 600 136 controller, Waters Prep degasser, and Waters MASSLYNX software (version 4.1). Employed mobile phases were 0.1% TFA in deionized water (eluent A) and 0.1% TFA in acetonitrile (eluent B). The flow rate was set at 1.5 mLmin$^{-1}$ over 15 minutes. The column eluate was monitored using a Waters 2998 Photodiode array detector set at 220 nm, 254 nm and 400 nm. Peptides were purified using a reverse-phase preparative HPLC column (Agilent Zorbax SB-C18 column 21.2×150 mm, 5 μm) on the same system mentioned above. The detection method and eluents were the same was mentioned above for the analytical system and the flow rate was set at 20 mLmin$^{-1}$. The collected fractions were then lyophilized to a solid and analyzed by ESI-MS. Purity of final products was determined by analytical RP-HPLC (220 nm).

Circular Dichroism (CD) Spectroscopy

CD spectra were obtained on a Jasco J-810 spectropolarimeter and recorded in the range of 180-260 nm. Peptide solutions were prepared with a 0.1M phosphate buffer solution to a concentration of 0.5 mM. The measurements were performed in quartz cuvettes with a path length of 1 mm and a scanning speed of 10-50 nm/min. Five individual data points were averaged by the instrument in order to obtain the reported CD spectrum. The measurements were carried out at 20° C. A blank solution of 0.1M phosphate buffer solution was run before every measurement in order to baseline correct for any UV-interference observed from the buffer.

Results

Table 7 provides sequences for the 14- and 15-mer peptides containing HABD2 and HABD1, respectively, as well as derivatives of these peptides where (i, i+4) staples were placed in cyclized versions. All peptides were amidated on the C-terminus and either non-acetylated, acetylated or biotinylated on the N-terminus. Those peptides with a biotin group on the N-terminus included an AEEA spacer to separate the peptide sequence from the biotin molecule. "Reverse" peptides are peptides in which the staple includes a lysine at the i position and a glutamic acid residue at the i+4 position. Mass spectrometry data are provided for each of these peptides in Table 14 at the end of this example.

TABLE 7

| Binding Domain | | Compound No. (SEQ ID NO.*) | Sequence |
|---|---|---|---|
| HABD2 | Linear | 132 (2) | Ac-VSKLRSQLVKRKQN-NH$_2$ |
| | | 284 (2) | Biotin-AEEA-VSKLRSQLVKRKQN-NH$_2$ |
| | Cyclo-4,8 | 133 (7) | H-(cyclo-4,8)-VSK[ERSQK]VKRKQN-NH$_2$ |
| | | 150 (7) | Ac-(cyclo-4,8)-VSK[ERSQK]VKRKQN-NH$_2$ |
| | | 285 (7) | Biotin-AEEA-(cyclo-4,8)-VSK[ERSQK]VKRKQN-NH$_2$ |
| | Cyclo-5,9 | 134 (8) | H-(cyclo-5,9)-VSKL[ESQLK]KRKQN-NH$_2$ |
| | | 151 (8) | Ac-(cyclo-5,9)-VSKL[ESQLK]KRKQN-NH$_2$ |
| | | 286 (8) | Biotin-AEEA-(cyclo-5,9)-VSKL[ESQLK]KRKQN-NH$_2$ |
| | Cyclo-6,10 | 135 (9) | H-(cyclo-6,10)-VSKLR[EQLVK]RKQN-NH$_2$ |
| | | 152 (9) | Ac-(cyclo-6,10)-VSKLR[EQLVK]RKQN-NH$_2$ |
| | | 287 (9) | Biotin-AEEA-(cyclo-6,10)-VSKLR[EQLVK]RKQN-NH$_2$ |
| | Cyclo-7,11 | 136 (10) | H-(cyclo-7,11)-VSKLRS[ELVKK]KQN-NH$_2$ |
| | | 153 (10) | Ac-(cyclo-7,11)-VSKLRS[ELVKK]KQN-NH$_2$ |
| | | 288 (10) | Biotin-AEEA-(cyclo-7,11)-VSKLRS[ELVKK]KQN-NH$_2$ |
| | Reverse Cyclo-5,9 | 154 (8) | Ac-(cyclo-5,9)-VSKL[KSQLE]KRKQN-NH$_2$ |
| | | 289 (8) | Biotin-AEEA-(cyclo-5,9)-VSKL[KSQLE]KRKQN-NH$_2$ |
| | Reverse Cyclo-6,10 | 155 (9) | Ac-(cyclo-6,10)-VSKLR[KQLVE]RKQN-NH$_2$ |
| | | 290 (9) | Biotin-AEEA-(cyclo-6,10)-VSKLR[KQLVE]RKQN-NH$_2$ |
| HABD1 | Linear | 156 (4) | Ac-NLKQKIKHVVKLKDE-NH$_2$ |
| | | 291 (4) | Biotin-AEEA-NLKQKIKHVVKLKDE-NH$_2$ |
| | Cyclo-4,8 | 157 (15) | Ac-(cyclo-4,8)-NLK[EKIKK]VVKLKDE-NH$_2$ |
| | | 292 (15) | Biotin-AEEA-(cyclo-4,8)-NLK[EKIKK]VVKLKDE-NH$_2$ |
| | Cyclo-5,9 | 158 (16) | Ac-(cyclo-5,9)-NLKQ[EIKHK]VKLKDE-NH$_2$ |
| | | 293 (16) | Biotin-AEEA-(cyclo-5,9)-NLKQ[EIKHK]VKLKDE-NH$_2$ |
| | Cyclo-6,10 | 159 (17) | Ac-(cyclo-6,10)-NLKQK[EKHVK]KLKDE-NH$_2$ |
| | | 294 (17) | Biotin-AEEA-(cyclo-6,10)-NLKQK[EKHVK]KLKDE-NH$_2$ |
| | Cyclo-7,11 | 160 (18) | Ac-(cyclo-7,11)-NLKQKI[EHVVK]LKDE-NH$_2$ |
| | | 295 (18) | Biotin-AEEA-(cyclo-7,11)-NLKQKI[EHVVK]LKDE-NH$_2$ |
| | Cyclo-8,12 | 161 (19) | Ac-(cyclo-8,12)-NLKQKIK[EVVKK]KDE-NH$_2$ |
| | | 296 (19) | Biotin-AEEA-(cyclo-8,12)-NLKQKIK[EVVKK]KDE-NH$_2$ |

*Each of the peptides of SEQ ID NO: 7-10 and 15-19 include substitutions at $X_1$ and $X_2$ positions with glutamic acid or lysine residues as shown in the sequences provided in the table.

CD data for the 14- and 15-mer peptides containing HABD2 (VSKLRSQLVKRKQN, SEQ ID NO: 2) and HABD1 (NLKQKIKHVVKLKDE, SEQ ID NO: 4) and cyclized derivatives thereof in water or 40% TFE/water are provided below in Tables 8 (water) and 9 (40% TFE/water). Tables 8 and 9 provide the mean residue ellipticity ([θ] deg cm$^2$ dmol$^{-1}$) at λ=222 and 208 nm for each peptide and ratios of ellipticities at 222/208. Each of the peptides was acetylated at its amino terminus and amidated at its carboxy terminus.

TABLE 8

| Compound Number (SEQ ID NO.*) | Sequence | [θ]222 | [θ]208 | [θ]222/[θ]208 |
|---|---|---|---|---|
| 132 (2) | Ac-VSKLRSQLVKRKQN-NH$_2$ | -1.10E+03 | -4.85E+03 | 0.13 |
| 150 (7) | Ac-(cyclo-4,8)-VSK[ERSQK]VKRKQN-NH$_2$ | -3.35E+03 | -6.30E+03 | 0.53 |
| 151 (8) | Ac-(cyclo-5,9)-VSKL[ESQLK]KRKQN-NH$_2$ | -6.45E+03 | -9.25E+03 | 0.70 |
| 152 (9) | Ac-(cyclo-6,10)-VSKLR[EQLLVK]RKQN-NH$_2$ | -4.85E+03 | -7.90E+03 | 0.61 |
| 153 (10) | Ac-(cyclo-7,11)-VSKLRS[ELVKK]KQN-NH$_2$ | -3.68E+03 | -6.79E+03 | 0.54 |
| 154 (8) | Ac-(cyclo-5,9)-VSKL[KSQLE]KRKQN-NH$_2$ | -9.74E+02 | -4.95E+03 | 0.20 |
| 155 (9) | Ac-(cyclo-6,10)-VSKLR[KQLVE]RKQN-NH$_2$ | -1.98E+05 | -5.30E+03 | 0.37 |
| 156 (4) | Ac-NLKQKIKRVVKLKDE-NH$_2$ | -1.01E+02 | -9.00E+02 | 0.11 |
| 157 (15) | Ac-(cyclo-4,8)-NLK[EKIKK]VVKLKDE-NH$_2$ | -2.46E+03 | -6.40E+03 | 0.38 |
| 158 (16) | Ac-(cyclo-5,9)-NLKQ[EIKHK]VKLKDE-NH$_2$ | -2.83E+03 | -6.60E+03 | 0.43 |
| 159 (17) | Ac-(cyclo-6,10)-NLKQK[EKHVK]KLKDE-NH$_2$ | -2.61E+03 | -5.95E+03 | 0.44 |
| 160 (18) | Ac-(cyclo-7,11)-NLKQKI[EHVVK]LKDE-NH$_2$ | -3.85E+03 | -6.98E+03 | 0.55 |
| 161 (19) | Ac-(cyclo-8,12)-NLKQKIK[EVVKK]KDE-NH$_2$ | -1.80E+03 | -5.85E+03 | 0.31 |

*Each of the peptides of SEQ ID NO: 7-10 and 15-19 include substitutions at X$_1$ and X$_2$ positions with glutamic acid or lysine residues as shown in the sequences provided in the table.

TABLE 9

| Compound Number (SEQ ID NO.*) | Sequence | [θ]222 | [θ]208 | [θ]222/[θ]208 |
|---|---|---|---|---|
| 132 (2) | Ac-VSKLRSQLVKRKQN-NH$_2$ | -1.14E+04 | -1.59E+04 | 0.72 |
| 150 (7) | Ac-(cyclo-4,8)-VSK[ERSQK]VKRKQN-NH$_2$ | -9.75E+03 | -1.21E+04 | 0.81 |
| 151 (8) | Ac-(cyclo-5,9)-VSKL[ESQLK]KRKQN-NH$_2$ | -1.33E+04 | -1.62E+04 | 0.82 |
| 152 (9) | Ac-(cyclo-6,10)-VSKLR[EQLVK]RKQN-NH$_2$ | -1.19E+04 | -1.50E+04 | 0.70 |
| 153 (10) | Ac-(cyclo-7,11)-VSKLRS[ELVKK]KQN-NH$_2$ | -8.53E+03 | -1.02E+04 | 0.74 |
| 154 (8) | Ac-(cyclo-5,9)-VSKL[KSQLE]KRKQN-NH$_2$ | -8.78E+03 | -1.18E+04 | 0.75 |
| 155 (9) | Ac-(cyclo-6,10)-VSKLR[KQLVE]RKQN-NH$_2$ | -1.28E+04 | -1.71E+04 | 0.75 |
| 156 (4) | Ac-NLKQKIKHVVKLKDE-NH$_2$ | -8.57E+03 | -1.03E+04 | 0.74 |
| 157 (15) | Ac-(cyclo-4,8)-NLK[EKIKK]VVKLKDE-NH$_2$ | -1.25E+04 | -1.56E+04 | 0.80 |
| 158 (16) | Ac-(cyclo-5,9)-NLKQ[EIKHK]VKLKDE-NH$_2$ | -1.24E+04 | -1.70E+04 | 0.84 |
| 159 (17) | Ac-(cyclo-6,10)-NLKQK[EKHVK]KLKDE-NH$_2$ | -1.26E+04 | 1.48E+04 | 0.85 |
| 160 (18) | Ac-(cyclo-7,11)-NLKQKI[EHVVK]LKDE-NH$_2$ | -1.42E+04 | -1.65E+04 | 0.86 |
| 161 (19) | Ac-(cyclo-8,12)-NLKQKIK[EVVKK]KDE-NH$_2$ | -1.60E+04 | -1.96E+04 | 0.82 |

*Each of the peptides of SEQ ID NO: 7-10 and 15-19 include substitutions at X$_1$ and X$_2$ positions with glutamic acid or lysine residues as shown in the sequences provided in the table.

Figure 12:
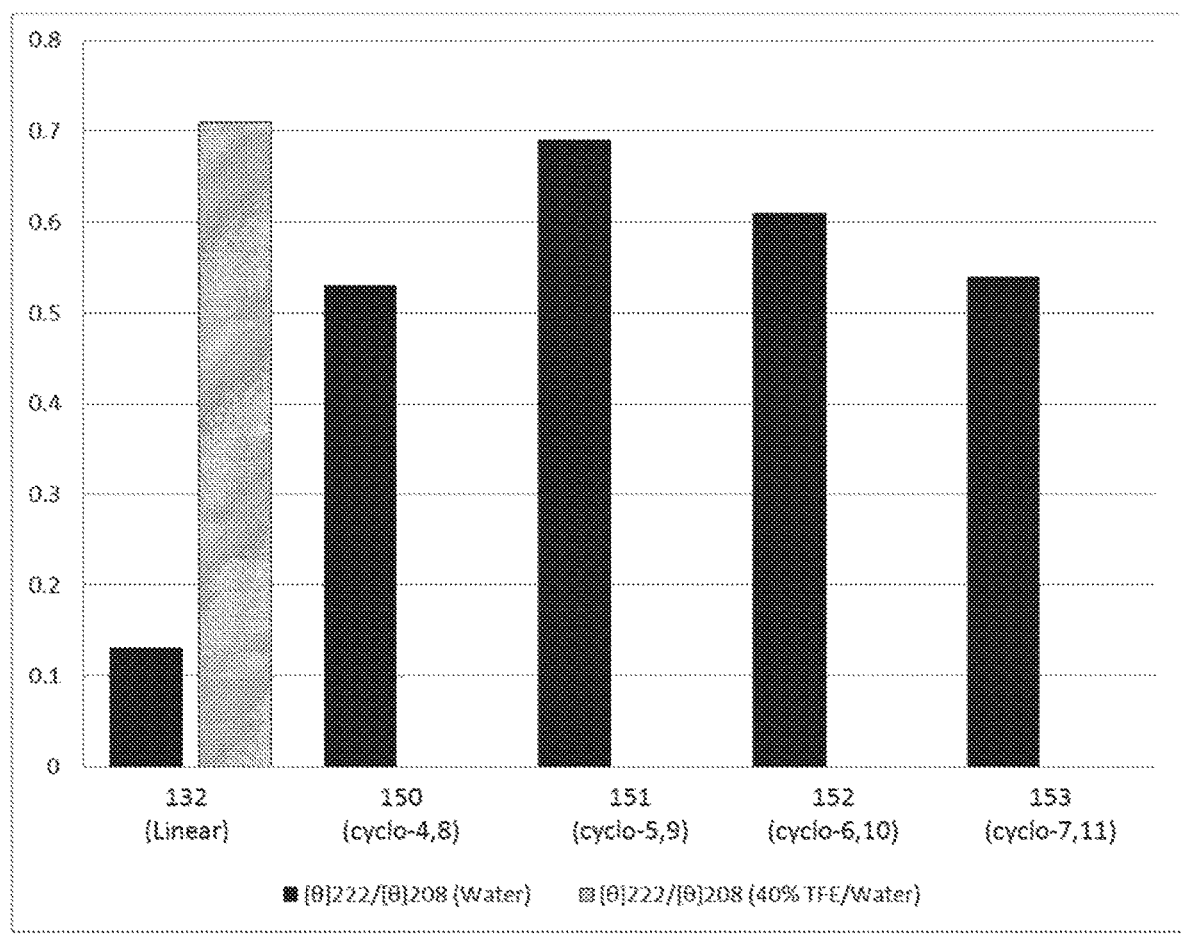
FIGS. 12-15 provide illustrative CD data for linear and cyclized peptides.
Figure 13:
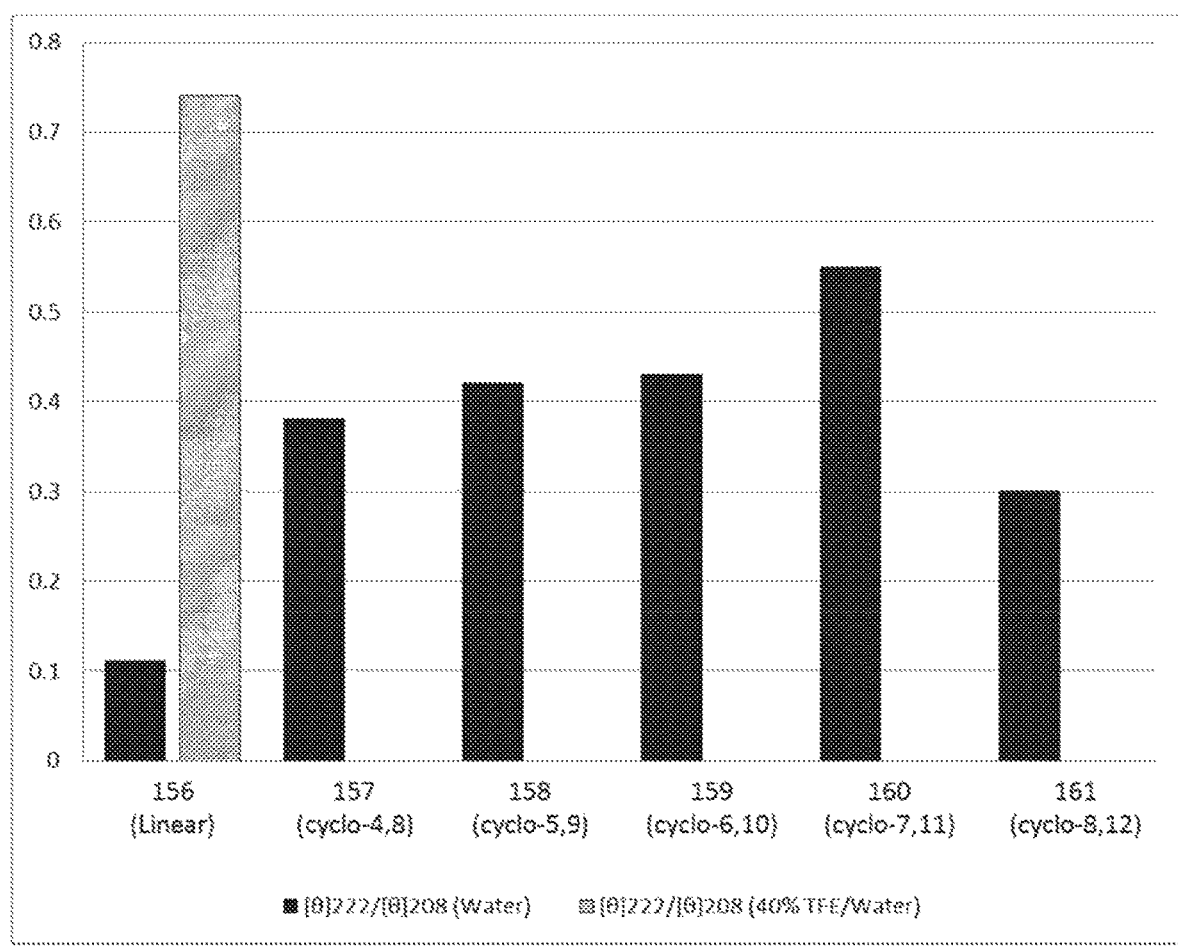

FIG. 12 shows the CD data for Ac-VSKLR-SQLVKRKQN-NH$_2$ (compound 132; SEQ ID NO: 2) and its cyclized derivatives. FIG. 13 shows the CD data for Ac-NLKQKIKHVVKLKDE-NH$_2$ (compound 156; SEQ ID NO: 4) and its cyclized derivatives.

Figure 23:
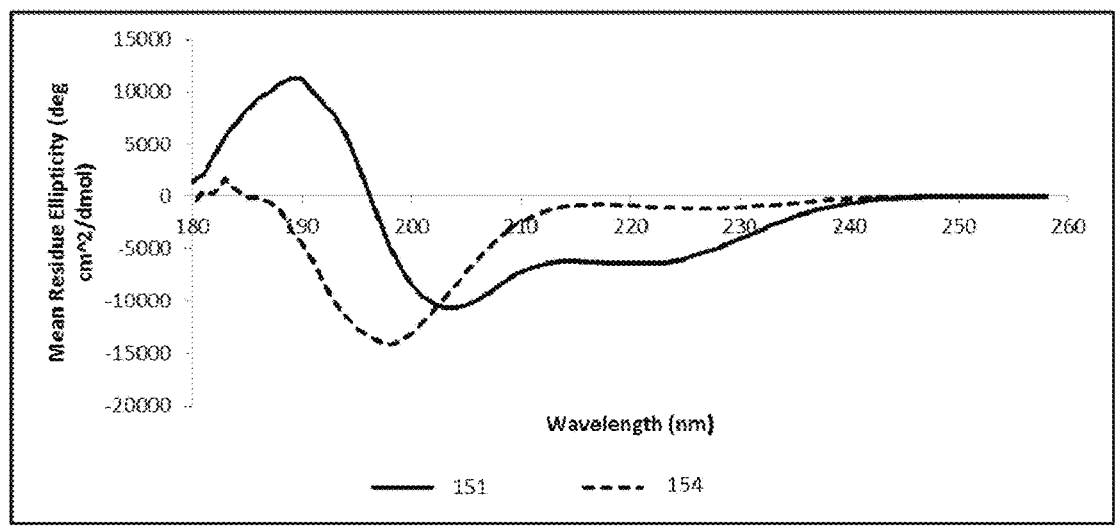
Figure 24:
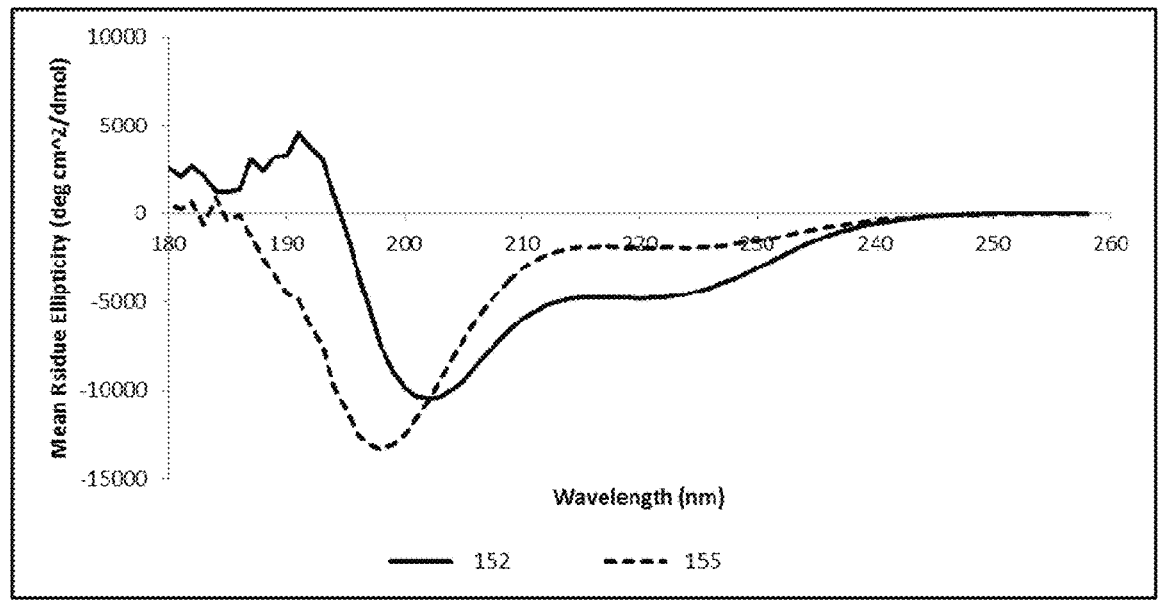
Figure 25:
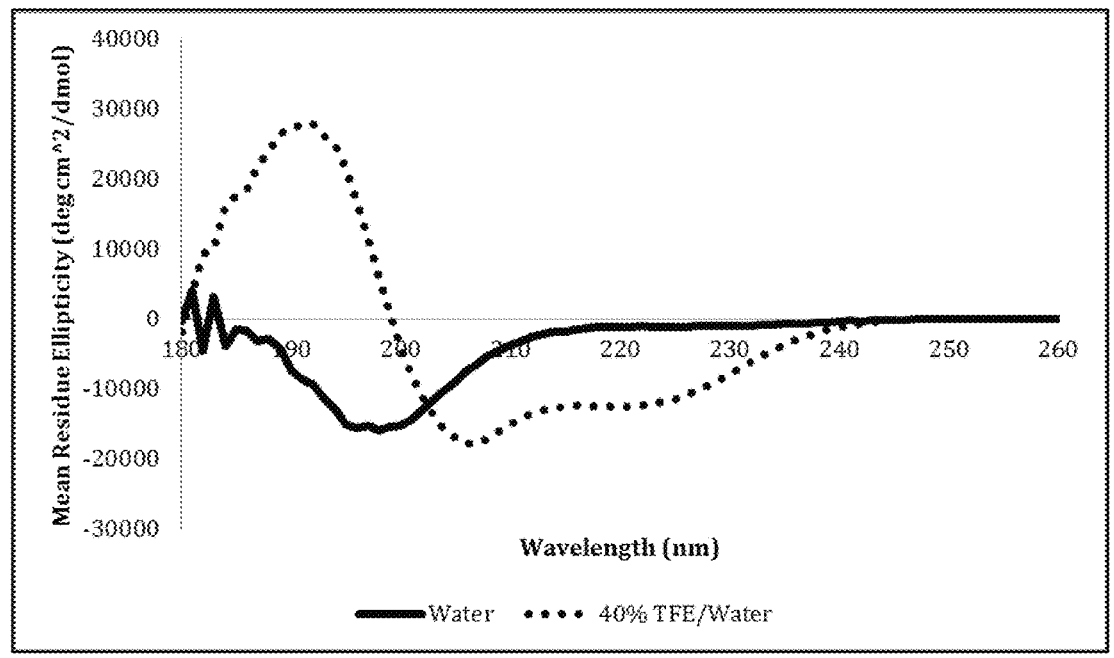
Figure 26:
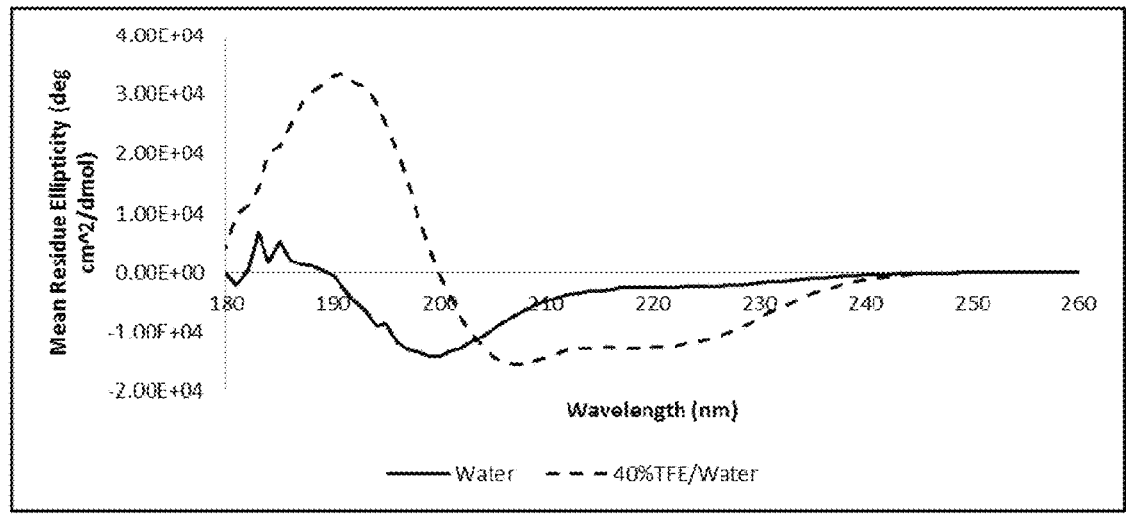
Figure 27:
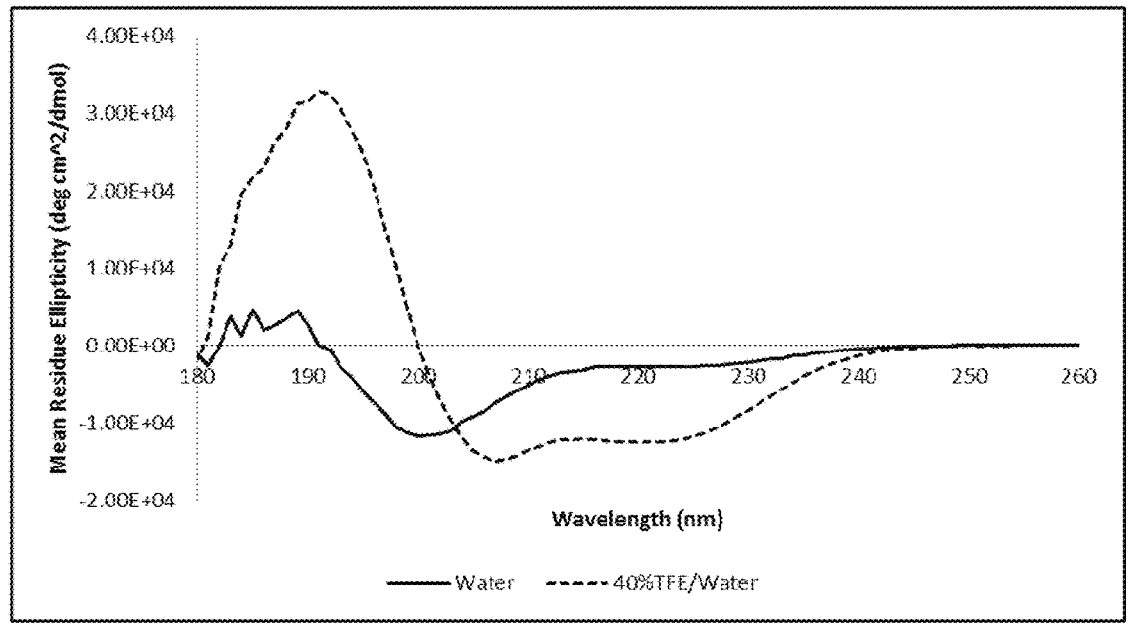
Figure 28:
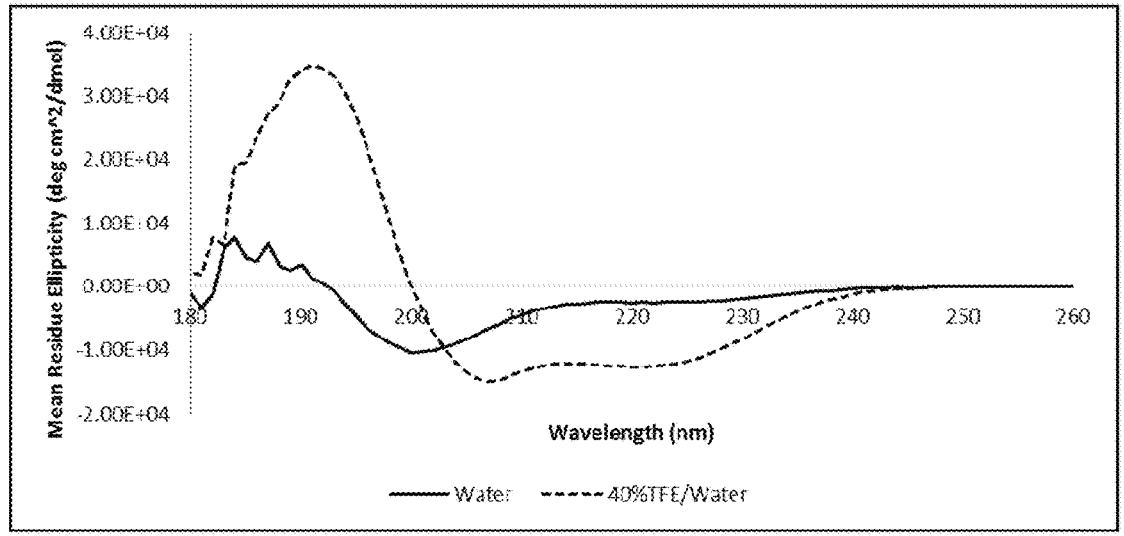
Figure 29:
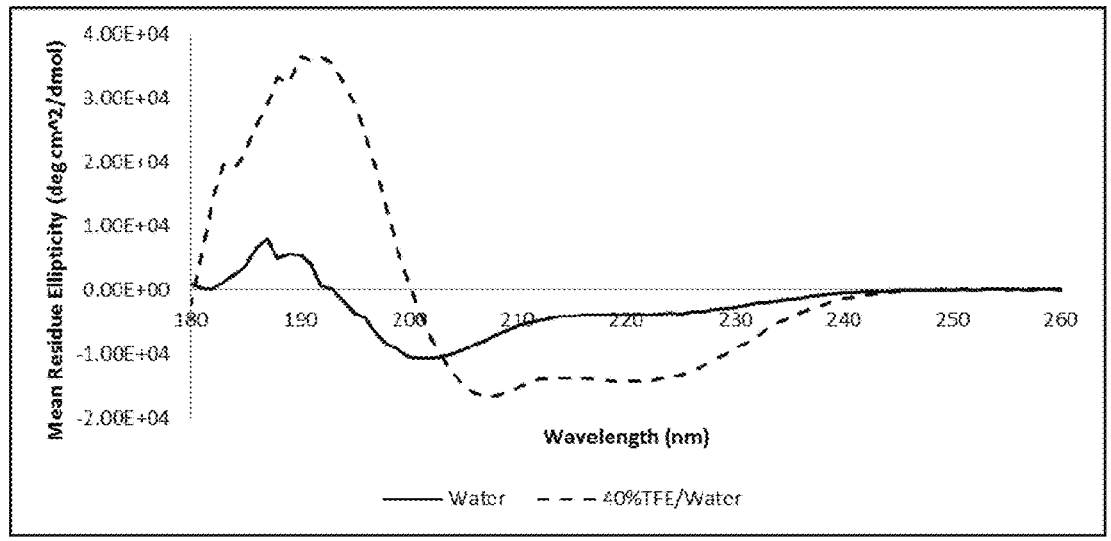
Figure 30:
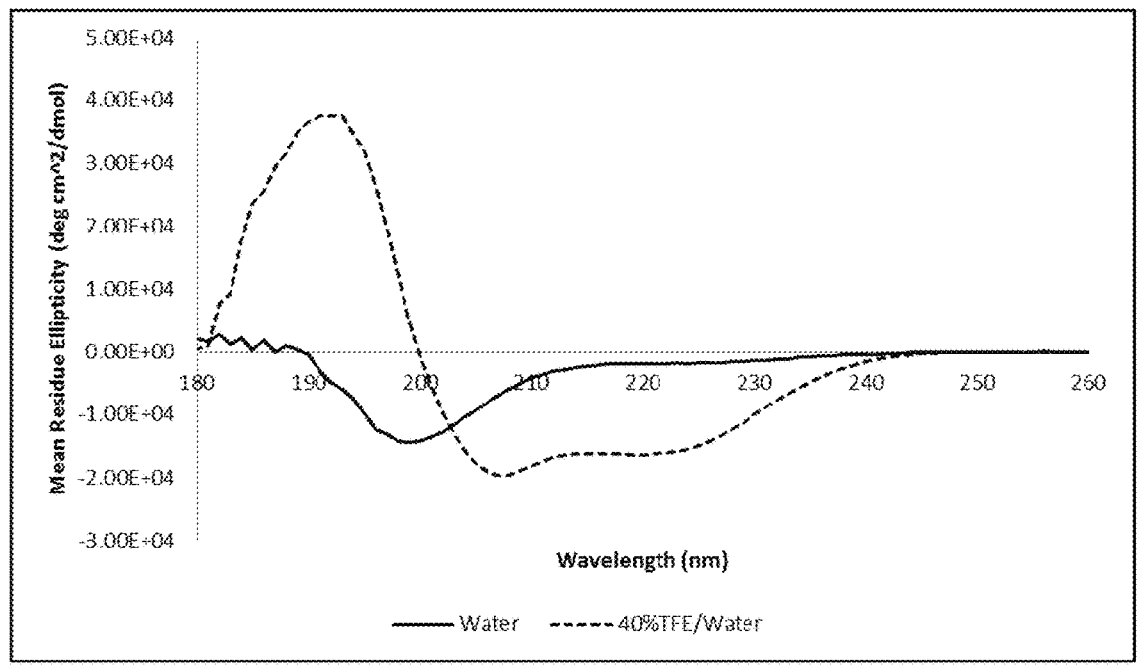
Figure 31:
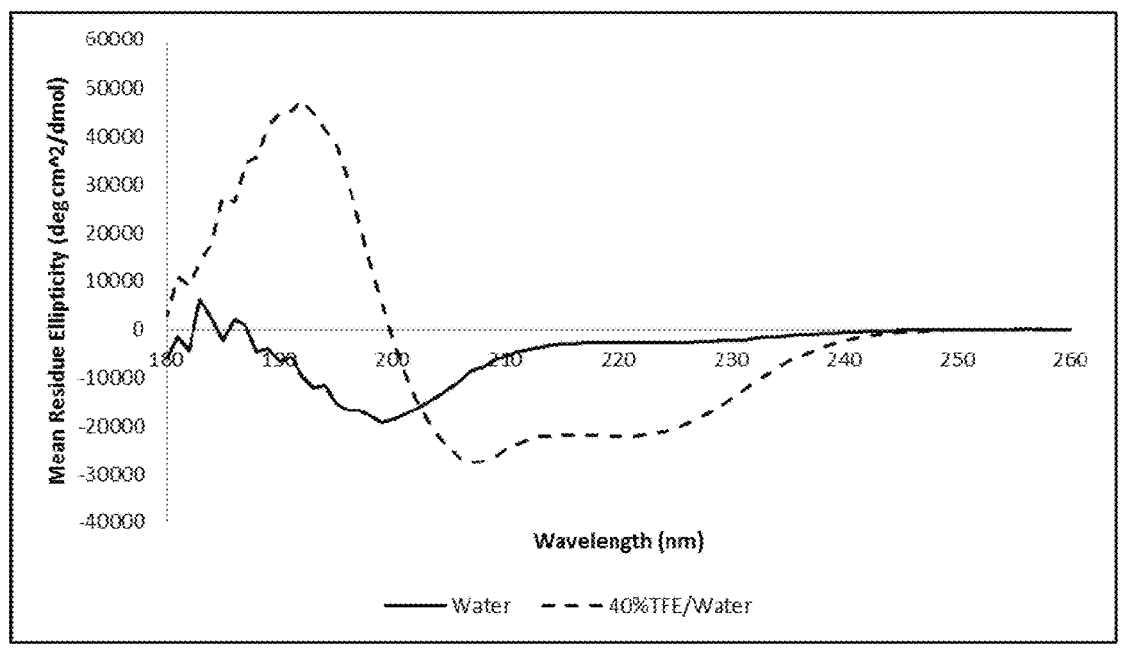
Figure 32:
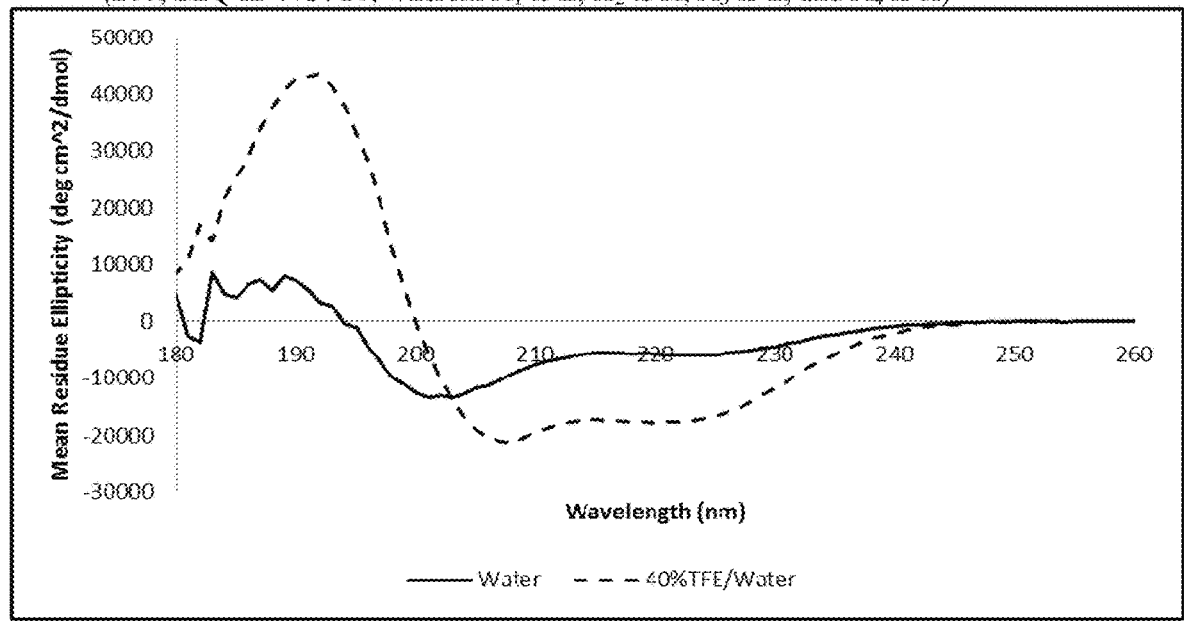
Figure 33:
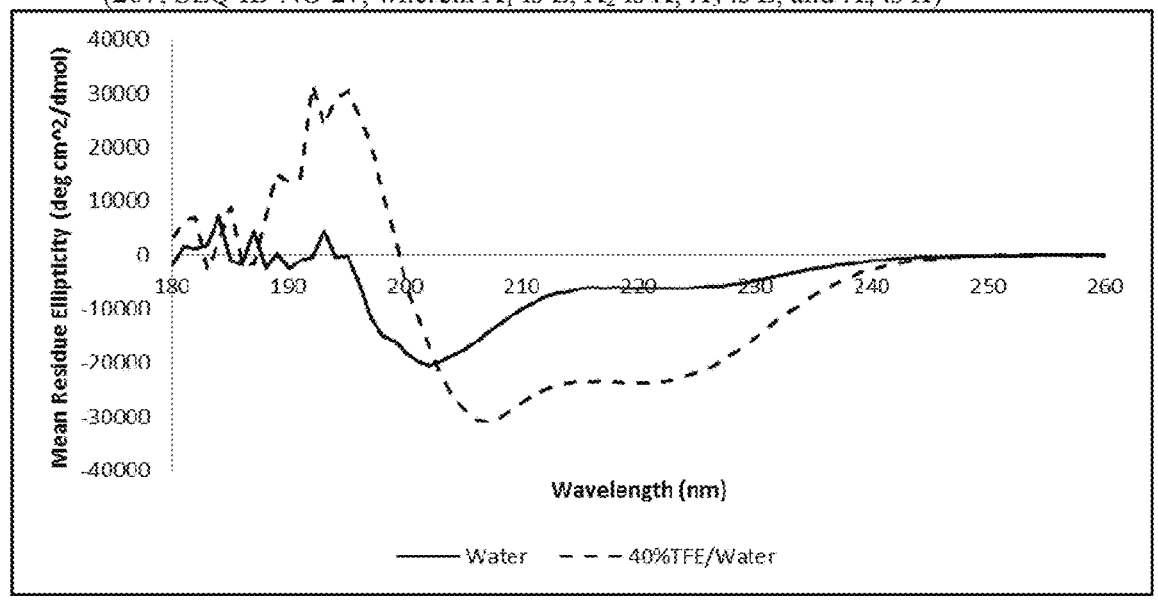
Figure 34:
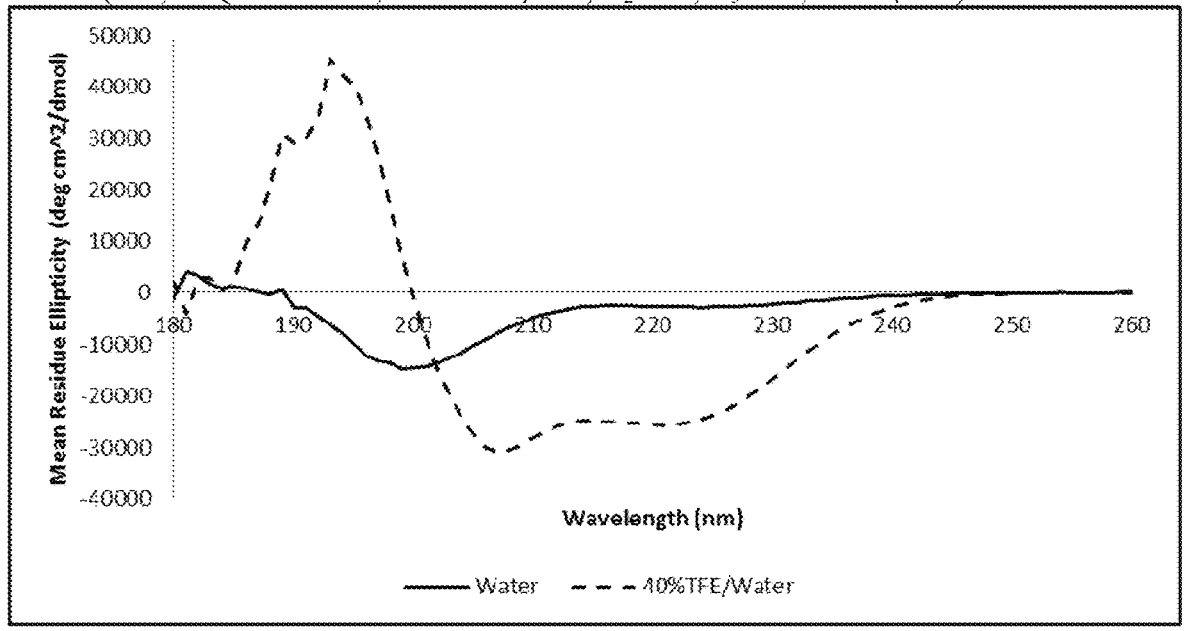
Figure 35:
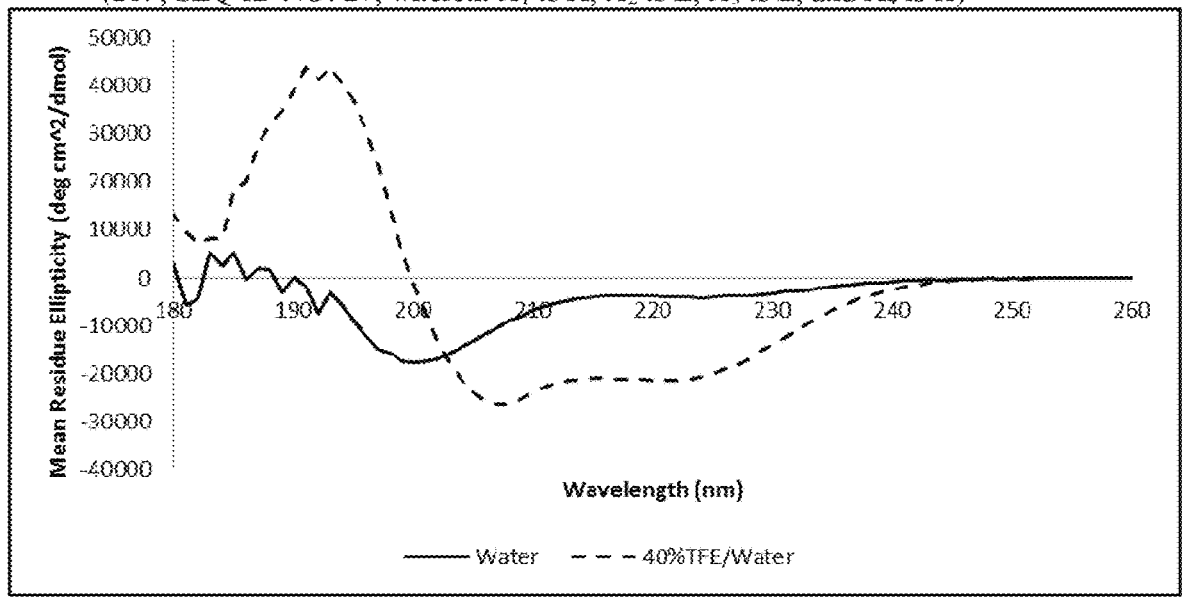
Figure 36:
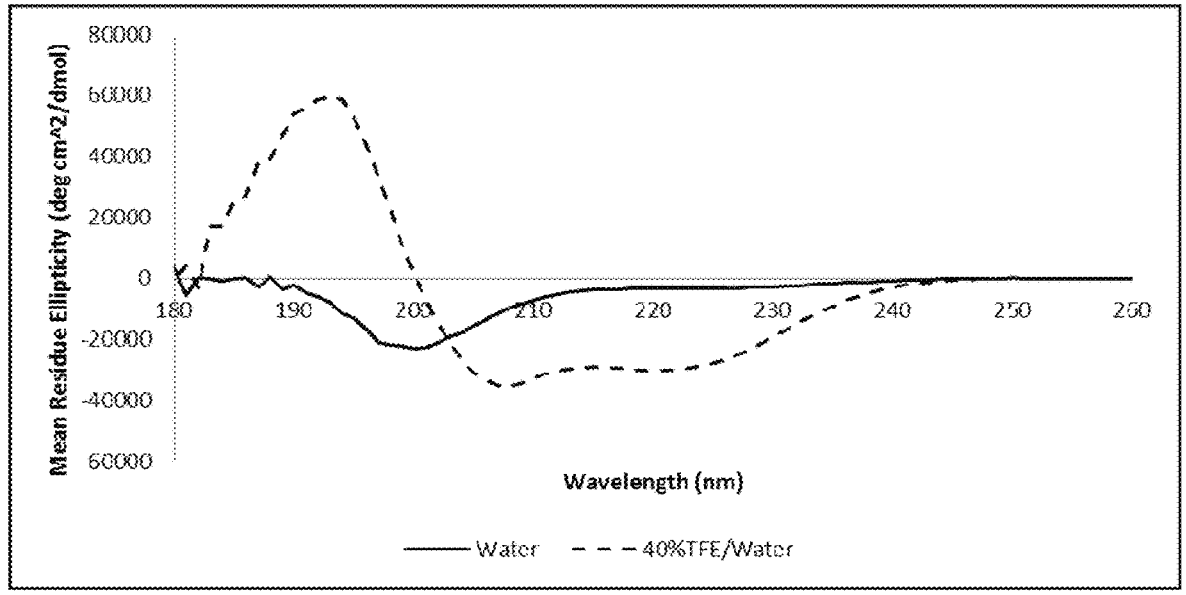
Figure 37:
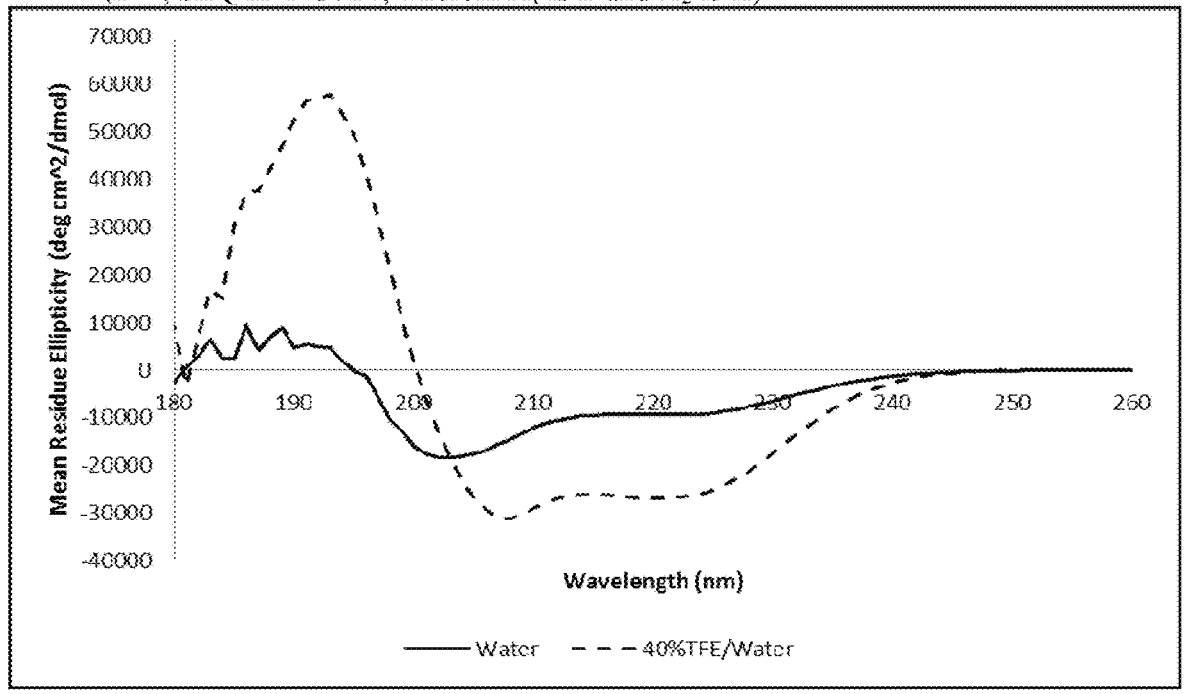
Figure 38:
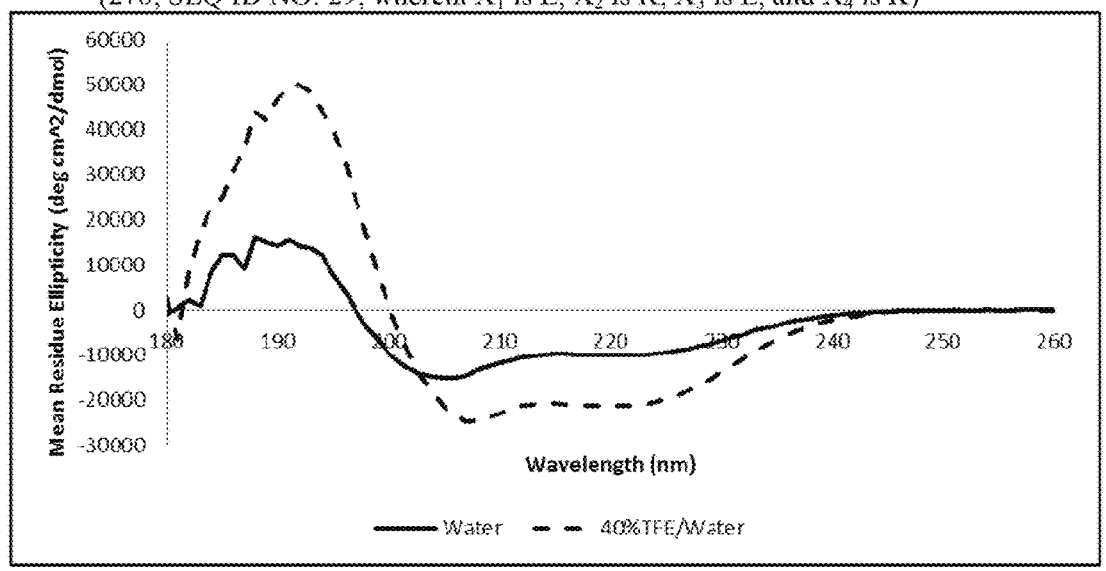

The CD spectra for each of compounds 132 and 150-155 in water and 40% TFE/water are provided in FIGS. 16-22. CD spectra comparing compounds 151 and 154 in water are provided in FIG. 23. CD spectra comparing compounds 152 and 155 in water are provided in FIG. 24. The CD spectra for each of compounds 156-161 in water are provided in FIGS. 25-30.

Table 10 provides sequences for a longer RHAMM fragment which includes most of HABD1 and all of HABD2 (KIKHVVKLKDENSQLKSEVSKLRSQLVKRK, SEQ ID NO: 5), and derivatives thereof in which two (i, i+4) staples were placed side-by-side. All sequences were amidated on the C-terminus and either acetylated or biotinylated on the N-terminus. Those peptides with a biotin group on the N-terminus included an AEEA spacer to separate the peptide sequence from the biotin molecule. "Reverse" peptides are peptides in which the staple includes a lysine at the i position and a glutamic acid residue at the i+4 position. Mass spectrometry data are provided for each of these peptides in Table 14 at the end of this example.

TABLE 10

| Binding Domain | | Compound No. (SEQ ID NO.*) | Sequence |
|---|---|---|---|
| HABD1 & HABD2 | Linear | 265 (5) | Ac-KIKHVVKLKDENSQLKSEVSKLRSQLVKRK-NH$_2$ |
| | | 270 (5) | Biotin-AEEA-KIKHVVKLKDENSQLKSEVSKLRSQLVKRK-NH$_2$ |
| | Cyclo-10-14, 15-19 | 266 (26) | Ac-(cyclo-10-14, cyclo-15-19)-KIKHVVKLK[EENSK][EKSEK]SKLRSQLVKRK-NH$_2$ |
| | | 271 (26) | Biotin-AEEA-(cyclo-10-14, cyclo-15-19)-KIKHVVKLK[EENSK][EKSEK]SKLRSQLVKRK-NH$_2$ |
| | Cyclo-11-15, 16-20 | 267 (27) | Ac-(cyclo-11-15, cyclo-16-20)-KIKHVVKLKD[ENSQK][ESEVK]KLRSQLVKRIK-NH$_2$ |
| | | 272 (27) | Biotin-AEEA-(cyclo-11-15, cyclo-16-20)-KIKHVVKLKD[ENSQK][ESEVK]KLRSQLVKRK-NH$_2$ |
| | Cyclo-10-14, Reverse Cyclo-15-19 | 268 (26) | Ac-(cyclo-10-14, cyclo-15-19)-KIKHVVKLK[EENSK][KKSEE]SKLRSQLVKRK-NH$_2$ |
| | | 273 (26) | Biotin-AEEA-(cyclo-10-14, cyclo-15-19)-KIKHVVKLK[EENSK][KKSEE]SKLRSQLVKRK-NH$_2$ |
| | Reverse Cyclo 10-14, Cyclo-15-19 | 269 (27) | Ac-(cyclo-10-14, cyclo-15-19)-KIKHVVKLK[KENSE][EKSEK]SKLRSQLVKRK-NH$_2$ |
| | | 274 (27) | Biotin-AEEA-(cyclo-10-14, cyclo-15-19)-KIKHVVKLK[KENSE][EKSEK]SKLRSQLVKRK-NH$_2$ |

*Each of the peptides of SEQ ID NO: 26 and 27 include substitutions at $X_1$ and $X_2$ positions with glutamic acid or lysine residues as shown in the sequences provided in the table.

Table 11 provides sequences for a longer RHAMM fragment which includes the entirety of both HABD1 and HABD2 (NLKQKIKHVVKLKDENSQLKSEVSKLRSQLVKRKQN, SEQ ID NO: 6) and derivatives thereof in which either HABD1, HABD2, or both were stapled. All sequences were amidated on the C-terminus and either acetylated or biotinylated on the N-terminus. Those peptides with a biotin group on the N-terminus included an AEEA spacer to separate the peptide sequence from the biotin molecule. Mass spectrometry data are provided for each of these peptides in Table 14 at the end of this example.

TABLE 11

| Binding Domain | | Compound No. (SEQ ID NO.*) | Sequence |
|---|---|---|---|
| | Linear | 275 (6) | Ac-NLKQKIKHVVKLKDENSQLKSEVSKLRSQLVKRKQN-NH$_2$ |
| | | 279 (6) | Biotin-AEEA--NLKQKIKHVVKLKDENSQLKSEVSKLRSQLVKRKQN-NH$_2$ |
| HABD2 | Cyclo-28-32 | 277 (28) | Ac-(cyclo-28-32)-NLKQKIKHVVKLKDENSQLKSEVSKLR[EQLVK]RKQN-NH$_2$ |
| | | 281 (28) | Biotin-AEEA-(cyclo-28-32)-NLKQKIKHVVKLKDENSQLKSEVSKLR[EQLVK]RKQN-NH$_2$ |
| HABD1 & HABD2 | Cyclo-7-11, 28-32 | 278 (29) | Ac-(cyclo-7-11, cyclo-28-32)-NLKQKI[EHVVK]LKDENSQLKSEVSKLR[EQLVK]RKQN-NH$_2$ |
| | | 282 (29) | Biotin-AEEA-(cyclo-7-11, cyclo-28-32)-NLKQKI[EHVVK]LKDENSQLKSEVSKLR[EQLVK]RKQN-NH$_2$ |

*Each of the peptides of SEQ ID NO: 28 and 29 include substitutions at $X_1$ and $X_2$ positions with glutamic acid or lysine residues as shown in the sequences provided in the table.

CD data for linear peptides having the sequences KIKHVVKLKDENSQLKSEVSKLRSQLVKRK (SEQ ID NO: 5) and NLKQKIKHVVKLKDENSQLKSEVSKLRSQLVKRKQN (SEQ ID NO: 6) and cyclized derivatives thereof in water or 40% TFE/water are provided below in Tables 12 (water) and 13 (40% TFE/water). Tables 12 and 13 provide the mean residue ellipticity ([0] deg cm$^2$ dmol$^{-1}$) at $\lambda$=222 and 208 nm for each peptide and ratios of ellipticities at 222/208. Each of the peptides was acetylated at its amino terminus and amidated at its carboxy terminus.

TABLE 12

| Compound Number (SEQ ID NO.*) | Sequence | [θ]222 | [θ]208 | [θ]222/[θ]208 |
|---|---|---|---|---|
| 265 (5) | Ac-KIKHVVKLKDENSQLKSEVSKLRSQLVKRK-NH$_2$ | -1.09E+04 | -2.73E+04 | 0.40 |
| 266 (26) | Ac-(cyclo-10-14, cyclo-15-19)-KIKHVVKLK[EENSK][EKSEK]SKLRSQLVKRK-NH$_2$ | -5.89E+03 | -9.36E+03 | 0.63 |
| 267 (27) | Ac-(cyclo-11-15, cyclo-16-20)-KIKHVVKLKD[ENSQK][ESEVK]KLRSQLVKRK-NH$_2$ | -6.14E+03 | -1.29E+04 | 0.48 |
| 268 (26) | Ac-(cyclo-10-14, cyclo-15-19)-KIKHVVKLK[EENSK][KKSEE]SKLRSQLVKRK-NH$_2$ | -2.71E+03 | -6.74E+03 | 0.40 |
| 269 (27) | Ac-(cyclo-10-14, cyclo-15-19)-KIKHVVKLK[KENSE][EKSEK]SKLRSQLVKRK-NH$_2$ | -3.99E+03 | -9.04E+03 | 0.44 |
| 275 (6) | Ac-NLKQKIKHVVKLKDENSQLKSEVSKLRSQLVKRKQN-NH$_2$ | -3.35E+03 | -9.71E+03 | 0.35 |
| 277 (28) | Ac-(cyclo-28-32)-NLKQKIKHVVKLKDENSQLKSEVSKLR[EQLVK]RKQN-NH$_2$ | -9.36E+03 | -1.46E+04 | 0.64 |
| 278 (29) | Ac-(cyclo-7-11, cyclo-28-32)-NLKQKI[EHVVK]LKDENSQLKSEVSKLR[EQLVK]RKQN-NH$_2$ | -9.95E+03 | -1.33E+04 | 0.74 |

*Each of the peptides of SEQ ID NO: 26, 27, 28 and 29 include substitutions at $X_1$ and $X_2$ positions with glutamic acid or lysine residues as shown in the sequences provided in the table.

TABLE 13

| Compound Number (SEQ ID NO.*) | Sequence | [θ]222 | [θ]208 | [θ]222/[θ]208 |
|---|---|---|---|---|
| 265 (5) | Ac-KIKHVVKLKDENSQLKSEVSKLRSQLVKRK-NH$_2$ | -2.18E04 | -2.72E04 | 0.80 |
| 266 (26) | Ac-(cyclo-10-14, cyclo-15-19)-KIKHVVKLK[EENSK][EKSEK]SKLRSQLVKRK-NH$_2$ | -1.77E04 | -2.11E04 | 0.84 |
| 267 (27) | Ac-(cyclo-11-15, cyclo-16-20)-KIKHVVKLKD[ENSQK][ESEVK]KLRSQLVKRK-NH$_2$ | -2.34E04 | -3.02E04 | 0.77 |
| 268 (26) | Ac-(cyclo-10-14, cyclo-15-19)-KIKHVVKLK[EENSK][KKSEE]SKLRSQLVKRK-NH$_2$ | -2.54E04 | -.304E04 | 0.83 |
| 269 (27) | Ac-(cyclo-10-14, cyclo-15-19)-KIKHVVKLK[KENSE][EKSEL]KLRSQLVKRK-NH$_2$ | -2.14E04 | -2.65E04 | 0.81 |
| 275 (6) | Ac-NLKQKIKHVVKLKDENSQLKSEVSKLRSQLVKRKQN-NH$_2$ | -2.96E04 | -3.52E04 | 0.83 |
| 277 (28) | Ac-(cyclo-28-32)-NLKQKIKHVVKLKDENSQLKSEVSKLR[EQLVK]RKQN-NH$_2$ | -2.65E04 | -3.10E04 | 0.85 |
| 278 (29) | Ac-(cyclo-7-11, cyclo-28-32)-NLKQKI[EHVVK]LKDENSQLKSEVSKLR[EQLVK]RKQN-NH$_2$ | -2.12E04 | -2.44E04 | 0.86 |

*Each of the peptides of SEQ ID NO: 26, 27, 28 and 29 include substitutions at $X_1$ and $X_2$ positions with glutamic acid or lysine residues as shown in the sequences provided in tlic table.

Figure 14:
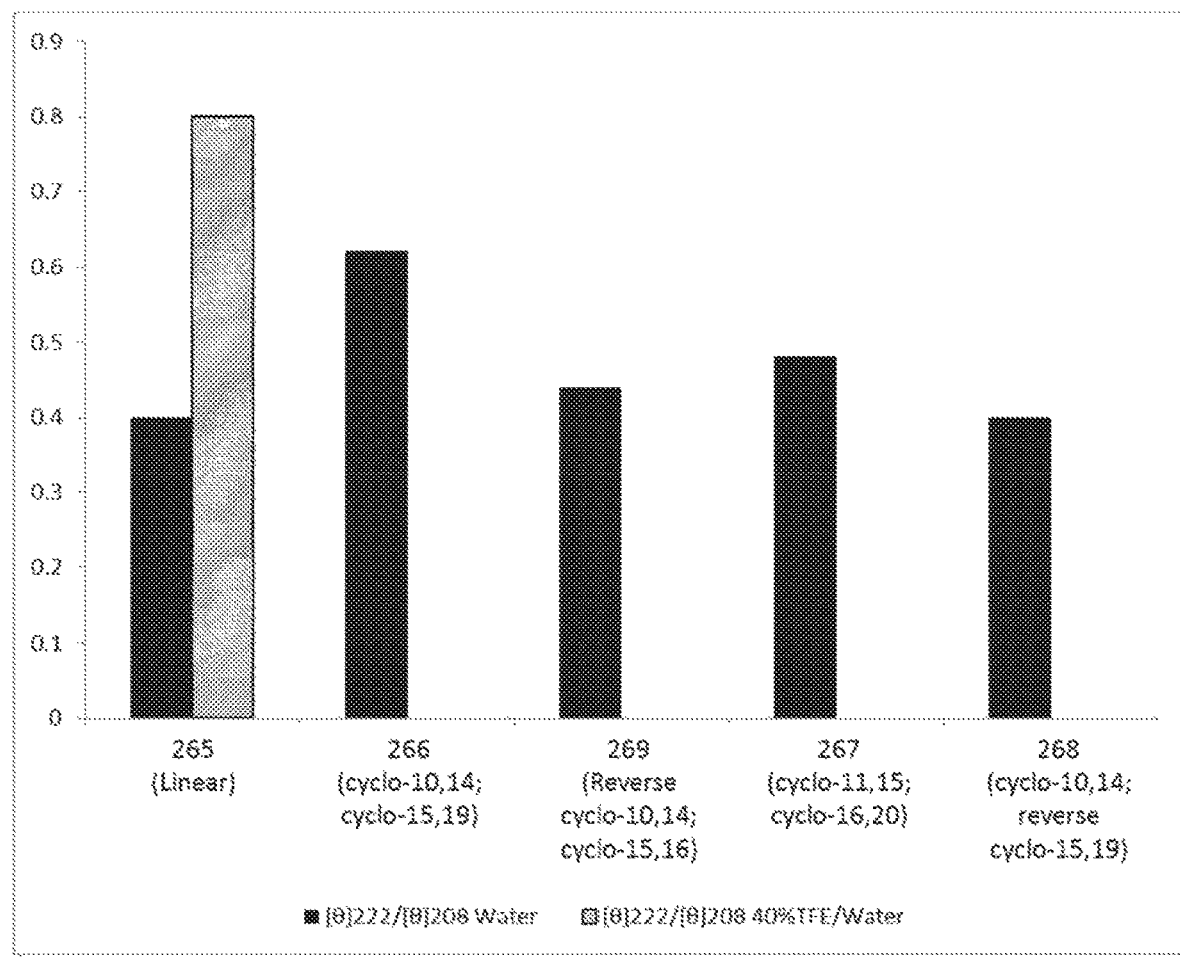
Figure 15:
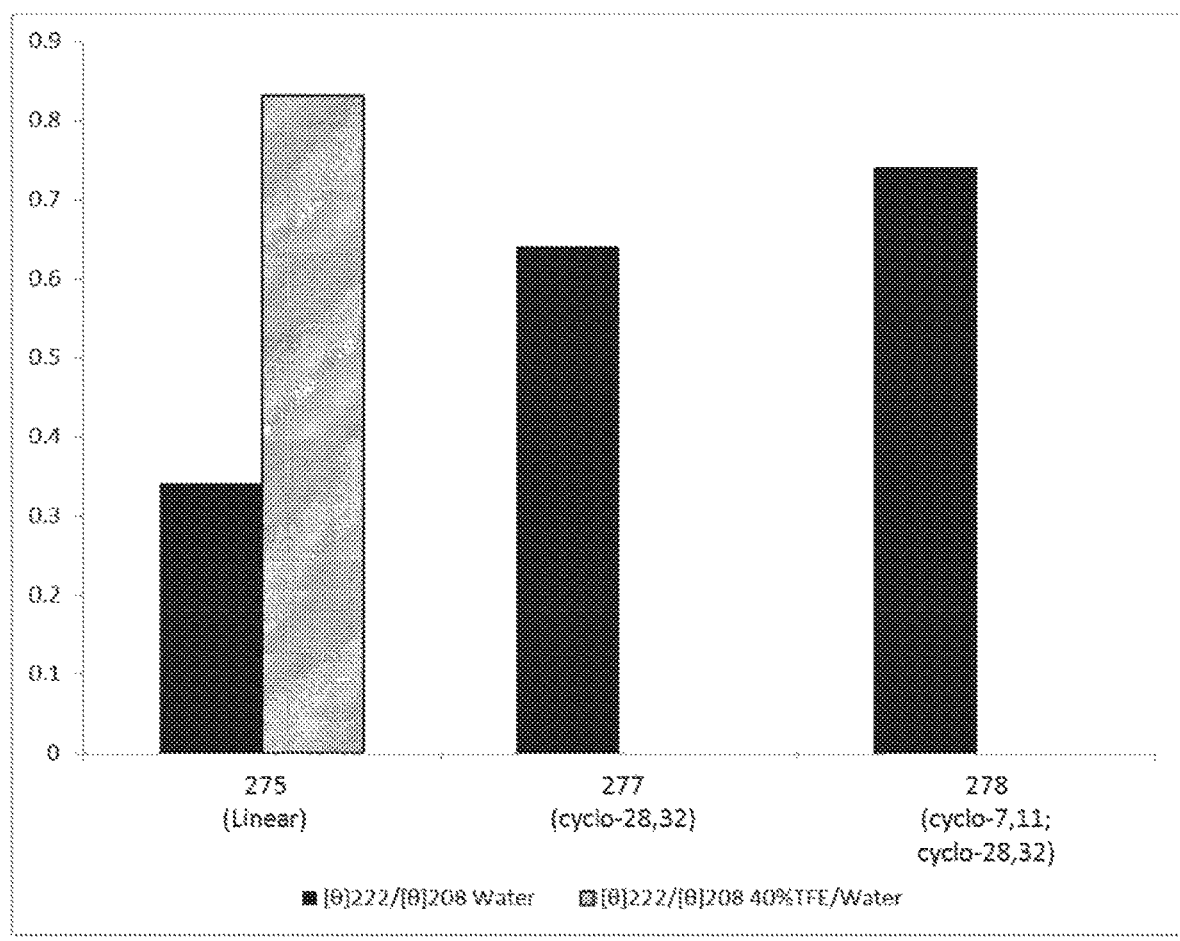
Figure 16:
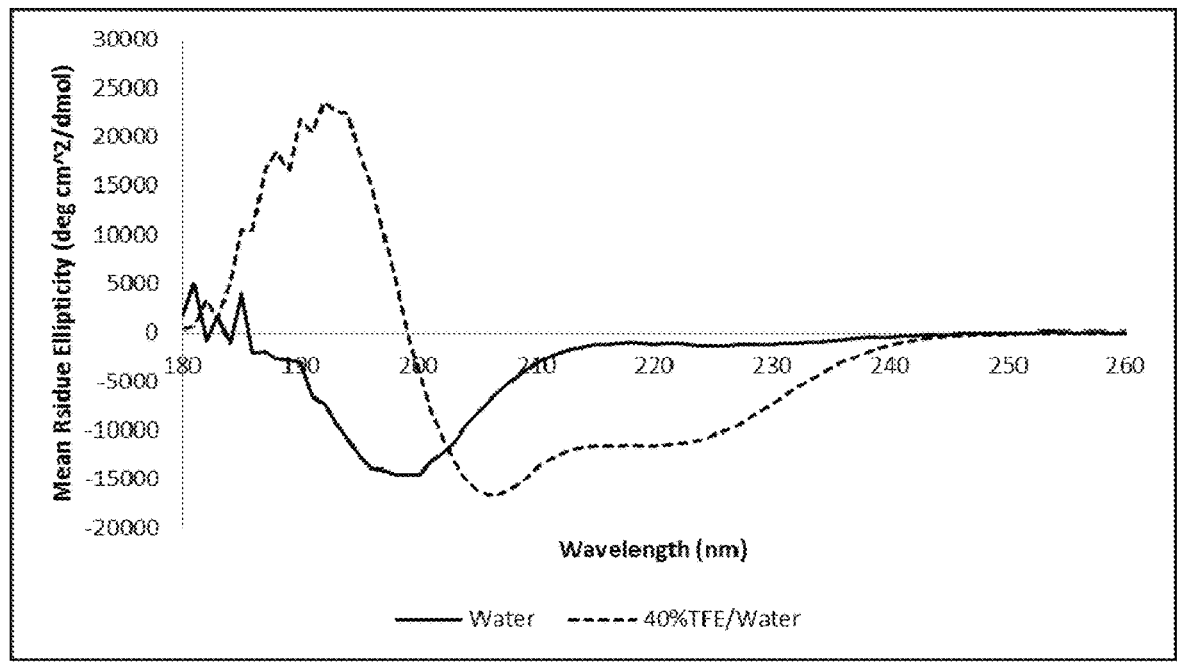
FIGS. 16-38 provide illustrative CD spectra for linear and cyclized peptides.
Figure 17:
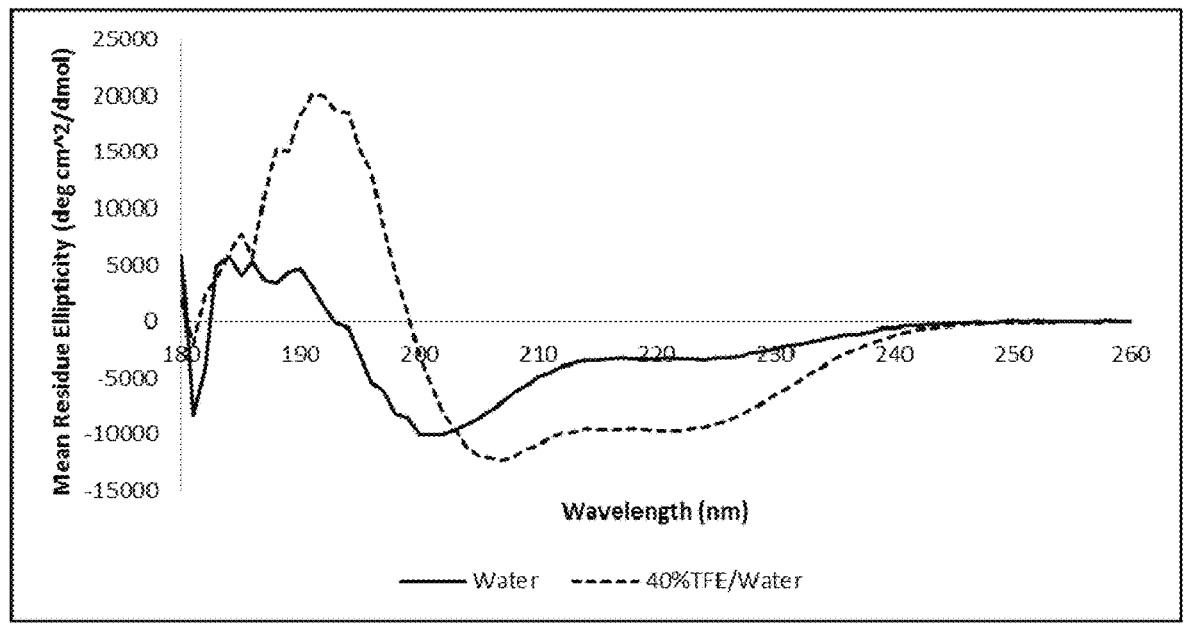
Figure 18:
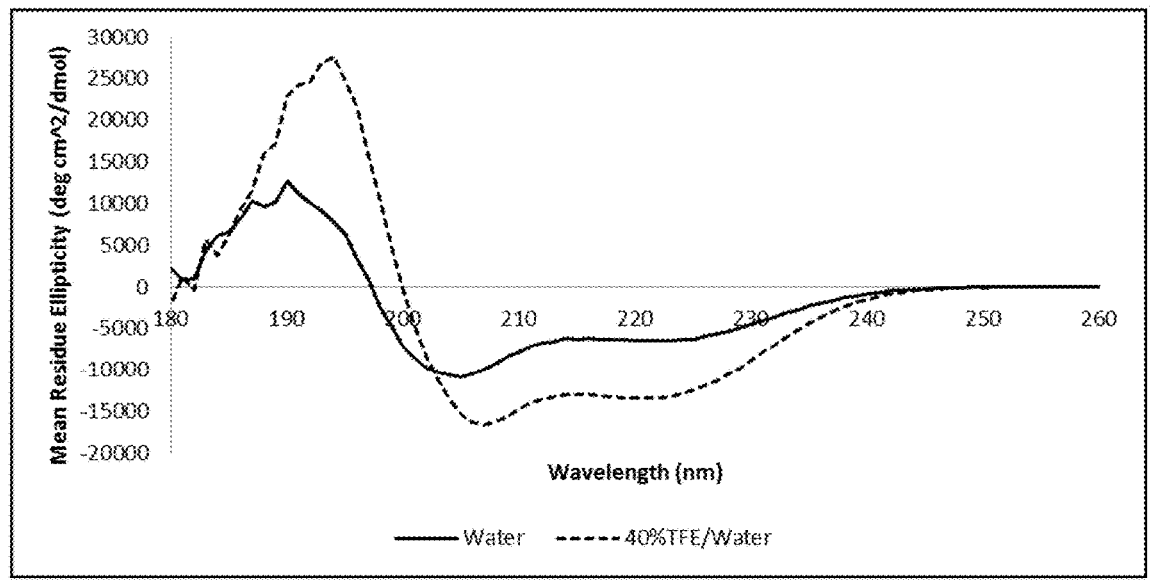
Figure 19:
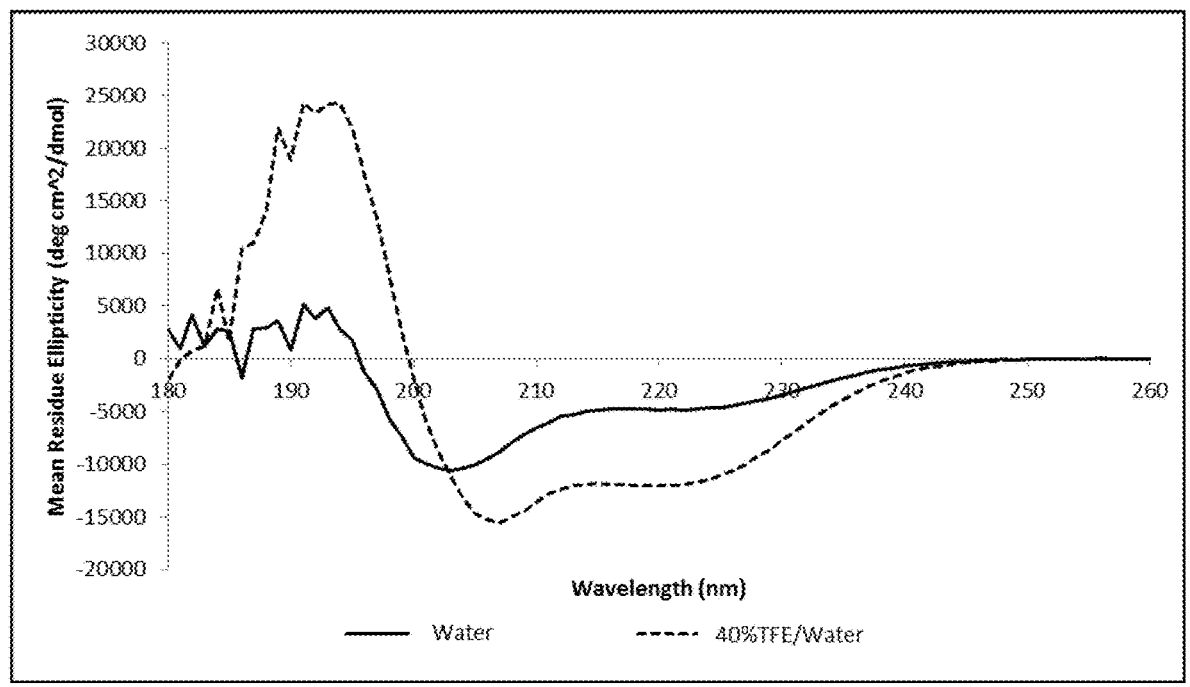
Figure 20:
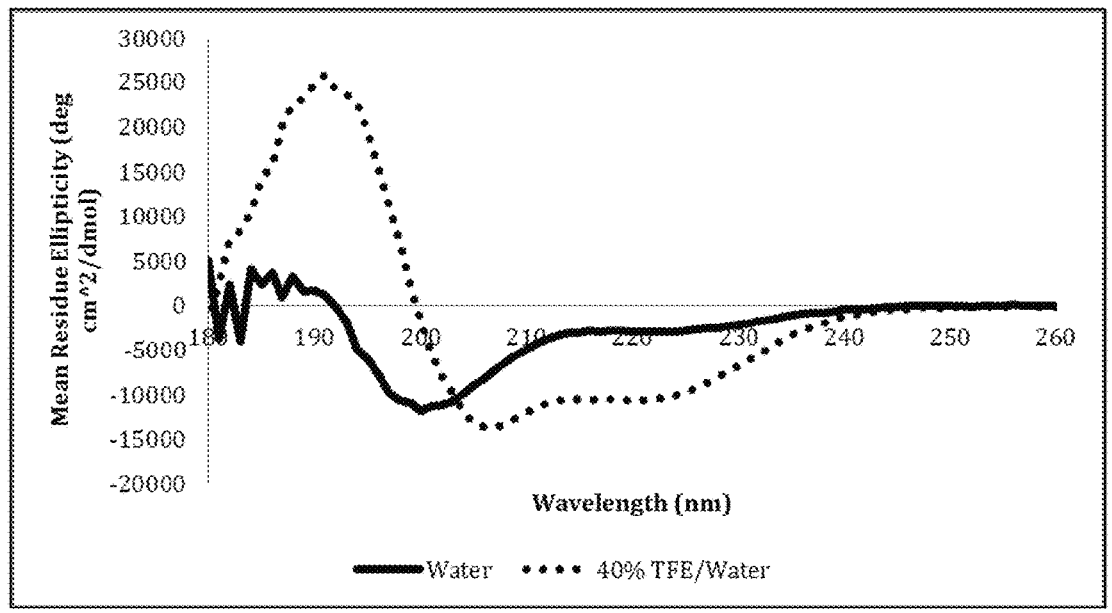
Figure 21:
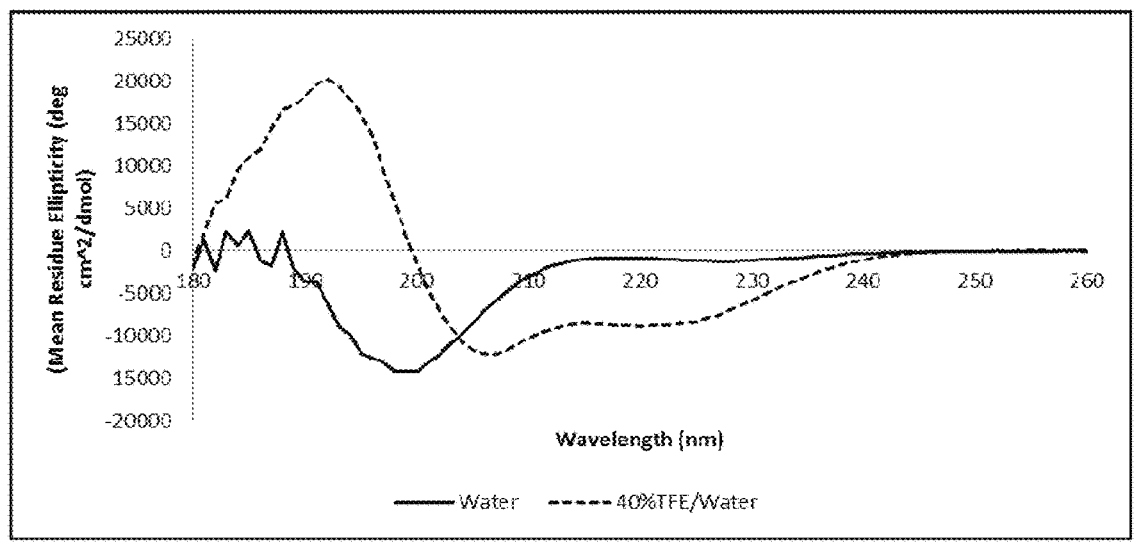
Figure 22:
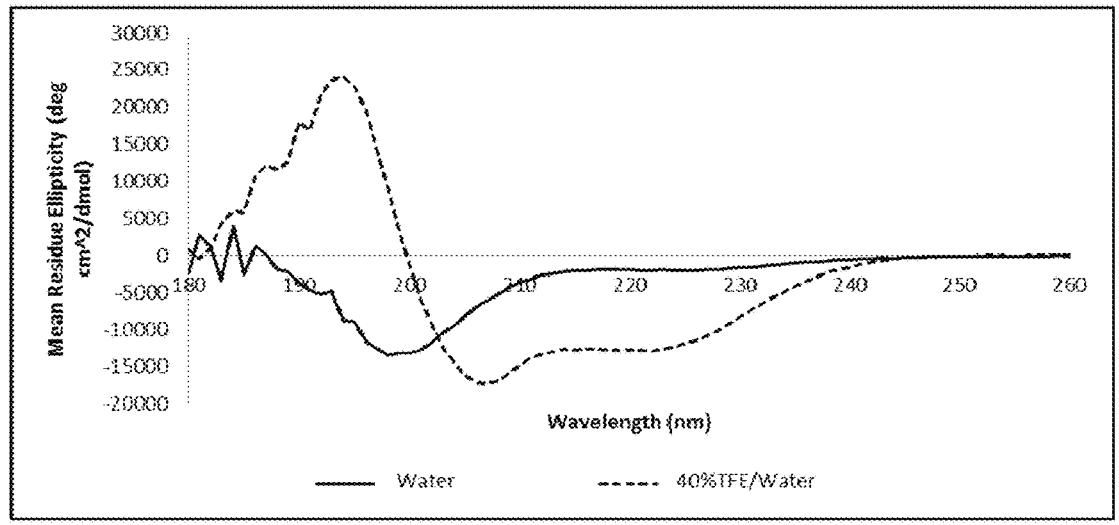

FIG. 14 shows the CD data for Ac-KIKHVVKLKDENSQLKSEVSKLRSQLVKRK-NH$_2$ (compound 265; SEQ ID NO: 5) and its cyclized derivatives. FIG. 15 shows the CD data for Ac-NLKQKIKHVVKLKDENSQLKSEVSKLRSQLVKRKQN-NH$_2$ (compound 275; SEQ ID NO: 6) and its cyclized derivatives.

The CD spectra for each of compounds 265-269, 275 and 277-278 in water are provided in FIGS. 31-38.

Discussion

Circular Dichroism (CD) spectroscopy is a tool that is used to study the secondary structure characteristics of a compound. Peptides and proteins can fold into organized structures, such as alpha helices and beta sheets, which are the result of complex hydrogen bonding and other interactions between amino acid side chains, as well as adopt a random coil formation, which lacks much of the organization of the other two structures. The CD spectrum of an alpha helix is characterized by two local minima at 208 nm and 222 nm. The ratio of the values of the molar ellipticities at these wavelengths ([θ]222/[θ]208) is a strong indication of the relative helicity of a compound; a compound is more helical when the ratio of these two values approaches 1.0. Synthetic constraints introduced to the peptide backbone can force a peptide chain to increase its helical character. These constraints can be introduced by staples, of varying types, which allow cyclization of the peptide backbone to take place.

RHAMM is known to have two binding domains for the polysaccharide hyaluronan (HA), both of which are predicted to have alpha helical character. However, truncation of these two regions to include only the sequence of each binding domain results in significant loss of alpha helical character when dissolved in water and studied by CD spectroscopy. The short linear RHAMM fragments investigated here, compounds 132 and 156, have nominal alpha helical character in water (Table 8, FIGS. 12-13). However, specific solvents, such as trifluoroethanol (TFE), can be used as co-solvents in CD spectroscopy, as they act by stabilizing the secondary structure of peptides and proteins in solution. Table 9 and FIGS. 12-13 summarize the effect of a 40% TFE/water solution on secondary structure of the fragmented linear RHAMM binding domains. The increase in the value of [θ]222/[θ]208 for compounds 132 and 156 from 0.23 to 0.72 and 0.11 to 0.74, respectively, suggests that these compounds have inherent alpha-helical properties, such as when they are part of a larger protein. In addition, the increase in molar ellipticity when the linear fragments are dissolved in a TFE/water mixture indicates the maximal helicity that each compound is capable of having.

In order to study the effect of stapling the peptide backbone on alpha-helicity, a (i, i+4) staple scan was performed on each of the peptide fragments. The staple scan excluded those residues believed to be important for HA-binding, which include specific Lys residues that make up the BX$_7$B binding motif of each binding domain. It was found that the peptides with the staples located closest to the center of the peptide, and away from either terminus, resulted in the highest degree of alpha helical character (Table 8, FIGS. 12-13). Notably, compound 151 resulted in a [θ]222/[θ]208 value of 0.70 in water, which is only slightly less helical than the maximum helicity of linear peptide, 132, in a 40% TFE/water solution, which produced a value of 0.72. Thus, by synthetically cyclizing the backbone of these peptide fragments at specific positions within the peptide sequence, it is possible to increase the helicity of the short peptide sequence to the maximum helicity as observed in the presence of a structure-stabilizing solvent, such as TFE.

In addition to the two HA-binding domains of RHAMM studied individually, longer RHAMM fragments were investigated. These included 30-mer peptides, in which two (i, i+4) staples were placed side-by-side in the coiled region between HABD1 and HABD2, as well as 36-mer peptides, which incorporated the staple positions that were found to produce the most helicity in the two binding domains alone. The linear peptide in both groups appeared to have greater alpha-helical character than the shorter linear peptide of each HA-binding domain alone, as seen by their higher [θ]222/[θ]208 values. This can be attributed to the longer peptide chain adopting some secondary structure, while those peptides that have suffered further truncation are too short in length to fold accordingly. In addition, contrary to the results of the shorter fragments, the stapled peptides with two staples positioned side-by-side of one another did not appear to improve helicity greatly compared to their linear counterpart; however, compound 266 showed a slight improvement in helicity from a [θ]222/[θ]208 value of 0.40 to 0.63. When the two adjacent staples were moved over by one residue producing compound 267, the [θ]222/[θ]208 value dropped to 0.48, which is an insubstantial improvement over the linear peptide. This suggests that compound 266 has some characteristics that may be important for secondary structure stabilization, such as the Lys residue that remains intact but has been removed in compound 267. On the other hand, the longer peptides that include staples at those positions that were determined to yield the highest degree of helicity in each binding domain alone showed greater improvement in the recovery of secondary structure by comparison to the linear peptide (Table 12, FIG. 15). Interestingly, when staples are placed in both HABD1 and HABD2 coincidentally, as in 278, the ensuing peptide produces a [θ]222/[θ]208 value of 0.74, suggesting that it has the greatest alpha-helical character of all of the peptides investigated, including those shorter fragments from which the staple positions were taken.

Alpha-helical character of a peptide depends on several factors, including peptide length, where longer peptides have greater helicity than truncated peptides, and amino acid sequence that produces natural helicity. It has also been proposed that specific residues, leucine and glutamine, have helix-stabilizing characteristics, and therefore, induce greater helicity. [21] This is observed in the shorter RHAMM fragments, where those peptides with the highest degree of alpha-helical character did not replace a Leu or Gln residue at either the i or (i+4) position, while those peptides where at least one Leu or Gln was replaced in order to create the staple had decreased helicity, such as in the cases of 157 and 161 in HABD1 and 150 and 153 in HABD2. In addition, it has been reported that a peptide's helicity depends on the order in which the Glu and Lys involved in forming the staple are placed within a peptide's sequence; maximum helicity is formed when Glu is in the i position and Lys is in the (i+4) position.[22] This was observed with all of the peptides that were studied. Those peptides that reversed the order of Glu and Lys residues for cyclization had significant loss of alpha-helical character and had [θ]222/[θ]208 values that were the same as or negligibly higher than their linear counterparts.

TABLE 14

Mass spectrometry data

| Compound No. (SEQ ID NO.*) | Sequence | Purity | Calculated | Found |
|---|---|---|---|---|
| 132 (2) | Ac-VSKLRSQLVKRKQN-NH$_2$ | >95% | $[M + 2H]^{2+}$ = 863.75<br>$[M + 3H]^{3+}$ = 575.95 | $[M + 2H]^{2+}$ = 863.69<br>$[M + 3H]^{3+}$ = 575.97 |

TABLE 14-continued

Mass spectrometry data

| Compound No. (SEQ ID NO.*) | Sequence | Purity | MS (ESI+) Calculated | Found |
|---|---|---|---|---|
| 133 (7) | H-(cyclo-4,8)-VSK[ERSQK]VKRKQN-NH$_2$ | >99% | [M + 3H]$^{3+}$ = 566.00<br>[M + 4H]$^{4+}$ = 424.75 | [M + 3H]$^{3+}$ = 566.04<br>[M + 4H]$^{4+}$ = 424.78 |
| 134 (8) | H-(cyclo-5,9)-VSKL[ESQLK]KRKON-NH$_2$ | >99% | [M + 3H]$^{3+}$ = 556.33<br>[M + 4H]$^{4+}$ = 417.49 | [M + 3H]$^{3+}$ = 556.36<br>[M + 4H]$^{4+}$ = 417.52 |
| 135 (9) | H-(cyclo-6,10)-VSKLR[EQLVK]RKQN-NH$_2$ | >98% | [M + 3H]$^{3+}$ = 569.68<br>[M + 4H]$^{4+}$ = 427.51 | [M + 3H]$^{3+}$ = 569.08<br>[M + 4H]$^{4+}$ = 427.06 |
| 136 (10) | H-(cyclo-7,11)-VSKLRS[ELVKK]KQN-NH$_2$ | >99% | [M + 3H]$^{3+}$ = 546.67<br>[M + 4H]$^{4+}$ = 410.25 | [M + 3H]$^{3+}$ = 546.63<br>[M + 4H]$^{4+}$ = 410.22 |
| 150 (7) | Ac-(cyclo-4,8)-VSK[ERSQK]VKRKQN-NH$_2$ | >99% | [M + 2H]$^{2+}$ = 869.89<br>[M + 3H]$^{3+}$ = 580.33 | [M + 2H]$^{2+}$ = 869.94<br>[M + 3H]$^{3+}$ = 580.22 |
| 151 (8) | Ac-(cyclo-5,9)-VSKL[ESQLK]KRKQN-NH$_2$ | >95% | [M + 2H]$^{2+}$ = 855.43<br>[M + 3H]$^{3+}$ = 570.62 | [M + 2H]$^{2+}$ = 855.51<br>[M + 3H]$^{3+}$ = 570.71 |
| 152 (9) | Ac-(cyclo-6,10)-VSKLR[EQLVK]RKQN-NH$_2$ | >95% | [M + 2H]$^{2+}$ = 876.10<br>[M + 3H]$^{3+}$ = 583.91 | [M + 2H]$^{2+}$ = 876.06<br>[M + 3H]$^{3+}$ = 583.95 |
| 153 (10) | Ac-(cyclo-7,11)-VSKLRS[ELVKK]KQN-NH$_2$ | >99% | [M + 2H]$^{2+}$ = 819.44<br>[M + 3H]$^{3+}$ = 546.63 | [M + 2H]$^{2+}$ = 819.86<br>[M + 3H]$^{3+}$ = 546.84 |
| 154 (8) | Ac-(cyclo-5,9)-VSKL[KSQLE]KRKQN-NH$_2$ | >99% | [M + 2H]$^{2+}$ = 855.43<br>[M + 3H]$^{3+}$ = 570.62 | [M + 2H]$^{2+}$ = 855.34<br>[M + 3H]$^{3+}$ = 570.64 |
| 155 (9) | Ac-(cyclo-6,10)-VSKLR[KQLVE]RKQN-NH$_2$ | >99% | [M + 2H]$^{2+}$ = 876.10<br>[M + 3H]$^{3+}$ = 583.91 | [M + 2H]$^{2+}$ = 876.63<br>[M + 3H]$^{3+}$ = 583.92 |
| 156 (4) | Ac-NLKQKIKHVVKLKDE-NH$_2$ | >99% | [M + 2H]$^{2+}$ = 931.75<br>[M + 3H]$^{3+}$ = 621.33 | [M + 2H]$^{2+}$ = 931.73<br>[M + 3H]$^{3+}$ = 621.32 |
| 157 (15) | Ac-(cyclo-4,8)-NLK[EKIKK]VVKLKDE-NH$_2$ | >99% | [M + 3H]$^{3+}$ = 612.38<br>[M + 4H]$^{4+}$ = 459.53 | [M + 3H]$^{3+}$ = 612.81<br>[M + 4H]$^{4+}$ = 459.90 |
| 158 (16) | Ac-(cyclo-5,9)-NLKQ[EIKHK]VKLKDE-NH$_2$ | >98% | [M + 2H]$^{2+}$ = 937.04<br>[M + 3H]$^{3+}$ = 635.03 | [M + 2H]$^{2+}$ = 937.79<br>[M + 3H]$^{3+}$ = 635.45 |
| 159 (17) | Ac-(cyclo-6,10)-NLKQK[EKHVK]KLKDE-NH$_2$ | >99% | [M + 2H]$^{2+}$ = 944.55<br>[M + 3H]$^{3+}$ = 630.03 | [M + 2H]$^{2+}$ = 944.90<br>[M + 3H]$^{3+}$ = 630.50 |
| 160 (18) | Ac-(cyclo-7,11)-NLKQK[EHVVK]LKDE-NH$_2$ | >99% | [M + 2H]$^{2+}$ = 922.53<br>[M + 3H]$^{3+}$ = 650.54 | [M + 2H]$^{2+}$ = 922.22<br>[M + 3H]$^{3+}$ = 650.67 |
| 161 (19) | Ac-(cyclo-8,12)-NLKQKIK[EVVKK]KDE-NH$_2$ | >98% | [M + 2H]$^{2+}$ = 925.56<br>[M + 3H]$^{3+}$ = 617.37 | [M + 2H]$^{2+}$ = 925.28<br>[M + 3H]$^{3+}$ = 617.80 |
| 284 (2) | Biotin-AEEA-VSKLRSQLVKRKQN-NH$_2$ | >95% | [M + 3H]$^{3+}$ = 690.07<br>[M + 4H]$^{4+}$ = 517.80 | [M + 3H]$^{3+}$ = 690.12<br>[M + 4H]$^{4+}$ = 517.32 |
| 285 (7) | Biotin-AEEA-(cyclo-4,8)-VSK[ERSQK]VKRKQN-NH$_2$ | >99% | [M + 3H]$^{3+}$ = 694.39<br>[M + 4H]$^{4+}$ = 521.04 | [M + 3H]$^{3+}$ = 694.30<br>[M + 4H]$^{4+}$ = 521.03 |
| 286 (8) | Biotin-AEEA-(cyclo-5,9)-VSKL[ESQLK]VRKQN-NH$_2$ | >95% | [M + 3H]$^{4+}$ = 684.72<br>[M + 4H]$^{3+}$ = 513.79 | [M + 3H]$^{4+}$ = 684.56<br>[M + 4H]$^{3+}$ = 513.92 |
| 287 (9) | Biotin-AEEA-(cyclo-6,10)-VSKLR[EQLVK]RKQN-NH$_2$ | >95% | [M + 3H]$^{3+}$ = 698.07<br>[M + 4H]$^{4+}$ = 523.80 | [M + 3H]$^{3+}$ = 698.01<br>[M + 4H]$^{4+}$ = 523.01 |
| 288 (10) | Biotin-AEEA-(cyclo-7,11)-VSKLRS[ELVKK]KQN-NH$_2$ | >90% | [M + 3H]$^{3+}$ = 675.05<br>[M + 4H]$^{4+}$ = 506.54 | [M + 3H]$^{3+}$ = 675.71<br>[M + 4H]$^{4+}$ = 506.83 |
| 289 (8) | Biotin-AEEA-(cyclo-5,9)-VSKL[KSQLE]KRKQN-NH$_2$ | >95% | [M + 3H]$^{3+}$ = 694.43<br>[M + 4H]$^{4+}$ = 521.07 | [M + 3H]$^{3+}$ = 694.29<br>[M + 4H]$^{4+}$ = 521.38 |
| 290 (9) | Biotin-AEEA-(cyclo-6,10)-VSKLR[KQLVE]RKQN-NH$_2$ | >95% | [M + 3H]$^{3+}$ = 684.72<br>[M + 4H]$^{4+}$ = 513.79 | [M + 3H]$^{3+}$ = 684.56<br>[M + 4H]$^{4+}$ = 513.92 |
| 291 (4) | Biotin-AAEA-NLKQKIKHVVKLKDE-NH$_2$ | >99% | [M + 3H]$^{3+}$ = 735.42<br>[M + 4H]$^{4+}$ = 511.82 | [M + 3H]$^{3+}$ = 735.30<br>[M + 4H]$^{4+}$ = 511.67 |

TABLE 14-continued

Mass spectrometry data

| Compound No. (SEQ ID NO.*) | Sequence | Purity | MS (ESI+) Calculated | Found |
|---|---|---|---|---|
| 292 (15) | Biotin-AEEA-(cyclo-6,10)NLK[EKIKK]VVKLKDE-NH$_2$ | >99% | $[M + 3H]^{3+}$ = 726.76<br>$[M + 4H]^{4+}$ = 545.32 | $[M + 3H]^{3+}$ = 726.16<br>$[M + 4H]^{4+}$ = 545.39 |
| 293 (16) | Biotin-AEEA-(cyclo-5,9)NLKQ[EIKHK]VKLKDE-NH$_2$ | >99% | $[M + 3H]^{3+}$ = 739.41<br>$[M + 4H]^{4+}$ = 554.81 | $[M + 3H]^{3+}$ = 739.33<br>$[M + 4H]^{4+}$ = 554.22 |
| 294 (17) | Biotin-AEEA-(cyclo-6,10)NLKQK[EKHVK]KLKDE-NH$_2$ | >99% | $[M + 3H]^{3+}$ = 744.42<br>$[M + 4H]^{4+}$ = 558.56 | $[M + 3H]^{3+}$ = 744.89<br>$[M + 4H]^{4+}$ = 558.96 |
| 295 (18) | Biotin-AEEA-(cyclo-7,11)NLKQKI[EHVVK]LKDE-NH$_2$ | >99% | $[M + 3H]^{3+}$ = 729.74<br>$[M + 4H]^{4+}$ = 547.55 | $[M + 3H]^{3+}$ = 729.79<br>$[M + 4H]^{4+}$ = 547.05 |
| 296 (19) | Biotin-AEEA-(cyclo-8,12)NLKQKIK[EVVKK]KDE-NH$_2$ | >99% | $[M + 3H]^{3+}$ = 731.76<br>$[M + 4H]^{4+}$ = 549.06 | $[M + 3H]^{3+}$ = 731.59<br>$[M + 4H]^{4+}$ = 549.25 |
| 265 (5) | Ac-KIKHVVKLKDENSQLKSEVSKLRSQLVKRK-NH$_2$ | >95% | $[M + 4H]^{4+}$ = 897.75<br>$[M + 5H]^{5+}$ = 718.24 | $[M + 4H]^{4+}$ = 898.16<br>$[M + 5H]^{5+}$ = 718.61 |
| 266 (26) | Ac-(cyclo-10-14, cyclo-15-19)-KIKHVVKLK[EENSK][EKSEK]SKLRSQLVKRK-NH$_2$ | >95% | $[M + 4H]^{4+}$ = 903.31<br>$[M + 5H]^{5+}$ = 722.85 | $[M + 4H]^{4+}$ = 903.95<br>$[M + 5H]^{5+}$ = 723.30 |
| 267 (27) | Ac-(cyclo-11-15, cyclo-16-20)-KIKHVVKLKD[ENSQK][ESEVK]KLRSQLVKRK-NH$_2$ | >95% | $[M + 4H]^{4+}$ = 902.80<br>$[M + 5H]^{5+}$ = 722.44 | $[M + 4H]^{4+}$ = 903.80<br>$[M + 5H]^{5+}$ = 722.82 |
| 268 (26) | Ac-(cyclo-10-14, cyclo-15-19)-KIKHVVKLK[EENSK][KKSEE]SKLRSQLVKRK-NH$_2$ | >95% | $[M + 4H]^{4+}$ = 903.31<br>$[M + 5H]^{5+}$ = 722.85 | $[M + 4H]^{4+}$ = 903.94<br>$[M + 5H]^{5+}$ = 723.30 |
| 269 (27) | Ac-(cyclo-10-14, cyclo-15-19)-KIKHVVKLK[KENSE][EKSEK]SKLRSQLVKRK-NH$_2$ | >95% | $[M + 4H]^{4+}$ = 903.31<br>$[M + 5H]^{5+}$ = 722.85 | $[M + 4H]^{4+}$ = 903.93<br>$[M + 5H]^{5+}$ = 723.35 |
| 270 (5) | Biotin-AEEA-KIKHVVKLKDENSQLKSEVSKLRSQLVKRK-NH$_2$ | >95% | $[M + 4H]^{4+}$ = 979.60<br>$[M + 5H]^{5+}$ = 783.88 | $[M + 4H]^{4+}$ = 980.57<br>$[M + 5H]^{5+}$ = 784.53 |
| 271 (26) | Biotin-AEEA-(cyclo-14-15, cyclo-15-19)-KIKHVVKLK[EENSK][EKSEK]SKLRSQLVKRK-NH$_2$ | >95% | $[M + 4H]^{4+}$ = 985.36<br>$[M + 5H]^{5+}$ = 788.49 | $[M + 4H]^{4+}$ = 986.35<br>$[M + 5H]^{5+}$ = 789.16 |
| 272 (27) | Biotin-AEEA-(cyclo-11-15, cyclo-16-20)-KIKHVVKLKD[ENSQK][ESEVK]KLRSQLVKRK-NH$_2$ | >95% | $[M + 4H]^{4+}$ = 984.86<br>$[M + 5H]^{5+}$ = 788.0 | $[M + 4H]^{4+}$ = 985.83<br>$[M + 5H]^{5+}$ = 723.15 |
| 273 (26) | Biotin-AEEA-(cyclo-10-14, cyclo-15-19)-KIKHVVKLK[EENSK][KKSEE]SKLRSQLVKRK-NH$_2$ | >95% | $[M + 4H]^{4+}$ = 985.36<br>$[M + 5H]^{5+}$ = 788.49 | $[M + 4H]^{4+}$ = 986.28<br>$[M + 5H]^{5+}$ = 789.24 |
| 274 (27) | Biotin-AEEA-(cyclo-10-14, cyclo-1519)-KIKHVVKLK[KENSE][EKSEK]SKLRSQLVKRK-NH$_2$ | >95% | $[M + 4H]^{4+}$ = 985.36<br>$[M + 5H]^{5+}$ = 788.49 | $[M + 4H]^{4+}$ = 986.28<br>$[M + 5H]^{5+}$ = 789.18 |
| 275 (6) | Ac-NLKQKIKHVVKLKDENSQLKSEVSKLRSQLVRKQN-NH$_2$ | >95% | $[M + 4H]^{4+}$ = 1078.89<br>$[M + 5H]^{5+}$ = 863.32 | $[M + 4H]^{4+}$ = 1079.71<br>$[M + 5H]^{5+}$ = 863.94 |
| 277 (28) | Ac-(cyclo-28-32)-NLKQKIKHVVKLKDENSQLKSEVSKLR[EQLVK]RKQN-NH$_2$ | >95% | $[M + 4H]^{4+}$ = 1084.90<br>$[M + 5H]^{5+}$ = 868.12 | $[M + 4H]^{4+}$ = 1085.71<br>$[M + 5H]^{5+}$ = 868.68 |
| 278 (29) | Ac-(cyclo-7-11, cyclo-28-32)-NLKQKI[EHVVK]LKDENSQLKSEVSKLR[EQLVK]RKQN-NH$_2$ | >95% | $[M + 4H]^{4+}$ = 1080.63<br>$[M + 5H]^{5+}$ = 864.71 | $[M + 4H]^{4+}$ = 1081.56<br>$[M + 5H]^{5+}$ = 868.68 |
| 279 (6) | Biotin-AEEA-NLKQKIKHVVKLKDENSQLKSEVSKLRSQLVKRKQN-NH$_2$ | >95% | $[M + 4H]^{4+}$ = 1160.95<br>$[M + 5H]^{5+}$ = 928.96 | $[M + 4H]^{4+}$ = 1161.99<br>$[M + 5H]^{5+}$ = 930.01 |
| 281 (28) | Biotin-AEEA-(cyclo-28-32)-NLKQKIKHVVKLKDENSQLKSEVSKLR[EQLVK]RKQN-NH$_2$ | >95% | $[M + 4H]^{4+}$ = 1166.95<br>$[M + 6H]^{6+}$ = 778.30 | $[M + 4H]^{4+}$ = 1168.13<br>$[M + 5H]^{5+}$ = 778.98 |
| 282 (19) | Biotin-AEEA-(cyclo-7-11, cyclo-28-32)-NLKQKIK[EHVVK]LKDENSQLKSEVSKLR[EQLVK]RKQN-NH$_2$ | >93% | $[M + 4H]^{4+}$ = 1162.69<br>$[M + 5H]^{5+}$ = 930.35 | $[M + 4H]^{4+}$ = 1163.91<br>$[M + 5H]^{5+}$ = 930.99 |

*Each of the peptides of SEQ ID NO: 7-10, 15-19, 26, 27, 28 and 29 include substitutions at X$_1$ and X$_2$ positions with &mane acid or lysine residues as shown in the sequences provided in the table.

Example 4

The biotinylated equivalents of compounds 132, 150-161, 265-269 and 275-278 (i.e., compounds 284-296 and 270-274 as shown in Tables 7, 10, and 11 above) were tested for their ability to directly bind to RHAMM using an ELISA assay. Each of these peptides was biotinylated at its amino-terminus, and an AEEA spacer was included to separate the peptide sequence from the biotin molecule.

HA coated plates were purchased (ECHELON). Peptides were dissolved in 2 mM PBS to constant molarity, aliquoted and stored at −20° C. until used in assays. 7 kDa biotin-labeled RHAMM (SEQ ID NO: 1) was synthesized and used as a positive control in these assays. Biotin labeled peptides were added to the HA coated wells (n=3 replicates/peptide) at either 0.8 or 0.08 μM and then incubated with shaking overnight at 4° C. Wells were washed free of excess unbound peptides using 200 μl PBS (4 times). 100 μl of Streptavidin-HRP was then added to each well and the plate was incubated at room temperature for 1 hr. The plate was then washed with 200 μl PBS/well 4 times and TMB Liquid Substrate System for ELISA (Sigma) was added to each well, incubated for 5-10 min at room temperature and color read at 450 nm Plate Reader (BioTek, SYNERGY H4, Hybrid Reader).

Figure 39:
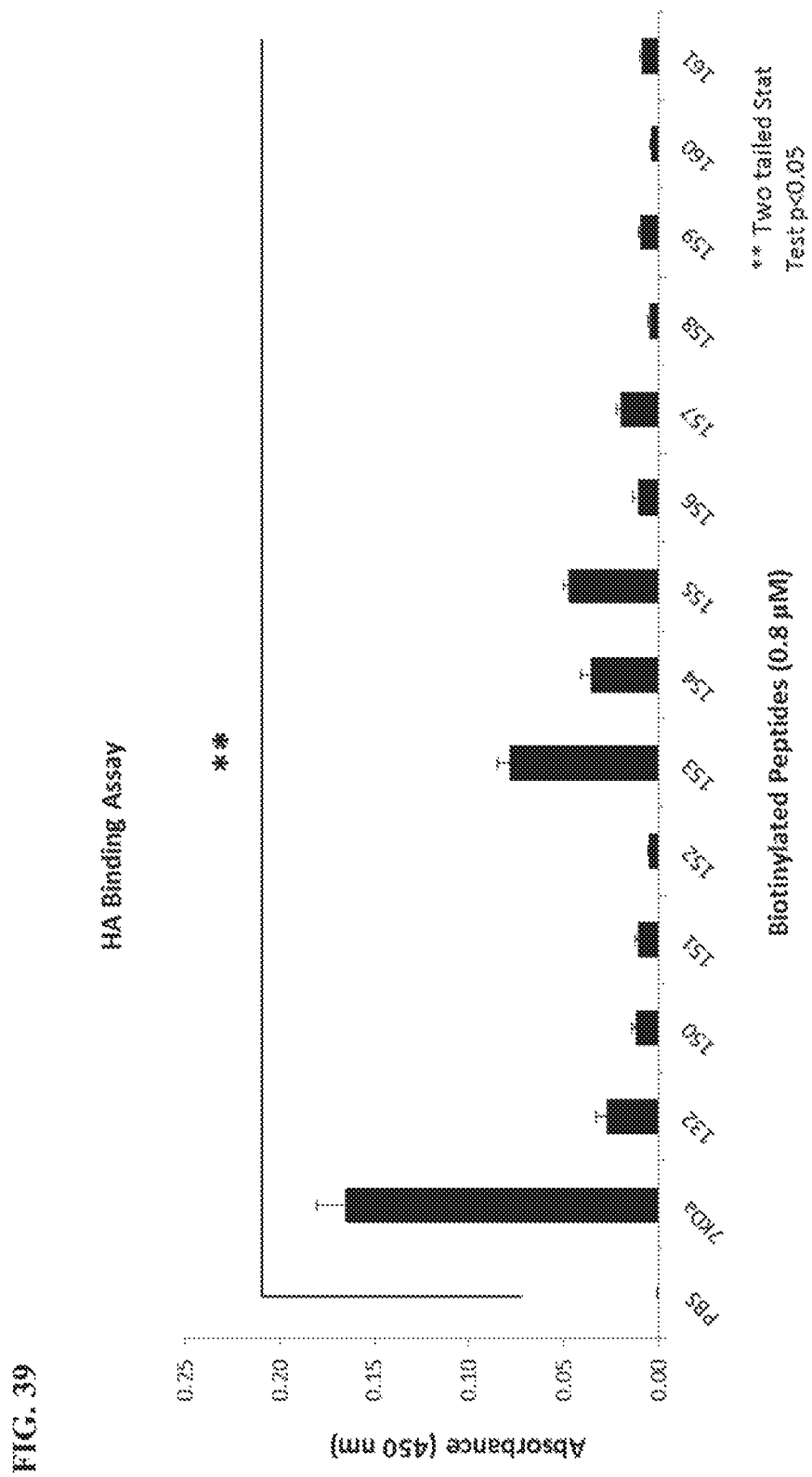
FIGS. 39 and 40 provide illustrative data from a direct HA-binding assay.
Figure 40:
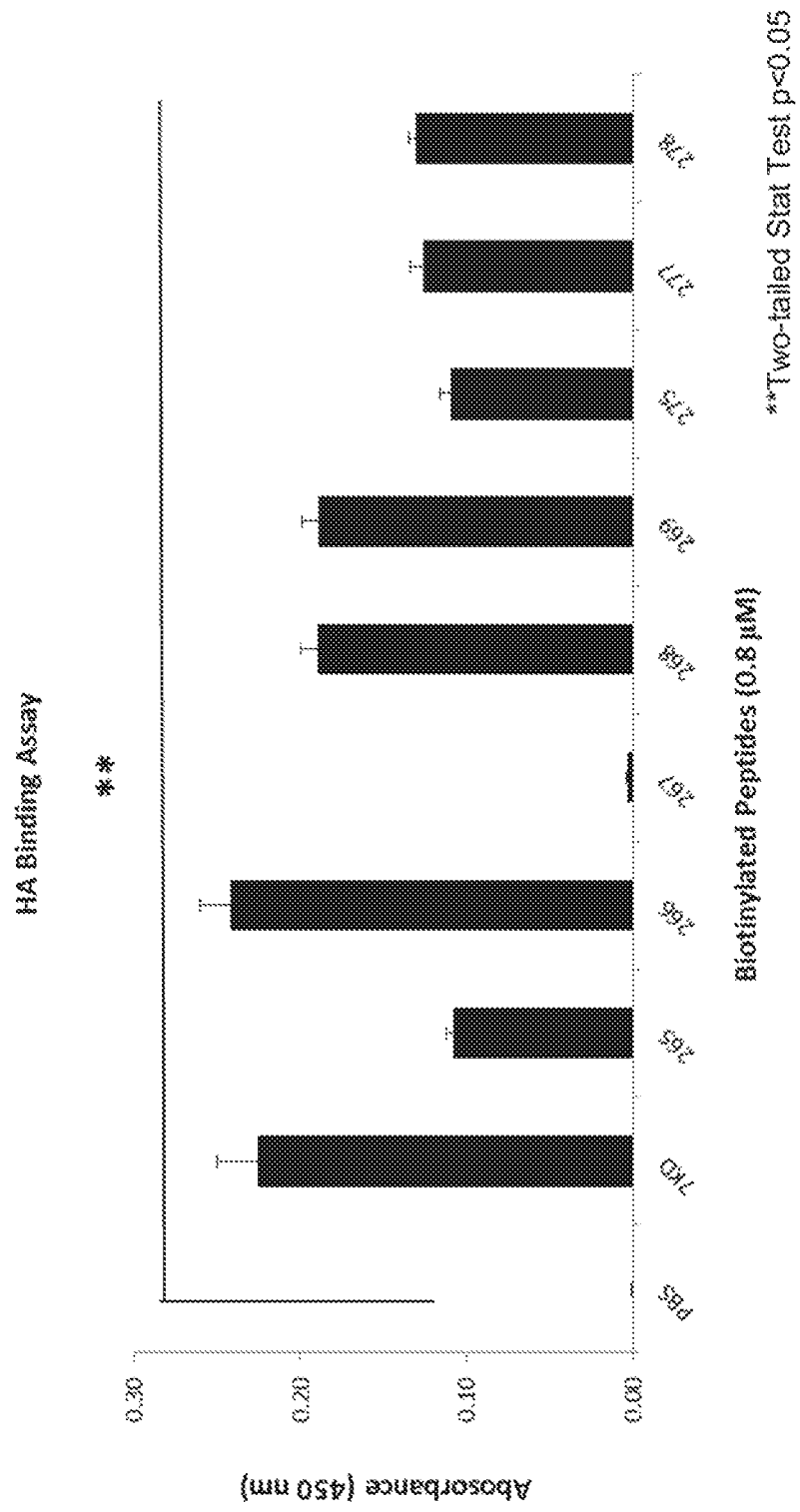

Direct HA-binding results for the biotinylated equivalents of compounds 132 and 150-161 are show in FIG. 39, and results for compounds 265-268 and 275-278 are shown in FIG. 40. All compounds tested exhibited HA-bind to RHAMM that was significantly above the negative (PBS only) control, with compounds 153, 154, 155, 157, 265, 266, 268, 269, and 275-278 exhibiting the highest binding ability.

Example 5

Compounds 132, 133, 150-152, 156-161, 265-269, 275, 277, and 278 were evaluated for their ability to inhibit cell migration. Cell migration assays were performed using Chemicon Assay Kits (ECM510 (Migration); Billerica, Mass., USA) according to the manufacturer's protocol. Briefly, sub-confluent cultures of RHAMM-overexpressing (LR21) cells were serum starved overnight. $7.5 \times 10^4$ cells were then plated in the upper chamber of a Boyden chamber, either in the presence or absence of 10 ng/mL of peptide. 30% fetal bovine serum in DMEM was used as the chemo-attractant in the lower chamber. The number of cells that had crossed the membrane after 20 hours was assessed using the CYQUANT GR Dye and lysis buffer solution provided in the kit. Fluorescence was measured with a fluorescent plate reader using a 480/520 nm filter set.

Figure 41:
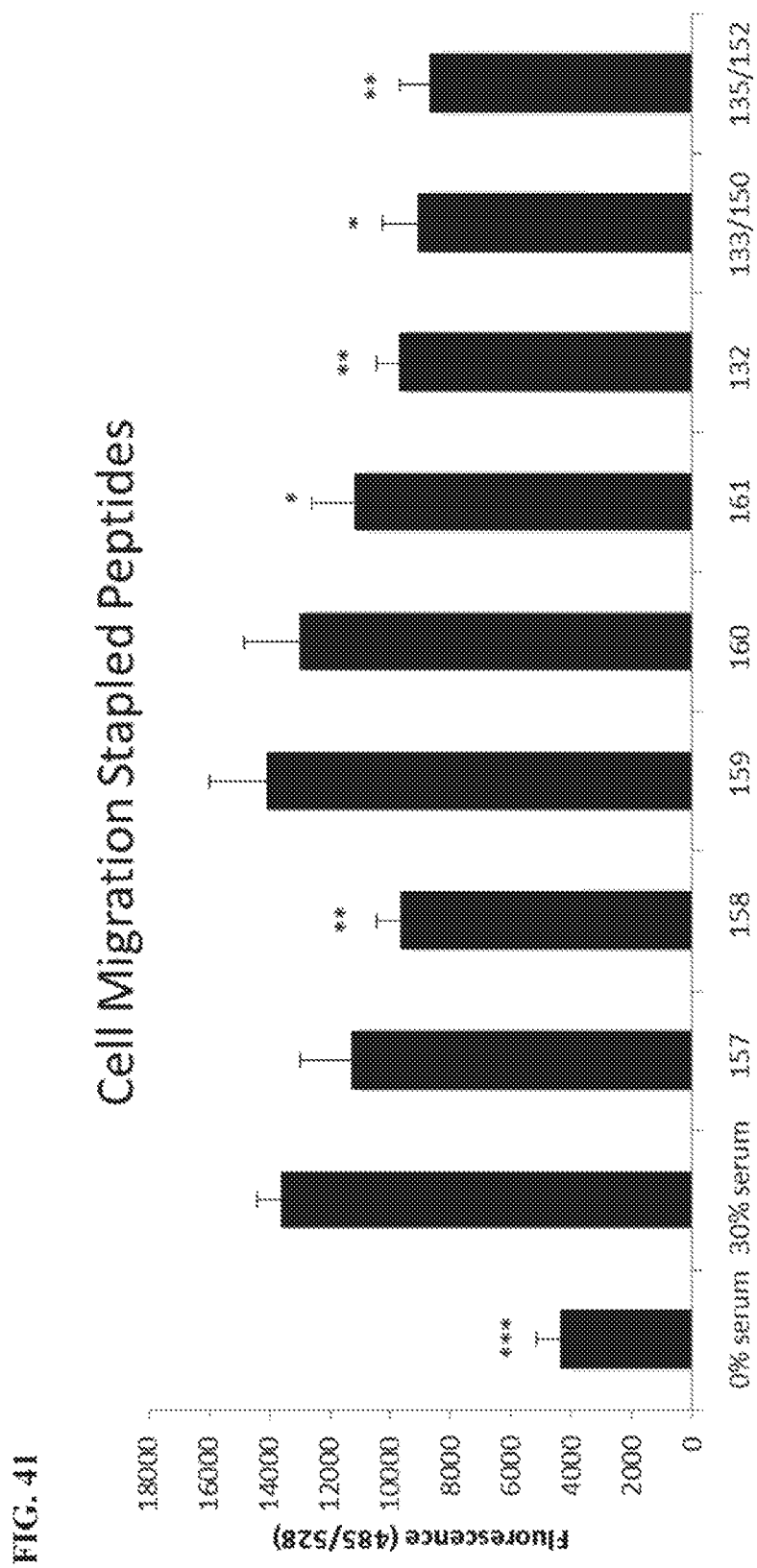
FIGS. 41-43 provide illustrative data from a cell migration assay.
Figure 42:
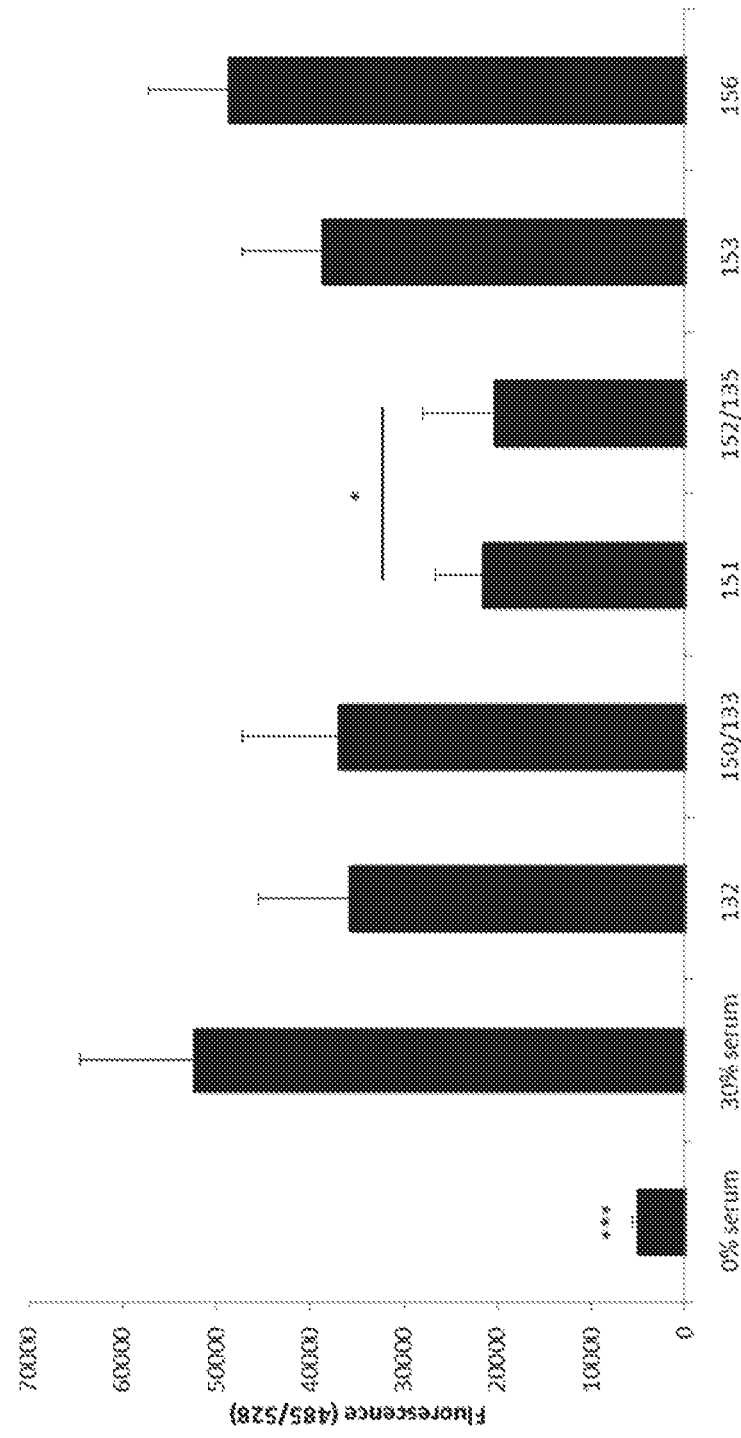
Figure 43:
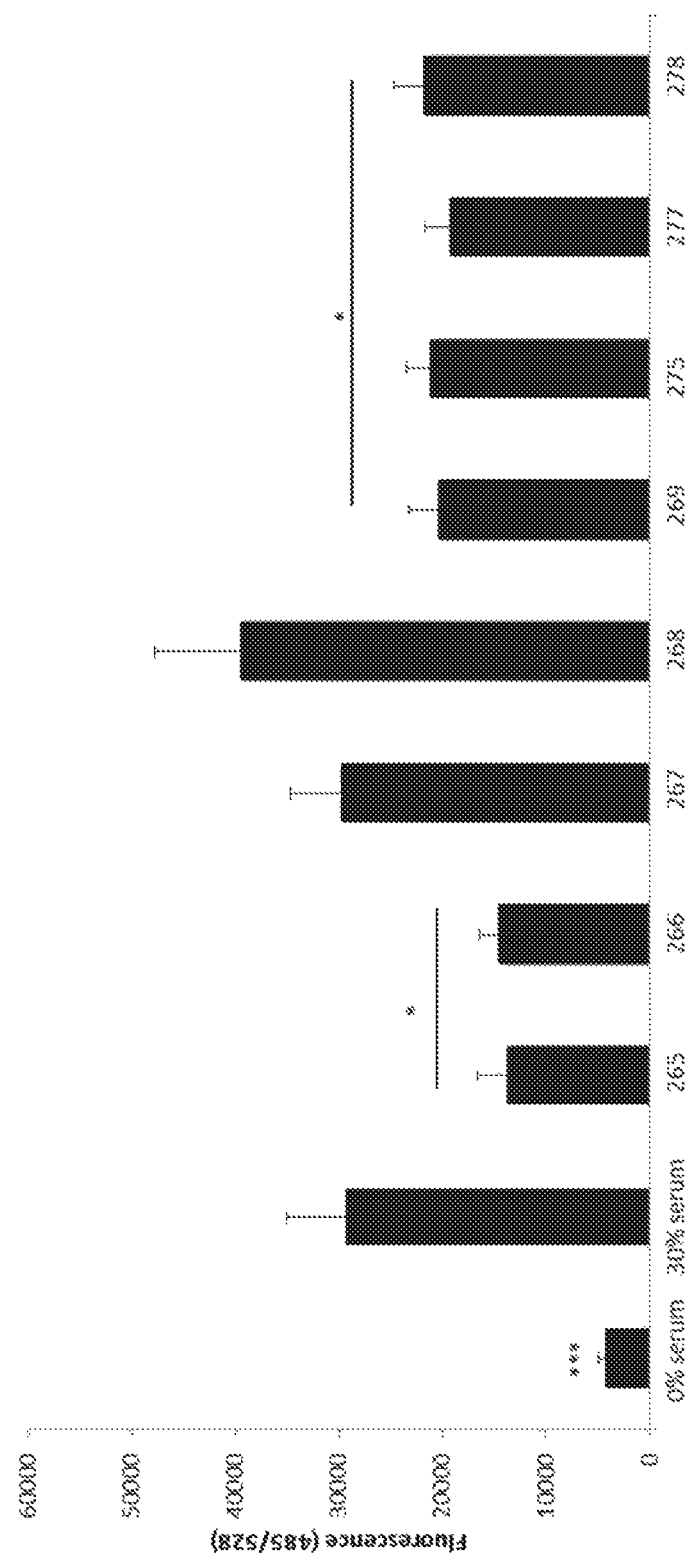

Results of the cell migration assays are shown in FIGS. 41-43. Values are the mean and SDM of n=3 replicates. *$p<0.05$, $p<0.01$. All statistics compare to 30% serum control. In FIGS. 41-43**, where bars are labeled with two compound numbers ("133/150" and "135/152") this means that the data were pooled for the indicated compounds, i.e., for the non-acetylated and acetylated versions of the indicated peptides. Compounds 132, 133/150, 151, 135/152, 158, 161, 265, 266, 269, 275, 277, and 278 were each found to significantly inhibit cell migration.

Example 6

Compounds 132, 133, 135, 150, 152, 157-161, 265-269, 275, 277, and 278 were evaluated for their ability to inhibit inflammation. To determine the effect of the peptides on inflammation, commercially available murine RAW 264.7 macrophages carrying a secreted embryonic alkaline phosphatase (SEAP) reporter that is inducible by NF-κB (RAW-Blue; InvivoGen, San Diego, Calif., USA) were used. Cells were grown to 80% confluence in DMEM containing 4.5 g/L glucose, 10% heat-inactivated fetal bovine serum, 2 mM L-glutamine, 50 μg/mL penicillin/streptomycin, 100 μg/mL Normocin (InvivoGen) at 37° C. in 5% $CO_2$. For peptide screening experiments, cells were scraped in growth medium, counted, and plated to flat-bottom 96-well plates at a density of $5 \times 10^4$ cells/well either in the presence or absence (control) of 200 ng/mL TLR1/TLR2 agonist PAM3CSK4 (InvivoGen). Peptides were added in 6 replicate wells at a dose of 10 ng/mL in the presence of PAM3CSK4. After 18 hours of stimulation, SEAP concentrations (indicating NF-κB activity) were measured in the supernatants collected from the RAW-Blue cells using QUANTI-BLUE reagent (InvivoGen). After 20 minutes of incubation at 37° C., SEAP levels were determined using spectrophotometry at a wavelength of 630 nm.

Figure 44:
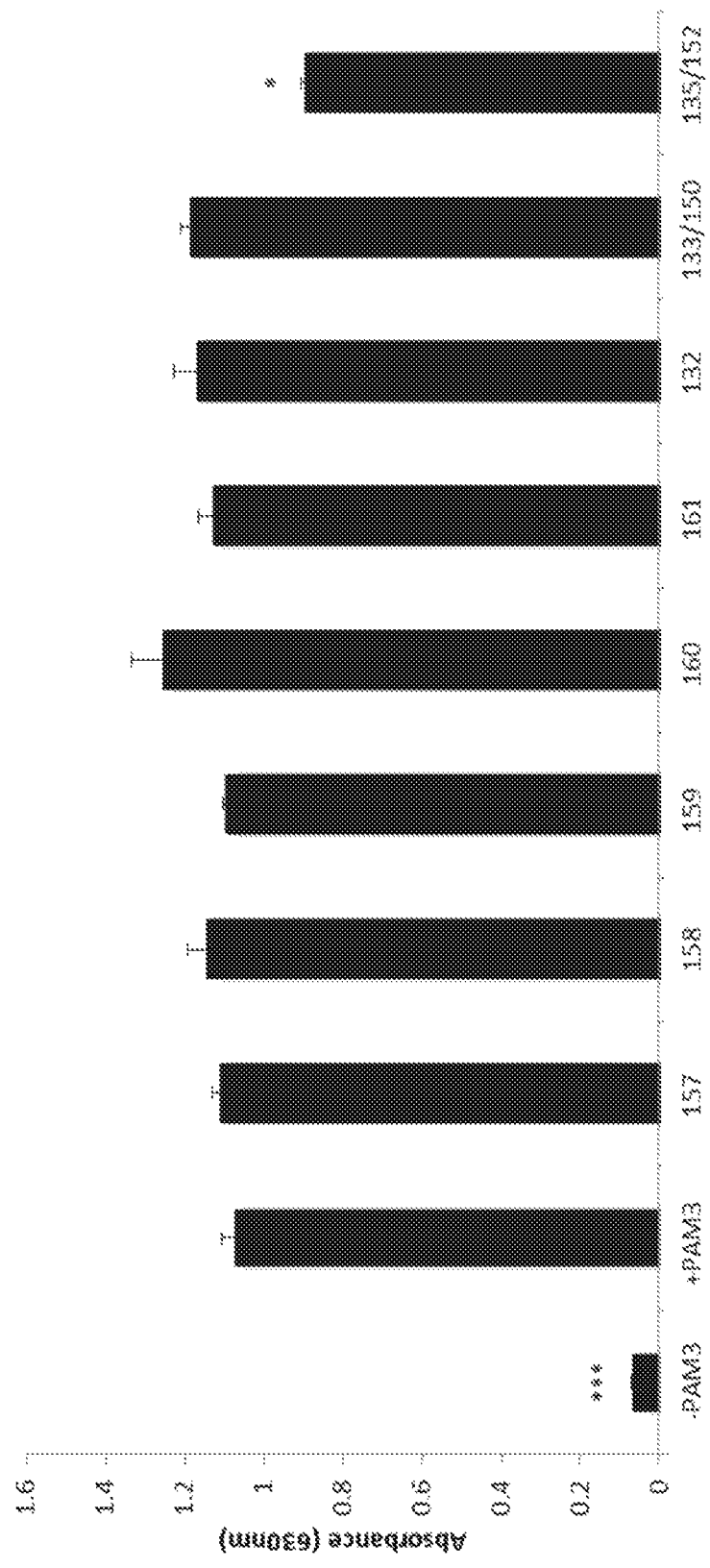
FIGS. 44-46 provide illustrative data from an assay that measures inflammation.
Figure 45:
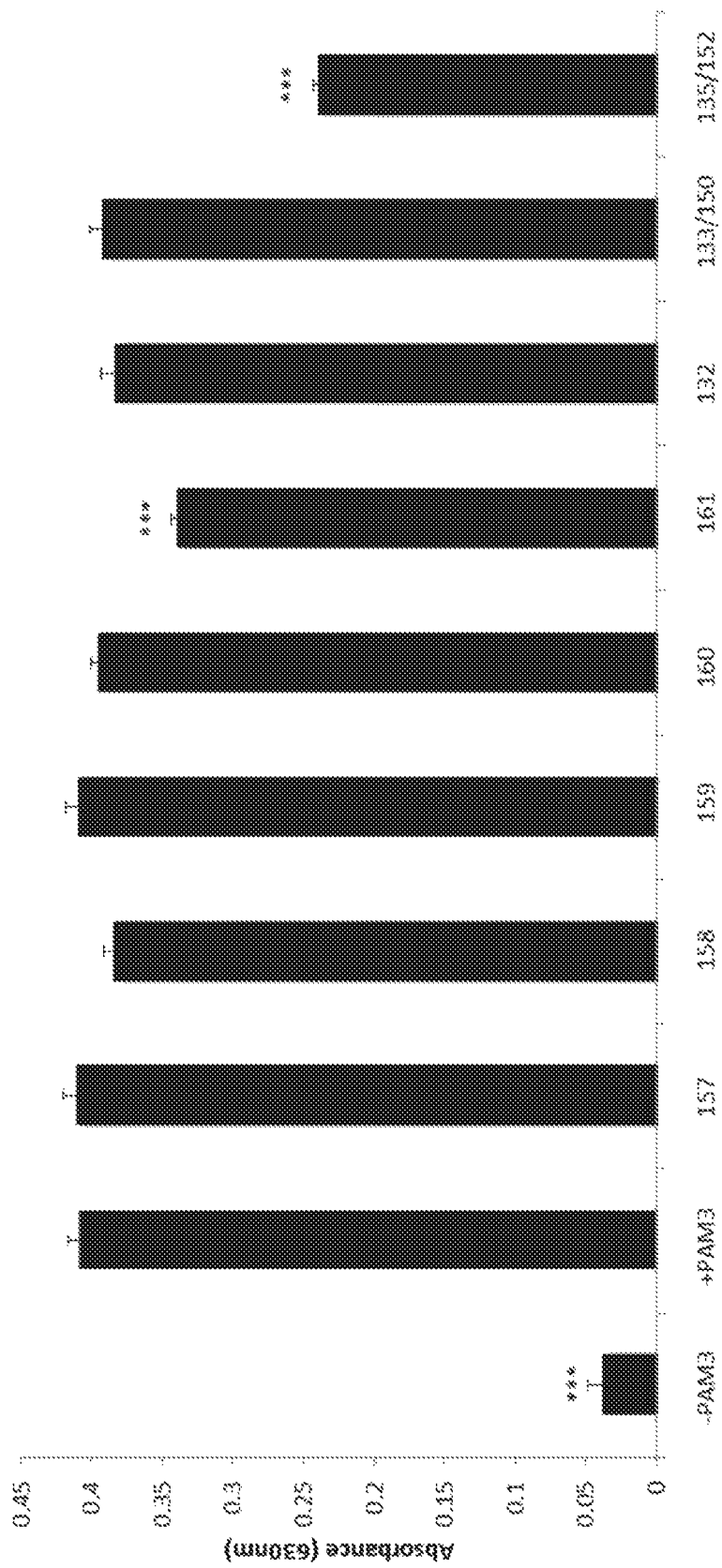
Figure 46:
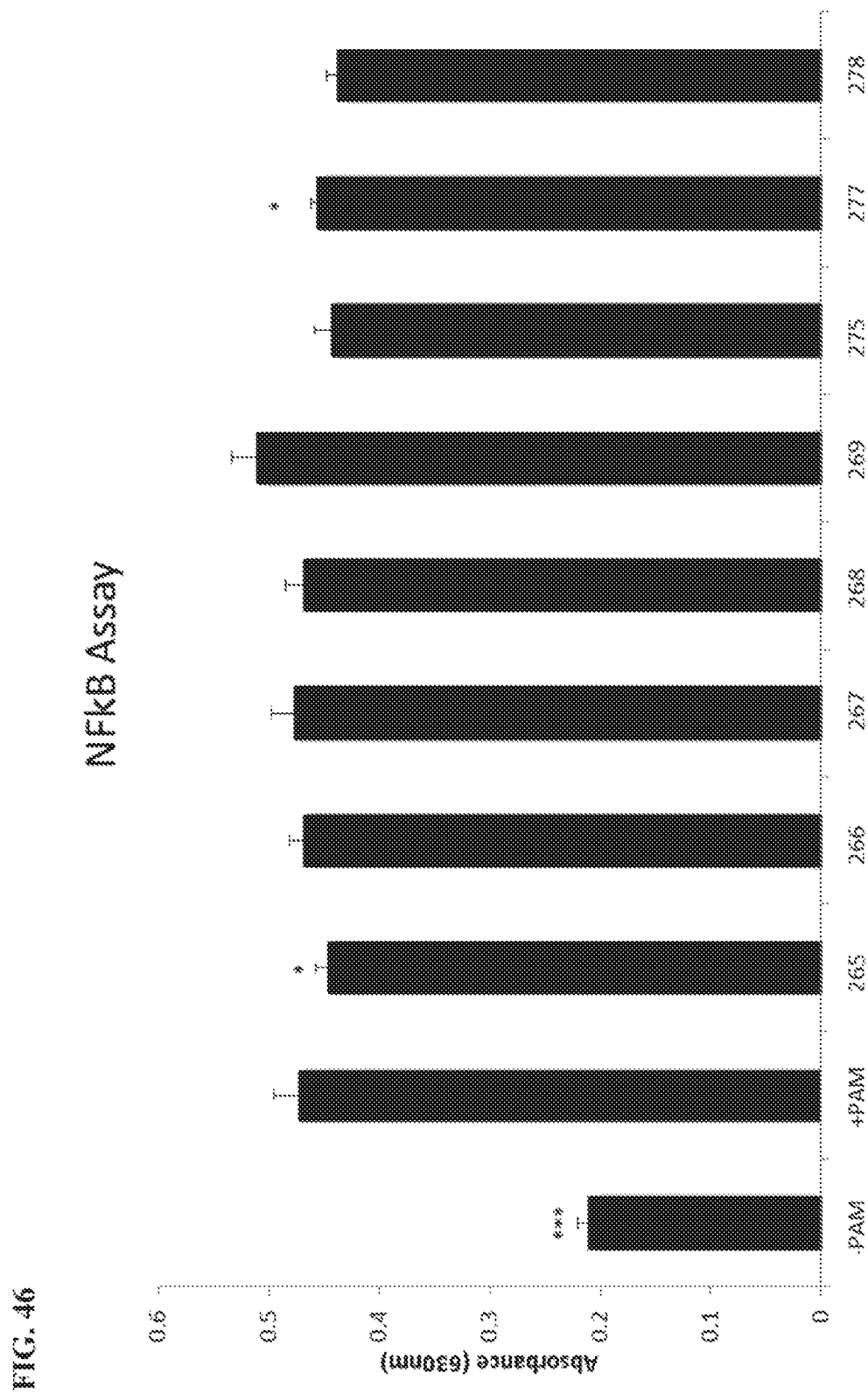

Results are shown in FIGS. 44-46. Values are the mean and SDM of n=3 replicates. *$p<0.05$ and *$p<0.001$ compared to +PAM3. In FIGS. 44 and 45**, where bars are labeled with two compound numbers ("133/150" and "135/152") this means that the data were pooled for the indicated compounds, i.e., for the non-acetylated and acetylated versions of the indicated peptides. Compounds 135, 152, 161, 265, and 277 each significantly inhibited inflammation using this assay.

Example 7

Compounds 132, 133, 135, 150, 152, 157-161, 265-269, 275, 277, and 278 were evaluated for their ability to inhibit fibrosis. IMR90 human fetal lung fibroblasts were obtained from ATCC and maintained in DMEM supplemented with 10% fetal bovine serum. In order to examine the effect of peptides on myofibroblast differentiation, 80% confluent cultures were serum starved overnight prior to addition of TGF-β (2 ng/mL, R&D Systems). Cells were treated with TGF-β for 24 hours prior to addition of peptides (10 ng/mL). 48 hours after addition of peptides, culture supernatants were collected and levels of active TGF-β measured using commercially available TGF-β ELISA (Quantikine, R&D Systems).

Figure 47:
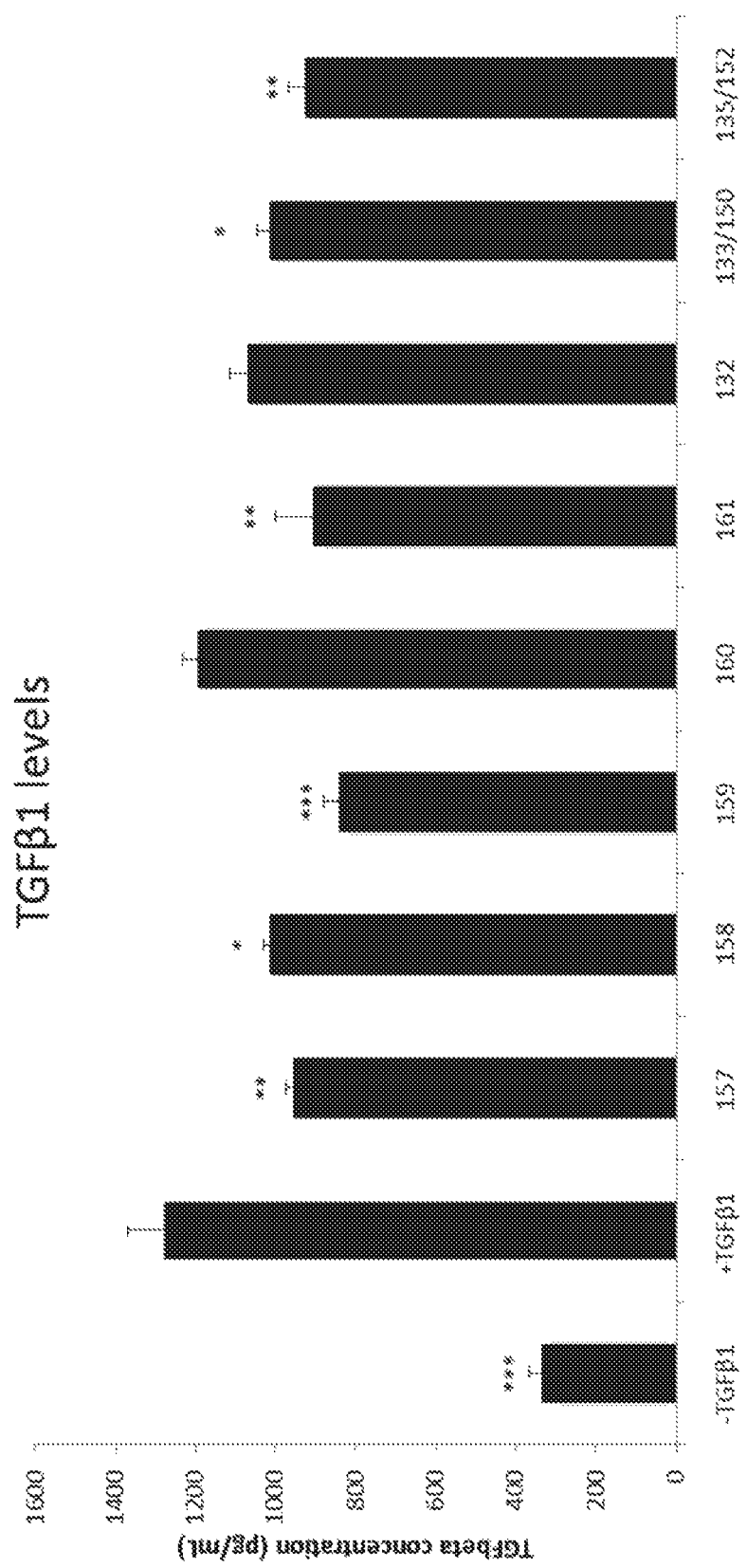
FIGS. 47 and 48 provide illustrative data from an assay that measures fibrosis.
Figure 48:
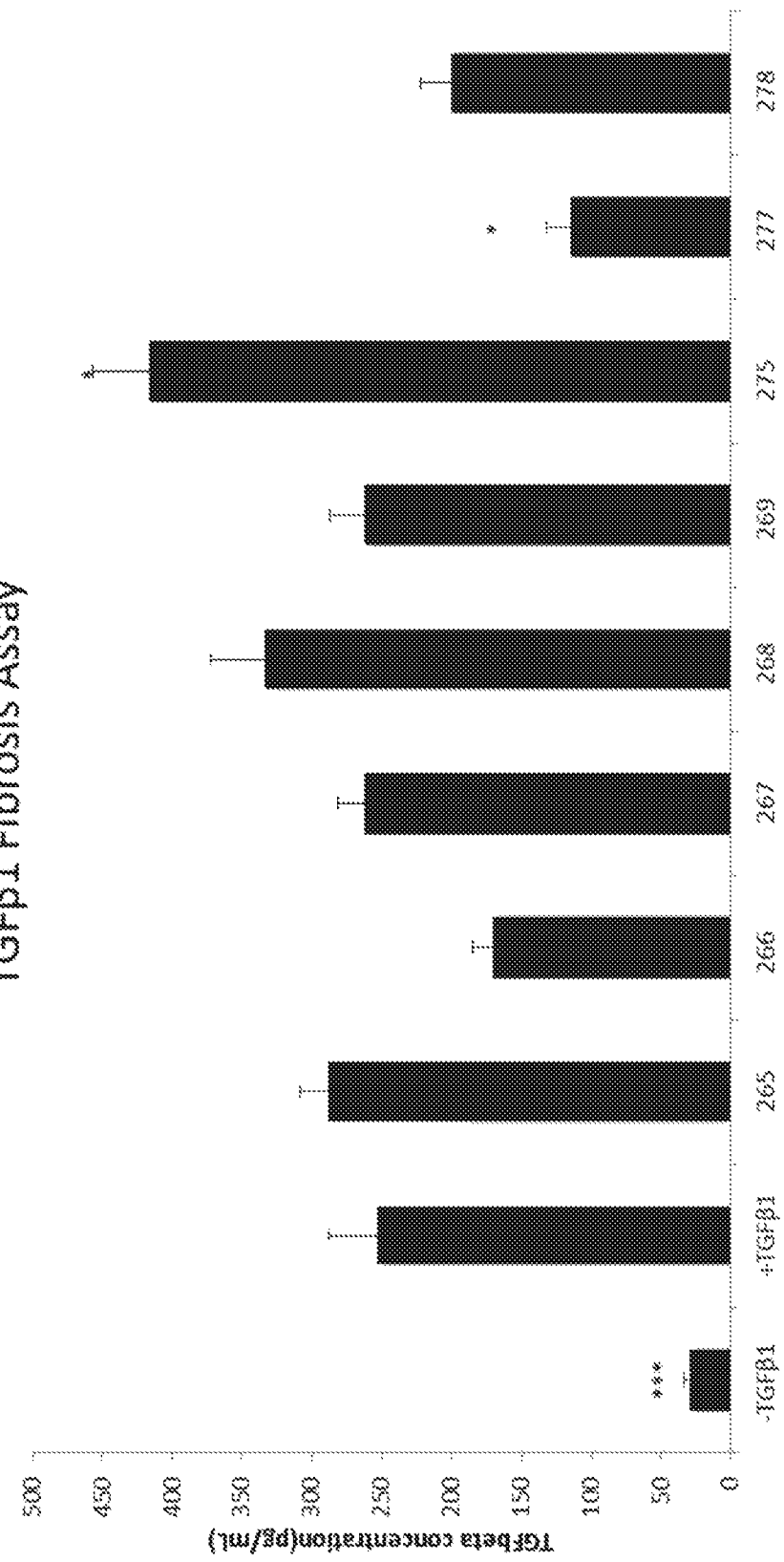

Results are shown in FIGS. 47 and 48. Values are the Mean and SDM n=3 replicates. *$p<0.05$, $p<0.01$, *$p<0.001$ when compared to the +TGFβ1 control. In FIG. 47, where bars are labeled with two compound numbers ("133/150" and "135/152") this means that the data were pooled for the indicated compounds, i.e., for the non-acetylated and acetylated versions of the indicated peptides. Compounds 133, 135, 150, 152, 157-159, 161, and 277 were found to significantly inhibit fibrosis using this assay. While the results were not statistically significant, compound 266 and 278 also showed a strong trend towards inhibition of fibrosis.

Example 8

Compounds 132, 133, 135, 150-153, 156, 265-269, and 275-278 were evaluated for their ability to inhibit cellular invasion. Invasion assays were performed using Chemicon Assay Kits ECM555 (Invasion); Billerica, Mass., USA) according to the manufacturer's protocol. Invasion assays are performed in an identical manner as the migration assays described above in Example 5, except that cells are required to invade through a layer of extracellular matrix (MATRIGEL) coating the filter that separates the upper and lower Boyden chambers. Briefly, sub-confluent cultures of RHAMM-overexpressing (LR21) cells were serum starved overnight before plating $7.5 \times 10^4$ cells in the upper chamber of a Boyden chamber either in the presence or absence of 10 ng/mL of peptide. 30% fetal bovine serum in DMEM was used as the chemo-attractant in the lower chamber. The number of cells that had crossed the membrane after 20 hours was assessed using the CYQUANT® GR Dye and lysis buffer solution provided in the kit. Fluorescence was measured with a fluorescent plate reader using 480/520 nm filter set.

Figure 49:
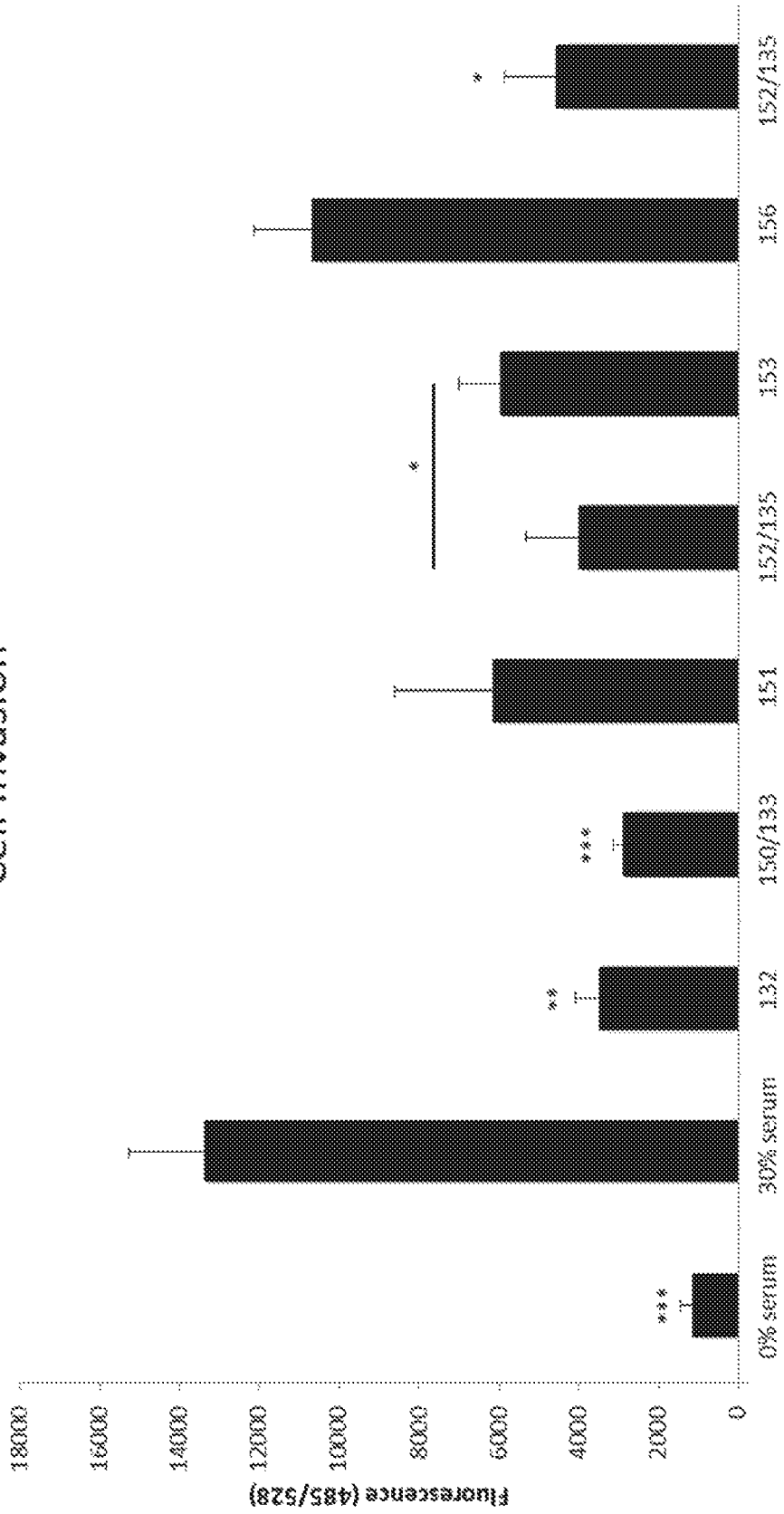
FIGS. 49 and 50 provide illustrative data from a cell invasion assay.
Figure 50:
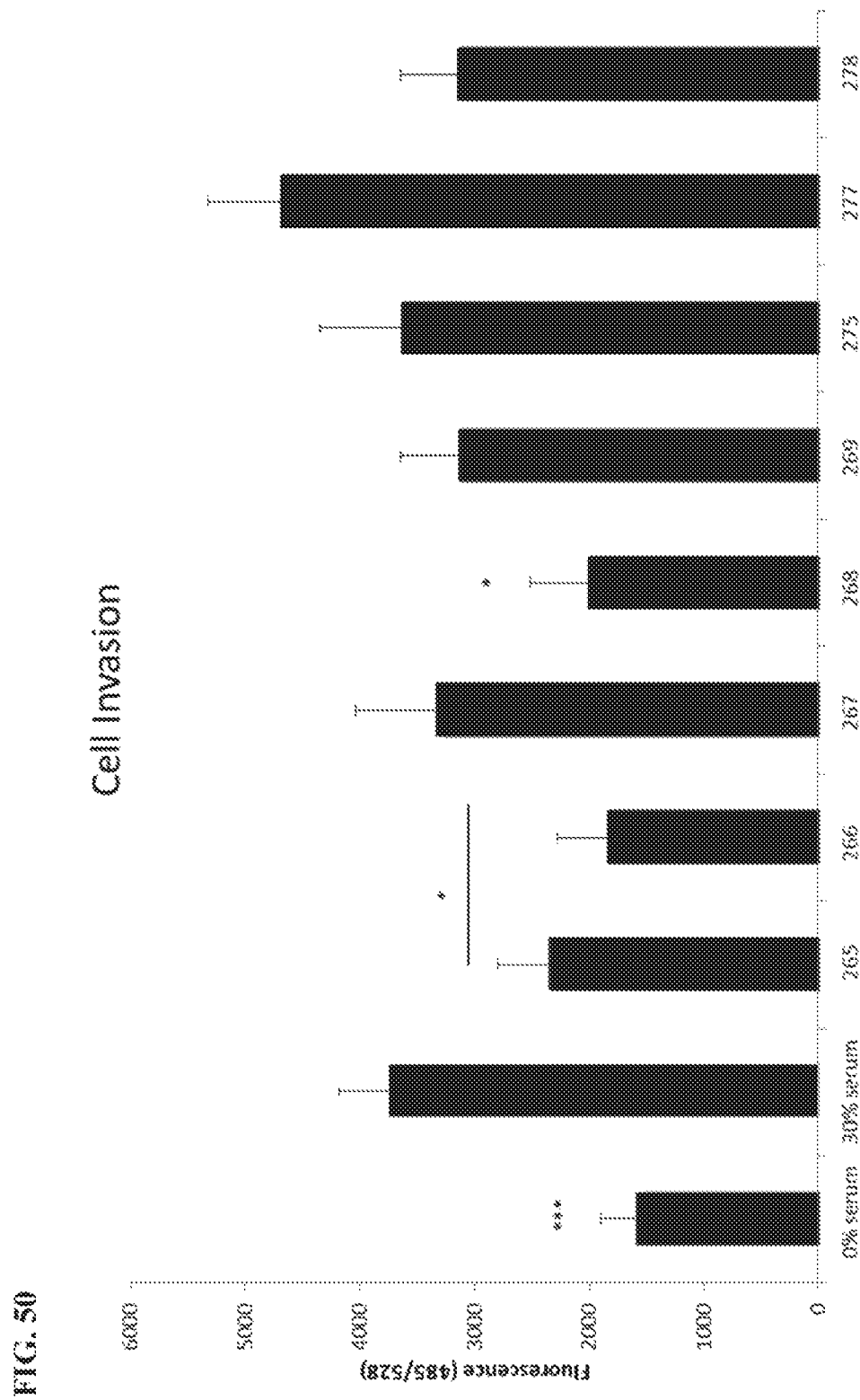

Results are shown in FIGS. 49 and 50. Values the mean and SDM of n=3 replicates. *p<0.05, p<0.01, *p<0.001 All statistics compared to 30% serum control. In FIG. 49, where bars are labeled with two compound numbers ("152/135") this means that the data were pooled for the indicated compound, i.e., for the non-acetylated and acetylated versions of the indicated peptide. Compounds 132, 133, 135, 150, 152, 153, 265, 266, and 268 all significantly inhibited cellular invasion using this assay.

Example 9

As documented in the Examples hereinabove, a variety of cyclized peptides were produced that contained the HA-binding domain 1 (HABD1), HA-binding domain 2 (HABD2), or both HABD1 and HABD2. These peptides were evaluated for helicity, direct HA binding and in a number of cell-based bioassays (effects on migration, invasion, NFkB activation, and TGFβ1 production) that are relevant to inflammation and fibrosis. The relationships amongst helicity, HA-binding, and biofunction were evaluated. Peptides were divided into three groups for this analysis: (1) peptides containing HABD1 ("HABD1"); (2) peptides containing HABD2 ("HABD2"); and peptides containing most or all of HABD1 and all of HABD2 ("HABD1+HABD2"). $R^2$ values were calculated to quantify the relationships between helicity, HA-binding, and biofunction were evaluated.

The results of this analysis for the HABD1 peptides are shown below in Tables 15 and 16. Table 15 provides a summary of the HA binding, biofunction, and helicity results for HABD1. Table 16 provides a function blocking scores for each of the tested peptides and provides $R^2$ values showing the relationship between HA binding and helicity ("HA binding vs. CD"), HA binding and function-blocking score ("HA binding vs. FBS") and helicity vs. function-blocking score ("CD vs. FBS"). The same type of summaries are provided for the HABD2 peptides in Tables 17 and 18 below, and for the HABD1+HABD2 peptides in Tables 19 and 20 below.

Function blocking scores were calculated as the total percent inhibition achieved by the peptide for all assays the peptides were tested in, divided by the number of assays. Assays included migration, invasion, inflammation and fibrosis assays. Not all peptides were tested all of the assays. All peptides were included for deriving $R^2$ values (Pearson's formula).

$R^2$ values were also calculated for individual cell functions vs. HA binding and helicity, for each the HABD1 peptides, the HABD2 peptides and the HABD1+HABD2 peptides. The linear relationship between HA binding levels and percent inhibition of migration, inflammation and fibrosis was assessed using R squared formulas (Pearson's formula). These results are shown below in Tables 21-23. The results for all peptides tested were used for these calculations.

TABLE 15

HABD1 linear and stapled peptide data summary

| Compound No.* | Staple position | HA direct binding (OD**) | Migration (% inhib.†) | Invasion (% inhib.†) | Inflammation (% Inhib.†) | Fibrosis (% inhib.†) | Helicity (CD) |
|---|---|---|---|---|---|---|---|
| 156 | Linear | 0.01 | 0 | 0 | ND | ND | 0.11 |
| 157 | Cyclo-4-8 | 0.02 | 0 | ND** | 0 | 38 | 0.38 |
| 158 | Cyclo-5-9 | 0.005 | 43 | ND | 0 | 31 | 0.43 |
| 159 | Cyclo-6-10 | 0.009 | 0 | ND | 0 | 50 | 0.44 |
| 160 | Cyclo-7-11 | 0.004 | 0 | ND | 0 | 0 | 0.55 |
| 161 | Cyclo-8-12 | 0.009 | 36 | ND | 6 | 38 | 0.31 |

*Compound 156 has the following sequence: Ac-NLKQKIKHVVKLKDE-NH$_2$ (SEQ ID NO: 4). Compounds 157-158 have the sequences of SEQ ID NOs. 15-19, with substitutions at $X_1$ and $X_2$ as described above in Example 3.
**ND = not determined; OD = optical density
†Values are given as % inhibition relative to positive control described as described above in the examples relating to for each assay.

TABLE 16

HABD1 function blocking scores and $R^2$ values

| Compound No.* | Staple position | Function blocking score (FBS) | HA binding | Helicity (CD) | $R^2$ value, HA binding vs. CD | $R^2$ value, MA binding vs. FBS | $R^2$ value, CD vs. FBS |
|---|---|---|---|---|---|---|---|
| 156 | Linear | 0 | 0.01 | 0.11 | 0.09 (neg**) | 0.06 (neg) | 0.03 |
| 157 | Cyclo-4-8 | 8.6 | 0.02 | 0.38 | | | |
| 158 | Cyclo-5-9 | 22 | 0.005 | 0.43 | | | |
| 159 | Cyclo-6-10 | 17 | 0.009 | 0.44 | | | |
| 160 | Cyclo-7-11 | 0 | 0.004 | 0.55 | | | |
| 161 | Cyclo-8-12 | 22 | 0.009 | 0.31 | | | |

*Compound 156 has the following sequence: Ac-NLKQKIKHVVKLKDE-NH$_2$ (SEQ ID NO: 4). Compounds 157-158 have the sequences of SEQ ID NOs. 15-19, with substitutions at $X_1$ and $X_2$ as described above in Example 3.
**neg = negative correlation or inverse correlation.

TABLE 17

HABD2 linear and stapled peptide data summary

| Compound No.* | Staple position | HA direct binding (OD**) | Migration (% inhib.†) | Invasion (% inhib.†) | Inflammation (% Inhib.†) | Fibrosis (% inhib.†) | Helicity (CD) |
|---|---|---|---|---|---|---|---|
| 132 | Linear | 0.03 | 36 | 66 | 0 | 0 | 0.13 |
| 150 | Cyclo-4-8 | 0.015 | 0 | 79 | 0 | 31 | 0.53 |
| 151 | Cyclo-5-9 | 0.01 | 59 | 0 | ND | ND | 0.70 |
| 135/152†† | Cyclo-6-10 | 0.005 | 60 | 75 | 40 | 38 | 0.61 |
| 153 | Cyclo-7-11 | 0.08 | 0 | 58 | ND | ND | 0.54 |
| 154 | Reverse cyclo 5-9 | 0.045 | ND** | ND | ND | ND | 0.20 |
| 155 | Reverse cyclo-6-10 | 0.05 | ND | ND | ND | ND | 0.37 |

*Compound 132 has the sequence Ac-VSKLRSQLVKRKQN-NH$_2$ (SEQ ID NO: 2). Compounds 135 and 150-155 have the sequences of SEQ ID NOs. 7-10, with substitutions at $X_1$ and $X_2$ as described above in Example 3.
**ND = not determined; OD = optical density
†Values are given as % inhibition relative to positive control described as described above in the examples relating to for each assay.
††Represents pooled data for compounds 135 (non-acetylated) and 152 (acetylated)

TABLE 18

HABD2 function blocking scopes and $R^2$ values

| Compound No.* | Staple position | Function blocking score (FBS) | HA binding | Helicity (CD) | $R^2$ value, HA binding vs. CD | $R^2$ value, HA binding vs. FBS†† | $R^2$ value, CD vs. FBS |
|---|---|---|---|---|---|---|---|
| 132 | Linear | 17 | 0.03 | 0.13 | 0.1 (neg†) | 0.29 | 0.23 |
| 150 | Cyclo-4-8 | 27 | 0.015 | 0.53 | | | |
| 151 | Cyclo-5-9 | 20 | 0.01 | 0.

TABLE 19-continued

HABD1 + HABD2 linear and stapled peptide data summary

| Compound No.* | Staple position | HA direct binding (OD**) | Migration (% inhib.†) | Invasion (% inhib.†) | Inflammation (% Inhib.†) | Fibrosis (% inhib.†) | Helicity (CD) |
|---|---|---|---|---|---|---|---|
| 278 | Cyclo-7-11 28-32 | 0.125 | 45 | 0 | 0 | 0 | 0.74 |

*Compound 265 has the sequence Ac-KIKHVVKLKDENSQLKSEVSKLRSQLVKRK-NH$_2$ (SEQ ID NO: 5). Compounds 266-269 have the sequences of SEQ ID NOs. 26 and 27, with substitutions at the $X_1$ and $X_2$ as described above in Example 3. Compound 275 has the sequence Ac-NLKQKIKHVVKLKDENSQLKSEVSKLRSQLVKRKQN-NH$_2$ (SEQ ID NO: 6). Compounds 277 and 278 have the sequences of SEQ ID NOs. 28 and 29, with substitutions at the $X_1$ and $X_2$ as described above in Example 3.
**OD = optical density.
†Values are given as % inhibition relative to positive control described as described above in the examples relating to for each assay.

TABLE 20

HABD1 + HABD2 function blocking scores and $R^2$ values

| Compound No.* | Staple position | Function blocking score (FBS) | HA binding | Helicity (CD) | $R^2$ value, HA binding vs. CD | $R^2$ value, HA binding vs. FBS | $R^2$ value, CB vs. FBS |
|---|---|---|---|---|---|---|---|
| 265 | Linear | 28 | 0.10 | 0.40 | 0.05 | 0.25 | 0.06 |
| 266 | Cyclo-10-14, 15-19 | 28 | 0.24 | 0.63 | | | |
| 267 | Cyclo-11-15, 16-20 | 0 | 0.01 | 0.48 | | | |
| 268 | Cyclo-10-14, reverse 15-19 | 14 | 0.19 | 0.40 | | | |
| 269 | Reverse Cycl-10-14, 15-19 | 13 | 0.19 | 0.44 | | | |
| 275 | Linear | 12 | 0.11 | 0.35 | | | |
| 277 | Cyclo-7-11 | 29 | 0.12 | 0.64 | | | |
| 278 | Cyclo-7-11 28-32 | 12 | 0.125 | 0.74 | | | |

*Compound 265 has the sequence Ac-KIKHVVKLKDENSQLKSEVSKLRSQLVKRK-NH$_2$ (SEQ ID NO: 5). Compounds 266-269 have the sequences of SEQ ID NOs. 26 and 27, with substitutions at the $X_1$ and $X_2$ as described above in Example 3. Compound 275 has the sequence Ac-NLKQKIKHVVKLKDENSQLKSEVSKLRSQLVKRKQN-NH$_2$ (SEQ ID NO: 6). Compounds 277 and 278 have the sequences of SEQ ID NOs. 28 and 29, with substitutions at the $X_1$ and $X_2$ as described above in Example 3.

TABLE 21

$R^2$ values for individual cell functions vs. HA binding and helicity of HABD1 peptides

| Variable | Migration | Inflammation | Fibrosis |
|---|---|---|---|
| HA binding | 0.13 (neg*) | 0.001 (neg) | 0.24 |
| Helicity (CD) | 0.001 | 0.5 (neg) | 0.5 (neg) |

*neg = negative correlation or inverse correlation.

TABLE 22

$R^2$ values for individual cell functions vs. HA binding and helicity of HABD2 peptides

| Variable | Migration | Invasion | Inflammation | Fibrosis |
|---|---|---|---|---|
| HA binding | 0.32 | 0.04 | 1.00 (neg) | 0.92 (neg) |
| Helicity (CD) | 0.03 | 0.20 (neg*) | 0.39 | 0.99 |

*neg = negative correlation or inverse correlation.

TABLE 23

$R^2$ values for individual cell functions vs. HA binding and helicity of HABD1 + HABD2 peptides

| Variable | Migration | Invasion | Inflammation | Fibrosis |
|---|---|---|---|---|
| HA binding | 0.1 | 0.25 | 0.07 (neg) | 0.02 |
| Helicity (CD) | 0.03 | 0.03 (neg*) | 0.02 (neg) | 0.23 |

*neg = negative correlation or inverse correlation.

It was found that the peptides that contained most or all of HABD1 and all of HABD2 and the leucine zipper linker between HABD1 and HABD2 (HABD1+HABD2 peptides) had a greater HA-binding ability than peptides containing only HABD1 or HABD2. In general, HA binding ability was correlated to blocking migration and invasion. In addition, strong helicity was generally associated with function blocking. HA binding was not correlated to helicity, and in fact there appears to be an inverse correlation.

Compound 152 was an outlier in that it was a strong function blocker, but bound poorly to HA. Correlation coefficients were strongly reduced by the inclusion of compound 152 in the analyses.

HA binding of the HABD2 peptides was strongly inversely correlated to fibrosis and inflammation, while helicity was strongly associated with blocking these functions. Overall, stapling increased bioactivity, but this does not appear to be related to HA binding.

REFERENCES

1. Petrey A C, de la Motte C A: Hyaluronan, a crucial regulator of inflammation. Front Immunol 2014, 5:101.
2. Bollyky P L, Bogdani M, Bollyky J B, Hull R L, Wight T N: The role of hyaluronan and the extracellular matrix in islet inflammation and immune regulation. Curr Diab Rep 2012, 12(5):471-480.
3. Tolg C, McCarthy J B, Yazdani A, Turley E A: Hyaluronan and RHAMM in Wound Repair and the "Cancerization" of Stromal Tissues. Biomed Res Int 2014, 2014: 103923.
4. Jiang D, Liang J, Noble P W: Hyaluronan as an immune regulator in human diseases. Physiol Rev 2011, 91(1): 221-264.
5. Hill D R, Rho H K, Kessler S P, Amin R, Homer C R, McDonald C, Cowman M K, de la Motte C A: Human milk hyaluronan enhances innate defense of the intestinal epithelium. J Biol Chem 2013, 288(40):29090-29104.
6. Sokolowska M, Chen L Y, Eberlein M, Martinez-Anton A, Liu Y, Alsaaty S, Qi H Y, Logun C, Horton M, Shelhamer J H: Low molecular weight hyaluronan activates cytosolic phospholipase A2alpha and eicosanoid production in monocytes and macrophages. J Biol Chem 2014, 289(7): 4470-4488.
7. Ebid R, Lichtnekert J, Anders H J: Hyaluronan is not a ligand but a regulator of toll-like receptor signaling in mesangial cells: role of extracellular matrix in innate immunity. ISRN Nephrol 2014, 2014:714081.
8. Foley J P, Lam D, Jiang H, Liao J, Cheong N, McDevitt T M, Zaman A, Wright J R, Savani R C: Toll-like receptor 2 (TLR2), transforming growth factor-beta, hyaluronan (HA), and receptor for HA-mediated motility (RHAMM) are required for surfactant protein A-stimulated macrophage chemotaxis. J Biol Chem 2012, 287(44):37406-37419.
9. Orian-Rousseau V: CD44, a therapeutic target for metastasising tumours. Eur J Cancer 2010, 46(7):1271-1277.
10. Takeda M, Ogino S, Umemoto R, Sakakura M, Kajiwara M, Sugahara K N, Hayasaka H, Miyasaka M, Terasawa H, Shimada I: Ligand-induced structural changes of the CD44 hyaluronan-binding domain revealed by NMR. J Biol Chem 2006, 281(52):40089-40095.
11. Teriete P, Banerji S, Noble M, Blundell C D, Wright A J, Pickford A R, Lowe E, Mahoney D J, Tammi M I, Kahmann J D et al: Structure of the regulatory hyaluronan binding domain in the inflammatory leukocyte homing receptor CD44. Mol Cell 2004, 13(4):483-496.
12. Rezvani K, de Lavallade H: Vaccination strategies in lymphomas and leukaemias: recent progress. Drugs 2011, 71(13):1659-1674.
13. Casalegno-Garduno R, Schmitt A, Schmitt M: Clinical peptide vaccination trials for leukemia patients. Expert Rev Vaccines 2011, 10(6):785-799.
14. Ziebell, M. R. and G. D. Prestwich, Interactions of peptide mimics of hyaluronic acid with the receptor for hyaluronan mediated motility (RHAMM). J Comput Aided Mol Des, 2004. 18(10): p. 597-614.
15. Arispe, N., J. C. Diaz, and M. Flora, Efficiency of histidine-associating compounds for blocking the Alzheimer's Abeta channel activity and cytotoxicity. Biophys J, 2008. 95(10): p. 4879-89.
16. Isidro-Llobet, A., M. Alvarez, and F. Albericio, Amino acid-protecting groups. Chem Rev, 2009. 109(6): p. 2455-504.
17. Shepherd, N. E., et al., Single turn peptide alpha helices with exceptional stability in water. J Am Chem Soc, 2005. 127(9): p. 2974-83.
18. Luo, P. and R. L. Baldwin, Mechanism of helix induction by trifluoroethanol: a framework for extrapolating the helix-forming properties of peptides from trifluoroethanol/water mixtures back to water. Biochemistry, 1997. 36(27): p. 8413-21.
19. Correa, D. H. A. and C. H. I. Ramos, The use of circular dichroism spectroscopy to study protein folding, form and function. Afr. J. Biochem. Res., 2009. 3(5): p. 164-173.
20. Pelton, J. T. and L. R. McLean, Spectroscopic methods for analysis of protein secondary structure. Anal Biochem, 2000. 277(2): p. 167-76.
21. Shepherd, N. E., et al., *Single turn peptide alpha helices with exceptional stability in water.* J Am Chem Soc, 2005. 127(9): p. 2974-83.
22. Houston, M. E., et al., *Lactam bridge stabilization of α-helical peptides: Ring size, orientation and positional effect.* Journal of Peptide Science, 1995. 1: p. 274-282.

In view of the above, it will be seen that the several objects of the invention are achieved and other advantageous results attained.

As various changes could be made in the above compounds, compositions, and methods without departing from the scope of the invention, it is intended that all matter contained in the above description and shown in the accompanying drawing shall be interpreted as illustrative and not in a limiting sense.

The invention claimed is:

1. A peptide comprising at least a portion of a RHAMM HA binding domain (HABD), wherein the peptide has a length of at least 7 amino acids and includes one or more amino acid substitutions relative to the sequence of a HABD of a naturally occurring RHAMM protein, wherein the one or more substitutions occur at position i, i+4, and/or i+7, and wherein the substitution allows for the formation of a covalent bond between the amino acid at position i and the amino acid at position i+4 or i+7.

2. The peptide of claim 1, wherein the substitution at position i, i+4, and/or i+7 comprises a substitution with a standard amino acid.

3. The peptide of claim 1, wherein the substitution at position i, i+4, and/or i+7 comprises a substitution with a non-standard amino acid.

4. The peptide of claim 1, wherein the amino acid at position i is covalently bonded to the amino acid at position i+4 or i+7.

5. The peptide of claim 1, wherein the covalent bond comprises a lactam bridge, a hydrocarbon bridge, a metal-ion clip, a hydrogen bond surrogate, or a heterocycle bridge.

6. The peptide of claim 5, wherein the covalent bond comprises a lactam bridge and the one or more amino acid substitutions comprise a substitution with a glutamic acid residue, a substitution with a lysine residue, or a combination thereof.

7. The peptide of claim 6, wherein the one or more amino acid substitutions comprise:

a substitution with a glutamic acid residue at position i;
a substitution with a glutamic acid residue at position i+4;
a substitution with a glutamic acid residue at position i+7;
a substitution with a lysine residue at position i;
a substitution with a lysine residue at position i+4; or
a substitution with a lysine residue at position i+7.

8. The peptide of claim 7, wherein the one or more amino acid substitutions comprise the substitution with the glutamic acid residue at position i, and the sequence of the HABD of the naturally occurring RHAMM protein comprises a lysine residue at position i+4 or position i+7.

9. The peptide of claim 7, wherein the one or more amino acid substitutions comprise the substitution with a glutamic acid residue at position i and further comprises the substitution with the lysine residue at position i+4 or the substitution with the lysine residue at position i+7.

10. The peptide of claim 5, wherein:
(a) the covalent bond comprises a lactam bridge and the one or more amino acid substitutions comprise:
a substitution with an ornithine residue at position i and a substitution with an L-2-aminoadipic acid residue at position i+4 or i+7; or
a substitution with an L-2-aminoadipic acid residue at position i and a substitution with an ornithine residue at position i+4 or i+7; or
(b) the covalent bond comprises a hydrocarbon bridge and the one or more amino acid substitutions comprise:
substitutions with allylglycine residues at positions i and i+4;

substitutions with alanine derivative S5 residues at positions i and i+4;
a substitution with alanine derivative R8 at position i and a substitution with alanine derivative S5 at one of positions i+4 and i+7; or
substitutions with alanine derivative R5 residues at positions i and i+4.

11. The peptide of claim 1, wherein the peptide comprises:
one or more first substitutions at a first position i, a first position i+4, and/or a first position i+7, wherein the one or more first substitutions allows for the formation of a covalent bond between the amino acid at first position i and the amino acid at first position i+4 or first position i+7; and
one or more second substitutions at a second position i, a second position i+4, and/or a second position i+7, wherein the one or more second substitutions allows for the formation of a covalent bond between the amino acid at second position i and the amino acid at second position i+4 or second position i+7.

12. The peptide of claim 1, wherein the RHAMM HABD comprises amino acids 14 to 24 of SEQ ID NO: 1, amino acids 36 to 45 of SEQ ID NO: 1, or both acids 14 to 24 and amino acids 36 to 45 of SEQ ID NO: 1.

13. The peptide of claim 1, wherein the amino acid sequence of the peptide comprises a sequence selected from SEQ ID NOs. 2-6 and includes the one or more amino acid substitutions.

14. The peptide of claim 1, wherein the amino acid sequence of the peptide comprises a sequence selected from SEQ ID NOs. 7-32.

15. The peptide of claim 14, wherein the amino acid sequence of the peptide comprises or consists of:
VSKX$_1$RSQX$_2$VKRKQN (SEQ ID NO: 7), wherein X$_1$ is glutamic acid and X$_2$ is lysine, and wherein X$_1$ is covalently bonded to X$_2$;
VSKLX$_1$SQLX$_2$KRKQN (SEQ ID NO: 8), wherein X$_1$ is glutamic acid and X$_2$ is lysine, and wherein X$_1$ is covalently bonded to X$_2$;
VSKLRX$_1$QLVX$_2$RKQN (SEQ ID NO: 9), wherein X$_1$ is glutamic acid and X$_2$ is lysine, and wherein X$_1$ is covalently bonded to X$_2$;
VSKLRSX$_1$LVKX$_2$KQN (SEQ ID NO: 10), wherein X$_1$ is glutamic acid and X$_2$ is lysine, and wherein X$_1$ is covalently bonded to X$_2$;
VSKX$_1$RSQX$_2$VKRKQN (SEQ ID NO: 7), wherein X$_1$ is lysine and X$_2$ is glutamic acid, and wherein X$_1$ is covalently bonded to X$_2$;
VSKLX$_1$SQLX$_2$KRKQN (SEQ ID NO: 8), wherein X$_1$ is lysine and X$_2$ is glutamic acid, and wherein X$_1$ is covalently bonded to X$_2$;
VSKLRX$_1$QLVX$_2$RKQN (SEQ ID NO: 9), wherein X$_1$ is lysine and X$_2$ is glutamic acid, and wherein X$_1$ is covalently bonded to X$_2$;
VSKLRSX$_1$LVKX$_2$KQN (SEQ ID NO: 10), wherein X$_1$ is lysine and X$_2$ is glutamic acid, and wherein X$_1$ is covalently bonded to X$_2$;
VSKX$_1$RSQX$_2$VKRKQN (SEQ ID NO: 7), wherein X$_1$ is ornithine and X$_2$ is L-2-aminoadipic acid, and wherein X$_1$ is covalently bonded to X$_2$;
VSKLX$_1$SQLX$_2$KRKQN (SEQ ID NO: 8), wherein X$_1$ is ornithine and X$_2$ is L-2-aminoadipic acid, and wherein X$_1$ is covalently bonded to X$_2$;
VSKLRX$_1$QLVX$_2$RKQN (SEQ ID NO: 9), wherein X$_1$ is ornithine and X$_2$ is L-2-aminoadipic acid, and wherein X$_1$ is covalently bonded to X$_2$;
VSKLRSX$_1$LVKX$_2$KQN (SEQ ID NO: 10), wherein X$_1$ is ornithine and X$_2$ is L-2-aminoadipic acid, and wherein X$_1$ is covalently bonded to X$_2$;
VSKX$_1$RSQX$_2$VKRKQN (SEQ ID NO: 7), wherein X$_1$ is L-2-aminoadipic acid and X$_2$ is ornithine, and wherein X$_1$ is covalently bonded to X$_2$;
VSKLX$_1$SQLX$_2$KRKQN (SEQ ID NO: 8), wherein X$_1$ is L-2-aminoadipic acid and X$_2$ is ornithine, and wherein X$_1$ is covalently bonded to X$_2$;
VSKLRX$_1$QLVX$_2$RKQN (SEQ ID NO: 9), wherein X$_1$ is L-2-aminoadipic acid and X$_2$ is ornithine, and wherein X$_1$ is covalently bonded to X$_2$;
VSKLRSX$_1$LVKX$_2$KQN (SEQ ID NO: 10), wherein X$_1$ is L-2-aminoadipic acid and X$_2$ is ornithine, and wherein X$_1$ is covalently bonded to X$_2$;
VSKX$_1$RSQX$_2$VKRKQN (SEQ ID NO: 7), wherein X$_1$ and X$_2$ are both alanine derivative S5, and wherein X$_1$ is covalently bonded to X$_2$;
VSKLX$_1$SQLX$_2$KRKQN (SEQ ID NO: 8), wherein X$_1$ and X$_2$ are both alanine derivative S5, and wherein X$_1$ is covalently bonded to X$_2$;
VSKLRX$_1$QLVX$_2$RKQN (SEQ ID NO: 9), wherein X$_1$ and X$_2$ are both alanine derivative S5, and wherein X$_1$ is covalently bonded to X$_2$;
VSKLRSX$_1$LVKX$_2$KQN (SEQ ID NO: 10), wherein X$_1$ and X$_2$ are both alanine derivative S5, and wherein X$_1$ is covalently bonded to X$_2$;
VSKX$_1$RSQX$_2$VKRKQN (SEQ ID NO: 7), wherein X$_1$ and X$_2$ are both allylglycine, and wherein X$_1$ is covalently bonded to X$_2$;
VSKLX$_1$SQLX$_2$KRKQN (SEQ ID NO: 8), wherein X$_1$ and X$_2$ are both allylglycine, and wherein X$_1$ is covalently bonded to X$_2$;
VSKLRX$_1$QLVX$_2$RKQN (SEQ ID NO: 9), wherein X$_1$ and X$_2$ are both allylglycine, and wherein X$_1$ is covalently bonded to X$_2$;
VSKLRSX$_1$LVKX$_2$KQN (SEQ ID NO: 10), wherein X$_1$ and X$_2$ are both allylglycine, and wherein X$_1$ is covalently bonded to X$_2$;
NLKX$_1$KIKX$_2$VVKLKDE (SEQ ID NO: 15), wherein X$_1$ is glutamic acid and X$_2$ is lysine, and wherein X$_1$ is covalently bonded to X$_2$;
NLKQX$_1$IKHX$_2$VKLKDE (SEQ ID NO: 16), wherein X$_1$ is glutamic acid and X$_2$ is lysine, and wherein X$_1$ is covalently bonded to X$_2$;
NLKQKX$_1$KHVX$_2$KLKDE (SEQ ID NO: 17), wherein X$_1$ is glutamic acid and X$_2$ is lysine, and wherein X$_1$ is covalently bonded to X$_2$;
NLKQKIX$_1$HVVX$_2$LKDE (SEQ ID NO: 18), wherein X$_1$ is glutamic acid and X$_2$ is lysine, and wherein X$_1$ is covalently bonded to X$_2$;
NLKQKIKX$_1$VVKX$_2$KDE (SEQ ID NO: 19), wherein X$_1$ is glutamic acid and X$_2$ is lysine, and wherein X$_1$ is covalently bonded to X$_2$;
NLKX$_1$KIKX$_2$VVKLKDE (SEQ ID NO: 15), wherein X$_1$ is lysine and X$_2$ is glutamic acid, and wherein X$_1$ is covalently bonded to X$_2$;
NLKQX$_1$IKHX$_2$VKLKDE (SEQ ID NO: 16), wherein X$_1$ is lysine and X$_2$ is glutamic acid, and wherein X$_1$ is covalently bonded to X$_2$;
NLKQKX$_1$KHVX$_2$KLKDE (SEQ ID NO: 17), wherein X$_1$ is lysine and X$_2$ is glutamic acid, and wherein X$_1$ is covalently bonded to X$_2$;
NLKQKIX$_1$HVVX$_2$LKDE (SEQ ID NO: 18), wherein X$_1$ is lysine and X$_2$ is glutamic acid, and wherein X$_1$ is covalently bonded to X$_2$;

NLKQKIKX$_1$VVKX$_2$KDE (SEQ ID NO: 19), wherein X$_1$ is lysine and X$_2$ is glutamic acid, and wherein X$_1$ is covalently bonded to X$_2$;
NLKX$_1$KIKX$_2$VVKLKDE (SEQ ID NO: 15), wherein X$_1$ is ornithine and X$_2$ is L-2-aminoadipic acid, and wherein X$_1$ is covalently bonded to X$_2$;
NLKQX$_1$IKHX$_2$VKLKDE (SEQ ID NO: 16), wherein X$_1$ is ornithine and X$_2$ is L-2-aminoadipic acid, and wherein X$_1$ is covalently bonded to X$_2$;
NLKQKX$_1$KHVX$_2$KLKDE (SEQ ID NO: 17), wherein X$_1$ is ornithine and X$_2$ is L-2-aminoadipic acid, and wherein X$_1$ is covalently bonded to X$_2$;
NLKQKIX$_1$HVVX$_2$LKDE (SEQ ID NO: 18), wherein X$_1$ is ornithine and X$_2$ is L-2-aminoadipic acid, and wherein X$_1$ is covalently bonded to X$_2$;
NLKQKIKX$_1$VVKX$_2$KDE (SEQ ID NO: 19), wherein X$_1$ is ornithine and X$_2$ is L-2-aminoadipic acid, and wherein X$_1$ is covalently bonded to X$_2$;
NLKX$_1$KIKX$_2$VVKLKDE (SEQ ID NO: 15), wherein X$_1$ is L-2-aminoadipic acid and X$_2$ is ornithine, and wherein X$_1$ is covalently bonded to X$_2$;
NLKQX$_1$IKHX$_2$VKLKDE (SEQ ID NO: 16), wherein X$_1$ is L-2-aminoadipic acid and X$_2$ is ornithine, and wherein X$_1$ is covalently bonded to X$_2$;
NLKQKX$_1$KHVX$_2$KLKDE (SEQ ID NO: 17), wherein X$_1$ is L-2-aminoadipic acid and X$_2$ is ornithine, and wherein X$_1$ is covalently bonded to X$_2$;
NLKQKIX$_1$HVVX$_2$LKDE (SEQ ID NO: 18), wherein X$_1$ is L-2-aminoadipic acid and X$_2$ is ornithine, and wherein X$_1$ is covalently bonded to X$_2$;
NLKQKIKX$_1$VVKX$_2$KDE (SEQ ID NO: 19), wherein X$_1$ is L-2-aminoadipic acid and X$_2$ is ornithine, and wherein X$_1$ is covalently bonded to X$_2$;
NLKX$_1$KIKX$_2$VVKLKDE (SEQ ID NO: 15), wherein X$_1$ and X$_2$ are both alanine derivative S5, and wherein X$_1$ is covalently bonded to X$_2$;
NLKQX$_1$IKHX$_2$VKLKDE (SEQ ID NO: 16), wherein X$_1$ and X$_2$ are both alanine derivative S5, and wherein X$_1$ is covalently bonded to X$_2$;
NLKQKX$_1$KHVX$_2$KLKDE (SEQ ID NO: 17), wherein X$_1$ and X$_2$ are both alanine derivative S5, and wherein X$_1$ is covalently bonded to X$_2$;
NLKQKIX$_1$HVVX$_2$LKDE (SEQ ID NO: 18), wherein X$_1$ and X$_2$ are both alanine derivative S5, and wherein X$_1$ is covalently bonded to X$_2$;
NLKQKIKX$_1$VVKX$_2$KDE (SEQ ID NO: 19), wherein X$_1$ and X$_2$ are both alanine derivative S5, and wherein X$_1$ is covalently bonded to X$_2$;
NLKX$_1$KIKX$_2$VVKLKDE (SEQ ID NO: 15), wherein X$_1$ and X$_2$ are both allylglycine, and wherein X$_1$ is covalently bonded to X$_2$;
NLKQX$_1$IKHX$_2$VKLKDE (SEQ ID NO: 16), wherein X$_1$ and X$_2$ are both allylglycine, and wherein X$_1$ is covalently bonded to X$_2$;
NLKQKX$_1$KHVX$_2$KLKDE (SEQ ID NO: 17), wherein X$_1$ and X$_2$ are both allylglycine, and wherein X$_1$ is covalently bonded to X$_2$;
NLKQKIX$_1$HVVX$_2$LKDE (SEQ ID NO: 18), wherein X$_1$ and X$_2$ are both allylglycine, and wherein X$_1$ is covalently bonded to X$_2$;
NLKQKIKX$_1$VVKX$_2$KDE (SEQ ID NO: 19), wherein X$_1$ and X$_2$ are both allylglycine, and wherein X$_1$ is covalently bonded to X$_2$;
NLKX$_1$KIKHVVX$_2$LKDE (SEQ ID NO: 20), wherein X$_1$ is glutamic acid and X$_2$ is lysine, and wherein X$_1$ is covalently bonded to X$_2$;
NLKQX$_1$IKHVVKX$_2$KDE (SEQ ID NO: 21), wherein X$_1$ is glutamic acid and X$_2$ is lysine, and wherein X$_1$ is covalently bonded to X$_2$;
NLKX$_1$KIKHVVX$_2$LKDE (SEQ ID NO: 20), wherein X$_1$ is lysine and X$_2$ is glutamic acid, and wherein X$_1$ is covalently bonded to X$_2$;
NLKQX$_1$IKHVVKX$_2$KDE (SEQ ID NO: 21), wherein X$_1$ is lysine and X$_2$ is glutamic acid, and wherein X$_1$ is covalently bonded to X$_2$;
NLKX$_1$KIKHVVX$_2$LKDE (SEQ ID NO: 20), wherein X$_1$ is ornithine and X$_2$ is L-2-aminoadipic acid, and wherein X$_1$ is covalently bonded to X$_2$;
NLKQX$_1$IKHVVKX$_2$KDE (SEQ ID NO: 21), wherein X$_1$ is ornithine and X$_2$ is L-2-aminoadipic acid, and wherein X$_1$ is covalently bonded to X$_2$;
NLKX$_1$KIKHVVX$_2$LKDE (SEQ ID NO: 20), wherein X$_1$ is L-2-aminoadipic acid and X$_2$ is ornithine, and wherein X$_1$ is covalently bonded to X$_2$;
NLKQX$_1$IKHVVKX$_2$KDE (SEQ ID NO: 21), wherein X$_1$ is L-2-aminoadipic acid and X$_2$ is ornithine, and wherein X$_1$ is covalently bonded to X$_2$;
NLKX$_1$KIKHVVX$_2$LKDE (SEQ ID NO: 20), wherein X$_1$ is alanine derivative R8 and X$_2$ is alanine derivative S5, and wherein X$_1$ is covalently bonded to X$_2$;
NLKQX$_1$IKHVVKX$_2$KDE (SEQ ID NO: 21), wherein X$_1$ is alanine derivative R8 and X$_2$ is alanine derivative S5, and wherein X$_1$ is covalently bonded to X$_2$;
KSEVSKLRX$_1$QLVKRKX$_2$NELR (SEQ ID NO: 11), wherein X$_1$ is glutamic acid and X$_2$ is lysine, and wherein X$_1$ is covalently bonded to X$_2$;
KSEVSKLRSX$_1$LVKRKQX$_2$ELR (SEQ ID NO: 12), wherein X$_1$ is glutamic acid and X$_2$ is lysine, and wherein X$_1$ is covalently bonded to X$_2$;
KSEVSKLRSQX$_1$VKRKQNX$_2$LR (SEQ ID NO: 13), wherein X$_1$ is glutamic acid and X$_2$ is lysine, and wherein X$_1$ is covalently bonded to X$_2$;
KSEVSKLRX$_1$QLVKRKX$_2$NELR (SEQ ID NO: 11), wherein X$_1$ is lysine and X$_2$ is glutamic acid, and wherein X$_1$ is covalently bonded to X$_2$;
KSEVSKLRSX$_1$LVKRKQX$_2$ELR (SEQ ID NO: 12), wherein X$_1$ is lysine and X$_2$ is glutamic acid, and wherein X$_1$ is covalently bonded to X$_2$;
KSEVSKLRSQX$_1$VKRKQNX$_2$LR (SEQ ID NO: 13), wherein X$_1$ is lysine and X$_2$ is glutamic acid, and wherein X$_1$ is covalently bonded to X$_2$;
KSEVSKLRX$_1$QLVKRKX$_2$NELR (SEQ ID NO: 11), wherein X$_1$ is ornithine and X$_2$ is L-2-aminoadipic acid, and wherein X$_1$ is covalently bonded to X$_2$;
KSEVSKLRSX$_1$LVKRKQX$_2$ELR (SEQ ID NO: 12), wherein X$_1$ is ornithine and X$_2$ is L-2-aminoadipic acid, and wherein X$_1$ is covalently bonded to X$_2$;
KSEVSKLRSQX$_1$VKRKQNX$_2$LR (SEQ ID NO: 13), wherein X$_1$ is ornithine and X$_2$ is L-2-aminoadipic acid, and wherein X$_1$ is covalently bonded to X$_2$;
KSEVSKLRX$_1$QLVKRKX$_2$NELR (SEQ ID NO: 11), wherein X$_1$ is L-2-aminoadipic acid and X$_2$ is ornithine, and wherein X$_1$ is covalently bonded to X$_2$;
KSEVSKLRSX$_1$LVKRKQX$_2$ELR (SEQ ID NO: 12), wherein X$_1$ is L-2-aminoadipic acid and X$_2$ is ornithine, and wherein X$_1$ is covalently bonded to X$_2$;
KSEVSKLRSQX$_1$VKRKQNX$_2$LR (SEQ ID NO: 13), wherein X$_1$ is L-2-aminoadipic acid and X$_2$ is ornithine, and wherein X$_1$ is covalently bonded to X$_2$;
KSEVSKLRX$_1$QLVKRKX$_2$NELR (SEQ ID NO: 11), wherein X$_1$ is alanine derivative R8 and X$_2$ is alanine derivative S5, and wherein X$_1$ is covalently bonded to X$_2$;

KSEVSKLRSX$_1$LVKRKQX$_2$ELR (SEQ ID NO: 12), wherein X$_1$ is alanine derivative R8 and X$_2$ is alanine derivative S5, and wherein X$_1$ is covalently bonded to X$_2$;

KSEVSKLRSQX$_1$VKRKQNX$_2$LR (SEQ ID NO: 13), wherein X$_1$ is alanine derivative R8 and X$_2$ is alanine derivative S5, and wherein X$_1$ is covalently bonded to X$_2$;

KIKHVVKLKX$_1$ENSQLKX$_2$EVSKLRSQLVKRK (SEQ ID NO: 22), wherein X$_1$ is glutamic acid and X$_2$ is lysine, and wherein X$_1$ is covalently bonded to X$_2$;

KIKHVVKLKDX$_1$NSQLKSX$_2$VSKLRSQLVKRK (SEQ ID NO: 23), wherein X$_1$ is glutamic acid and X$_2$ is lysine, and wherein X$_1$ is covalently bonded to X$_2$;

KIKHVVKLKDEX$_1$SQLKSEX$_2$SKLRSQLVKRK (SEQ ID NO: 24), wherein X$_1$ is glutamic acid and X$_2$ is lysine, and wherein X$_1$ is covalently bonded to X$_2$;

KIKHVVKLKDENX$_1$QLKSEVX$_2$KLRSQLVKRK (SEQ ID NO: 25), wherein X$_1$ is glutamic acid and X$_2$ is lysine, and wherein X$_1$ is covalently bonded to X$_2$;

KIKHVVKLKX$_1$ENSQLKX$_2$EVSKLRSQLVKRK (SEQ ID NO: 22), wherein X$_1$ is lysine and X$_2$ is glutamic acid, and wherein X$_1$ is covalently bonded to X$_2$;

KIKHVVKLKDX$_1$NSQLKSX$_2$VSKLRSQLVKRK (SEQ ID NO: 23), wherein X$_1$ is lysine and X$_2$ is glutamic acid, and wherein X$_1$ is covalently bonded to X$_2$;

KIKHVVKLKDEX$_1$SQLKSEX$_2$SKLRSQLVKRK (SEQ ID NO: 24), wherein X$_1$ is lysine and X$_2$ is glutamic acid, and wherein X$_1$ is covalently bonded to X$_2$;

KIKHVVKLKDENX$_1$QLKSEVX$_2$KLRSQLVKRK (SEQ ID NO: 25), wherein X$_1$ is lysine and X$_2$ is glutamic acid, and wherein X$_1$ is covalently bonded to X$_2$;

KIKHVVKLKX$_1$ENSQLKX$_2$EVSKLRSQLVKRK (SEQ ID NO: 22), wherein X$_1$ is ornithine and X$_2$ is L-2-aminoadipic acid, and wherein X$_1$ is covalently bonded to X$_2$;

KIKHVVKLKDX$_1$NSQLKSX$_2$VSKLRSQLVKRK (SEQ ID NO: 23), wherein X$_1$ is ornithine and X$_2$ is L-2-aminoadipic acid, and wherein X$_1$ is covalently bonded to X$_2$;

KIKHVVKLKDEX$_1$SQLKSEX$_2$SKLRSQLVKRK (SEQ ID NO: 24), wherein X$_1$ is ornithine and X$_2$ is L-2-aminoadipic acid, and wherein X$_1$ is covalently bonded to X$_2$;

KIKHVVKLKDENX$_1$QLKSEVX$_2$KLRSQLVKRK (SEQ ID NO: 25), wherein X$_1$ is ornithine and X$_2$ is L-2-aminoadipic acid, and wherein X$_1$ is covalently bonded to X$_2$;

KIKHVVKLKX$_1$ENSQLKX$_2$EVSKLRSQLVKRK (SEQ ID NO: 22), wherein X$_1$ is L-2-aminoadipic acid and X$_2$ is ornithine, and wherein X$_1$ is covalently bonded to X$_2$;

KIKHVVKLKDX$_1$NSQLKSX$_2$VSKLRSQLVKRK (SEQ ID NO: 23), wherein X$_1$ is L-2-aminoadipic acid and X$_2$ is ornithine, and wherein X$_1$ is covalently bonded to X$_2$;

KIKHVVKLKDEX$_1$SQLKSEX$_2$SKLRSQLVKRK (SEQ ID NO: 24), wherein X$_1$ is L-2-aminoadipic acid and X$_2$ is ornithine, and wherein X$_1$ is covalently bonded to X$_2$;

KIKHVVKLKDENX$_1$QLKSEVX$_2$KLRSQLVKRK (SEQ ID NO: 25), wherein X$_1$ is L-2-aminoadipic acid and X$_2$ is ornithine, and wherein X$_1$ is covalently bonded to X$_2$;

KIKHVVKLKX$_1$ENSQLKX$_2$EVSKLRSQLVKRK (SEQ ID NO: 22), wherein X$_1$ is alanine derivative R8 and X$_2$ is alanine derivative S5, and wherein X$_1$ is covalently bonded to X$_2$;

KIKHVVKLKDX$_1$NSQLKSX$_2$VSKLRSQLVKRK (SEQ ID NO: 23), wherein X$_1$ is alanine derivative R8 and X$_2$ is alanine derivative S5, and wherein X$_1$ is covalently bonded to X$_2$;

KIKHVVKLKDEX$_1$SQLKSEX$_2$SKLRSQLVKRK (SEQ ID NO: 24), wherein X$_1$ is alanine derivative R8 and X$_2$ is alanine derivative S5, and wherein X$_1$ is covalently bonded to X$_2$;

KIKHVVKLKDENX$_1$QLKSEVX$_2$KLRSQLVKRK (SEQ ID NO: 25), wherein X$_1$ is alanine derivative R8 and X$_2$ is alanine derivative S5, and wherein X$_1$ is covalently bonded to X$_2$;

KIKHVVKLKX$_1$ENSX$_2$X$_3$KSEX$_4$SKLRSQLVKRK (SEQ ID NO: 26), wherein X$_1$ is glutamic acid, X$_2$ is lysine, X$_3$ is glutamic acid, X$_4$ is lysine, and wherein X$_1$ is covalently bonded to X$_2$ and X$_3$ is covalently bonded to X$_4$;

KIKHVVKLKDX$_1$NSQX$_2$X$_3$SEVX$_4$KLRSQLVKRK (SEQ ID NO: 27), wherein X$_1$ is glutamic acid, X$_2$ is lysine, X$_3$ is glutamic acid, X$_4$ is lysine, and wherein X$_1$ is covalently bonded to X$_2$ and X$_3$ is covalently bonded to X$_4$;

KIKHVVKLKX$_1$ENSX$_2$X$_3$KSEX$_4$SKLRSQLVKRK (SEQ ID NO: 26), wherein X$_1$ is lysine, X$_2$ is glutamic acid, X$_3$ is lysine, X$_4$ is glutamic acid, and wherein X$_1$ is covalently bonded to X$_2$ and X$_3$ is covalently bonded to X$_4$;

KIKHVVKLKDX$_1$NSQX$_2$X$_3$SEVX$_4$KLRSQLVKRK (SEQ ID NO: 27), wherein X$_1$ is lysine, X$_2$ is glutamic acid, X$_3$ is lysine, X$_4$ is glutamic acid, and wherein X$_1$ is covalently bonded to X$_2$ and X$_3$ is covalently bonded to X$_4$;

KIKHVVKLKX$_1$ENSX$_2$X$_3$KSEX$_4$SKLRSQLVKRK (SEQ ID NO: 26), wherein X$_1$ is glutamic acid, X$_2$ is lysine, X$_3$ is lysine, X$_4$ is glutamic acid, and wherein X$_1$ is covalently bonded to X$_2$ and X$_3$ is covalently bonded to X$_4$;

KIKHVVKLKDX$_1$NSQX$_2$X$_3$SEVX$_4$KLRSQLVKRK (SEQ ID NO: 27), wherein X$_1$ is glutamic acid, X$_2$ is lysine, X$_3$ is lysine, X$_4$ is glutamic acid, and wherein X$_1$ is covalently bonded to X$_2$ and X$_3$ is covalently bonded to X$_4$;

KIKHVVKLKX$_1$ENSX$_2$X$_3$KSEX$_4$SKLRSQLVKRK (SEQ ID NO: 26), wherein X$_1$ is lysine, X$_2$ is glutamic acid, X$_3$ is glutamic acid, X$_4$ is lysine, and wherein X$_1$ is covalently bonded to X$_2$ and X$_3$ is covalently bonded to X$_4$;

KIKHVVKLKDX$_1$NSQX$_2$X$_3$SEVX$_4$KLRSQLVKRK (SEQ ID NO: 27), wherein X$_1$ is lysine, X$_2$ is glutamic acid, X$_3$ is glutamic acid, X$_4$ is lysine, and wherein X$_1$ is covalently bonded to X$_2$ and X$_3$ is covalently bonded to X$_4$;

KIKHVVKLKX$_1$ENSX$_2$X$_3$KSEX$_4$SKLRSQLVKRK (SEQ ID NO: 26), wherein X$_1$ is ornithine, X$_2$ is L-2-aminoadipic acid, X$_3$ is ornithine, X$_4$ is L-2-aminoadipic acid, and wherein X$_1$ is covalently bonded to X$_2$ and X$_3$ is covalently bonded to X$_4$;

KIKHVVKLKDX$_1$NSQX$_2$X$_3$SEVX$_4$KLRSQLVKRK (SEQ ID NO: 27), wherein X$_1$ is ornithine, X$_2$ is L-2-aminoadipic acid, X$_3$ is ornithine, X$_4$ is L-2-aminoadipic acid, and wherein X$_1$ is covalently bonded to X$_2$ and X$_3$ is covalently bonded to X$_4$;

KIKHVVKLKX₁ENSX₂X₃KSEX₄SKLRSQLVKRK
(SEQ ID NO: 26), wherein X₁ is L-2-aminoadipic acid, X₂ is ornithine, X₃ is L-2-aminoadipic acid, X₄ is ornithine, and wherein X₁ is covalently bonded to X₂ and X₃ is covalently bonded to X₄;

KIKHVVKLKDX₁NSQX₂X₃SEVX₄KLRSQLVKRK
(SEQ ID NO: 27), wherein X₁ is L-2-aminoadipic acid, X₂ is ornithine, X₃ is L-2-aminoadipic acid, X₄ is ornithine, and wherein X₁ is covalently bonded to X₂ and X₃ is covalently bonded to X₄;

KIKHVVKLKX₁ENSX₂X₃KSEX₄SKLRSQLVKRK
(SEQ ID NO: 26), wherein X₁ is ornithine, X₂ is L-2-aminoadipic acid, X₃ is L-2-aminoadipic acid, X₄ is ornithine, and wherein X₁ is covalently bonded to X₂ and X₃ is covalently bonded to X₄;

KIKHVVKLKDX₁NSQX₂X₃SEVX₄KLRSQLVKRK
(SEQ ID NO: 27), wherein X₁ is ornithine, X₂ is L-2-aminoadipic acid, X₃ is L-2-aminoadipic acid, X₄ is ornithine, and wherein X₁ is covalently bonded to X₂ and X₃ is covalently bonded to X₄;

KIKHVVKLKX₁ENSX₂X₃KSEX₄SKLRSQLVKRK
(SEQ ID NO: 26), wherein X₁ is L-2-aminoadipic acid, X₂ is ornithine, X₃ is ornithine, X₄ is L-2-aminoadipic acid, and wherein X₁ is covalently bonded to X₂ and X₃ is covalently bonded to X₄;

KIKHVVKLKDX₁NSQX₂X₃SEVX₄KLRSQLVKRK
(SEQ ID NO: 27), wherein X₁ is L-2-aminoadipic acid, X₂ is ornithine, X₃ is ornithine, X₄ is L-2-aminoadipic acid, and wherein X₁ is covalently bonded to X₂ and X₃ is covalently bonded to X₄;

KIKHVVKLKX₁ENSX₂X₃KSEX₄SKLRSQLVKRK
(SEQ ID NO: 26), wherein X₁, X₂, X₃, and X₄ are each allylglycine, and wherein X₁ is covalently bonded to X₂ and X₃ is covalently bonded to X₄;

KIKHVVKLKDX₁NSQX₂X₃SEVX₄KLRSQLVKRK
(SEQ ID NO: 27), wherein X₁, X₂, X₃, and X₄ are each allylglycine, and wherein X₁ is covalently bonded to X₂ and X₃ is covalently bonded to X₄;

KIKHVVKLKX₁ENSX₂X₃KSEX₄SKLRSQLVKRK
(SEQ ID NO: 26), wherein X₁, X₂, X₃, and X₄ are each alanine derivative S5, and wherein X₁ is covalently bonded to X₂ and X₃ is covalently bonded to X₄;

KIKHVVKLKDX₁NSQX₂X₃SEVX₄KLRSQLVKRK
(SEQ ID NO: 27), wherein X₁, X₂, X₃, and X₄ are each alanine derivative S5, and wherein X₁ is covalently bonded to X₂ and X₃ is covalently bonded to X₄;

NLKQKIKHVVKLKDENSQLKSEVSKLRX₁QLVX₂RKQN (SEQ ID NO: 28), wherein X₁ is glutamic acid and X₂ is lysine, and wherein X₁ is covalently bonded to X₂;

NLKQKIX₁HVVX₂LKDENSQLKSEVSKLRX₃QLVX₄RKQN (SEQ ID NO: 29), wherein X₁ is glutamic acid, X₂ is lysine, X₃ is glutamic acid, X₄ is lysine, and wherein X₁ is covalently bonded to X₂ and X₃ is covalently bonded to X₄;

NLKQKIKHVVKLKDENSQLKSEVSKLX₁SQLX₂KRKQN (SEQ ID NO: 30), wherein X₁ is glutamic acid and X₂ is lysine, and wherein X₁ is covalently bonded to X₂;

NLKQKIX₁HVVX₂LKDENSQLKSEVSKLRSQLVKRKQN (SEQ ID NO: 31), wherein X₁ is glutamic acid and X₂ is lysine, and wherein X₁ is covalently bonded to X₂; or NLKQKIX₁HVVX₂LKDENSQLKSEVSKLX₃SQLX₄KRKQN (SEQ ID NO: 32), wherein X₁ is glutamic acid, X₂ is lysine, X₃ is glutamic acid, X₄ is lysine, and wherein X₁ is covalently bonded to X₂ and X₃ is covalently bonded to X₄.

16. The peptide of claim 15, wherein the amino acid sequence of the peptide comprises or consists of:

VSKX₁RSQX₂VKRKQN (SEQ ID NO: 7), wherein X₁ is glutamic acid and X₂ is lysine, and wherein X₁ is covalently bonded to X₂;

VSKLX₁SQLX₂KRKQN (SEQ ID NO: 8), wherein X₁ is glutamic acid and X₂ is lysine, and wherein X₁ is covalently bonded to X₂;

VSKLRX₁QLVX₂RKQN (SEQ ID NO: 9), wherein X₁ is glutamic acid and X₂ is lysine, and wherein X₁ is covalently bonded to X₂;

VSKLRSX₁LVKX₂KQN (SEQ ID NO: 10), wherein X₁ is glutamic acid and X₂ is lysine, and wherein X₁ is covalently bonded to X₂;

VSKLX₁SQLX₂KRKQN (SEQ ID NO: 8), wherein X₁ is lysine and X₂ is glutamic acid, and wherein X₁ is covalently bonded to X₂;

VSKLRX₁QLVX₂RKQN (SEQ ID NO: 9), wherein X₁ is lysine and X₂ is glutamic acid, and wherein X₁ is covalently bonded to X₂;

NLKX₁KIKX₂VVKLKDE (SEQ ID NO: 15), wherein X₁ is glutamic acid and X₂ is lysine, and wherein X₁ is covalently bonded to X₂;

NLKQX₁IKHX₂VKLKDE (SEQ ID NO: 16), wherein X₁ is glutamic acid and X₂ is lysine, and wherein X₁ is covalently bonded to X₂;

NLKQKX₁KHVX₂KLKDE (SEQ ID NO: 17), wherein X₁ is glutamic acid and X₂ is lysine, and wherein X₁ is covalently bonded to X₂;

NLKQKIX₁HVVX₂LKDE (SEQ ID NO: 18), wherein X₁ is glutamic acid and X₂ is lysine, and wherein X₁ is covalently bonded to X₂;

NLKQKIKX₁VVKX₂KDE (SEQ ID NO: 19), wherein X₁ is glutamic acid and X₂ is lysine, and wherein X₁ is covalently bonded to X₂;

KIKHVVKLKX₁ENSX₂X₃KSEX₄SKLRSQLVKRK
(SEQ ID NO: 26), wherein X₁ is glutamic acid, X₂ is lysine, X₃ is glutamic acid, X₄ is lysine, and wherein X₁ is covalently bonded to X₂ and X₃ is covalently bonded to X₄;

KIKHVVKLKDX₁NSQX₂X₃SEVX₄KLRSQLVKRK
(SEQ ID NO: 27), wherein X₁ is glutamic acid, X₂ is lysine, X₃ is glutamic acid, X₄ is lysine, and wherein X₁ is covalently bonded to X₂ and X₃ is covalently bonded to X₄;

KIKHVVKLKX₁ENSX₂X₃KSEX₄SKLRSQLVKRK
(SEQ ID NO: 26), wherein X₁ is glutamic acid, X₂ is lysine, X₃ is lysine, X₄ is glutamic acid, and wherein X₁ is covalently bonded to X₂ and X₃ is covalently bonded to X₄;

KIKHVVKLKX₁ENSX₂X₃KSEX₄SKLRSQLVKRK
(SEQ ID NO: 26), wherein X₁ is lysine, X₂ is glutamic acid, X₃ is glutamic acid, X₄ is lysine, and wherein X₁ is covalently bonded to X₂ and X₃ is covalently bonded to X₄;

NLKQKIKHVVKLKDENSQLKSEVSKLRX₁QLVX₂RKQN (SEQ ID NO: 28), wherein X₁ is glutamic acid and X₂ is lysine, and wherein X₁ is covalently bonded to X₂; or NLKQKIX₁HVVX₂LKDENSQLKSEVSKLRX₃QLVX₄RKQN (SEQ ID NO: 29), wherein X₁ is glutamic acid, X₂ is lysine, X₃ is glutamic acid, X₄ is lysine, and wherein X₁ is covalently bonded to X₂ and X₃ is covalently bonded to X₄.

17. The peptide of claim 16, wherein the amino acid sequence of the peptide comprises or consists of:
VSKX$_1$RSQX$_2$VKRKQN (SEQ ID NO: 7), wherein X$_1$ is glutamic acid and X$_2$ is lysine, and wherein X$_1$ is covalently bonded to X$_2$;
VSKLRX$_1$QLVX$_2$RKQN (SEQ ID NO: 9), wherein X$_1$ is glutamic acid and X$_2$ is lysine, and wherein X$_1$ is covalently bonded to X$_2$;
NLKX$_1$KIKX$_2$VVKLKDE (SEQ ID NO: 15), wherein X$_1$ is glutamic acid and X$_2$ is lysine, and wherein X$_1$ is covalently bonded to X$_2$;
NLKQX$_1$IKHX$_2$VKLKDE (SEQ ID NO: 16), wherein X$_1$ is glutamic acid and X$_2$ is lysine, and wherein X$_1$ is covalently bonded to X$_2$;
KIKHVVKLKX$_1$ENSX$_2$X$_3$KSEX$_4$SKLRSQLVKRK (SEQ ID NO: 26), wherein X$_1$ is glutamic acid, X$_2$ is lysine, X$_3$ is glutamic acid, X$_4$ is lysine, and wherein X$_1$ is covalently bonded to X$_2$ and X$_3$ is covalently bonded to X$_4$; or
KIKHVVKLKDX$_1$NSQX$_2$X$_3$SEVX$_4$KLRSQLVKRK (SEQ ID NO: 27), wherein X$_1$ is glutamic acid, X$_2$ is lysine, X$_3$ is glutamic acid, X$_4$ is lysine, and wherein X$_1$ is covalently bonded to X$_2$ and X$_3$ is covalently bonded to X$_4$.

18. The peptide of claim 16, wherein the amino acid sequence of the peptide comprises VSKLRX$_1$QLVX$_2$RKQN (SEQ ID NO: 9), wherein X$_1$ is glutamic acid and X$_2$ is lysine, and wherein X$_1$ is covalently bonded to X$_2$.

19. The peptide of claim 1, wherein the peptide is acetylated at its amino-terminus.

20. The peptide of claim 1, wherein the peptide is amidated at its carboxy-terminus.

21. A pharmaceutical composition comprising one or more peptides of claim 1 and a pharmaceutically acceptable carrier.

22. A method for treating a subject suffering from a disorder or condition associated with elevated levels of hyaluronic acid (HA) or RHAMM comprising administering to the subject an effective amount of one or more peptides of claim 1 or a pharmaceutical composition comprising one or more peptides of claim 1 and a pharmaceutically acceptable carrier.

23. The peptide of claim 1, wherein the peptide has a length of at least 8 amino acids.

24. The peptide of claim 1, wherein the peptide comprises 50 amino acids or fewer.

* * * * *